(12) United States Patent
Flanagan et al.

(10) Patent No.: US 9,744,188 B2
(45) Date of Patent: Aug. 29, 2017

(54) METHODS OF PROMOTING NEURONAL OUTGROWTH BY GYPICAN 2 THAT BINDS TO RECEPTOR PROTEIN TYROSINE PHOSPHATASE SIGMA

(75) Inventors: John G. Flanagan, Weston, MA (US); Yingjie Shen, Brighton, MA (US); Edith Yvonne Jones, Oxford (GB); Alexandru Radu Aricescu, Oxford (GB); Charlotte Hannah Coles, Bonn (DE)

(73) Assignees: PRESIDENT AND FELLOWS OF HARVARD COLLEGE, Cambridge, MA (US); THE CHANCELLOR, MASTERS AND SCHOLARS OF THE UNIVERSITY OF OXFORD, Oxford (GB)

(*) Notice: Subject to any disclaimer, the term of this patent is extended or adjusted under 35 U.S.C. 154(b) by 0 days.

(21) Appl. No.: 13/985,629

(22) PCT Filed: Feb. 17, 2012

(86) PCT No.: PCT/US2012/025738
§ 371 (c)(1),
(2), (4) Date: Oct. 23, 2013

(87) PCT Pub. No.: WO2012/112953
PCT Pub. Date: Aug. 23, 2012

(65) Prior Publication Data
US 2014/0045762 A1 Feb. 13, 2014

Related U.S. Application Data

(60) Provisional application No. 61/444,620, filed on Feb. 18, 2011.

(51) Int. Cl.
| | | |
|---|---|---|
| *A61K 38/00* | (2006.01) |
| *A61K 38/18* | (2006.01) |
| *A61K 49/00* | (2006.01) |
| *C07K 14/475* | (2006.01) |
| *C07K 14/48* | (2006.01) |
| *C07K 14/00* | (2006.01) |
| *A61K 31/727* | (2006.01) |
| *A61K 45/06* | (2006.01) |
| *A61K 31/737* | (2006.01) |
| *A61K 38/17* | (2006.01) |

(52) U.S. Cl.
CPC .......... *A61K 31/727* (2013.01); *A61K 31/737* (2013.01); *A61K 38/177* (2013.01); *A61K 45/06* (2013.01)

(58) Field of Classification Search
CPC .... A61K 31/727; A61K 31/737; A61K 47/26; A61K 35/454; C07K 14/705; C12N 2502/02; C12N 5/0619; G01N 2333/4722; G01N 2800/28
See application file for complete search history.

(56) References Cited

U.S. PATENT DOCUMENTS

| | | | | |
|---|---|---|---|---|
| 6,020,323 | A * | 2/2000 | Cohen et al. | 514/53 |
| 6,143,730 | A * | 11/2000 | Parish et al. | 514/54 |
| 7,754,432 | B2 * | 7/2010 | Rosenberg et al. | 435/7.1 |
| 8,530,169 | B2 * | 9/2013 | Rosenberg et al. | 435/7.1 |
| 2002/0045185 | A1 | 4/2002 | McCarthy et al. | |
| 2004/0024181 | A1 * | 2/2004 | Gangolli et al. | 530/350 |
| 2004/0138255 | A1 | 7/2004 | Huang et al. | |
| 2006/0183712 | A1 * | 8/2006 | McKeehan et al. | 514/56 |
| 2006/0293275 | A1 * | 12/2006 | Nakamura et al. | 514/53 |
| 2007/0010484 | A1 | 1/2007 | Eisenbach-Schwartz et al. | |
| 2007/0134234 | A1 | 6/2007 | Smith et al. | |
| 2008/0152689 | A1 | 6/2008 | Baird et al. | |
| 2009/0036405 | A1 * | 2/2009 | Kennedy | 514/56 |
| 2009/0117112 | A1 | 5/2009 | Smith et al. | |
| 2012/0083465 | A1 * | 4/2012 | Kennedy | 514/56 |
| 2012/0231014 | A1 * | 9/2012 | Flanagan et al. | 424/158.1 |

FOREIGN PATENT DOCUMENTS

| | | |
|---|---|---|
| WO | 99/66959 | 6/1999 |
| WO | 02/060471 A2 | 8/2001 |
| WO | 02/083182 | 10/2002 |
| WO | 2011/022462 A2 | 2/2011 |

OTHER PUBLICATIONS

Kurosawa et al. Glycoconjugate J. 2001. 18:499-507.*
Akita et al., Biochem J., 383:129-138 (2004). "Hepar sulphate proteoglycans interact with neurocan and promote neurite outgrowth from cerebellar granule cells."
Bandtlow et al., Physiol. Rev. 80:1267-1290 (2000) "Proteoglycans in the Developing Brain: New Conceptual Insights for Old Proteins."
Blight, Nature Neuroscience Supplement. 5:1051-1054 (2002). "Miracles and molecules- progress in spinal cord repair."
Bowie et al., Science, 247(4948):1306-1310 (1990). "Deciphering the Message in Protein Sequences: Tolerance to Amino Acid Substitutions."
Burgess et al., The Journal of Cell Biology, 111:2129-2138 (1990). "Possible Dissociation of the Heparin-binding and Mitogenic Activites of Heparin-binding (Acidic Fibroblast) Growth Factor-1 from Its Receptor-binding Activities by Site-directed Mutagenesis of a Single Lysine Residue."

(Continued)

*Primary Examiner* — Chang-Yu Wang
(74) *Attorney, Agent, or Firm* — Nixon Peabody LLP; David S. Resnick; Shayne Y. Huff

(57) ABSTRACT

Disclosed herein are methods of inducing neuronal outgrowth of a neuron. The methods comprise contacting the neuron with an agent that binds receptor protein tyrosine phosphatase δ (RPTPδ), to thereby induce neuronal outgrowth of the neuron. The agent may induces clustering of RPTPδ and/or inhibit binding of chondroitin sulfate proteoglycan (CSPG) to RPTPδ. Examples of suitable agents are heparan sulfate proteoglycan, heparan sulfate, heparan sulfate oligosaccharides, or heparin oligosaccharides. Additional agents are also disclosed. The neuron can be a CNS neuron or peripheral neuron. Also disclosed herein are methods of treating neuronal injury in a subject comprising, administering to the subject an agent that binds RPTPδ. Administration may be to a site of neuronal injury, to thereby induce neuronal outgrowth at the site of neuronal injury.

9 Claims, 66 Drawing Sheets

(56) References Cited

OTHER PUBLICATIONS

Case et al., Curr Biol 15, R749 (2005). "Regeneration of the adult central nervous system."
Coles et al., Science, 332:484-488 (2011). "Proteoglycan-specific molecular switch for RPTsigma clustering and neuronal extension."
Dobbertin et al., Molecular and Cellular Neuroscience, 24:951-971 (2003). "Regulation of RPTPbeta/phosphacan expression and glycosaminoglycan epitopes in injured brain and cytokine-treated glia."
Duan et al., Science Signaling, 3:pe6 (2010). "A New Role for RPTP in Spinal Cord Injury: Signaling Chondroitin Sulfate Proteoglycan Inhibition."
Endo et al., J Bone Miner Res, 11:535 ((1996). "Human Protein Tyrosine Phosphatase-sigma: Alternative Splicing and Inhibition by Bisphosphates."
Flanagan et al., Annu. Rev. Neurosci., 21:309-345 (1998). "The Ephrins and EPH Receptors in Neural Development."
Fox et al., Current Biology, 15:1701-1711 (2005). "The heparan sulfate proteoglycan syndecan is an in vivo ligand for the drosophila LAR receptor tyrosine phosphatase".
Fry et al., Glia 58:423-433 (2010). "Corticospinal tract regeneration after spinal cord injury in receptor protein tyrosine phosphatase sigma deficient mice."
Galtrey et al., Brain Res. Rev. 54:1-18 (2007). "The role of chondroitin sulfate proteoglycans in regeneration and plasticity in the central nervous system."
Groves et al., Nat Struct Mol Biol 17:659-665 (2010). "Molecular mechanisms in signal transduction at the membrane."
Harmer et al., Biochem J 393:741-748 (2006), "Multimers of the fibroblast growth factor (FGF)-FGF receptor-saccharide complex are formed on long oligomers of heparin."
Hoke, Nature Clinical Practice Neurology, 2(8):448-454 (2006). "Mechanisms of Disease: what factors limit the success of peripheral nerve regeneration in humans?".
Johnson et al., Physiol. Rev. 83:1-24 (2003). "Receptor Protein Tyrosine Phosphatases in Nervous System Development."
Johnson et al., Neuron, 49(4):517-531 (2006). "The HSPGs Syndecan and Dallylike bind the receptor phosphatase LAR and exert distinct effects on synaptic development."
Jones et al., Experimental Neurology, 182:399-411 (2003). "The chondroitin sulfate proteoglycans neurocan, brevican, phosphacan, and versican are differentially regulated following spinal cord injury."
Kantor et al., Neuron 44:961-975 (2004). "Semaphorin 5A is a Bifunctional Axon Guidance Cue Regulated by Heparan and Chondroitin Sulfate Proteoglycans."
Kinnunen et al., The Journal of Biological Chemistry, 271(4):2243-2248 (1996). "Neurite Outgrowth in Brain Neurons Induced by Heparin-binding Growth-associated Molecule (HB-GAM) Depends on the Specific Interaction of HB-GAM with Heparan Sulfate at the Cell Surface."
Kirkham et al., BMC Neuroscience, 7:50 (2006). "Neural stem cells from protein tyrosine phosphatase sigma knockout mice generate an altered neuronal phenotype in culture."
Ledig, et al., J. Cell Biol 147:375-388 (1999). "The receptor tyrosine phosphatase CRYPalpha promotes intraretinal axon growth."
Matsumoto, et al., J Neurosci 27(16):4342-4350 (2007). "Netrin-1/DCC Signaling in Commissural Axon Guidance Requires Cell-Autonomous Expression of Heparan Sulfate."
McLean et al., J. Neurosci. 22:5481-4591 (2002). "Enhanced Rate of Nerve Regeneration and Directional Errors After Sciatic Nerve Injury in Receptor Protein Tyrosine Phosphatase ς Knock-Out Mice."
Murphy et al., J. Biol Chem., 279;27239-27245 (2004). "Interchain Proteolysis in teh Absence of a Dimerization Stimulus, Can Initiate Apoptosis-associated Caspase-8 Activation."
Pawson et al, Science, 300:445-452 (2003). "Assembly of Cell Regulatory Systems Through Protein Interaction Domains."
Pulido et al., PNAS, 92:11686-11690 (1995). "The LAR/PTP delta/PTP sigma subfamily of transmembrane protein-tyrosine-phosphatases: multiple human LAR, PTP delta, and PTP sigma isoforms are expressed in a tissue-specific manner and associate with the LAR-interacting protein LIP.1."
Robles et al., J. Neurosci. 25(33):7669-7681 (2005). "Src-Dependent Tyrosine Phosphorylation at the Tips of Growth Cone Filopodia Promotes Extension."
Sajnani-Perez et al., Molecular and Cellular Neuroscience, 22:37-48 (2003). "Isoform-specific binding of the tyrosine phosphatase PTPsigma to a ligand in developing muscle."
Sajnani et al., Journal of Neurobiology. 65(1):59-71 (2005). "PTPsigma promotes retinal neurite outgrowth non-cell autonomously."
Sapieha et al., Mol. Cell. Neuro. 28:625-635 (2005). "Receptor tyrosine phosphatase sigma inhibits axon regrowth in the adult injured CNS."
Schmidt et al., Annu. Rev. Biomed. Engl., 5:293-347 (2003). "Neural Tissue Engineering: strategies for Repair and Regeneration."
Shen et al., Science 326:592-596 (2009). "PTPsigma is a receptor for Chondroitin Sulfate Proteoglycan, an inhibitor of neural regeneration."
Silver et al., Nat. Rev. Neurosci. 5:146-156 (2004). "Regeneration beyond the glial scar."
Spivak-Kroizman et al., Cell 79:1015-1024 (1994). "Heparin-induced oligomenzation of FGF molecules is responsible for FGF receptor dimerization, activation, and cell proliferation."
Thompson et al., Mol. Cell. Neuro. 23:681-692 (2003). "Receptor protein tyrosine phosphatase sigma inhibits axonal regeneration and the rate of axon extension."
Van Vactor et al., Curr. Opin. Neurobiol. 16:40-51 (2006). "Heparan sulfate proteoglycans and the emergence of neuronal connectivity."
Vearing et al., Growth Factors, 23:67-76 (2005). "Eph receptor signalling dimerisation just isn't enough".
Wu et al., J. Cell Biol. 123:653-664 (1993). "Regulated tyrosine phosphorylation at the tips of growth cone filopodia."
Aricescu et al., Molecular and Cellular Biology, 22(6):1881-1892 (2002). "Heparan sulfate proteoglycans are ligands for receptor protein tyrosine phosphate sigma."

* cited by examiner

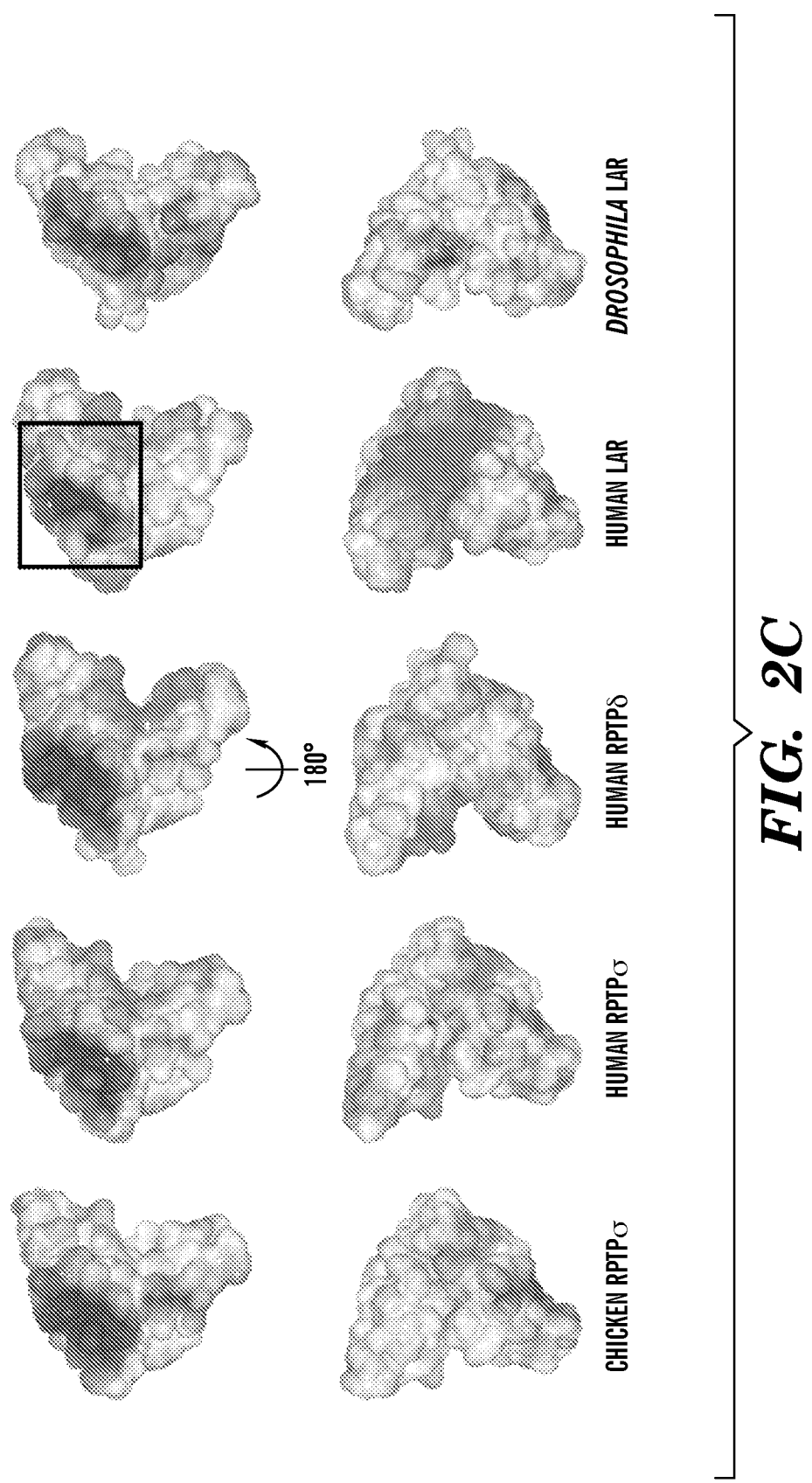

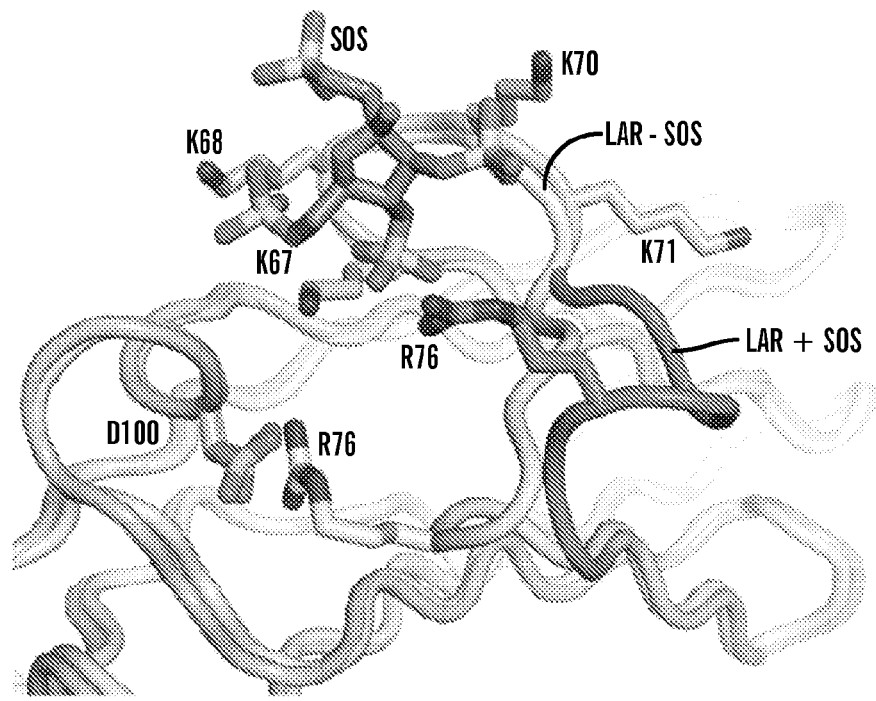
FIG. 2D
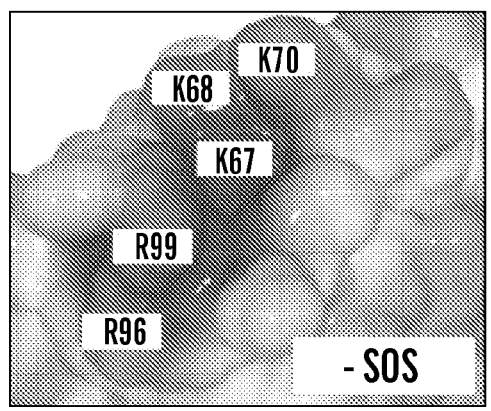 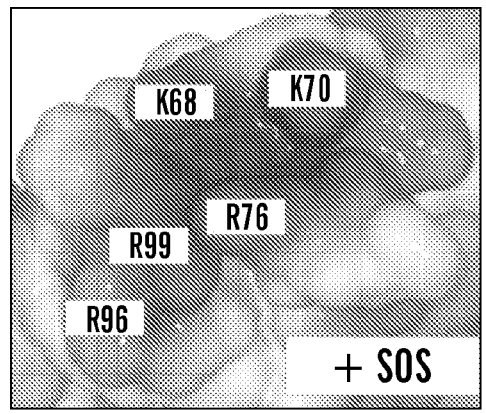
FIG. 2E  FIG. 2F

| REFERENCE STRUCTURE | MOVING STRUCTURE | RESIDUE RANGE USED FOR ALIGNMENT | EQUIVALENT RESIDUES | SEQUENCE IDENTITY OF EQUIVALENCES (%) | rmsd OF EQUIVALENCES (Å) |
|---|---|---|---|---|---|
| HUMAN RPTPσ $14_122$ Ig1 | CHICKEN RPTPσ $14_122$ Ig1 | 29 TO 125 | 97 | 92 | 0.27 |
| HUMAN RPTPσ $14_122$ Ig1 | HUMAN RPTPσ C2 Ig1 | 30 TO 126 | 96 | 100 | 0.45 |
| HUMAN RPTPσ $14_122$ Ig1 | HUMAN LAR $P3_221$ Ig1 | 30 TO 126 | 97 | 71 | 0.76 |
| HUMAN RPTPσ $14_122$ Ig1 | HUMAN RPTPδ $P3_221$ Ig1 | 21 TO 117 | 97 | 73 | 0.70 |
| HUMAN RPTPσ $14_122$ Ig1 | HUMAN RPTPδ C2 A Ig1 | 21 TO 117 | 95 | 75 | 1.00 |
| HUMAN RPTPσ $14_122$ Ig1 | HUMAN RPTPδ C2 B Ig1 | 21 TO 117 | 97 | 73 | 0.84 |
| HUMAN RPTPσ $14_122$ Ig1 | *DROSOPHILA* LAR C2 Ig1 | 35 TO 228 | 91 | 44 | 0.99 |
| HUMAN RPTPσ $14_122$ Ig2 | CHICKEN RPTPσ $14_122$ Ig2 | 132 TO 225 | 94 | 96 | 0.19 |
| HUMAN RPTPσ $14_122$ Ig2 | HUMAN RPTPσ C2 Ig2 | 133 TO 226 | 94 | 100 | 0.76 |
| HUMAN RPTPσ $14_122$ Ig2 | HUMAN LAR $P3_221$ Ig2 | 133 TO 226 | 94 | 89 | 0.50 |
| HUMAN RPTPσ $14_122$ Ig2 | HUMAN RPTPδ $P3_221$ Ig2 | 124 TO 117 | 88 | 82 | 1.41 |
| HUMAN RPTPσ $14_122$ Ig2 | HUMAN RPTPδ C2 A Ig2 | 124 TO 117 | 89 | 83 | 1.25 |
| HUMAN RPTPσ $14_122$ Ig2 | HUMAN RPTPδ C2 B Ig2 | 124 TO 117 | 87 | 82 | 1.45 |
| HUMAN RPTPσ $14_122$ Ig2 | *DROSOPHILA* LAR C2 Ig2 | 138 TO 228 | 92 | 46 | 1.26 |

| STRUCTURE | INTERDOMAIN INTERFACE (Å$^2$) | ΔG (kcal/mol) | Ig1-Ig2 ANGLE DEVIATION (*) | SURFACE COMPLEMENTARITY STATISTIC |
|---|---|---|---|---|
| HUMAN RPTPσ $14_122$ | 640 | -6.9 | 0.0 | 0.681 |
| CHICKEN RPTPσ $14_122$ | 659 | -7.8 | 2.2 | 0.723 |
| HUMAN RPTPσ C2 | 662 | -7.4 | -5.0 | 0.739 |
| HUMAN LAR $P3_221$ | 662 | -7.7 | -7.8 | 0.718 |
| HUMAN RPTPδ $P3_221$ | 654 | -6.9 | -5.9 | 0.693 |
| HUMAN RPTPδ C2 A | 694 | -6.0 | -10.2 | 0.700 |
| HUMAN RPTPδ C2 B | 644 | -6.9 | -3.7 | 0.683 |
| *DROSOPHILA* LAR C2 | 588 | 0.0 | 11.3 | 0.590 |

*FIG. 7C*

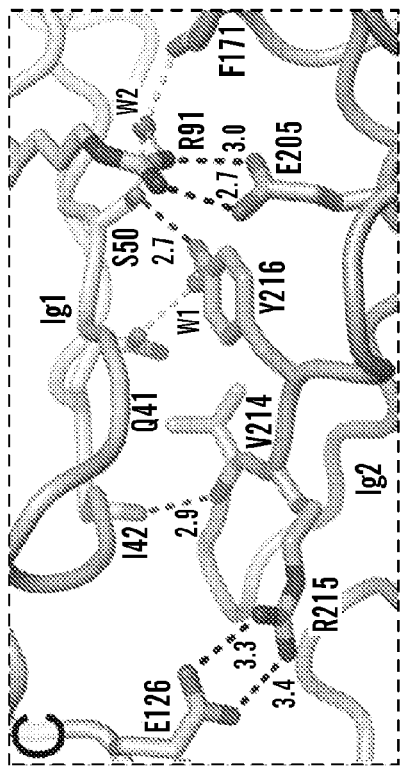
*FIG. 8C*
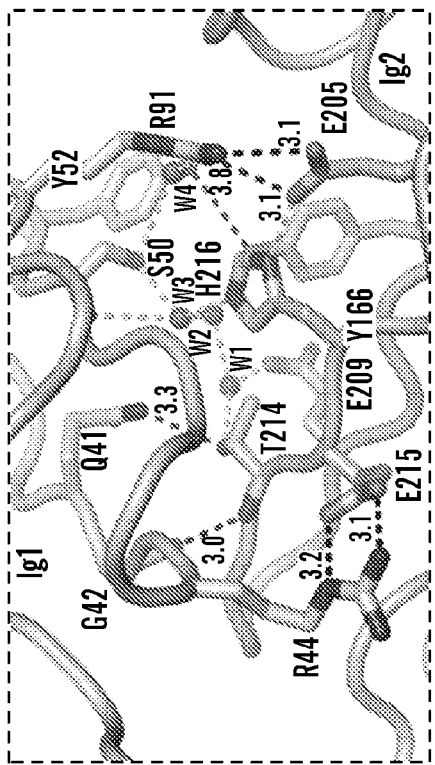
*FIG. 8F*
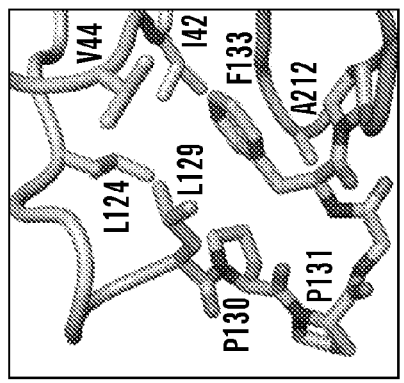
*FIG. 8B*
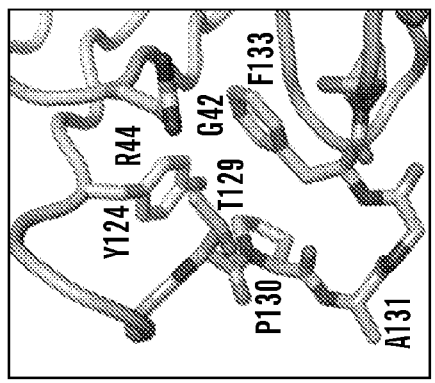
*FIG. 8E*
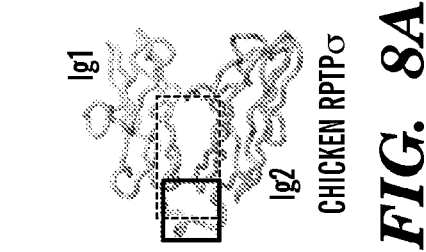
*FIG. 8A* CHICKEN RPTPσ
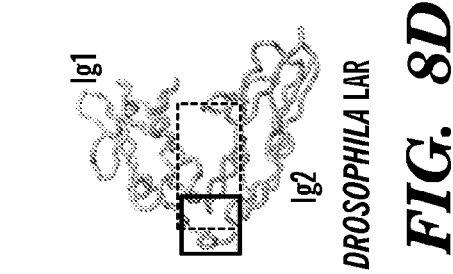
*FIG. 8D* DROSOPHILA LAR

```
                                                                                             Ig2
                                                                            ────────────────────────────────
                                                    d              a    c      b
                 128  DQLPSG ENIDMGPQLKWERIRIATMLCAASGNPDEI TWF KDFLP VDPAASNGRIKQLRSGAIQIESSEEIDQGKY E CVA T M SAGVRY SSPANLYVRV  227
RPTPS_human
RPTPS_mouse      128  DQLPPG ENIDMGPQLKWERIRIATMLCAASGNPDEI TWF KDFLP VDPAASNGRIKQLRSGAIQIESSEEIDQGKY E CVA T M SAGVRY SSPANLYVRV  227
RPTPS_chick      127  DQLPRG ENIDMGPQLKWERIRIATMLCAASGNPDEI TWF KDFLP VDPSTSNGRIKQLRSGGIQIESSEEIDQGKY E CVA S M SAGVRY SSPANLYVRV  226
RPTPS_xenopus    119  DQLPSG ENIDMGPQLKWERIRIATMLCAASGNPDEI TWF KDFLP VDPAASNGRIKQLRSGAIQIENSEEIDQGKY E CVA T M SAGVRY SSPANLYVRV  218
RPTPS_zebrafish  187  DLLPRG ENIDMGPQLKWERIRIATMLCAASGNPDEI TWF KDFLP VDKTSNGRIKQLRSGAIQIENIEEIDQGKY E CVA S N VEGVRY SSPANLYVRV  286
RPTPD_human      119  DQLPRG ETIDMGPQLKWERIRIATMLCAASGNPDEI TWF KDFLP VDTSNANGRIKQLRSGAIQIEQSEEIDQGKY E CVA T M SAGTRY SAPANLYVRV  218
RPTPD_mouse      126  DQLPRG ETIDMGPQLKWERIRIATMLCAASGNPDEI TWF KDFLP VDTSNANGRIKQLRSGAIQIEQSEEIDQGKY E CVA T M SAGTRY SAPANLYVRV  225
RPTPD_chick      127  DQLPRG ESIDMGPQLKWERSRIATMLCAASGNPDEI SWF KDFLP VDTSNANGRIKQLRSGAIQIEISEEIDQGKY E CVA T M SAGTRY SAPANLYVRV  226
RPTPD_xenopus    126  DQLPRG ESIDMGPQLKWERIRIATMLCAASGNPDEI TWF KDYLP VDTSNANGRIKQLRSGAIQIEQSEEIDQGKY E CVA T M SAGTRY SAPANLYVRV  225
RPTPD_zebrafish  127  DQLPAG ESIDMGPQLKWERSRIATMLCAASGNPDEI TWF KDFLP IDT-HIHGRIKQLRSGAIQIDQSEEIDQGKY E CVA T M SEGTRY STPANLYVRV  225
RPTPF_human      128  EQLPRG ESIDMGPQLKWEKIRIATMLCAASGGNPDEI SWF KDFLP VDPATSNGRIKQLRSGAIQIESSEESDQGKY E CVA T M SAGTRY SAPANLYVRV  227
RPTPF_mouse      128  DQLPSS ETIDMGPQLKWERGRIATMLCAAGGNPDEI SWF KDFLP VDPAASNGRIKQLRSGAIQIESSEESDQGKY E CVA T M SAGTRY SAPANLYVRV  227
RPTPF_chick      129  DHLPAG ETIDMGPQLKWEKARIATMLCAAGGNPDEI SWF KDFLP VDTA-SNGRIKQLRSGAIQIESSEESDQGKY E CVA T M SAGTRY SAPANLYVRV  228
RPTPF_xenopus    125  EQLPAG ETIDMGPQLKWEKIRIATMLCAASGNPDEI TWF KDFLP VDTSSNGRIKQLRSGAIQIENSEESDQGKY E CVA T M SAGTRY SAPANLYVRV  224
RPTPF_zebrafish  130  NQLPRG ETIDMGPQLKWERIRIATMLCAASGNPDEI TWF KDFLP VDING-NGRIKQLRSGAIQIENSEESDQGKY E CVA T M SAGTRY SAPANLYVRV  228
RPTPF_drosophila 133  DKLPAG EVITQQPGCTRVIEVGHTVLMTCKAIGNPTNI YW I KN QTK V DMSN--PRVSLKDEFLQIENSREEDQGKY E CVA E NS MGTEH SKATNLYKV  229
                             ▲                                              *                           ▲**
                             ▲
```

Human PTPsigma transcript variant 4, amino acid sequence

MAPTWGPGMVSVVGPMGLLVVLLVGGCAAEEPPRFIKEPKDQIGVSGGVASFVCQATGDPKPRVT
WNKKGKKVNSQRFETIEFDESAGAVLRIQPLRTPRDENVYECVAQNSVGEITVHAKLTVLREDQL
PSGFPNIDMGPQLKVVERTRTATMLCAASGNPDPEITWFKDFLPVDPSASNGRIKQLRSGALQIE
SSEETDQGKYECVATNSAGVRYSSPANLYVRELREVRRVAPRFSILPMSHEIMPGGNVNITCVAV
GSPMPYVKWMQGAEDLTPEDDMPVGRNVLELTDVKDSANYTCVAMSSLGVIEAVAQITVKSLPKA
PGTPMVTENTATSITITWDSGNPDPVSYYVIEYKSKSQDGPYQIKEDITTTRYSIGGLSPNSEYE
IWVSAVNSIGQGPPSESVVTRTGEQAPASAPRNVQARMLSATTMIVQWEEPVEPNGLIRGYRVYY
TMEPEHPVGNWQKHNVDDSLLTTVGSLLEDETYTVRVLAFTSVGDGPLSDPIQVKTQQGVPGQPM
NLRAEARSETSITLSWSPPRQESIIKYELLFREGDHGREVGRTFDPTTSYVVEDLKPNTEYAFRL
AARSPQGLGAFTPVVRQRTLQSISPKNFKVKMIMKTSVLLSWEFPDNYNSPTPYKIQYNGLTLDV
DGRTTKKLITHLKPHTFYNFVLTNRGSSLGGLQQTVTAWTAFNLLNGKPSVAPKPDADGFIMVYL
PDGQSPVPVQSYFIVMVPLRKSRGGQFLTPLGSPEDMDLEELIQDISRLQRRSLRHSRQLEVPRP
YIAARFSVLPPTFHPGDQKQYGGFDNRGLEPGHRYVLFVLAVLQKSEPTFAASPFSDPFQLDNPD
PQPIVDGEEGLIWVIGPVLAVVFIICIVIAILLYKNKPDSKRKDSEPRTKCLLNNADLAPHHPKD
PVEMRRINFQTPGMLSHPPIPIADMAEHTERLKANDSLKLSQEYESIDPGQQFTWEHSNLEVNKP
KNRYANVIAYDHSRVILQPIEGIMGSDYINANYVDGYRCQNAYIATQGPLPETFGDFWRMVWEQR
SATIVMMTRLEEKSRIKCDQYWPNRGTETYGFIQVTLLDTIELATFCVRTFSLHKNGSSEKREVR
QFQFTAWPDHGVPEYPTPFLAFLRRVKTCNPPDAGPIVVHCSAGVGRTGCFIVIDAMLERIKPEK
TVDVYGHVTLMRSQRNYMVQTEDQYSFIHEALLEAVGCGNTEVPARSLYAYIQKLAQVEPGEHVT
GMELEFKRLANSKAHTSRFISANLPCNKFKNRLVNIMPYESTRVCLQPIRGVEGSDYINASFIDG
YRQQKAYIATQGPLAETTEDFWRMLWENNSTIVVMLTKLREMGREKCHQYWPAERSARYQYFVVD
PMAEYNMPQYILREFKVTDARDGQSRTVRQFQFTDWPEQGVPKSGEGFIDFIGQVHKTKEQFGQD
GPISVHCSAGVGRTGVFITLSIVLERMRYEGVVDIFQTVKMLRTQRPAMVQTEDEYQFCYQAALE
YLGSFDHYAT (SEQ ID NO: 1)

*FIG. 26*

The human PTPsigma transcript variant 4, nucleotide sequence

```
   1 cctcgcgccg cccgcccggc agcccggccg gcgcgcgcac gccgcgagcc gctggcgctc
  61 gggctccgct cggatcccat gcaacagcca cgatgtgaag cggggcagag ccgggggagc
 121 ccagcccagc cagcctccag acgttgcccc atctgacgct cggctcgagg cctctctgtg
 181 agggaccggg gggccatccc cctccagggc ggagatcgga ggtcgctgcc aagcatggcg
 241 cccacctggg gccctggcat ggtgtctgtg gttggtccca tgggcctcct tgtggtcctg
 301 ctcgttggag gctgtgcagc agaagagccc cccaggttta tcaaagaacc caaggaccag
 361 atcggcgtgt cgggggggtgt ggcctctttc gtgtgtcagg ccacgggtga ccccaagcca
 421 cgagtgacct ggaacaagaa gggcaagaag gtcaactctc agcgctttga gacgattgag
 481 tttgatgaga gtgcaggggc agtgctgagg atccagccgc tgaggacacc gcgggatgaa
 541 aacgtgtacg agtgtgtggc ccagaactcg gttggggaga tcacagtcca tgccaagctt
 601 actgtcctcc gagaggacca gctgccctct ggcttcccca acatcgacat gggcccacag
 661 ttgaaggtgg tggagcggac acggacagcc accatgctct gtgcagccag cggcaaccct
 721 gaccctgaga tcacctggtt caaggacttc ctgcctgtgg atcctagtgc cagcaatgga
 781 cgcatcaaac agctgcgatc aggagccctg cagattgaaa gcagtgagga aaccgaccag
 841 ggcaaatatg agtgtgtggc caccaacagc gccggcgtgc gctactcctc acctgccaac
 901 ctctacgtgc gagagcttcg agaagtccgc cgcgtggccc cgcgcttctc catcctgccc
 961 atgagccacg agatcatgcc aggggcaac gtgaacatca cctgcgtggc cgtgggctcg
1021 cccatgccat acgtgaagtg gatgcagggg gccgaggacc tgaccccga ggatgacatg
1081 cccgtgggtc ggaacgtgct ggaactcaca gatgtcaagg actcggccaa ctacacctgc
1141 gtggccatgt ccagcctggg cgtcattgag gcggttgctc agatcacggt gaaatctctc
1201 cccaaagctc ccgggactcc catggtgact gagaacacag ccaccagcat caccatcacg
1261 tgggactcgg caacccaga tcctgtgtcc tattacgtca tcgaatataa atccaagagc
1321 caagacgggc cgtatcagat taaagaggac atcaccacca cacgttacag catcggcggc
1381 ctgagcccca actcggagta cgagatctgg gtgtcggccg tcaactccat cggccaggggg
1441 cccccccagcg agtccgtggt cacccgcaca ggcgagcagg ccccggccag cgcgccgcgg
1501 aacgtgcaag cccggatgct cagcgcgacc accatgattg tgcagtggga ggagccggtg
1561 gagcccaacg gcctgatccg cggctaccgc gtctactaca ccatggaacc ggagcacccc
1621 gtgggcaact ggcagaagca caacgtggac gacagcctgc tgaccaccgt gggcagcctg
1681 ctggaggacg agacctacac cgtgcgggtg ctcgccttca cctccgtcgg cgacgggccc
1741 ctctcggacc ccatccaggt caagacgcag cagggagtgc cgggccagcc catgaacctg
1801 cgggccgagg ccaggtcgga gaccagcatc acgctgtcct ggagccccccc gcggcaggag
1861 agtatcatca agtacgagct cctcttccgg gaaggcgacc atggccggga ggtgggaagg
1921 accttcgacc cgacgacttc ctacgtggtg gaggacctga agcccaacac ggagtacgcc
1981 ttccgcctgg cggcccgctc gccgcagggc ctgggcgcct cacccccgt ggtgcggcag
2041 cgcacgctgc agtccatctc gcccaagaac ttcaaggtga aatgatcat gaagacatca
2101 gttctgctca gctgggagtt ccctgacaac tacaactcac ccacaccta caagatccag
2161 tacaatgggc tcacactgga tgtggatggc cgtaccacca agaagctcat cacgcacctc
```

*FIG. 27*

```
2221 aagccccaca ccttctacaa ctttgtgctg accaatcgcg gcagcagcct gggcggcctc
2281 cagcagacgg tcaccgcctg gactgccttc aacctgctca acggcaagcc cagcgtcgcc
2341 cccaagcctg atgctgacgg cttcatcatg gtgtatcttc ctgacggcca gagcccgtg
2401 cctgtccaga gctatttcat tgtgatggtg ccactgcgca agtctcgtgg aggccaattc
2461 ctgaccccgc tgggtagccc agaggacatg gatctggaag agctcatcca ggacatctca
2521 cggctacaga ggcgcagcct gcggcactcg cgtcagctgg aggtgccccg gccctatatt
2581 gcagctcgct tctctgtgct gccacccacg ttccatcccg gcgaccagaa gcagtatggc
2641 ggcttcgata accggggcct ggagcccggc caccgctatg tcctcttcgt gcttgccgtg
2701 cttcagaaga gcgagcctac ctttgcagcc agtcccttct cagacccctt ccagctggat
2761 aacccggacc cccagcccat cgtggatggc gaggaggggc ttatctgggt gatcgggcct
2821 gtgctggccg tggtcttcat aatctgcatt gtcattgcta tcctgctcta caagaacaaa
2881 cccgacagta aacgcaagga ctcagaaccc cgcaccaaat gcctcctgaa caatgccgac
2941 ctcgcccctc accacccaa ggaccctgtg gaaatgagac gcattaactt ccagactcca
3001 ggcatgctta gccacccgcc aattcccatc gcagacatgg cggagcacac ggagcggctc
3061 aaggccaacg acagcctcaa gctctcccag gagtatgagt ccatcgaccc tggacagcag
3121 ttcacatggg aacattccaa cctggaagtg aacaagccga agaaccgcta tgccaacgtc
3181 atcgcctatg accactcccg tgtcatcctc cagcccattg aaggcatcat gggcagtgat
3241 tacatcaatg ccaactacgt ggacggctac cggtgtcaga acgcgtacat gccacgcag
3301 gggccgctgc ctgagacctt tgggacttc tggcgtatgg tgtgggagca gcggtcggcg
3361 accatcgtca tgatgacgcg gctggaggag aagtcacgga tcaagtgtga tcagtattgg
3421 cccaacagag gcacggagac ctacggcttc atccaggtca cgttgctaga taccatcgag
3481 ctggccacat tctgcgtcag gacattctct ctgcacaaga atggctccag tgagaaacgc
3541 gaggtccgcc agttccagtt tacggcgtgg ccggaccatg gcgtgccga tacccaacg
3601 cccttcctgg ctttcctgcg gagagtcaag acctgcaacc cgccagatgc cggccccatc
3661 gtggttcact gcagtgccgg tgtgggccgc acaggctgct ttatcgtcat cgacgccatg
3721 cttgagcgga tcaagccaga gaagacagtc gatgtctatg ccacgtgac gctcatgagg
3781 tcccagcgca actacatggt gcagacggag gaccagtaca gcttcatcca cgaggccctg
3841 ctggaggccg tgggctgtgg caacacagaa gtgcccgcac gcagcctcta tgcctacatc
3901 cagaagctgg cccaggtgga gcctggcgaa cacgtcactg gcatggaact cgagttcaag
3961 cggctggcta actccaaggc ccacacgtca cgcttcatca gtgccaatct gccttgtaac
4021 aagttcaaga accgcctggt gaacatcatg ccctatgaga gcacacgggt ctgtctgcaa
4081 cccatccggg gtgtggaggg ctctgactac atcaacgcca gcttcattga tggctacagg
4141 cagcagaagg cctacatcgc gacacagggg ccgctggcgg agaccacgga agacttctgg
4201 cgcatgctgt gggagaacaa ttcgacgatc gtggtgatgc tgaccaagct gcgggagatg
4261 ggccgggaga agtgtcacca gtactggccg gccgagcgct ctgcccgcta ccagtacttt
4321 gtggtagatc cgatggcaga atacaacatg cctcagtata tcctgcgaga gttcaaggtc
4381 acagatgccc gggatggcca gtcccggact gtccggcagt ccagttcac agactggccg
4441 gaacagggtg tgccaaagtc ggggagggc ttcatcgact tcattggcca agtgcataag
4501 actaaggagc agtttggcca ggacggcccc atctctgtcc actgcagtgc cggcgtgggc
```

```
4561 aggacgggcg tcttcatcac gcttagcatc gtgctggagc ggatgcggta tgaaggcgtg
4621 gtggacatct ttcagacggt gaagatgcta cgaacccagc ggccggccat ggtgcagaca
4681 gaggatgagt accagttctg ttaccaggcg gcactggagt acctcggaag ctttgaccac
4741 tatgcaacct aaagccatgg ttcccccag gcccgacacc actggccccg gatgcctctg
4801 cccctcccgg gcggacctcc tgaggcctgg accccagtg ggcagggcag gaggtggcag
4861 cggcagcagc tgtgtttctg caccatttcc gaggacgacg cagcccctcg agccccccca
4921 ccggccccgg ccgccccagc gacctccctg gcaccggccg ccgccttcaa atacttggca
4981 cattcctcct ttccttccaa ttccaaaacc agattccggg gtgggggtg ggggatggt
5041 gagcaaatag gagtgctccc cagaaccaga ggagggtggg gcacagacca tagacggacc
5101 cctcgtcctc ccccagcggt ggtaggggga cccgggggc tcctccccgc tctgcagcct
5161 ggggacactg ggctgggacc agaatccagc tttcttttaa aactctcagt gtaactgtat
5221 cccgtgacat ttcattttt ttaaatagtg tattttttt tccatttttt tttttaagag
5281 aaacaaacaa aagactcgcc agtcaatgac tttcaaagag aactaacttt ggcttattca
5341 tattctgttc aaagacagtc tattttttca ctgtagaaag cgtccttgtg tgatagttac
5401 gttcgcaaac gcgcacgcca ggcccatggc tgtaccttgg cttttttttt tttttttttt
5461 ttttaattt ttcctaccat cagaaagtgt gctttgctca cagaagaatg ggatgtcctt
5521 ttttctttct tggcttttt tttccccctt tttgtttcat ttttataaat taaattttca
5581 gacatatcaa atacagttct gagggtaagg tcatggggga gctcggaccc agtggcgttg
5641 ggtgcggttg aggggacgc tgctgtaaga ggagagagat gacagtggtc ctcctctgag
5701 agcctgagct gtctccccgt ctcccgcccc caaggagaca gagaggatcc tacttcttcg
5761 gggacagtgg ctgtatggct gtgctgcccc acatcaggga ccctttcccc ctgggactgt
5821 ggggcagttt gggagcaaaa ccagaaggac aggcccccct ctacccgcct accctgagca
5881 agcgagttgt tcctctttgt acaagggcag gtctgcggtt actttcaaca ctgtttattc
5941 cagcggaagc agccgggtgg ttttcccacc cccgtgtatg tagatatatc gactttgtat
6001 taaaggaaga tcgtctga (SEQ ID NO: 2)
```

FIG. 27 (cont.)

The human PTPσ transcript variant 3 amino acid sequence

MAPTWGPGMVSVVGPMGLLVVLLVGGCAAEEPPRFIKEPKDQIGVSGGVASFVCQATG
DPKPRVTWNKKGKKVNSQRFETIEFDESAGAVLRIQPLRTPRDENVYECVAQNSVGEIT
VHAKLTVLREDQLPSGFPNIDMGPQLKVVERTRTATMLCAASGNPDPEITWFKDFLPVD
PSASNGRIKQLRSGALQIESSEETDQGKYECVATNSAGVRYSSPANLYVRVRRVAPRFSI
LPMSHEIMPGGNVNITCVAVGSPMPYVKWMQGAEDLTPEDDMPVGRNVLELTDVKDS
ANYTCVAMSSLGVIEAVAQITVKSLPKAPGTPMVTENTATSITITWDSGNPDPVSYYVIE
YKSKSQDGPYQIKEDITTTRYSIGGLSPNSEYEIWVSAVNSIGQGPPSESVVTRTGEQAPA
SAPRNVQARMLSATTMIVQWEEPVEPNGLIRGYRVYYTMEPEHPVGNWQKHNVDDSL
LTTVGSLLEDETYTVRVLAFTSVGDGPLSDPIQVKTQQGVPGQPMNLRAEARSETSITLS
WSPPRQESIIKYELLFREGDHGREVGRTFDPTTSYVVEDLKPNTEYAFRLAARSPQGLGA
FTPVVRQRTLQSISPKNFKVKMIMKTSVLLSWEFPDNYNSPTPYKIQYNGLTLDVDGRTT
KKLITHLKPHTFYNFVLTNRGSSLGGLQQTVTAWTAFNLLNGKPSVAPKPDADGFIMVY
LPDGQSPVPVQSYFIVMVPLRKSRGGQFLTPLGSPEDMDLEELIQDISRLQRRSLRHSRQL
EVPRPYIAARFSVLPPTFHPGDQKQYGGFDNRGLEPGHRYVLFVLAVLQKSEPTFAASPF
SDPFQLDNPDPQPIVDGEEGLIWVIGPVLAVVFIICIVIAILLYKNKPDSKRKDSEPRTKCL
LNNADLAPHHPKDPVEMRRINFQTPGMLSHPPIPIADMAEHTERLKANDSLKLSQEYESI
DPGQQFTWEHSNLEVNKPKNRYANVIAYDHSRVILQPIEGIMGSDYINANYVDGYRCQN
AYIATQGPLPETFGDFWRMVWEQRSATIVMMTRLEEKSRIKCDQYWPNRGTETYGFIQ
VTLLDTIELATFCVRTFSLHKNGSSEKREVRQFQFTAWPDHGVPEYPTPFLAFLRRVKTC
NPPDAGPIVVHCSAGVGRTGCFIVIDAMLERIKPEKTVDVYGHVTLMRSQRNYMVQTE
DQYSFIHEALLEAVGCGNTEVPARSLYAYIQKLAQVEPGEHVTGMELEFKRLANSKAHT
SRFISANLPCNKFKNRLVNIMPYESTRVCLQPIRGVEGSDYINASFIDGYRQQKAYIATQG
PLAETTEDFWRMLWENNSTIVVMLTKLREMGREKCHQYWPAERSARYQYFVVDPMAE
YNMPQYILREFKVTDARDGQSRTVRQFQFTDWPEQGVPKSGEGFIDFIGQVHKTKEQFG
QDGPISVHCSAGVGRTGVFITLSIVLERMRYEGVVDIFQTVKMLRTQRPAMVQTEDEYQ
FCYQAALEYLGSFDHYAT (SEQ ID NO: 3)

FIG. 28

Human PTPσ transcript variant 3 nucleotide sequence:

```
   1 cctcgcgccg cccgcccggc agcccggccg gcgcgcgcac gccgcgagcc gctggcgctc
  61 gggctccgct cggatcccat gcaacagcca cgatgtgaag cggggcagag ccgggggagc
 121 ccagcccagc cagcctccag acgttgcccc atctgacgct cggctcgagg cctctctgtg
 181 agggaccggg gggccatccc cctccagggc ggagatcgga ggtcgctgcc aagcatggcg
 241 cccacctggg gccctggcat ggtgtctgtg gttggtccca tgggcctcct tgtggtcctg
 301 ctcgttggag gctgtgcagc agaagagccc cccaggttta tcaaagaacc caaggaccag
 361 atcggcgtgt cgggggggtgt ggcctctttc gtgtgtcagg ccacgggtga ccccaagcca
 421 cgagtgacct ggaacaagaa gggcaagaag gtcaactctc agcgctttga cacgattgag
 481 tttgatgaga gtgcaggggc agtgctgagg atccagccgc tgaggacacc gcgggatgaa
 541 aacgtgtacg agtgtgtggc ccagaactcg gttggggaga tcacagtcca tgccaagctt
 601 actgtcctcc gagaggacca gctgccctct ggcttcccca acatcgacat gggcccacag
 661 ttgaaggtgg tggagcggac acggacagcc accatgctct gtgcagccag cggcaaccct
 721 gaccctgaga tcacctggtt caaggacttc ctgcctgtgg atcctagtgc cagcaatgga
 781 cgcatcaaac agctgcgatc aggagccctg cagattgaaa gcagtgagga aaccgaccag
 841 ggcaaatatg agtgtgtggc caccaacagc gccggcgtgc gctactcctc acctgccaac
 901 ctctacgtgc gagtccgccg cgtggccccg cgcttctcca tcctgcccat gagccacgag
 961 atcatgccag ggggcaacgt gaacatcacc tgcgtggccg tgggctcgcc catgccatac
1021 gtgaagtgga tgcagggggc cgaggacctg accccgagg atgacatgcc cgtgggtcgg
1081 aacgtgctgg aactcacaga tgtcaaggac tcggccaact acacctgcgt ggccatgtcc
1141 agcctgggcg tcattgaggc ggttgctcag atcacggtga atctctcccc aaagctcccc
1201 gggactccca tggtgactga aacacagcc accagcatca ccatcacgtg ggactcgggc
1261 aacccagatc ctgtgtccta ttacgtcatc gaatataaat ccaagagcca agacgggccg
1321 tatcagatta aagaggacat caccaccaca cgttacagca tcggcggcct gagccccaac
1381 tcggagtacg agatctgggt gtcggccgtc aactccatcg ccaggggccc cccagcgag
1441 tccgtggtca cccgcacagg cgagcaggcc ccggccagcg cgccgcggaa cgtgcaagcc
1501 cggatgctca gcgcgaccac catgattgtg cagtgggagg agccggtgga gcccaacggc
1561 ctgatccgcg gctaccgcgt ctactacacc atggaaccgg agcacccgt gggcaactgg
1621 cagaagcaca cgtggacga cagcctgctg accaccgtgg gcagcctgct ggaggacgag
1681 acctacaccg tgcgggtgct cgccttcacc tccgtcggcg acgggcccct ctcggacccc
1741 atccaggtca agacgcagca gggagtgccg ggccagccca tgaacctgcg ggccgaggcc
1801 aggtcggaga ccagcatcac gctgtcctgg agccccccgc ggcaggagag tatcatcaag
1861 tacgagctcc tcttccggga aggcgaccat ggccgggagg tgggaaggac cttcgacccg
1921 acgacttcct acgtggtgga ggacctgaag cccaacacgg agtacgcctt ccgcctggcg
1981 gcccgctcgc cgcagggcct gggcgccttc accccgtgg tgcggcagcg cacgctgcag
2041 tccatctcgc ccaagaactt caaggtgaaa atgatcatga agacatcagt tctgctcagc
2101 tgggagttcc ctgacaacta caactcaccc acacctaca agatccagta caatgggctc
2161 acactggatg tggatggccg taccaccaag aagctcatca cgcacctcaa gccccacacc
2221 ttctacaact ttgtgctgac caatcgcggc agcagcctgg gcggcctcca gcagacggtc
```

*FIG. 29*

```
2281 accgcctgga ctgccttcaa cctgctcaac ggcaagccca gcgtcgcccc caagcctgat
2341 gctgacggct tcatcatggt gtatcttcct gacggccaga gccccgtgcc tgtccagagc
2401 tatttcattg tgatggtgcc actgcgcaag tctcgtggag gccaattcct gacccgctg
2461 ggtagcccag aggacatgga tctggaagag ctcatccagg acatctcacg gctacagagg
2521 cgcagcctgc ggcactcgcg tcagctggag gtgccccggc cctatattgc agctcgcttc
2581 tctgtgctgc cacccacgtt ccatcccggc gaccagaagc agtatggcgg cttcgataac
2641 cggggcctgg agcccggcca ccgctatgtc ctcttcgtgc ttgccgtgct tcagaagagc
2701 gagcctacct ttgcagccag tcccttctca gacccttcc agctggataa cccggacccc
2761 cagcccatcg tggatggcga ggagggcctt atctgggtga tcgggcctgt gctggccgtg
2821 gtcttcataa tctgcattgt cattgctatc ctgctctaca agaacaaacc cgacagtaaa
2881 cgcaaggact cagaaccccg caccaaatgc ctcctgaaca atgccgacct cgcccctcac
2941 caccccaagg accctgtgga aatgagacgc attaacttcc agactccagg catgcttagc
3001 cacccgccaa ttcccatcgc agacatggcg gagcacacgg agcggctcaa ggccaacgac
3061 agcctcaagc tctcccagga gtatgagtcc atcgaccctg acagcagtt cacatgggaa
3121 cattccaacc tggaagtgaa caagccgaag aaccgctatg ccaacgtcat cgcctatgac
3181 cactcccgtg tcatcctcca gcccattgaa ggcatcatgg gcagtgatta catcaatgcc
3241 aactacgtgg acggctaccg gtgtcagaac gcgtacattg ccacgcaggg gccgctgcct
3301 gagacctttg gggacttctg gcgtatggtg tgggagcagc ggtcggcgac catcgtcatg
3361 atgacgcggc tggaggagaa gtcacggatc aagtgtgatc agtattggcc aacagaggc
3421 acggagacct acggcttcat ccaggtcacg ttgctagata ccatcgagct ggccacattc
3481 tgcgtcagga cattctctct gcacaagaat ggctccagtg agaaacgcga ggtccgccag
3541 ttccagttta cggcgtggcc ggaccatggc gtgcccgaat acccaacgcc cttcctggct
3601 ttcctgcgga gagtcaagac ctgcaacccg ccagatgccg gccccatcgt ggttcactgc
3661 agtgccggtg tgggccgcac aggctgcttt atcgtcatcg acgccatgct tgagcggatc
3721 aagccagaga agacagtcga tgtctatggc cacgtgacgc tcatgaggtc ccagcgcaac
3781 tacatggtgc agacggagga ccagtacagc ttcatccacg aggccctgct ggaggccgtg
3841 ggctgtggca acacagaagt gcccgcacgc agcctctatg cctacatcca gaagctggcc
3901 caggtggagc ctggcgaaca cgtcactggc atggaactcg agttcaagcg gctggctaac
3961 tccaaggccc acacgtcacg cttcatcagt gccaatctgc cttgtaacaa gttcaagaac
4021 cgcctggtga acatcatgcc ctatgagagc acgggtct gtctgcaacc catccggggt
4081 gtggagggct ctgactacat caacgccagc ttcattgatg gctacaggca gcagaaggcc
4141 tacatcgcga cacaggggcc gctggcggag accacggaag acttctggcg catgctgtgg
4201 gagaacaatt cgacgatcgt ggtgatgctg accaagctgc gggagatggg ccgggagaag
4261 tgtcaccagt actggccggc cgagcgctct gcccgctacc agtactttgt ggtagatccg
4321 atggcagaat acaacatgcc tcagtatatc ctgcgagagt tcaaggtcac agatgcccgg
4381 gatggccagt cccggactgt ccggcagttc cagttcacag actggccgga acagggtgtg
4441 ccaaagtcgg gggagggctt catcgacttc attggccaag tgcataagac taaggagcag
4501 tttggccagg acggccccat ctctgtccac tgcagtgccg gcgtgggcag gacgggcgtc
4561 ttcatcacgc ttagcatcgt gctggagcgg atgcggtatg aaggcgtggt ggacatcttt
```

*FIG. 29 (cont.)*

```
4621 cagacggtga agatgctacg aacccagcgg ccggccatgg tgcagacaga ggatgagtac
4681 cagttctgtt accaggcggc actggagtac ctcggaagct ttgaccacta tgcaacctaa
4741 agccatggtt ccccccaggc ccgacaccac tggccccgga tgcctctgcc cctcccgggc
4801 ggacctcctg aggcctggac ccccagtggg cagggcagga ggtggcagcg gcagcagctg
4861 tgtttctgca ccatttccga ggacgacgca gcccctcgag ccccccacc ggccccggcc
4921 gccccagcga cctccctggc accggccgcc gccttcaaat acttggcaca ttcctccttt
4981 ccttccaatt ccaaaaccag attccggggt gggggtggg gggatggtga gcaaatagga
5041 gtgctcccca gaaccagagg agggtgggc acagaccata gacggacccc tcgtcctccc
5101 ccagcggtgg taggggggacc cgggggggctc ctccccgctc tgcagcctgg ggacactggg
5161 ctgggaccag aatccagctt tcttttaaaa ctctcagtgt aactgtatcc cgtgacattt
5221 catttttttt aaatagtgta ttttttttc cattttttt tttaagagaa acaaacaaaa
5281 gactcgccag tcaatgactt tcaaagagaa ctaactttgg cttattcata ttctgttcaa
5341 agacagtcta tttttcact gtagaaagcg tccttgtgtg atagttacgt tcgcaaacgc
5401 gcacgccagg cccatggctg taccttggct tttttttttt tttttttttt tttaattttt
5461 cctaccatca gaaagtgtgc tttgctcaca gaagaatggg atgtcctttt ttctttcttg
5521 gctttttttt tccccctttt tgtttcattt ttataaatta aattttcaga catatcaaat
5581 acagttctga gggtaaggtc atgggggagc tcggacccag tggcgttggg tgcggttgag
5641 ggggacgctg ctgtaagagg agagagatga cagtggtcct cctctgagag cctgagctgt
5701 ctccccgtct cccgccccca aggagacaga gaggatccta cttcttcggg gacagtggct
5761 gtatggctgt gctgccccac atcagggacc cttcccccct gggactgtgg ggcagtttgg
5821 gagcaaaacc agaaggacag gcccccctct acccgcctac cctgagcaag cgagttgttc
5881 ctctttgtac aagggcaggt ctgcggttac tttcaacact gtttattcca gcggaagcag
5941 ccgggtggtt ttcccacccc cgtgtatgta gatatatcga ctttgtatta aaggaagatc
6001 gtctga (SEQ ID NO: 4)
```

Human PTPσ transcript variant 1 amino acid sequence:

```
MAPTWGPGMVSVVGPMGLLVVLLVGGCAAEEPPRFIKEPKDQIGVSGGVASFVCQATGDPKPRVTWNKKG
KKVNSQRFETIEFDESAGAVLRIQPLRTPRDENVYECVAQNSVGEITVHAKLTVLREDQLPSGFPNIDMG
PQLKVVERTRTATMLCAASGNPDPEITWFKDFLPVDPSASNGRIKQLRSETFESTPIRGALQIESSEETD
QGKYECVATNSAGVRYSSPANLYVRELREVRRVAPRFSILPMSHEIMPGGNVNITCVAVGSPMPYVKWMQ
GAEDLTPEDDMPVGRNVLELTDVKDSANYTCVAMSSLGVIEAVAQITVKSLPKAPGTPMVTENTATSITI
TWDSGNPDPVSYYVIEYKSKSQDGPYQIKEDITTTRYSIGGLSPNSEYEIWVSAVNSIGQGPPSESVVTR
TGEQAPASAPRNVQARMLSATTMIVQWEEPVEPNGLIRGYRVYYTMEPEHPVGNWQKHNVDDSLLTTVGS
LLEDETYTVRVLAFTSVGDGPLSDPIQVKTQQGVPGQPMNLRAEARSETSITLSWSPPRQESIIKYELLF
REGDHGREVGRTFDPTTSYVVEDLKPNTEYAFRLAARSPQGLGAFTPVVRQRTLQSKPSAPPQDVKCVSV
RSTAILVSWRPPPPETHNGALVGYSVRYRPLGSEDPEPKEVNGIPPTTTQILLEALEKWTQYRITTVAHT
EVGPGPESSPVVVRTDEDVPSAPPRKVEAEALNATAIRVLWRSPAPGRQHGQIRGYQVHYVRMEGAEARG
PPRIKDVMLADAQWETDDTAEYEMVITNLQPETAYSITVAAYTMKGDGARSKPKVVVTKGAVLGRPTLSV
QQTPEGSLLARWEPPAGTAEDQVLGYRLQFGREDSTPLATLEFPPSEDRYTASGVHKGATYVFRLAARSR
GGLGEEAAEVLSIPEDTPRGHPQILEAAGNASAGTVLLRWLPPVPAERNGAIVKYTVAVREAGALGPARE
TELPAAAEPGAENALTLQGLKPDTAYDLQVRAHTRRGPGPFSPPVRYRTFLRDQVSPKNFKVKMIMKTSV
LLSWEFPDNYNSPTPYKIQYNGLTLDVDGRTTKKLITHLKPHTFYNFVLTNRGSSLGGLQQTVTAWTAFN
LLNGKPSVAPKPDADGFIMVYLPDGQSPVPVQSYFIVMVPLRKSRGGQFLTPLGSPEDMDLEELIQDISR
LQRRSLRHSRQLEVPRPYIAARFSVLPPTFHPGDQKQYGGFDNRGLEPGHRYVLFVLAVLQKSEPTFAAS
PFSDPFQLDNPDPQPIVDGEEGLIWVIGPVLAVVFIICIVIAILLYKNKPDSKRKDSEPRTKCLLNNADL
APHHPKDPVEMRRINFQTPDSGLRSPLREPGFHFESMLSHPPIPIADMAEHTERLKANDSLKLSQEYESI
DPGQQFTWEHSNLEVNKPKNRYANVIAYDHSRVILQPIEGIMGSDYINANYVDGYRCQNAYIATQGPLPE
TFGDFWRMVWEQRSATIVMMTRLEEKSRIKCDQYWPNRGTETYGFIQVTLLDTIELATFCVRTFSLHKNG
SSEKREVRQFQFTAWPDHGVPEYPTPFLAFLRRVKTCNPPDAGPIVVHCSAGVGRTGCFIVIDAMLERIK
PEKTVDVYGHVTLMRSQRNYMVQTEDQYSFIHEALLEAVGCGNTEVPARSLYAYIQKLAQVEPGEHVTGM
ELEFKRLANSKAHTSRFISANLPCNKFKNRLVNIMPYESTRVCLQPIRGVEGSDYINASFIDGYRQQKAY
IATQGPLAETTEDFWRMLWENNSTIVVMLTKLREMGREKCHQYWPAERSARYQYFVVDPMAEYNMPQYIL
REFKVTDARDGQSRTVRQFQFTDWPEQGVPKSGEGFIDFIGQVHKTKEQFGQDGPISVHCSAGVGRTGVF
ITLSIVLERMRYEGVVDIFQTVKMLRTQRPAMVQTEDEYQFCYQAALEYLGSFDHYAT
```
(SEQ ID NO: 5)

*FIG. 30*

Human PTPσ transcript variant 1 nucleotide sequence

```
   1 cctcgcgccg cccgcccggc agcccggccg gcgcgcgcac gccgcgagcc gctggcgctc
  61 gggctccgct cggatcccat gcaacagcca cgatgtgaag cggggcagag ccgggggagc
 121 ccagcccagc cagcctccag acgttgcccc atctgacgct cggctcgagg cctctctgtg
 181 agggaccggg gggccatccc cctccagggc ggagatcgga ggtcgctgcc aagcatggcg
 241 cccacctggg gccctggcat ggtgtctgtg gttggtccca tgggcctcct tgtggtcctg
 301 ctcgttggag gctgtgcagc agaagagccc ccaggttta tcaaagaacc caaggaccag
 361 atcggcgtgt cggggggtgt ggcctctttc gtgtgtcagg ccacgggtga ccccaagcca
 421 cgagtgacct ggaacaagaa gggcaagaag gtcaactctc agcgctttga gacgattgag
 481 tttgatgaga gtgcagggc agtgctgagg atccagccgc tgaggacacc gcgggatgaa
 541 aacgtgtacg agtgtgtggc ccagaactcg gttggggaga tcacagtcca tgccaagctt
 601 actgtcctcc gagaggacca gctgccctct ggcttcccca acatcgacat ggggcccacag
 661 ttgaaggtgg tggagcggac acggacagcc accatgctct gtgcagccag cggcaaccct
 721 gaccctgaga tcacctggtt caaggacttc ctgcctgtgg atcctagtgc cagcaatgga
 781 cgcatcaaac agctgcgatc agaaaacctt gaaagcactc cgattcgagg agccctgcag
 841 attgaaagca gtgaggaaac cgaccagggc aaatatgagt gtgtggccac caacagcgcc
 901 ggcgtgcgct actcctcacc tgccaacctc tacgtgcgag agcttcgaga agtccgccgc
 961 gtggccccgc gcttctccat cctgcccatg agccacgaga tcatgccagg gggcaacgtg
1021 aacatcacct gcgtggccgt gggctcgccc atgccatacg tgaagtggat gcagggggcc
1081 gaggacctga ccccgagga tgacatgccc gtgggtcgga acgtgctgga actcacagat
1141 gtcaaggact cggccaacta cacctgcgtg gccatgtcca gcctgggcgt cattgaggcg
1201 gttgctcaga tcacggtgaa atctctcccc aaagctcccg ggactccat ggtgactgag
1261 aacacagcca ccagcatcac catcacgtgg gactcgggca cccagatcc tgtgtcctat
1321 tacgtcatcg aatataaatc caagagccaa gacgggccgt atcagattaa agaggacatc
1381 accaccacac gttacagcat cggcggcctg agccccaact cggagtacga gatctgggtg
1441 tcggccgtca actccatcgg ccaggggccc ccagcgagt ccgtggtcac ccgcacaggc
1501 gagcaggccc cggccagcgc gccgcggaac gtgcaagccc ggatgctcag cgcgaccacc
1561 atgattgtgc agtgggagga gccggtggag cccaacggcc tgatccgcgg ctaccgcgtc
1621 tactacacca tggaaccgga gcaccccgtg ggcaactggc agaagcacaa cgtggacgac
1681 agcctgctga ccaccgtggg cagcctgctg gaggacgaga cctacaccgt gcgggtgctc
1741 gccttcacct ccgtcggcga cgggcccctc tcggacccca tccaggtcaa gacgcagcag
1801 ggagtgccgg gccagcccat gaacctgcgg gccgaggcca ggtcggagac cagcatcacg
1861 ctgtcctgga gccccccgcg gcaggagagt atcatcaagt acgagctcct cttccgggaa
1921 ggcgaccatg gccgggaggt gggaaggacc ttcgacccga cgacttccta cgtggtggag
1981 gacctgaagc ccaacacgga gtacgccttc cgcctggcgg cccgctcgcc gcagggcctg
2041 ggcgccttca cccccgtggt gcggcagcgc acgctgcagt ccaaaccgtc agccccccct
2101 caagacgtta aatgtgtcag cgtgcgctcc acggccattt tggtaagttg gcgcccgccg
2161 ccgccggaaa cgcacaacgg ggccctggtg ggctacagcg tccgctaccg accgctgggc
2221 tcagaggacc cggaacccaa ggaggtgaac ggcatccccc cgaccaccac tcagatcctg
2281 ctggaggcct tggagaagtg gacccagtac cgcatcacga ctgtcgctca cagaggtg
2341 ggaccagggc ccgagagctc gcccgtggtc gtccgcaccg acgaggatgt gcccagcgcg
2401 ccgccgcgga aggtggaggc ggaggcgctc aacgccacgg ccatccgcgt gctgtggcgc
2461 tcgcccgcgc ccggccggca gcacggccag atccgcggct accaggtcca ctacgtgcgc
2521 atggagggcg ccgaggcccg cggggccgcg cgcatcaagg acgtcatgct ggccgatgcc
2581 cagtgggaga cggatgacac ggccgaatat gagatggtca tcacaaactt gcagcctgag
2641 accgcgtact ccatcacggt agccgcctac accatgaagg gcgatggcgc tcgcagcaaa
```

*FIG. 31*

2701 cccaaggtgg ttgtgaccaa gggagcagtg ctgggccgcc caaccctgtc ggtgcagcag
2761 accccccgagg gcagcctgct ggcacgctgg gagccccccgg ctggcaccgc ggaggaccag
2821 gtgctgggct accgcctgca gtttggccgt gaggactcga cgcccctggc caccctggag
2881 ttcccgccct ccgaggaccg ctacacggca tcaggcgtgc acaaggggc cacgtatgtg
2941 ttccggcttg cggcccggag ccgcggcggc ctgggcgagg aggcagccga ggtcctgagc
3001 atcccggagg acacgccccg tggccacccg cagattctgg aggcggccgg caacgcctcg
3061 gccgggaccg tccttctccg ctggctgcca cccgtgcccg ccgagcgcaa cggggccatc
3121 gtcaaataca cggtggccgt gcgggaggcc ggtgccctgg gccctgcccg agagactgag
3181 ctgccggcag cggctgagcc gggcgcggag aacgcgctca cgctgcaggg cctgaagccc
3241 gacacggcct atgacctcca agtgcgagcc cacacgcgcc ggggcccctgg cccccttcagc
3301 ccccccgtcc gctaccggac gttcctgcgg gaccaagtct cgcccaagaa cttcaaggtg
3361 aaaatgatca tgaagacatc agttctgctc agctgggagt tccctgacaa ctacaactca
3421 cccacaccct acaagatcca gtacaatggg ctcacactgg atgtggatgg ccgtaccacc
3481 aagaagctca tcacgcacct caagccccac accttctaca actttgtgct gaccaatcgc
3541 ggcagcagcc tgggcggcct ccagcagacg gtcaccgcct ggactgcctt caacctgctc
3601 aacggcaagc ccagcgtcgc ccccaagcct gatgctgacg gcttcatcat ggtgtatctt
3661 cctgacggcc agagccccgt gcctgtccag agctatttca ttgtgatggt gccactgcgc
3721 aagtctcgtg gaggccaatt cctgaccccg ctgggtagcc cagaggacat ggatctggaa
3781 gagctcatcc aggacatctc acggctacag aggcgcagcc tgcggcactc gcgtcagctg
3841 gaggtgcccc ggccctatat tgcagctcgc ttctctgtgc tgccacccac gttccatccc
3901 ggcgaccaga agcagtatgg cggcttcgat aaccggggcc tggagcccgg ccaccgctat
3961 gtcctcttcg tgcttgccgt gcttcagaag agcgagccta cctttgcagc cagtcccttc
4021 tcagacccct tccagctgga taacccggac ccccagccca tcgtggatgg cgaggagggg
4081 cttatctggg tgatcgggcc tgtgctggcc gtggtcttca taatctgcat tgtcattgct
4141 atcctgctct acaagaacaa acccgacagt aaacgcaagg actcagaacc ccgcaccaaa
4201 tgcctcctga acaatgccga cctcgccccct caccacccca aggaccctgt ggaaatgaga
4261 cgcattaact tccagactcc agattcaggc ctcaggagcc ccctcaggga gccgggggttt
4321 cactttgaaa gcatgcttag ccaccccgcca attcccatcg cagacatggc ggagcacacg
4381 gagcggctca aggccaacga cagcctcaag ctctcccagg agtatgagtc catcgacccct
4441 ggacagcagt tcacatggga acattccaac ctggaagtga acaagccgaa gaaccgctat
4501 gccaacgtca tcgcctatga ccactcccgt gtcatcctcc agcccattga aggcatcatg
4561 ggcagtgatt acatcaatgc caactacgtg gacggctacc ggtgtcagaa cgcgtacatt
4621 gccacgcagg ggccgctgcc tgagaccttt ggggacttct ggcgtatggt gtgggagcag
4681 cggtcggcga ccatcgtcat gatgacgcgg ctggaggaga agtcacggat caagtgtgat
4741 cagtattggc ccaacagagg cacggagacc tacggcttca tccaggtcac gttgctagat
4801 accatcgagc tggccacatt ctgcgtcagg acattctctc tgcacaagaa tggctccagt
4861 gagaaacgcg aggtccgcca gttccagttt acggcgtggc cggaccatgg cgtgcccgaa
4921 tacccaacgc ccttcctggc tttcctgcgg agagtcaaga cctgcaaccc gccagatgcc
4981 ggccccatcg tggttcactg cagtgccggt gtgggccgca caggctgctt tatcgtcatc
5041 gacgccatgc ttgagcggat caagccagag aagacagtcg atgtctatgg ccacgtgacg
5101 ctcatgaggt cccagcgcaa ctacatggtg cagacggagg accagtacag cttcatccac
5161 gaggccctgc tgaggccgt gggctgtggc aacacagaag tgcccgcacg cagcctctat
5221 gcctacatcc agaagctggc ccaggtggag cctggcgaac acgtcactgg catggaactc
5281 gagttcaagc ggctggctaa ctccaaggcc cacacgtcac gcttcatcag tgccaatctg
5341 ccttgtaaca agttcaagaa ccgcctggtg aacatcatgc cctatgagag cacacgggtc

*FIG. 31 (cont.)*

5401 tgtctgcaac ccatccgggg tgtggagggc tctgactaca tcaacgccag cttcattgat
5461 ggctacaggc agcagaaggc ctacatcgcg acacaggggc cgctggcgga gaccacggaa
5521 gacttctggc gcatgctgtg ggagaacaat tcgacgatcg tggtgatgct gaccaagctg
5581 cgggagatgg gccgggagaa gtgtcaccag tactggccgg ccgagcgctc tgcccgctac
5641 cagtactttg tggtagatcc gatggcagaa tacaacatgc ctcagtatat cctgcgagag
5701 ttcaaggtca cagatgcccg ggatggccag tcccggactg tccggcagtt ccagttcaca
5761 gactggccgg aacagggtgt gccaaagtcg ggggagggct tcatcgactt cattggccaa
5821 gtgcataaga ctaaggagca gtttggccag gacggcccca tctctgtcca ctgcagtgcc
5881 ggcgtgggca ggacgggcgt cttcatcacg cttagcatcg tgctggagcg gatgcggtat
5941 gaaggcgtgg tggacatctt tcagacggtg aagatgctac gaacccagcg gccggccatg
6001 gtgcagacag aggatgagta ccagttctgt taccaggcgg cactggagta cctcggaagc
6061 tttgaccact atgcaaccta aagccatggt tcccccagg cccgacacca ctggccccgg
6121 atgcctctgc ccctccgggg cggacctcct gaggcctgga ccccagtgg gcagggcagg
6181 aggtggcagc ggcagcagct gtgtttctgc accatttccg aggacgacgc agcccctcga
6241 gccccccac cggccccggc cgccccagcg acctccctgg caccggccgc cgccttcaaa
6301 tacttggcac attcctcctt tccttccaat tccaaaacca gattccgggg tgggggtgg
6361 ggggatggtg agcaaatagg agtgctcccc agaaccagag gagggtgggg cacagaccat
6421 agacggaccc ctcgtcctcc cccagcggtg gtaggggac ccggggggct cctccccgct
6481 ctgcagcctg gggacactgg gctgggacca gaatccagct ttcttttaaa actctcagtg
6541 taactgtatc ccgtgacatt tcattttttt taaatagtgt atttttttt ccatttttt
6601 ttttaagaga aacaaacaaa agactcgcca gtcaatgact ttcaaagaga actaactttg
6661 gcttattcat attctgttca aagacagtct atttttcac tgtagaaagc gtccttgtgt
6721 gatagttacg ttcgcaaacg cgcacgccag gcccatggct gtaccttggc ttttttttt
6781 tttttttt ttttaatttt tcctaccatc agaaagtgtg ctttgctcac agaagaatgg
6841 gatgtccttt ttcttctt ggcttttttt ttcccccttt ttgtttcatt tttataaatt
6901 aaatttcag acatatcaaa tacagttctg agggtaaggt catggggag ctcggaccca
6961 gtggcgttgg gtgcggttga gggggacgct gctgtaagag gagagagatg acagtggtcc
7021 tcctctgaga gcctgagctg tctccccgtc tcccgccccc aaggagacag agaggatcct
7081 acttcttcgg ggacagtggc tgtatggctg tgctgcccca catcagggac cctttcccc
7141 tgggactgtg gggcagtttg ggagcaaaac cagaaggaca ggccccctc tacccgccta
7201 ccctgagcaa gcgagttgtt cctctttgta caagggcagg tctgcggtta ctttcaacac
7261 tgtttattcc agcggaagca gccgggtggt tttcccaccc ccgtgtatgt agatatatcg
7321 actttgtatt aaaggaagat cgtctga (SEQ ID NO: 6)

*FIG. 31 (cont.)*

Murine amino acid sequence:

MAPTWSPSVVSVVGPVGLFLVLLARGCLAEEPPRFIREPKDQIGVSGGVASFVCQATGDPKPRVTWNK
KGKKVNSQRFETIDFDESSGAVLRIQPLRTPRDENVYECVAQNSVGEITIHAKLTVLREDQLPPGFPN
IDMGPQLKVVERTRTATMLCAASGNPDPEITWFKDFLPVDPSASNGRIKQLRSGALQIESSEETDQGK
YECVATNSAGVRYSSPANLYVRVRRVAPRFSILPMSHEIMPGGNVNITCVAVGSPMPYVKWMQGAEDL
TPEDDMPVGRNVLELTDVKDSANYTCVAMSSLGVIEAVAQITVKSLPKAPGTPVVTENTATSITVTWD
SGNPDPVSYYVIEYKSKSQDGPYQIKEDITTTRYSIGGLSPNSEYEIWVSAVNSIGQGPPSESVVTRT
GEQAPASAPRNVQARMLSATTMIVQWEEPVEPNGLIRGYRVYYTMEPEHPVGNWQKHNVDDSLLTTVG
SLLEDETYTVRVLAFTSVGDGPLSDPIQVKTQQGVPGQPMNLRAEAKSETSIGLSWSAPRQESVIKYE
LLFREGDRGREVGRTFDPTTAFVVEDLKPNTEYAFRLAARSPQGLGAFTAVVRQRTLQAKPSAPPQDV
KCTSLRSTAILVSWRPPPPETHNGALVGYSVRYRPLGSEDPDPKEVNNIPPTTTQILLEALEKWTEYR
VTAVAYTEVGPGPESSPVVVRTDEDVPSAPPRKVEAEALNATAIRVLWRSPTPGRQHGQIRGYQVHYV
RMEGAEARGPPRIKDIMLADAQEMVITNLQPETAYSITVAAYTMKGDGARSKPKVVVTKGAVLGRPTL
SVQQTPEGSLLARWEPPADAAEDPVLGYRLQFGREDAAPATLELAAWERRFAAPAHKGATYVFRLAAR
GRAGLGEEAAAALSIPEDAPRGFPQILGAAGNVSAGSVLLRWLPPVPAERNGAIIKYTVSVREAGAPG
PATETELAAAAQPGAETALTLRGLRPETAYELRVRAHTRRGPGPFSPPLRYRLARDPVSPKNFKVKMI
MKTSVLLSWEFPDNYNSPTPYKIQYNGLTLDVDGRTTKKLITHLKPHTFYNFVLTNRGSSLGGLQQTV
TARTAFNMLSGKPSVAPKPDNDGFIVVYLPDGQSPVTVQNYFIVMVPLRKSRGGQFPVLLGSPEDMDL
EELIQDISRLQRRSLRHSRQLEVPRPYIAARFSILPAVFHPGNQKQYGGFDNRGLEPGHRYVLFVLAV
LQKNEPTFAASPFSDPFQLDNPDPQPIVDGEEGLIWVIGPVLAVVFIICIVIAILLYKNKPDSKRKDS
EPRTKCLLNNADLAPHHPKDPVEMRRINFQTPGMLSHPPIPITDMAEHMERLKANDSLKLSQEYESID
PGQQFTWEHSNLEANKPKNRYANVIAYDHSRVILQPLEGIMGSDYINANYVDGYRRQNAYIATQGPLP
ETFGDFWRMVWEQRSATVVMMTRLEEKSRIKCDQYWPNRGTETYGFIQVTLLDTMELATFCVRTFSLH
KNGSSEKREVRHFQFTAWPDHGVPEYPTPFLAFLRRVKTCNPPDAGPIVVHCSAGVGRTGCFIVIDAM
LERIKTEKTVDVYGHVTLMRSQRNYMVQTEDQYGFIHEALLEAVGCGNTEVPARSLYTYIQKLAQVEP
GEHVTGMELEFKRLASSKAHTSRFITASLPCNKFKNRLVNILPYESSRVCLQPIRGVEGSDYINASFI
DGYRQQKAYIATQGPLAETTEDFWRALWENNSTIVVMLTKLREMGREKCHQYWPAERSARYQYFVVDP
MAEYNMPQYILREFKVTDARDGQSRTVRQFQFTDWPEQGAPKSGEGFIDFIGQVHKTKEQFGQDGPIS
VHCSAGVGRTGVFITLSIVLERMRYEGVVDIFQTVKVLRTQRPAMVQTEDEYQFCFQAALEYLGSFDH
YAT (SEQ ID NO: 7)

*FIG. 32*

Murine nucleotide sequence

```
   1 aggggtgacg tcaccggctg ggggcgcgcg agccgcagtg gggttttgcc ccgcccgcca
  61 ggcagctcgg gccgcgcgca cacgcggagc cgccggagcc cgggccgacc cgtgccggg
 121 agcagcatgc ggagcccgca gacgctgccc ctctggacac ctcagcctga ggcctctccg
 181 tgagtcacgg gggtaccatc ccccaccagg gcagaggctg gaggccactg ccaagcatgg
 241 cgcccacctg gagtcccagc gtggtgtctg tggtgggtcc tgtggggctc ttcctcgtac
 301 tgctggccag aggatgcttg gctgaagaac cacccaggtt tatcagagag cccaaggatc
 361 agattggagt gtcgggaggc gtggcctcct tcgtgtgcca ggccacgggt gatcctaagc
 421 cacgggtgac ctggaacaag aagggcaaga agtgaactc acagcgcttc gagaccattg
 481 actttgacga gagctctggg gcggtcctga ggatccagcc acttcggacg cctcgggatg
 541 agaacgtgta cgagtgtgtg cccagaact cggtgggcga atcacaatt catgcaaagc
 601 tcaccgtcct tcgagaggac cagctgcctc ctggcttccc caacattgac atgggccccc
 661 agttgaaggt tgtagagcgc acacgcacag ccaccatgct ctgtgctgcc agcgggaacc
 721 cggaccctga gatcacctgg tttaaggact tcctgcctgt ggaccccagt gccagcaacg
 781 ggcggatcaa gcagcttcga tcaggtgccc tgcagattga gagcagcgag gagacagacc
 841 agggcaagta cgagtgtgtg gccaccaaca gcgctgggg gcgctactca tcacctgcca
 901 acctctacgt gcgagtccgc cgtgtggccc cacgcttctc catcctgccc atgagccacg
 961 agatcatgcc cggtgggaat gtgaatatca cttgtgtggc cgtgggctca cccatgccct
1021 acgtgaaatg gatgcagggg gccgaggacc tgacgcctga ggatgacatg cccgtgggtc
1081 ggaatgttct agaactcacg gatgtcaagg actcagctaa ctacacttgt gtggccatgt
1141 ccagcctggg tgtgatcgag gccgtggccc agatcactgt aaaatctctc cccaaagccc
1201 ctgggactcc tgtggtgacg gagaacactg ccaccagtat cactgtcaca tgggactcgg
1261 gcaaccctga ccccgtgtcc tactacgtaa ttgagtataa gtccaaaagc caggatgggc
1321 cgtatcagat caaagaagac atcaccacca cgcgctacag catcggaggc ctgagcccca
1381 attctgagta tgagatctgg gtgtcagctg tcaactccat tggccagggc cctcccagtg
1441 aatcggtggt gacccgcaca ggtgagcagg caccagccag cgctcccagg aatgttcagg
1501 cccgcatgct cagcgccacc accatgatcg tgcagtggga ggagcctgtg agcccaatg
1561 gcctgatccg tggctaccgt gtctactata ccatggagcc ggaacaccca gtgggcaact
1621 ggcagaaaca caatgtggac gacagtctcc tgaccactgt gggcagcctg ctggaagacg
1681 agacctacac cgtgcgcgtg ctcgccttca gtcggtgg cgacggacca ctgtcagacc
1741 ccatccaggt caagacccag cagggagttc ctggccagcc catgaacttg cgggctgagg
1801 ccaagtcaga gaccagcatt gggctctcgt ggagtgcacc acgacaggag agtgtcatta
1861 agtatgaact gctcttccgg gagggcgacc gaggccgaga ggtggggcga accttcgacc
1921 caaccacagc ctttgtggtg gaggacctca gcccaatac ggagtatgcg ttccggctgg
1981 cggcgcgctc gccgcagggc ctgggcgcct tcaccgcggt cgtgcgccag cgcacgctgc
2041 aggccaaacc gtcagccccc cctcaagacg ttaagtgcac cagcttgcgc tccacggcca
2101 tattggtaag ttggcgcccg ccaccgccag aaactcacaa cggggccctc gtgggctaca
```

FIG. 33

```
2161 gcgtccgcta ccgaccgctg ggctcagagg acccggaccc caaggaggtg aacaacatac
2221 cccccgaccac cactcagatc cttctggaag ctttggagaa atggacggag taccgtgtca
2281 ccgccgtggc ttacacagag gtgggaccag ggcccgagag ctcgcccgtg gtcgtccgca
2341 ccgatgagga cgtgcccagc gcgcccccgc ggaaggtgga ggcggaggcg ctcaacgcca
2401 cagccatccg agtgctgtgg cgctcgccca cgcccggccg gcagcacggg cagatccgcg
2461 gctaccaggt ccactatgtg cgcatggagg gtgccgaggc ccgcgggcca ccgcgcatca
2521 aggacatcat gctggcggat gcccaggaaa tggtgataac gaacctccag cctgagactg
2581 cttactctat cacagtagcc gcgtatacca tgaaaggcga tggcgctcgc agcaaaccga
2641 aggtggtggt gaccaaggga gcagtgctgg gccgccccac cctgtcggtg cagcagaccc
2701 ccgagggcag cctgctggcg cgctgggagc ccccccgcgga cgcggccgag gacccggtgc
2761 ttggctaccg cctgcagttt gggcgcgaag acgcggcccc ggccacgttg gagctggctg
2821 cgtgggagcg gcggttcgcg gcgcctgcac acaagggcgc cacctatgtg ttccggctgg
2881 cagcgcgggg ccgcgcgggg ttgggcgagg aggccgcggc agcgctgagc atccccgagg
2941 acgctccgcg cggcttcccg cagatcttgg gcgccgcggg caacgtgtcc gcgggctccg
3001 tgctactgcg ctggctgcca cccgtgcccg ccgagcgcaa cggcgccatc atcaagtaca
3061 cggtgtccgt gcgggaggcc ggcgcccctg ggcccgcgac cgagacggag ctggcggcgg
3121 ccgcccagcc gggggccgag acagcgctca cgctgcgagg gctgcggccg gagacggcct
3181 acgagttacg cgtgcgcgca cacacgcgtc gcggcccggg ccccttctca cccccgctgc
3241 gctacaggct cgcgcgggac ccagtctccc caaagaactt caaggtgaag atgatcatga
3301 agacttcagt gctgctgagc tgggagttcc ccgacaacta taactcaccc acaccctaca
3361 agattcagta caatgggctc accctggatg tggacggccg cacgaccaag aagctgatca
3421 cacacctcaa gccacacacc ttctataatt tcgtgctcac caaccgtggc agcagcctgg
3481 ggggcctgca gcagacggtc actgccagga ccgcctttaa catgctcagt ggcaagccta
3541 gcgtcgcccc gaagcccgac aatgacggtt tcatcgtggt ctacctgcct gatggccaga
3601 gtcctgtgac cgtgcagaac tacttcattg tgatggtccc acttcggaag tctcgaggtg
3661 gccagttccc tgtcctacta ggtagtccag aggacatgga tctggaggag ctcatccagg
3721 acatctcccg gctgcagagg cgcagcctgc gccactccag acagctggag gtgcctcggc
3781 cctacatcgc cgctcgattc tccatcctgc cagctgtctt ccatcctggg aaccagaagc
3841 aatatggtgg ctttgacaac aggggcttgg agccaggcca ccgctatgtc ctctttgtgc
3901 ttgctgtgtt gcagaagaat gagcctacat ttgcagccag tcccttctca gaccccttcc
3961 agctggacaa cccggaccct cagcccattg tggacggcga ggagggcctc atctgggtga
4021 ttgggcctgt gctggccgtg gtcttcatca tctgcatcgt gattgccatc ctgctgtaca
4081 agaacaaacc tgacagcaaa cgcaaggact cagagccccg caccaaatgc ttactgaaca
4141 atgccgacct tgcccccccat caccccaagg accctgtgga aatgcgacgc atcaacttcc
4201 agacaccagg tatgctcagc cacccacccca tccccatcac agacatggcg gagcacatgg
4261 agagactcaa agccaacgac agcctgaagc tctcccagga gtacgagtcc attgaccccg
4321 ggcagcaatt cacgtgggaa cattcgaacc tggaggccaa caagcccaag aaccgctatg
```

*FIG. 33 (cont.)*

```
4381 ccaacgtcat cgcctatgac cactcacgag tcatcctgca gcccctagaa ggcatcatgg
4441 gtagtgatta catcaatgcc aactatgtgg acggctaccg gcggcagaat gcatacattg
4501 ccacgcaggg gccctgcct gagacctttg gggacttctg gcggatggtg tgggagcagc
4561 gatcggccac tgtggtcatg atgacgcgac tggaggagaa atcacggatc aaatgtgacc
4621 aatactggcc taaccgaggc accgagacat acggcttcat ccaggtcacc tactagata
4681 ccatggagct ggctaccttc tgcgtcagga cttttctct acacaagaat ggctctagcg
4741 agaagcgtga ggtgcgacat ttccagttca cggcatggcc cgaccacggg gtacctgagt
4801 accccacgcc cttcctggca ttcctgcgaa gagtcaagac ctgcaacccg cctgatgctg
4861 gccccattgt ggtccactgc agcgcgggtg tggggcgcac tggctgcttc atcgtaattg
4921 acgccatgct agagcgcatc aagacagaga agaccgtgga tgtgtatgga catgtgacac
4981 tcatgcggtc gcagcgcaac tacatggtgc agacagagga tcagtatggc ttcatccacg
5041 aggcgctgct ggaggctgtg ggctgcggca ataccgaggt ccctgctcgc agcctctaca
5101 cctacatcca gaagctggcc caggtggagc ctggcgagca cgtcacgggc atggagcttg
5161 agttcaagag gctcgccagt tccaaggcac acacttcgcg cttcatcacc gccagcctgc
5221 cttgcaacaa gtttaagaac cgactggtga acatcctgcc gtacgagagc tcgcgtgtct
5281 gcctgcagcc catccgcggt gtggagggct ctgactacat caatgccagc tttatcgacg
5341 gctatagaca gcagaaagcc tacattgcaa cacaggggcc actggcagag accacagagg
5401 acttctggcg agctctgtgg gagaacaact ctactattgt cgtaatgctc accaagctcc
5461 gagaaatggg ccgggaaaag tgccaccagt actggccagc cgagcgctct gcccgctacc
5521 agtactttgt ggttgacccg atggcagagt ataacatgcc acagtacatt ctgcgtgagt
5581 ttaaggtcac agatgcccgg gatggccagt cccggaccgt ccgacagttc cagttcacgg
5641 actggccaga gcagggtgca cccaagtcag ggaaggctt cattgacttc atcggccaag
5701 tgcataagac caaggagcag tttggccagg acggacccat ctcagtgcac tgcagcgccg
5761 gagtgggcag gaccggagtg ttcatcaccc tgagcatcgt gcttgagcgg atgcgctacg
5821 agggcgtggt ggacatttc cagacagtga aggtgcttcg gacccagagg cctgccatgg
5881 tgcagacaga ggacgagtac cagttctgct tccaggcggc tttggaatac ctgggcagtt
5941 ttgatcatta tgcaacataa gccatgggcc ccgcccaaca cctcagccct gcgccaagtg
6001 ccctggatgt gagcctaggc ccgccgctgg gcaggatgcg gcccagggag acctcctctt
6061 cgcggagaca ggcgctgcct tcctcattcc cttctgattc caaaacgagg ttccagggtg
6121 ggggttggg gtggagagag aaggagccac tgctccccag gctggggtca cacagggacc
6181 gacctctgct tccgcactcc cctgcctgcc ttttggcaac attttttttc ttatttttt
6241 ttaatagtgt atattttttt tcttttcctt tttttctttt ttttttttaa gaaaaaaca
6301 aaatcgtgcc ggtcaaaact ttgaaaaaga aacaagatca ctgtttgtgc ctctgtggga
6361 ggcctatttt ttcatagtta gtgtgccgtg tggcggctat gtgcggccac ttcgacggct
6421 tctgtgtgtg catctttccc acatgcccga cactgccccc atccccatgt gaatggtgcg
6481 cttagttttt attttaacc ttttacttt ttttttaatc aatcttcaga catatcagat
6541 atggagggtg aggcgctggg ggcactcggg ccagactaca gggacatggc caccaaggac
```

*FIG. 33 (cont.)*

```
6601 acagtggctg gccttgctgc tccagtccct ggcacaccag ggagggtcct cgtctactca
6661 tgacctctgt gccccgcatg gaggacctgg gactacggga cacttggggg atatccaacc
6721 ccctggagca actgaggtct ctctttgtag gagagtgggt cagtactcgt ccccgctgtt
6781 ttttgggcag aagcagcagg tgacgcccct gtatgtagat aaaccaactt tgtattaaag
6841 aaagattcgt ccgacctaga aaaaaaaaaa aaaa (SEQ ID NO:  8)
```

FIG. 33 (cont.)

| CONSTRUCT | SPACE GROUP | PROTEIN CONCENTRATION | CRYSTALLISATION CONDITION | TEMP (°C) | FREEZING PROCEDURE |
|---|---|---|---|---|---|
| CHICK RPTPσ Ig1-2 SeMet | $14_122$ | 7 mg/ml | 10% w/v PEG 6k<br>0.1 M CITRATE<br>pH 5 | 6.5 | 30% PEG 400 |
| CHICK RPTPσ Ig1-2 | $14_122$ | 7 mg/ml | 20% w/v PEG 8k<br>0.1 M CHES<br>pH 9.6 | 20.5 | 30% PEG 400 |
| HUMAN RPTPσ Ig1-2 † | $14_122$ | 11 mg/ml | 0.2 M SODIUM SULPHATE<br>20% w/v PEG 3350<br>pH 6.6 | 20.5 | PERFLUOROPOLYETHER OIL<br>PFO-X125/03 |
| HUMAN RPTPσ Ig1-2 | C2 | 10.5 mg/ml | 0.2 M $NH_4I$<br>20% w/v PEG 3350<br>pH 6.2 | 20.5 | PERFLUOROPOLYETHER OIL<br>PFO-X125/03 |
| HUMAN RPTPδ Ig1-2 | $P3_221$ | 6 mg/ml | 0.085 M TRI-SODIUM CITRATE DIHYDRATE<br>25% PEG 4k<br>15% GLYCEROL<br>pH 5.6 | 20.5 | EXTRA 15% GLYCEROL |
| HUMAN RPTPδ Ig1-2 | C2 | 6 mg/ml | 20% w/v PEG 3350<br>0.2 M AMMONIUM DI-HYDROGEN PHOSPATE | 20.5 | 30% ETHYLENE GLYCOL |
| HUMAN RPTP LAR Ig1-2 | $P3_221$ | 9 mg/ml | 0.1 M SODIUM ACETATE TRIHYDRATE<br>20% ISOPROPANOL<br>20% w/v PEG 4k<br>0.25 mM HEPARIN dp10<br>pH 5.6 | 20.5 | 25% ETHYLENE GLYCOL |
| *DROSOPHILA* RPTP LAR Ig1-2 | C2 | 12 mg/ml | 25% w/v PEG 1500<br>0.1 M SPG SYSTEM<br>35 mM AMMONIUM SULPHATE<br>pH 5.0 | 20.5 | 25% GLYCEROL |
| HUMAN RPTPσ Ig1-3 R227Q+R228N | I222 | 6.7 mg/ml | 20% w/v PEG 3350<br>0.2 M SODIUM IODIDE<br>0.1 M bis-Tris PROPANE<br>pH 7.5 | 20.5 | 30% GLYCEROL |
| HUMAN RPTP LAR Ig1-2 +25 mM SUCROSE OCTASULPHATE | $P3_221$ | 9 mg/ml | 0.1 M MES<br>30% w/v PEG 6k<br>pH 6.0 | 20.5 | 30% PROPYLENE GLYCOL |

*FIG. 35*

| Data collection | | | | | | | | | |
|---|---|---|---|---|---|---|---|---|---|
| Protein | Chick RPTPσ Ig1-2 SeMet | Chick RPTPσ Ig1-2 | Human RPTPσ Ig1-2 | Human RPTPσ Ig1-2 | Human RPTPδ Ig1-2 | Human RPTPδ Ig1-2 | Human RPTP LAR Ig1-2 | Drosophila RPTP LAR Ig1-2 | Human RPTP LAR Ig1-2 + SOS | Human RPTPσ Ig1-3 |
| PDB accession code | XXXX | XXXX | XXXX | XXXX | XXXX | XXXX | XXXX | XXXX | XXXX | XXXX |
| Beamline | ESRF-BM14 | ESRF-BM14 | Diamond-I03 | ESRF-ID14EH3 | Diamond-I02 | Diamond-I02 | Diamond-I03 | ESRF-ID23EH2 | Diamond-I04 | Diamond-I04 |
| Resolution (Å) | 50.0-3.1 (3.2-3.1) | 74-1.65 (1.7-1.65) | 40-2.3 (2.38-2.3) | 29-2.55 (2.6-2.55) | 50-2.0 (2.06-2.0) | 49-1.35 (1.4-1.35) | 48-2.2 (2.26-2.2) | 50-1.8 (1.85-1.8) | 40-2.05 (2.12-2.05) | 50-2.6 (2.7-2.6) |
| Spacegroup | I422 | I422 | I422 | C2 | C2 | P3₂21 | P3₂21 | C2 | P3₂21 | I222 |
| Cell dimensions | | | | | | | | | | |
| $a, b, c$ (Å) | 104.9, 104.9, 92.0 | 104.8, 104.8, 94.6 | 104.2, 104.2, 94.9 | 124.2, 29.4, 61.4 | 161.2, 31.7, 92.3 | 48.7, 48.7, 145.9 | 77.0, 77.0, 68.7 | 124.2, 29.1, 49.4 | 78.8, 78.8, 71.9 | 71.7, 90.0, 143.3 |
| $\alpha, \beta, \gamma$ (°) | 90.0, 90.0, 90.0 | 90.0, 90.0, 90.0 | 90.0, 90.0, 90.0 | 90.0, 92.6, 90.0 | 90.0, 112.0, 90.0 | 90.0, 90.0, 120.0 | 90.0, 90.0, 120.0 | 90.0, 107.3, 90.0 | 90.0, 90.0, 120.0 | 90.0, 90.0, 90.0 |
| Wavelength (Å) | 0.9783 | 0.9763 | 1.0600 | 0.9310 | 0.9795 | 0.9795 | 0.9765 | 0.8726 | 0.9763 | 0.9786 |
| Unique reflections | 4922 (475) | 31882 (2319) | 12003 (1176) | 7438 (474) | 30633 (2991) | 45165 (3237) | 12272 (872) | 16271 (1610) | 16614 (1638) | 14979 (1469) |
| Completeness (%) | 100 (100) | 100 (100) | 100 (99.9) | 98.1 (84.8) | 99.8 (99.8) | 99.9 (99.8) | 99.7 (98.2) | 100 (100) | 100 (100) | 99.9 (99.9) |
| $R_{merge}$ (%)[b] | 14.9 (86.2) | 11.8 (88.5) | 13.7 (66.5) | 8.2 (66.6) | 7.4 (60.3) | 11.4 (81.6) | 9.2 (83.1) | 8.1 (53.3) | 10.2 (94.3) | 13.0 (87.0) |
| I/σI | 33.6 (5.6) | 26.2 (4.2) | 13.6 (3.7) | 13.7 (2.6) | 16.8 (2.1) | 17.4 (3.1) | 19.1 (3.6) | 19.6 (3.1) | 24.7 (2.7) | 14.6 (2.3) |
| Redundancy | 35.7 (36.9) | 26.0 (18.6) | 18.3 (18.3) | 3.5 (3.1) | 3.6 (3.6) | 15.0 (10.4) | 10.7 (10.6) | 5.6 (5.4) | 9.9 (10.0) | 7.2 (7.4) |

FIG. 36

| | 7.4-1.65 | 40-2.3 | 29-2.55 | 50-2.0 | 49-1.35 | 48-2.2 | 50-1.8 | 40-2.05 | 50-2.6 |
|---|---|---|---|---|---|---|---|---|---|
| Resolution range (Å) | | | | | | | | | |
| Number of reflections | 30925 | 11897 | 7196 | 28407 | 42829 | 11593 | 16006 | 15755 | 13846 |
| $R_{work}$ (%)$^c$ | 17.0 | 19.9 | 20.2 | 21.8 | 13.7 | 19.3 | 18.1 | 19.5 | 24.8 |
| $R_{free}$ (%)$^d$ | 20.4 | 23.3 | 26.0 | 24.8 | 17.0 | 23.1 | 22.2 | 22.7 | 28.9 |
| Number of protein atoms | 1677 | 1546 | 1524 | 3079 | 1657 | 1518 | 1505 | 1506 | 2119 |
| Number of chloride ions | 1 | 1 | 3 | . | 1 | . | . | . | 4 |
| Number of sodium ions | . | 1 | . | . | . | . | . | . | . |
| Number of sulphate ions | 1 | . | . | . | . | . | . | . | . |
| Number of phosphate ions | . | . | . | 3 | . | . | . | . | . |
| Number of iodide ions | . | . | 4 | . | . | . | . | . | 4 |
| Number of PEG molecules | 3 | . | . | . | 1 | . | . | . | . |
| Number of citrate molecules | . | . | . | . | . | . | . | . | . |
| Number of BSP molecules | . | . | . | . | . | . | . | . | 1 |
| Number of SOS atoms | . | . | . | . | . | . | . | 28 | . |
| Number of NAG molecules | . | . | . | . | . | . | . | . | 2 |
| Number of glycine molecules | . | . | . | . | . | . | 1 | . | . |
| Number of water molecules | 273 | 81 | 29 | 139 | 259 | 58 | 115 | 97 | 21 |
| r.m.s.d. bonds (Å) | 0.009 | 0.007 | 0.005 | 0.009 | 0.014 | 0.004 | 0.007 | 0.014 | 0.006 |
| r.m.s.d. angles (deg) | 1.296 | 1.006 | 0.831 | 1.43 | 1.660 | 0.848 | 1.138 | 1.237 | 0.955 |

*FIG. 36 (cont.)*

| | | | | | | | | | |
|---|---|---|---|---|---|---|---|---|---|
| Average B factor (Å²): | | | | | | | | | |
| - protein | 20.2 | 38.3 | 30.6 | 43.8 | 13.7 | 40.4 | 31.1 | 43.9 | 69.0 |
| - chloride ions | 12.8 | 31.9 | 19.2 | - | 16.4 | - | - | - | 53.3 |
| - sodium ions | - | 25.4 | - | - | - | - | - | - | - |
| - sulphate ions | 59.4 | - | - | - | - | - | - | - | - |
| - phosphate ions | - | - | - | 68.3 | - | - | - | - | - |
| - iodide ions | - | - | 61.1 | - | - | - | - | - | 45.3 |
| - PEG molecules | 40.1 | - | - | - | - | - | - | - | - |
| - citrate molecules | - | - | - | - | 24.3 | - | - | - | - |
| - B3P molecules | - | - | - | - | - | - | - | - | 51.5 |
| - SOS molecules | - | - | - | - | - | - | - | 147.3 | - |
| - NAG molecules | - | - | - | - | - | - | - | - | 76.0 |
| - Glycine molecules | - | - | - | - | - | - | 62.1 | - | - |
| - water molecules | 29.7 | 37.5 | 22.3 | 39.5 | 25.3 | 35.3 | 35.6 | 44.0 | 42.2 |
| Ramachandran plot (% residues): | | | | | | | | | |
| - favoured | 98.5 | 98.0 | 94.9 | 97.1 | 99.0 | 97.5 | 98.5 | 98.0 | 96.0 |
| - additionally allowed | 1.5 | 1.5 | 5.1 | 2.9 | 1.0 | 2.5 | 1.5 | 2.0 | 4.0 |
| - disallowed | 0 | 0.5 | 0 | 0 | 0 | 0 | 0 | 0 | 0 |

[a] Numbers in parentheses refer to the appropriate outer shell.

[b] $R_{merge} = \Sigma_{hkl}\Sigma_j |I_j - \langle I \rangle| / \Sigma_{hkl}\Sigma_j |I_j|$, where $hkl$ specifies unique indices, $j$ indicates equivalent observations of $hkl$, and $\langle I \rangle$ is the mean value.

[c] $R_{work} = \Sigma_{hkl} ||F_o| - |F_c|| / \Sigma_{hkl} |F_o|$, where $|F_o|$ and $|F_c|$ are the observed and calculated structure factor amplitudes, respectively.

[d] $R_{free}$ is calculated as per $R_{work}$ for a 5% subset of reflections which was not used in the crystallographic refinement.

*FIG. 36 (cont.)*

| Protein and construct name | GAG added | Protein concentration at peak | Number of N-glyc sites | Theoretical MW (+ N-glyc) | MALS MW (± error) | Dominant oligomeric state |
|---|---|---|---|---|---|---|
| | | µg/ml | | kDa | | |
| *RPTPσ* | | | | | | |
| sEcto | none | 151 | 2 | 91.0 (93.7) | 107.2 (1.1) | monomer |
| sEcto | none | 709 | 2 | 91.0 (93.7) | 128.5 (1.0) | monomer |
| sEcto | heparin-dp10 | 147 | 2 | 91.0 (93.7) | 318 (2.4) | di/trimer |
| Ig1-2 | none | 211 | 0 | 23.7 (23.7) | 27.2 (1.4) | monomer |
| Ig1-2 | heparin-dp10 | 383 | 0 | 23.7 (23.7) | 69.8 (0.9) | di/trimer |
| Ig1-3 | none | 589 | 2 | 34.9 (37.6) | 44.2 (0.2) | monomer |
| Ig1-3 | heparin-dp10 | 434 | 2 | 34.9 (37.6) | 84.7 (0.6) | dimer |
| Ig1-FN3 | none | 173 | 2 | 64.3 (67.0) | 75.3 (0.6) | monomer |
| Ig1-FN3 | heparin-dp10 | 156 | 2 | 64.3 (67.0) | 211.6 (1.9) | di/trimer |
| Ig1-FN3 | none | 69 | 2 | 64.3 (67.0) | 68.7 (0.8) | monomer |
| Ig1-FN3 | heparin-dp4 | 62 | 2 | 64.3 (67.0) | 73.9 (0.9) | monomer |
| Ig1-FN3 | heparin-dp6 | 55 | 2 | 64.3 (67.0) | 77.4 (0.8) | monomer |
| Ig1-FN3 | heparin-dp8 | 26 | 2 | 64.3 (67.0) | 113.5 (0.7) | dimer |
| Ig1-FN3 | heparin-dp10 | 31 | 2 | 64.3 (67.0) | 119.8 (1.7) | dimer |
| Ig1-FN3 | heparin-dp20 | 38 | 2 | 64.3 (67.0) | 207 (1.3) | trimer |
| Ig1-FN3 | heparin-dp30 | 41 | 2 | 64.3 (67.0) | 275.7 (2.8) | tetramer |

*FIG. 37*

| | | | | | | |
|---|---|---|---|---|---|---|
| Ig1-FN3 | HS | 39 | 2 | 64.3 (67.0) | 219.0 (1.3) | trimer |
| Ig1-FN3 | HS (x5) | 38 | 2 | 64.3 (67.0) | 242.3 (1.5) | tri/tetramer |
| Ig1-FN3 | CS | 52 | 2 | 64.3 (67.0) | 67.7 (1.4) | monomer |
| Ig1-FN3 | CS (x5) | 29 | 2 | 64.3 (67.0) | 80.8 (1.4) | monomer |
| Ig1-FN3 | dp10 + CS (x5) | 36 | 2 | 64.3 (67.0) | 101.8 (1.8) | mono/dimer |
| Ig1-FN3 | HS + CS (x5) | 44 | 2 | 64.3 (67.0) | 171.3 (1.2) | di/trimer |
| Ig1-FN3 $\Delta$K | none | 83 | 2 | 64.3 (67.0) | 66 (0.3) | monomer |
| Ig1-FN3 $\Delta$K | heparin-dp10 | 81 | 2 | 64.3 (67.0) | 66.5 (0.7) | monomer |
| Ig1-FN3 $\Delta$K | heparin-dp30 | 77 | 2 | 64.3 (67.0) | 70.6 (2.1) | monomer |
| RPTP$\delta$ | | | | | | |
| Ig1-FN3 | none | 52 | 2 | 64.1 (66.8) | 72 (2.3) | monomer |
| Ig1-FN3 | heparin-dp10 | 48 | 2 | 64.1 (66.8) | 147.4 (1.7) | dimer |
| Ig1-FN3 | CS | 27 | 2 | 64.1 (66.8) | 72.6 (3.6) | monomer |
| LAR | | | | | | |
| Ig1-FN3 | none | 86 | 2 | 63.8 (66.5) | 66.2 (0.8) | monomer |
| Ig1-FN3 | heparin-dp10 | 85 | 2 | 63.8 (66.5) | 66.1 (0.4) | monomer |
| Ig1-FN3 | heparin-dp30 | 45 | 2 | 63.8 (66.5) | 107.2 (4.2) | mono/dimer |
| Ig1-FN3 | CS | 85 | 2 | 63.8 (66.5) | 65.9 (0.9) | monomer |
| DLAR | | | | | | |
| Ig1-FN3 | none | 73 | 3 | 64.5 (68.5) | 71.3 (2.9) | monomer |
| Ig1-FN3 | heparin-dp10 | 61 | 3 | 64.5 (68.5) | 82.3 (1.9) | monomer |
| Ig1-FN3 | heparin-dp20 | 42 | 3 | 64.5 (68.5) | 171.6 (10.1) | di/trimer |
| Ig1-FN3 | heparin-dp30 | 48 | 3 | 64.5 (68.5) | 234 (2.7) | trimer |

*FIG. 37 (cont.)*

METHODS OF PROMOTING NEURONAL OUTGROWTH BY GYPICAN 2 THAT BINDS TO RECEPTOR PROTEIN TYROSINE PHOSPHATASE SIGMA

CROSS-REFERENCE TO RELATED APPLICATIONS

This application is a 35 U.S.C. §371 National Phase Entry Application of International Application No. PCT/US2012/025738 filed Feb. 17, 2012, which designates the U.S., and which claims the benefit under 35 U.S.C. §119(e) of U.S. Provisional Application No. 61/444,620, filed Feb. 18, 2011, the contents of which are incorporated herein by reference in their entireties.

GOVERNMENT SUPPORT

This invention was supported by the National Institutes for Health (NIH) Grant No. EY11559 and HD29417 and the Government of the United States has certain rights thereto.

SEQUENCE LISTING

The instant application contains a Sequence Listing which has been submitted in ASCII format via EFS-Web and is hereby incorporated by reference in its entirety. Said ASCII copy, created on Aug. 8, 2013, is named 002806-069132_SequenceListing.txt and is 130,283 bytes in size.

FIELD OF THE INVENTION

The invention relates to the treatment of neuronal injury.

BACKGROUND

Type IIa receptor protein tyrosine phosphatases (RPTPs) are cell surface receptors important for nervous system development, function and repair (1-3). Vertebrate family members (RPTPσ, LAR and RPTPδ) and invertebrate orthologues (e.g. Drosophila DLAR) localise to axonal growth cones, regulating neuronal growth and guidance and participating in excitatory synapse formation and maintenance (1, 4-8). RPTPσ$^{-/-}$ mice exhibit neurological and neuroendocrine defects (9-10) as well as increased nerve regeneration (11-15), while RPTPδ-deficient mice show impaired learning and memory (16); RPTPσ and δ double-mutant mice have a developmental loss of motor neurons leading to paralysis (17).

Type IIa RPTP extracellular regions interact with HSPGs and CSPGs (5, 7, 12, 18). These proteoglycans modulate neuronal growth, guidance and connectivity, typically with CSPGs inhibiting and HSPGs promoting axon extension (19-23). Up-regulation of CSPGs in glial scar tissue after neural injury is an important factor limiting CNS axon sprouting and regeneration (2, 21, 24-25). In adult mouse dorsal root ganglion (DRG) sensory axons, this CSPG inhibitory effect is mediated, at least in part, by RPTPσ (12). In contrast, in developing chick retinal ganglion cell axons, RPTPσ was reported to promote growth in response to basal lamina (26). These observations posed a potential conundrum, namely that of RPTPσ interactions eliciting opposing effects on neuronal outgrowth.

SUMMARY

One aspect of the invention relates to a method of inducing neuronal outgrowth of a neuron comprising, contacting the neuron with an agent that binds receptor protein tyrosine phosphatase σ (RPTPσ), to thereby induce neuronal outgrowth of the neuron. In one embodiment, the agent induces clustering of RPTPσ. In one embodiment, the agent inhibits binding of chondroitin sulfate proteoglycan (CSPG) to RPTPσ. In one embodiment, the agent is heparan sulfate proteoglycan, heparan sulfate, heparin oligosaccharide, or heparan sulfate oligosaccharide. In one embodiment, the heparin oligosaccharide or heparan sulfate oligosaccharide contains 8 or more saccharide units and less than 67 saccharide units. In one embodiment, the heparin oligosaccharide or heparan sulfate oligosaccharide contains 10 or more saccharide units and less than 67 saccharide units. In one embodiment, the heparan sulfate proteoglycan is glypican 2 or a derivative thereof. In one embodiment, the agent binds to the first immunoglobulin-like domain of RPTPσ. In one embodiment, the agent is in solution. In one embodiment, the agent is contained in a matrix. Contacting can occur in vitro or in vivo. In one embodiment, the neuron is located at a site of injured or diseased tissue. In one embodiment, the method further comprises contacting said neuron with a second agent that promotes neuronal outgrowth. In one embodiment, the second agent reduces inhibition of neuronal outgrowth. The neuron contacted can be either a central nervous system neuron or a peripheral nervous system neuron.

Another aspect of the invention relates to a method of treating neuronal injury in a subject comprising, administering to the subject an agent that binds RPTPσ to thereby induce neuronal outgrowth. In one embodiment, the method further comprises selecting a subject in need of treatment for neuronal injury. In one embodiment, the agent is administered at a site of neuronal injury, to thereby induce neuronal outgrowth at the site of neuronal injury. In one embodiment, the agent induces clustering of the RPTPσ. In one embodiment, the agent inhibits binding of chondroitin sulfate proteoglycan (CSPG) to the RPTPσ. In one embodiment, the neuronal injury is selected from the group consisting of stroke, spinal cord injury, traumatic brain injury, peripheral nerve injury, skin burn, and eye injury (e.g., affecting optic nerve fibers or corneal nerves). In one embodiment, the neuronal injury is acute. In one embodiment, the agent is heparan sulfate proteoglycan, heparan sulfate, heparin oligosaccharide, or heparan sulfate oligosaccharide. In one embodiment, the heparin oligosaccharide or heparan sulfate oligosaccharide contains 8 or more saccharide units and less than 67 saccharide units. In one embodiment, the heparin oligosaccharide or heparan sulfate oligosaccharide contains 10 or more saccharide units and less than 67 saccharide units. In one embodiment, the heparan sulfate proteoglycan is glypican 2 or a derivative thereof. In one embodiment, the method further comprises contacting said neuron with a second agent that promotes neuronal outgrowth. In one embodiment, the agent is in solution. In one embodiment, the agent is contained in a matrix. In one embodiment, the agent directly binds to the RPTPσ. In one embodiment, the agent binds to the first immunoglobulin-like domain of RPTPσ. Administration of the agent can be systemic or localized. In one embodiment, administration is by method selected from the group consisting of oral, intramuscular injection, subcutaneous or intradermal injection, intravenous injection, buccal administration, transdermal, rectal, colonic, vaginal, intranasal, and inhalation. In one embodiment, localized administration is by implantation of a matrix that contains the agent. In one embodiment, implantation is by injection and the matrix is a gel that solidifies in the body of the subject.

Another aspect of the invention relates to a method of promoting neural outgrowth in the nervous system of a subject, comprising administering to the subject an agent that binds RPTPσ, to contact a neuron and thereby induce neural (axonal) outgrowth of the neuron. In one embodiment, the agent induces clustering of the RPTPσ. In one embodiment, the method further comprises selecting a subject in need of treatment for neuronal injury. In one embodiment, the agent inhibits binding of chondroitin sulfate proteoglycan (CSPG) to the RPTPσ. In one embodiment, the agent is heparan sulfate proteoglycan, heparan sulfate, heparin oligosaccharide, or heparan sulfate oligosaccharide. In one embodiment, the heparin oligosaccharide or heparan sulfate oligosaccharide contains 8 or more saccharide units and less than 67 saccharide units. In one embodiment, the heparin oligosaccharide or heparan sulfate oligosaccharide contains 10 or more saccharide units and less than 67 saccharide units. In one embodiment, the heparan sulfate proteoglycan is glypican 2 or a derivative thereof. In one embodiment, the agent is in solution. In one embodiment, the agent is contained in a matrix. In one embodiment, the CNS neuron is located at or adjacent to a site of diseased or injured tissue. In one embodiment, the injured tissue results from an injury selected from the group consisting of stroke, spinal cord injury, traumatic brain injury, peripheral nerve injury, skin burn, and eye injury. In one embodiment, the injured tissue results from an acute injury. In one embodiment, the injury injured tissue results from a chronic injury. In one embodiment, the diseased tissue is at a site of neuronal degeneration. In one embodiment, the diseased tissue results from a neurodegenerative disease. Administration can be either systemic or localized. In one embodiment, administration is by method selected from the group consisting of oral, intramuscular injection, subcutaneous or intradermal injection, intravenous injection, buccal administration, transdermal, rectal, colonic, vaginal, intranasal, and inhalation. In one embodiment, localized administration is by implantation of a matrix that contains the agent. In one embodiment, implantation is by injection and the matrix is a gel that solidifies in the body of the subject.

In one embodiment of any of the above therapeutic methods, the method further comprises selecting a subject in need of treatment for neuronal injury or in need of neuronal outgrowth, prior to administration of the agent.

DEFINITIONS

As used herein, the term axonal "growth" or "outgrowth" (also referred to herein as "neuronal outgrowth") includes the process by which axons or dendrites extend from a neuron. The outgrowth can result in a new neuritic projection or in the extension of a previously existing cellular process. Axonal outgrowth may include linear extension of an axonal process by five cell-diameters or more. Neuronal growth processes, including neuritogenesis, can be evidenced by detection of neuronal growth markers such as GAP-43 (e.g., detected by methods such as immunostaining for GAP-43). "Stimulating axonal growth" means promoting axonal outgrowth. The term neurite outgrowth may also be used in place of axonal outgrowth throughout the application.

"Central nervous system (CNS) neurons" include the neurons of the brain, the cranial nerves and the spinal cord. The term CNS neuron is not intended to include support-cells or protection-cells such as astrocytes, oligodentrocytes, microglia, ependyma and the like, nor is it intended to include peripheral nervous system (e.g., somatic, autonomic, sympathetic or parasympathetic nervous system) neurons. Although, in some embodiments, such cells are also, contacted with the agents described herein.

"Peripheral nervous system (PNS) neurons" includes the neurons which reside or extend outside of the CNS. PNS is intended to include the neurons commonly understood as categorized in the peripheral nervous system, including sensory neurons and motor neurons. The term PNS neuron is not intended to include support or protection cells such as Schwann cells, satellite glia, enteric glia, and the like, nor is it intended to include CNS nervous system neurons, although, in some embodiments, such cells are also contacted with the agents described herein.

The term "patient" or "subject" or "animal" or "host" may be used interchangeably herein, and refers to any animal. The animal can be a human or a non-human animal. The subject may be a human, but can also be a mammal in need of veterinary treatment, e.g., domestic animals or game animals, farm animals, and laboratory animals (e.g., rats, mice, guinea pigs, primates, and the like). Usually the animal is a mammal or vertebrate such as a primate, rodent, lagomorph, domestic animal or game animal. Primates include human and non-human primates, Non-human primates include chimpanzees, cynomologous monkeys, spider monkeys, and macaques, e.g., Rhesus or Pan. Rodents and lagomorphs include mice, rats, woodchucks, ferrets, rabbits and hamsters. Domestic and game animals include cows, horses, pigs, sheep, deer, bison, buffalo, mink, felines, e.g., domestic cat, canines, e.g., dog, wolf and fox, avian species, e.g., chicken, turkey, emu and ostrich, and fish, e.g., trout, catfish and salmon. Subject includes any subset of the foregoing, e.g., all of the above, but excluding one or more groups or species such as humans, primates or rodents. Other subsets of subjects include subjects of a given species or group of species of varying ages, e.g., young humans, e.g., about 1 week of age to about 9 years of age, adolescent humans, e.g., about 10-19 years of age, adult humans, e.g., about 20-100 years of age, and mature adult or elderly humans, e.g., at least about 55 years of age, at least about 60 years of age, at least about 65 years of age or a range of ages such as about 60-100 years of age. Thus, as used herein, prevention or treatment of a disease, condition or symptom may include or exclude any subset of subjects that are grouped by age. A subject can be male or female.

A subject can be one who has been diagnosed with or identified as suffering from neuronal injury or having a disorder characterized by neuronal injury or degeneration (e.g., atrophy/wasting). A subject can be one who is not currently being treated with an agent described herein (e.g., heparin oligosaccharide). A subject can be one who has been previously diagnosed with a disease that is being treated with a therapeutic regimen comprising an agent described herein (e.g., heparin oligosaccharide) wherein the disease is not a disease characterized by neuronal injury or degeneration. A subject can be one who has suffered a traumatic neuronal injury.

"Contacting" as the term is used herein with respect to a cell (e.g., a neuron) refers to any mode of agent delivery or "administration," either to cells or to whole organisms, in which the agent is brought into contact with one or more cells, in sufficient amount to exhibit its effect on the cell. "Contacting" includes both in vivo and in vitro methods of bringing an agent described herein into proximity with a cell. For example, when neuronal outgrowth of a neuron is stimulated in vitro, agents can be administered, for example, by transfection, lipofection, electroporation, viral vector infection, or by addition to growth medium. In vivo contacting is achieved by administration to a subject, as described herein. Suitable modes of administration can be determined by those skilled in the art and such modes of administration may vary between agents.

The term "antibody" refers to an immunoglobulin protein that is capable of binding an antigen. Antibody as used herein is meant to include antibody fragments, e.g. F(ab')2, Fab', Fab, capable of binding the antigen or antigenic fragment of interest.

The term "humanized antibody" is used herein to describe complete antibody molecules, i.e. composed of two complete light chains and two complete heavy chains, as well as antibodies consisting only of antibody fragments, e.g. Fab, Fab', F(ab')2, and Fv, wherein the CDRs are derived from a non-human source and the remaining portion of the Ig molecule or fragment thereof is derived from a human antibody, preferably produced from a nucleic acid sequence encoding a human antibody.

The terms "human antibody" and "humanized antibody" are used herein to describe an antibody of which all portions of the antibody molecule are derived from a nucleic acid sequence encoding a human antibody. Such human antibodies are most desirable for use in antibody therapies, as such antibodies would elicit little or no immune response in the human subject. The term "chimeric antibody" is used herein to describe an antibody molecule as well as antibody fragments, as described above in the definition of the term "humanized antibody." The term "chimeric antibody" encompasses humanized antibodies. Chimeric antibodies have at least one portion of a heavy or light chain amino acid sequence derived from a first mammalian species and another portion of the heavy or light chain amino acid sequence derived from a second, different mammalian species.

Preferably, the variable region is derived from a non-human mammalian species and the constant region is derived from a human species. Specifically, the chimeric antibody is preferably produced from a nucleotide sequence from a non-human mammal encoding a variable region and a nucleotide sequence from a human encoding a constant region of an antibody.

BRIEF DESCRIPTION OF THE DRAWINGS

FIGS. 1A-1F are photographs of immunostained mouse DRG neurons in culture following the indicated treatment. FIGS. 1A, 1C, and 1E are wild-type DRG neurons. FIGS. 1B, 1D and 1F are RPTPσ$^{-/-}$ P8 mouse DRG neurons. Neurons were grown on a poly-D-lysine/laminin mixture alone (control) or supplemented with either neurocan or glypican-2 proteoglycans and imaged 48 hours later by GAP-43 immunostaining. FIG. 1G is a bar graph of data obtained from neurite measurements of representative cells from experiments referred to in FIG. 1A to 1F. The data indicate statistically significant neurocan inhibition and glypican-2 promotion of outgrowth. FIG. 1H is a bar graph of data from experiments that indicate these effects are largely mediated via RPTPσ, and the proteoglycan GAG chains are essential for their interactions with RPTPσ. Pre-treatment of neurocan with chondroitinase ABC (ChABC) or glypican-2 with heparitinase III (HPNIII) dramatically reduced binding to RPTPσ in solid phase binding assays. n=3 mice for each genotype, except RPTPσ$^{-/-}$ on neurocan, where n=4. *P<0.001, P<0.01, Student's t-test. Scale bar, 100 µm.

FIG. 2A-FIG. 2F show the structure of the proteoglycan binding region of type IIa RPTPs. FIG. 2A is a schematic of the domain organisation of the type IIa RPTP family. N, amino terminus (extracellular); SP, secretion signal peptide; TM, transmembrane helix; C, carboxy terminus (intracellular); Ig, immunoglobulin-like domain; FN3, fibronectin type III domain. The ectodomain may be remodeled by alternative splicing, yielding multiple receptor isoforms with distinct expression patterns (1). Protein constructs illustrated here were used in subsequent biophysical assays and crystallographic studies. Residue numbering corresponds to chicken RPTPσ. FIG. 2B is a ribbon diagram of chicken RPTPσ Ig1-2. Six residues have previously been shown to be important for binding to HSPGs and CSPGs (12, 18) and are illustrated as blue sticks. FIG. 2C is a solvent-accessible surface representations of Ig1-2 crystal structures from chicken RPTPσ, human RPTPσ, human RPTPδ, human LAR and Drosophila LAR, coloured by the electrostatic potential contoured at ±5 kT/e (red, acidic; blue, basic). FIG. 2D is a model that shows how sucrose octasulfate (SOS) induces movement of the proteoglycan binding Lys-loop in human LAR (green) relative to the apo-protein (wheat); the R76-D100 salt bridge is disrupted to allow this conformational change. R76, together with K67 and K68, are involved in binding to the sulfate substituents from the five-membered ring of the SOS ligand. Surface representations of the boxed region in FIG. 2C are shown for apo-LAR in FIG. 2E, and for SOS-bound LAR in FIG. 2F, crystal structures highlight the malleability of the proteoglycan binding surface; colors as in FIG. 2C.

FIG. 3A models the dimensions of the RPTPσ proteoglycan binding surface taken from the chicken RPTPσ Ig1-2 crystal structure. FIG. 3B and FIG. 3C are graphs of data which indicate that Neurocan-alkaline phosphatase (NC-AP, a representative CSPG) and Glypican-2-AP (Glyp2-AP, a representative HSPG) bind to immobilised mouse RPTPσ sEcto-Fc with comparable affinities. $K_d$ values were obtained from the binding curves, assuming a one-to-one binding event. FIGS. 3D-3G are graphs of data collected from size-exclusion chromatography coupled to multi-angle light scattering (SEC-MAL, used to investigate the oligomerisation state of human RPTPσ Ig1-FN3 in solution with an excess of varying length GAGs. The data indicate that heparin dp8 is the minimum length of heparin oligosaccharide required to promote oligomerisation. FIG. 3D shows the results of experiments where the protein was incubated alone (red), with dp4 (orange), dp6 (purple), dp8 (green) dp10 (blue), dp20 (light green) or dp30 (grey). The data in FIG. 3E indicate that the addition of longer heparin oligosaccharides results in the formation of larger RPTP oligomers. The data in FIG. 3F indicate that the oligomerisation state of a quadruple K67A/K68A/K70A/K71A mutant of human RPTPσ Ig1-FN3 (Ig1-FN3 ΔK) was insensitive to the addition of heparin. FIG. 3G shows the results of experiments where heparan sulfate but not chondroitin sulfate induces oligomerisation of human RPTPσ Ig1-FN3; "×5" indicate increased GAG amounts (28). Refractive index traces (scaled within each panel) and measured molecular weights are represented by bold and dashed lines respectively. Refractive index peaks indicated by an asterisk correspond to excess glycan ligand. FIG. 3H is a proposed model for RPTPσ clustering along the highly sulfated domains of heparan sulfate. An unperturbed helical structure for heparin (PDB accession code 1HPN) is used in this model, which is scaled relative to the Ig1-2 molecule.

FIGS. 4A-F show immunolocalization of CS (red), with GAP43 neuronal marker (green) and DAPI nuclear stain (blue). Colors are merged in E and F. Boxed areas in A and E are enlarged in B and F. Filled arrowheads point to high CS labeling over ECM adjacent to non-neuronal cells. Open arrowheads point to dark areas of low CS labeling overlap with cell bodies and axons. GAP43 labeled axon in F grows over a non-neuronal cell at lower left. FIGS. 4M-O show labeling of a neuron, including cell body and neurites (arrowheads). FIGS. 4P-4S show a growth cone (arrowhead) with axon shaft (arrow) at higher magnification. DIC image is in FIG. 4S. Both HS and RPTPσ show punctate labeling, in similar although not identical patterns. Scale bar: 60 μm (FIGS. 4A, C-E, G, I-K, M-O) and 6 μm (FIGS. 4P-S). FIG. 4T shows an illustration of a model for type IIa RPTP-proteoglycan interactions and their distinct functional consequences. Islands of high/intermediate sulfation on HS chains (shown in pink/yellow) stabilise receptor oligomers, causing an uneven distribution of tyrosine phosphatase activity, formation of microdomains with high phosphotyrosine levels and supporting neuronal extension. Conversely, secreted CS (blue chains), present in glial scar tissues, is unable to induce tight RPTPσ oligomerization, competing with HS and inhibiting axon growth. Regulatory mechanisms might include shedding (1); crystal structure of human RPTPσ Ig1-3 reveals an exposed furin-like protease cleavage site in the Ig2-3 linker (scissors; FIG. 17).

FIG. 7A-FIG. 7C is a collection of illustrations and tables which indicate the structural alignment of the type IIa RPTPs illustrates the conserved architecture of the two N-terminal domains across the type IIa RPTP family. (A) Ig1 domains from human RPTP LAR (P3$_2$21) and RPTPδ (P3$_2$21) crystal structures were aligned with the Ig1 domain from human RPTPσ (I4$_1$22) using SHP (S22), to obtain an overlay of the human RPTP structures. (B) Ig1 from chicken RPTPσ (I4$_1$22) and DLAR (C2) structures were similarly aligned with the Ig1 from $_1$human RPTPσ (I4$_1$22). (C) Structural comparison of the Ig1-Ig2 domain interface for the type IIa RPTPs. Ig1-Ig2 angle deviation represents the angle required to realign the Ig2 domains (containing the residues listed) from the Ig1-2 structures on human RPTPσ I4$_1$22 Ig2 after having first superposed each Ig1-2 structure to align with human RPTPσ I4$_1$22 Ig1 and was calculated from the rotation matrix obtained for the Ig2 domain transformation in SHP. Interface surface areas per domain and the change in free energy for the Ig1-Ig2 interaction were estimated for each structure (using residues equivalent to 29-130 and 131-226 as molecule A and molecule B respectively), in the PISA prediction program (EBI, EMBL) and the surface complementarity was calculated using SC (S30). Although the buried surface area at the Ig1-Ig2 domain interface is comparable and the interdomain angle variation is small across the structures, the ΔG value and surface complementarity score for this domain arrangement in the DLAR structure are both notably less favorable.

FIG. 8A-FIG. 8F is a collection of illustrations that show comparison of the Ig1-Ig2 interdomain interactions observed in chicken RPTPσ and Drosophila LAR (DLAR) Ig1-2 crystal structures. Chicken RPTPσ: (A) Ribbon representation of the Ig1-2 crystal structure, highlighting the linker region (solid box) and the domain interface (dashed box). (B) Sidechains of hydrophobic residues L124, L129, P130 and F133, which lie on the Ig1-Ig2 Pro-rich loop, also pack closely with I42, V44 and A212 in a hydrophobic interdomain region, (C) Two salt bridges R91-E205 and E126-R215 and a network of hydrogen bonds involving the hydroxyl groups of S50 and Y216, the sidechain amide of Q41, the backbone carbonyls of I42 and F171, the backbone amide of V214 and two water molecules (purple spheres), hold Ig1 and Ig2 in a rigid arrangement. The interdomain interactions, including the two highlighted water molecules, observed in the chick RPTPσ Ig1-2 structure are present in the three human RPTP structures and the residues involved are also highly conserved across species (FIG. 6). DLAR: (D) Ribbon representation of the Ig1-2 crystal structure, highlighting the linker region (solid box) and the domain interface (dashed box), (E) Sidechains of P130 and F133 from the Ig1-Ig2 loop, pack with the carbon backbones of the Y124 and R44 sidechains, but this hydrophobic region is less extensive than in the chicken RPTPσ structure. (F) Two salt bridges R91-E205 and R44-E215 and a network of hydrogen bonds involving the backbone carbonyl of G42, the backbone amide of T214, the sidechain amide of Q41, the carboxyl group of E209, the imidazole group of H216, the hydroxyl groups of S50, Y52, Y166 and T214 and four water molecules, hold Ig1 and Ig2 in a similarly rigid arrangement. Interdomain interactions directly between protein residues and through water molecules are illustrated with black and grey dashed lines respectively. Blue and red atoms represent nitrogen and oxygen. Notably, there is a charge swap in residue 215 between the vertebrate (R215) and *Drosophila* (D215) crystal structures, which forms an interdomain salt bridge in all proteins.

FIG. 9 is a Sequence alignment of the two N-terminal Ig domains (SEQ ID NOS 9-24, respectively, in order of appearance) of the type IIa RPTP family members across species (sequences from FIG. 6). Hydrophobic amino acids (AVFMILWY) are coloured green, acidic (DE) are red, basic (RKH) are blue and residues (STCNGQP) are magenta. The bold and dashed lines represent interdomain salt bridges that are either conserved or nonconserved between RPTP Ig1-2 crystal structures. Residues highlighted with black asterisks appear to be involved in interdomain hydrogen bonding interactions and those indicated with black arrows pack in a hydrophobic region near to the rigid interdomain linker.

FIG. 18A, shows strong CS labeling over the ECM, whereas areas corresponding to cells showed little or no CS labeling above background. FIG. 18 B shows a control treated with chondroitinase ABC to remove CS. (C and D) Immunolocalization of HS (red), with GAP43 (green) and DAPI (blue). Colors are merged in the right-hand panel. FIG. 18C, shows strong HS labeling over cells including neurites, with additional faint labeling above background over the ECM. FIG. 18 D shows a control treated with combined heparinase I, II and III, to remove HS. (E-G) Immunolocalization of RPTPσ (green), combined with HS labeling (red) in FIGS. 18 E and F, or GAP43 neuronal marker (red) in FIG. 18 G. The right-hand Figures show DIC images. FIG. 18G shows a negative control for RPTPσ labeling with secondary antibody only. RPTP and HS overlapped in similar although not identical patterns in cells, as well as in puncta within the growth cone. Some additional scattered dots were seen outside the cells and may be cell fragments based on DIC and DAPI images. A similar pattern, with punctate labeling in the growth cone and scattered dots outside the cell, was reported for RPTPσ previously (35). Scale bar: 60 μm (FIGS. 18 A-E), 6 μm (FIGS. 18F and G).

FIG. 23A shows, on the left hand side, a graph of biotin-labeled heparin oligosaccharide 67-mer (HS67) binding to the PTPσ extracellular domain fused to an Fc tag. The measured dissociation constant ($K_D$) was 2.3 nM. The graph on the right hand side shows the ability of unlabeled HS67 to outcompete the CSPG neurocan, fused to an AP tag, for binding to the PTPσ extracellular domain, fused to an Fc tag. The inhibition constant (Ki), calculated from the Cheng-Prusoff equation, was 2.2 nM, very consistent with the $K_D$ for this oligosaccharide. FIG. 23B shows the results of competition experiments with heparin oligosaccharides of a range of different lengths (HS6 through HS67, corresponding to 6 through 67 monosaccharide units). All lengths tested showed evidence of competition with CSPG. Lengths of HS17 and above showed the strongest ability to compete, with Ki values in the low nanomolar range.

FIG. 26 shows the human PTPsigma transcript variant 4, amino acid sequence.

FIG. 27 shows the human PTPsigma transcript variant 4, nucleotide sequence.

FIG. 28 shows the human PTPσ transcript variant 3 amino acid.

FIG. 29 shows the human PTPσ transcript variant 3 nucleotide sequence.

FIG. 30 shows the human PTPσ transcript variant 1 amino acid sequence.

FIG. 31 shows the human PTPσ transcript variant 1 nucleotide.

FIG. 32 shows the murine PTPσ amino acid sequence.

FIG. 33 shows the murine PTPσ nucleotide sequence.

FIG. 35 is a table showing the crystallization conditions and freezing methods used. Crystallisation trials were set up with human RPTPσ Ig1-3 wildtype protein. Crystals were obtained within 80 days. Subsequent structure determination showed clear density for Ig1-2, but no space within the crystal lattice for a third Ig domain. This suggested a proteolytic cleavage of the protein within the flexible linker between Ig domains two and three, which contains a putative $^{225}$RVRR$^{228}$ furin motif. To obtain crystals of human RPTPσ Ig1-3 a double point mutation R227Q+R228N was necessary to disrupt this motif.

FIG. 36 is a table showing crystallographic data collection and refinement statistics.

FIG. 37 is a table showing the summary of MALS experiments. Heparin experiments were performed with different batches of heparin oligomers and tested at 1:2 and 1:5 protein:heparin ratios respectively. The approximate molecular weight of heparin dp10 is ~3.3 kDa, dp20 is ~6.6 kDa and dp30~10 kDa. CS (Sigma, C4384) and HS (Iduron, GAG-HS01) mixtures used in these experiments contain GAG fragments 10-50 kDa in mass. All Ig1-FN3 proteins were injected at ~10 µM. The molecular weight values listed in this table (MALS MW) were measured at the peak in the refractive index trace for a given experiment. The error in the measured molecular weights is the uncertainty statistic provided by the Astra software (Wyatt Technologies).

DETAILED DESCRIPTION

Figure 1A:
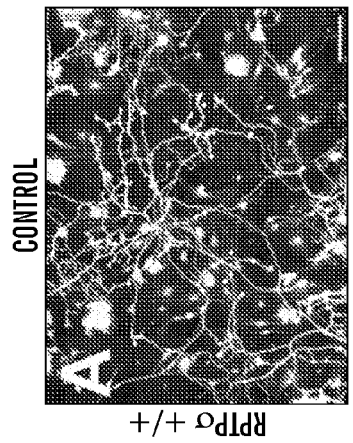
FIG. 1A-FIG. 1H show the results of experiments that demonstrate RPTPσ-GAG interactions modulate contrasting growth responses of sensory neurons.
Figure 1B:
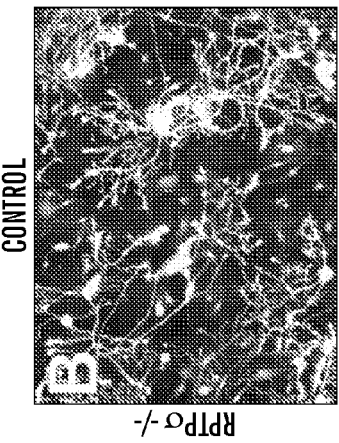
Figure 1C:
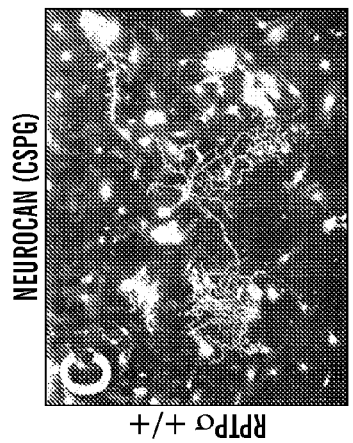
Figure 1D:
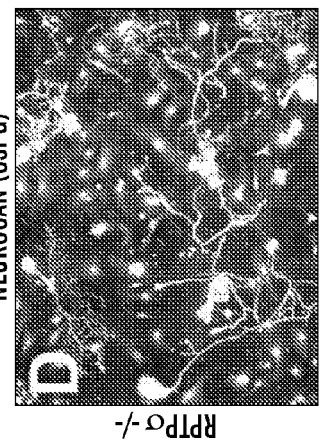
Figure 1E:
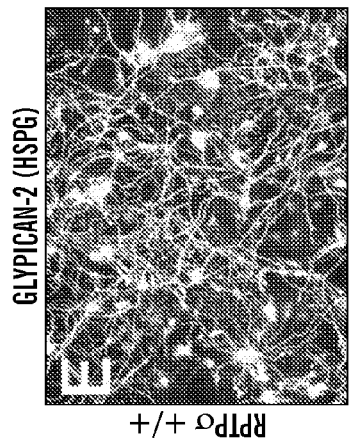
Figure 1F:
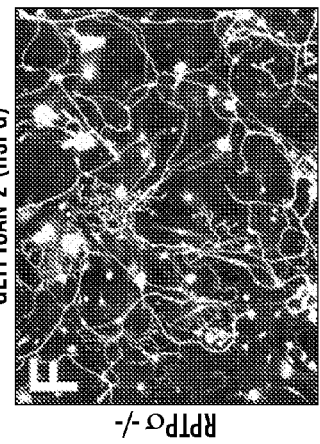
Figure 1G:
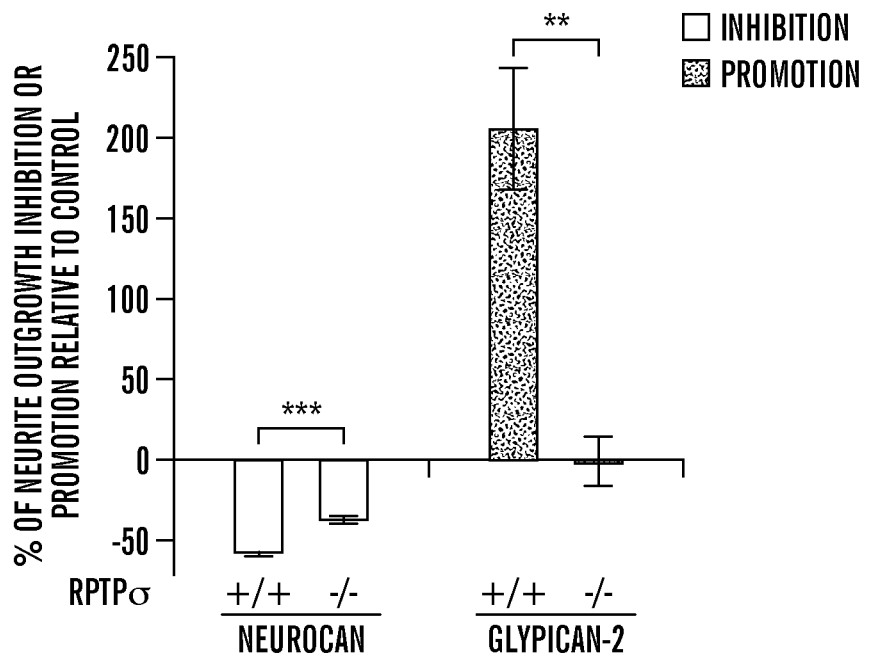

Aspects of the present invention relate to the findings that certain agents that bind to receptor protein tyrosine phosphatase σ (RPTPσ) on a neuron, can induce neuronal outgrowth of that neuron. Examples of such agents are described herein.

In one respect, the present invention relates to a method of inducing neuronal outgrowth of a neuron. This is achieved, for example, by contacting the neuron with an effective amount of an agent that binds RPTPσ, to thereby induce neuronal outgrowth of the neuron. Contact can be to the cell body or cell process. Such agents are described herein. The contacting can occur in vitro or in vivo. In vitro, the agent, for example, can be added to a cell culture containing the neuron. In vivo, the agent can be administered to a subject, such that an effective amount of the agent comes in contact with the neuron (herein referred to as the target neuron), to thereby induce the neuronal outgrowth. In one embodiment, the neuron is a central nervous system neuron. In one embodiment, the neuron is a peripheral nervous system neuron.

Without being bound by theory, it is thought that the agent induces neuronal outgrowth by inducing the clustering of RPTPσ and/or inhibiting CSPG binding to the RPTPσ of the neuron.

The neuron can further be contacted with a second agent that promotes neuronal outgrowth, as discussed herein.

When the method is performed in vivo, by administration of the agent to a subject, neuronal outgrowth in the subject is promoted. As such, another aspect of the present invention relates to a method of promoting neural outgrowth in the nervous system of a subject (e.g, CNS or PNS). The method comprises administering a therapeutically effective amount of the agent to contact the neuron, and thereby induce neural outgrowth of the contacted neuron(s).

The neuron contacted in vivo may be located at a site of injured or diseased tissue. Such injury or disease can impair normal neuronal function by disrupting normal neural connections. Examples of specific types of injury or disease that can disrupt normal neural connections are provided herein. The induction of neuronal outgrowth at such sites can have therapeutic effects. As such, another aspect of the present invention relates to a method of treating neuronal injury in a subject. The method comprises administering an agent that binds RPTPσ to a site of neuronal injury in the subject, to thereby induce neuronal outgrowth at the site of neuronal injury.

In one embodiment, the treatment comprises adjusting an already ongoing therapeutic regimen of the subject such that at least one symptom of neuronal damage is reduced. Without limitation, a therapeutic regime can be adjusted by modulating the frequency of administration of the agent (e.g., heparin oligosaccharide) and/or by altering the site or mode of administration.

In one embodiment, the method further comprises diagnosing a subject for neuronal injury (e.g., acute and/or traumatic injury) and/or neuronal degeneration, prior to treating the subject as described herein. In one embodiment of the methods described herein, the method further comprises selecting a subject with neuronal injury or degeneration before treating the subject as described herein. The method may further comprise selecting a subject in need of treatment of neuronal injury, degeneration or disease, prior to such treatment. Such selection may involve identification within a subject of such nerve damage, or the site of the nerve damage.

In one embodiment, neuronal outgrowth induced is sufficient to at least partially restore nerve function to an injured area (e.g., through an injured spinal cord). The restored function can be achieved by either 1) promoting regeneration of damaged neurons (axons) to restore the injured neural pathway, 2) promoting sprouting or plasticity of new connections that can compensate functionally (possibly distinct from the damaged connections, and 3) a combination of the two.

The methods herein utilize an "effective amount" of the agent. An "effective amount" of an agent refers to an amount sufficient to achieve a desired effect, as described herein (e.g., neuronal outgrowth of a contacted neuron). In one embodiment, the effective amount is sufficient to cause clustering of RPTPσ when contacted to a cell expressing that receptor. In one embodiment, the effective amount is sufficient to compete with CSPG for binding of RPTPσ when contacted to a cell expressing that receptor.

The methods of treating or treatment of a subject, described herein, utilize a therapeutically effect amount of the agent. The term "therapeutically effective amount" refers to an amount effective, at dosages and for periods of time necessary, to achieve the desired therapeutic result in a subject. As used herein, the term "therapeutically effective amount" refers to an amount of agent such that treatment of a patient with that amount can be associated with a medically desirable change (a therapeutic result) in neuronal outgrowth, nerve function, or that can reduce, or ameliorate neuronal damage. A therapeutic result in the subject may be, e.g., lessening of symptoms, prolonged survival, improved mobility, and the like. A therapeutic result need not be a "cure." A therapeutically effective amount of an agent as defined herein may vary according to factors such as the disease state, age, and weight of the subject, and the ability of the agent to elicit a desired response in the subject. Dosage regimens may be adjusted to provide the optimum therapeutic response. A therapeutically effective amount is also one in which any toxic or detrimental effects of the active compound are outweighed by the therapeutically beneficial effects.

Agents that Bind to Receptor Protein Tyrosine Phosphatase σ (RPTPσ) to Induce Neuronal Outgrowth In one embodiment the agent binds RPTPσ to inhibit the binding of CSPG. In one embodiment the agent binds the first immunoglobulin-like domain of RPTPσ (e.g., via the Ig1GAG binding site).

In one embodiment the agent binds RPTPσ to induce clustering of the receptor. In one embodiment the agent that induces clustering binds the first immunoglobulin-like domain of RPTPσ (e.g., via the Ig1GAG binding site). In one embodiment, the agent is multivalent. Without being bound by theory, it is expected that agents which bind RPTPσ multivalently will thereby induce clustering.

Agents that promote clustering of RPTPσ useful in the methods described herein include heparan sulfate proteoglycans, heparan sulfates, heparin oligosaccharides and heparan sulfate oligosaccharides. In one embodiment the heparan sulfate proteoglycan is glypican 2 or a derivative or modification thereof. In one embodiment, the heparin oligosaccharide or heparan sulfate oligosaccharide contains 8 or more saccharide units. In one embodiment, the heparin oligosaccharide or heparan sulfate oligosaccharide contains less than 67 oligosaccharide units. Such agents are described in more detail below.

Additional agents that specifically bind to one or more sites of RPTPσ (e.g., to thereby induce clustering and/or inhibit binding of CSPG) are also known or can be generated by the skilled practitioner. In one embodiment, the agent is an antibody or comprises a functional fragment of an antibody that binds to the RPTPσ. Examples of a functional fragment of an antibody include, without limitation, F(ab')2, Fab', Fab, capable of binding the RPTPσ. The antibody or functional fragment thereof may be humanized for use in a human subject. The antibody or functional fragment thereof may be chimeric.

When obtained or otherwise derived from a natural source, the agent for use in the methods described herein can be obtained from a whole animal or alternatively cell culture. In one embodiment, the agent is obtained or derived from a natural source that is of the same species as the subject on which the method is performed. In one embodiment, the agent is obtained or derived from a natural source that is of a different species as the subject on which the method is performed. The various animal species described herein for a "subject" also provide suitable sources of the agent.

One such agent that can be used in the methods of the invention is a glycosaminoglycan. The glycosaminoglycan can arise in and be purified from natural sources. The agent may be a fragment of the natural glycoasminoglycan (e.g., those described herein), and/or it may be further chemically modified. In some embodiments, the oligosaccharides described herein may be derived from a larger glycosaminoglycan (e.g., by purification, fragmentation, and/or modification). Several classes of glycosaminoglycans exist, including 1) heparan sulfate and heparin, 2) chondroitin sulfate, and 3) dermatan sulfate and keratan sulfates.

Another example of an agent that can be used to induce neuronal outgrowth is a heparin oligosaccharide. A variety of heparin oligosaccharides are known in the art and commercially available. Heparin oligosaccharides are typically described by virtue of the number of repeated unit or alternatively by their molecular weight. For example, octasaccharide have a molecular weight of about 2400 Da. Decasaccharides have a molecular weight of about 3000 Da. In one embodiment, the heparin oligosaccharide contains 8 or more saccharide units (this may also be referred to as having 4 or more di-saccharide units). In one embodiment, the heparin oligosaccharide contains 10 or more saccharide units (5 or more di-saccharide units). In one embodiment, the heparin oligosaccharide contains 20 or more saccharide units (10 or more di-saccharide units). In one embodiment, the heparin oligosaccharide contains about 30 or more saccharide units (15 or more di-saccharide units; approximately 9000 Da). Larger heparin polymers (e.g. heparin polysaccharides that contain about 67 or more saccharide units, approximately 20,000 Da) are also expected to induce neuronal outgrowth when used in the methods described herein. Such larger heparin oligosaccharides are typically referred to in the art as heparin polysaccharides. In one embodiment, the heparin oligosaccharide contains about 17, 23, 30, or 67 monosaccharide units. In one embodiment, the heparin olidosaccharide has a molecular weight of 1800, 2400, 3000, 5000, 7000, 9000, or 20,000 Da.

Another example of an agent that can be used to induce neuronal outgrowth is a heparan sulfate or a heparan sulfate oligosaccharide. Heparan sulfate oligosaccharides can be described by virtue of the number of repeated unit or alternatively by their molecular weight. In one embodiment, the heparan sulfate oligosaccharide contains 8 or more saccharide units (this may also be referred to as having 4 or more di-saccharide units). In one embodiment, the heparan sulfate oligosaccharide contains 10 or more saccharide units (5 or more di-saccharide units). In one embodiment, the heparan sulfate oligosaccharide contains 20 or more saccharide units (10 or more di-saccharide units). In one embodiment, the heparan sulfate oligosaccharide contains about 30 or more saccharide units (15 or more di-saccharide units). Larger heparan sulfate polymers (e.g. heparan sulfate polysaccharides that contain about 67 or more saccharide units) are also expected to induce neuronal outgrowth when used in the methods described herein. Such larger heparan sulfate oligosaccharides are typically referred to in the art as heparan sulfate polysaccharides. In one embodiment, the heparin sulfate oligosaccharide contains about 17, 23, 30, or 67 monosaccharide units.

The heparin oligosaccharide or heparan sulfate oligosaccharide can be derived from a natural or synthetic source, as described herein. In one embodiment, the heparin oligosaccharide or heparan sulfate oligosaccharide is derived by degradation (e.g., chemical) of HSPG. The heparin oligosaccharide may be further chemically modified, (e.g., to facilitate storage or administration).

In addition to length, a variety of carbohydrates of different structures (referred to as structural variants) are expected to exhibit the same activity as the heparin oligosaccharides described herein. Such carbohydrates are described below, by way of non-limiting example. Many such structural variants are available commercially (e.g., from Seikagaku, Neoparin, Northstar, Iduron). For heparan sulfate, five positions can be modified to produce the structural variants: 2-sulfation of the uronic acid, and N-deacetylation, N-sulphation, 3-sulfation and 6-sulfation of the glucosamine. Chondroitin sulfate also exists in forms denoted A, C, D and E, referring to differential sulfation at C2 of the uronic acid, or C4 or C6 of the GalNAc. Heparan sulfate and chondroitin sulfate carbohydrates are available with each of these positions oversulfated or desulfated (Gallagher, J. T. Biochem Soc Trans, 2006. 34: 438 41; Lepenies, B et al., Applications of synthetic carbohydrates to chemical biology. Curr Opin Chem Biol, 2010. 14: 404-11; Mulloy, B. Adv Pharmacol, 2006. 53: 49-67; Seeberger, P. H. Nature, 2007. 446: 1046-51). In addition to HS and CS, other saccharides expected to exhibit similar function include dermatan and keratin sulfates (DSPGs and KSPGs) since they are reported to inhibit axon regeneration (Smith-Thomas, et al., J Cell Sci, 1995. 108: 1307-15), as well as synthetic polymers such as dextran sulfate.

One model to explain the opposing effects of HSPG and chondroitinsulfate proteoglycan (CSPG) mediated by PTPσ is that the distribution of sulfate groups (typically 1-2 per disaccharide) along an individual chondroitin sulfate chain is relatively uniform, while heparan sulfate has a distinct modular composition, with regions of high sulfation (3 groups per disaccharide), flanked by intermediately modified transition zones and variably spaced by largely unmodified sections almost devoid of sulfation (Murphy, et al. J Biol Chem, 2004. 279: 27239-45). Although other chemical differences between heparan sulfate and chondroitin sulfate may contribute to differential effects on RPTPσ, these observations suggest a model where the islands of high sulfation present in heparan sulfate, but not chondroitin sulfate, may promote close packing of RPTPσ molecules along these regions. Therefore, oligosaccharides that mimic these islands of high sulfation density may be predicted to have particularly high effectiveness in promoting neurite growth. As such, a highly sulfated carbohydrate mimetic of heparin, heparan sulfate, chondroitin sulfate, dermatan sulfate or keratan sulfate is also envisioned for use in the methods described herein.

Heparin is well known to be an anticoagulant, and since this may create undesirable side effects, polymers with reduced or absent anticoagulant activity that also envisioned for use in the methods and formulations described herein. Anticoagulation by heparin is mediated mostly through its binding to anti-thrombin, and structural features of the saccharide chain that cause anticoagulant activity of heparin are known (Avci, et al., Curr Pharm Des, 2003. 9: 2323-35; Gandhi et al., Drug Discov Today, 2010. 15: 1058-69; Lever et al., Nat Rev Drug Discov, 2002. 1: 140-8.7-9). In particular, most of the anticoagulant activity of heparin resides in a specific 5-mer saccharide sequence.

Figure 34:
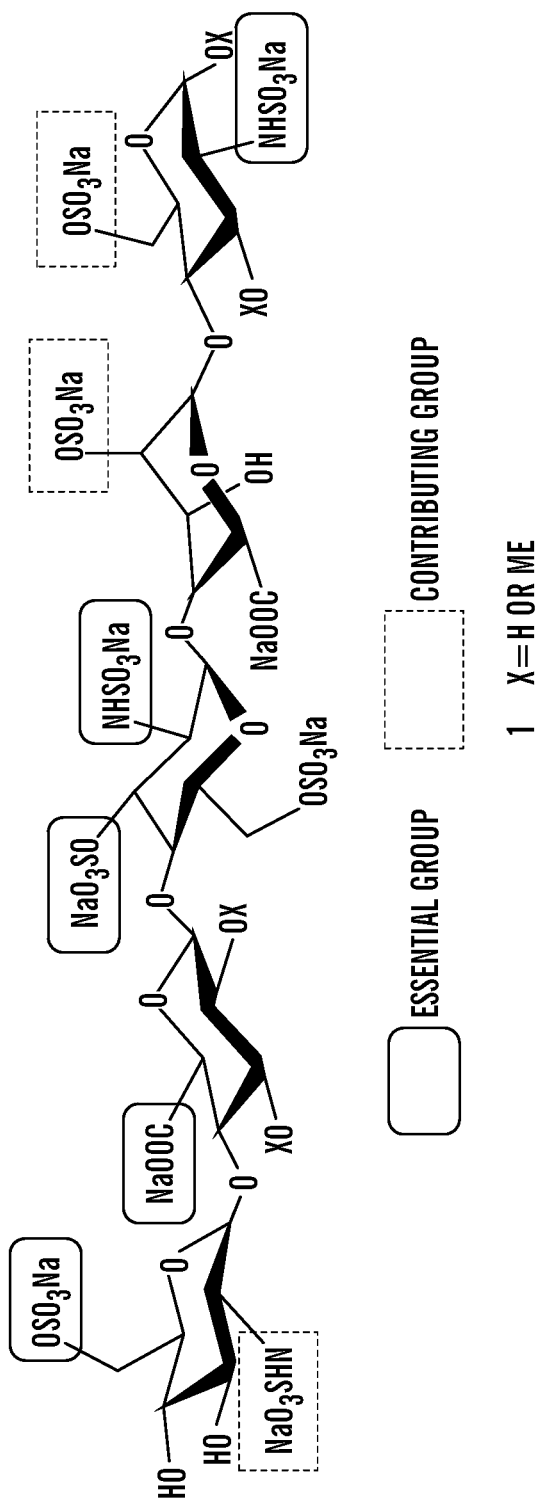
FIG. 34 is a schematic representation of a pentasaccharide which comprises the anti-thrombin binding domain and is responsible for the anticoagulant (From Gandhi, N. S., Mancera, R. L., 2010, 15: 1058-69).

Structural and functional studies have shown that a unique pentasaccharide (sometimes referred to as AGA*IA, DEFGH, or antithormbin binding domain (ABD)) comprises the anti-thrombin binding domain and is responsible for the anticoagulant activity of heparin. This pentasaccharide sequence is composed on three glucosamine residues (D, F, and H), a glucuronic acid residue E, and an iduronic acid residue (G). The sulfo group at C-3 of the central glucosamine residue (F) is a marker for the anti-thrombin bind site. The actual sequence of ABD is GlcNAc/NS6S→GlcA→GlcNS3S6S→IdoA2S→GlcNS6S (where GlcNS6S is a glucosamine comprising a sulfo group on the nitrogen and a sulfate group on C6, GlcA is glucoronic acid, GlcNS3S6S is a glucosamine comprising a sulfo group on the nitrogen and a sulfate group on C3 and C6, and IdoA2S is iduronic acid comprising a sulfate group on C2) and is shown in FIG. 34. See for example, Avci, F. Y., Karst, N. A., Linhardt, R. J., Curr Pharm Des, 2003, 9: 2323-35; Gandhi, N. S., Mancera, R. L., 2010, 15: 1058-69; and Lever, R. and Page, C. P., Nat Rev Drug Discov, 2002, 1: 140-8. The structural requirements for the binding of heparin to anti-thrombin are shown in FIG. 34. As shown in FIG. 34, charged sulfate groups (highlighted in the full boxes) are essential for activation of anti-thrombin while other charged sulfate groups (highlighted in the dashed boxes) are required to increase the biological activity. Moreover, hydrophobic interactions between the heparin pentasaccharide and anti-thrombin can also contribute to increasing the binding affinity. It is well known in the art that removal of N-sulfo groups in residue D results in a 50% loss of anti-Xa activity; removal of either of the O-sulfo groups in residues G or H results in a 75% loss of activity; and removal of any one of the 6-O-sulfo groups on residue D, carboxyl on residue E, 3-O-sulfo or N-sulfo on residue F, carboxyl on residue G, or N-sulfo group on residue H results in a 95% loss of activity.

A heparin or heparin derivative with reduced anticoagulant activity can be obtained by making one or more modification in the anti-thrombin binding pentasaccharide. Modifications can include one or more of changing, modifying, replacing, or substituting a charged sulfate group that is considered to be essential or required for anticoagulant activity. Exemplary modifications can include one or more of removing one or more of the sulfo groups, replacing one or more of the sulfo groups with a phospho group, replacing one or more of the sulfo groups with carboxylic group or carbonyl group, replacing one or more of the sulfo groups with an alkyl group (e.g., methyl, ethyl, propyl, butyl, isopropyl, pentyl, t-butyl, hexyl, and the like), alkylating one or more of the sulfate groups (e.g. with a methyl, ethyl, propyl, butyl, isopropyl, pentyl, t-butyl, or hexyl group), replacing the sulfo group on one or more of the nitrogens with an acyl (e.g., acetyl) group, replacing one or more of the saccharides with another saccharide (e.g., by a modified or unmodified allose, altrose, glucose, mannose, gulose, idose, galactose, or talose), replacing one or more of the saccharides with a non-saccharide linker, removing one or more of the saccharides, replacing the sodium cation from one or more of the sulfate groups with a different cation, replacing one or more of the sulfate groups with a 1,1-dihalogen alkyl group (e.g., 1,1-difluoroalkyl), replacing one or more of the sulfate groups with a 1,1-difluoromethylesulfate group, replacing one or more of the sulfate groups with a 1,1-difluoromethyletetazole group, and the like.

A heparin comprising a modified ABD can have anticoagulant activity that is at least 5%, 10%, 20%, 30%, 40%, 50%, 60%, 70%, 80% or 90% less than the anticoagulant activity of an heparin comprising a unmodified ABD. While not crucial, a heparin comprising a modified ABD can be free of any anticoagulant activity. Methods for determining anticoagulant activity are well known in the art and can be used to determine the anticoagulant activity of a heparin comprising a modified ABD.

Some exemplary non-anticoagulant heparin and heparin sulfates mimetics include, but are not limited to, Pentosan polysulfate, and Heparin tetrasaccharide.

Non-linear branched sulfated carbohydrates are also envisioned for use in the methods described herein, including without limitation, heparin-BSA, as well as glycodendrimers which can be produced with defined branched structures using click chemistry by methods known in the art (Lepenies, et al., Curr Opin Chem Biol, 2010. 14: 404-11). PTPσ activation may require higher-oligomerization, than dimerization, to promote neurite extension (FIG. 25), reminiscent of the requirement of Eph receptors for large scale clustering (Flanagan, et al., Annu. Rev. Neurosci., 1998. 21: 309-345; Vearing, et al., Growth Factors, 2005. 23: 67-76). Therefore, the branched polymers that can cluster receptors in an extended two-dimensional array are also envisioned.

Heparan Sulfate Proteoglycan (HSPG)

One type of glycosaminoglycan is heparan sulfate proteoglycan (HSPG). The biosynthesis of HSPGs leads to the production of molecules with great structural heterogeneity with respect to the size of the polysaccharide chain, the ratio of iduronic (IdoA) to glucuronic acid (GlcA) units, and the amount and distribution of sulfate groups along the carbohydrate backbone.

Different HSPG's associate with the cell surface by a variety of mechanisms. HSPGs can link to the plasma membrane through a hydrophobic transmembrane domain of their core protein or through a glycosyl-phosphatidylinositol (GPI) anchor covalently bound to the core protein (transmembrane HSPGs). Also, HSPGs can interact with the cell by non-covalent linkage to different cell-surface macromolecules (peripheral membrane HSPGs). Transmembrane HSPGs are glypican (Doolittle, R. F. (1992) Protein Sci. 1, 191-200), cerebroglycan (Stipp, et al. (1994) J. Cell Biol. 124, 149-160), betaglycan (Massagué, J. (1992) Cell 69, 1067-1070), CD44 (Brown, et al. (1991) J. Cell Biol. 113, 207-221), and the members of the syndecan family (Bernfield, M., Kokenyesi, (1992) Annu. Rev. Cell Biol. 8, 165-193): syndecan 1, fibroglycan (syndecan 2), N-syndecan (syndecan 3) and ryudocan (syndecan 4). Glypican and cerebroglycan are typical GPI-anchored HSPGs. Syndecans and betaglycan are typical transmembrane HSPGs characterized by a core protein composed of an extracellular domain, a single membrane-spanning domain and a short cytoplasmic domain (28 to 34 amino acid residues). In the extracellular domain are present the consensus sequences for glycosylation and a conserved putative proteolytic cleavage site. The cytoplasmic domain of syndecans can interact with the cytoskeleton and contains four conserved tyrosine residues, one of them hypothesized to be substrate for enzymatic phosphorylation. Perlecan and dystroglycan are associated with the extracellular matrix. Perlecan is a typical peripheral membrane HSPG that interacts with the cell surface through its core protein (Lopez-Casillas et al. (1991) Cell 67, 785-795). The cell-adhesion motif Arg-Gly-Asp within the core protein of perlecan binds integrins b1 or b3 present on endothelial cell surface (Hayashi et al. (1992) J. Cell Biol. 119, 945-959). However, HSPGs may associate to the cell surface and/or ECM also through their GAG-chain, as demonstrated by the observation that half of the total content of HSPGs in endothelial cells can be released after incubation with soluble heparin (Lowe-Krentz, et al. (1992) Mol. Cell. Biochem. 109, 51-60). Agrin and collagen XVIII are two other HSPGs that are found in the brain.

HSPGs exist also in soluble form following their mobilization from the cell surface. Transmembrane HSPGs are released after proteolytic digestion of their core protein (Saksela et al. (1988) J. Cell Biol. 107, 743-751). GAG-chain-associated HSPGs are released by exogenous GAGs by a simple law mass action (Lowe-Krentz, et al. (1992) Mol. Cell. Biochem. 109, 51-60) or by enzymatic digestion of their polysaccharidic backbone (Bashkin et al. (1989) Biochemistry 28, 1737-1743). GPI-anchored HSPGs can be released by action of endogenous phospholipase (Brunner et al. (1991) J. Cell Biol. 114, 1275-1283).

In one embodiment, the agent used in the methods of the invention is purified and/or isolated prior to its use. Purified materials are typically "substantially pure", meaning that a molecule or fragment thereof has been separated from the components that naturally accompany it. Typically, the polypeptide is substantially pure when it is at least 60%, 70%, 80%, 90%, 95%, or even 99%, by weight, free from the proteins and other organic molecules with which it is associated naturally. For example, a substantially pure molecule may be obtained by extraction from a natural source or by chemical synthesis. "Isolated" as the term is used herein, refers to the molecule or a mixture of molecules, having been removed from its natural location and environment. In the case of an isolated or purified domain or fragment of a naturally occurring molecule, the domain or fragment is substantially free from flanking portions that occur naturally.

The use of combinations of 2 or more agents (e.g., those described herein) is also envisioned. For example, combinations of different lengths of heparin oligosaccharides, combinations of different HSPGs, or derivatives thereof, etc. In one embodiment, the agent used is a mixture of unfractionated heparin.

Other Agents

The methods described herein can further include administration or contacting a cell (e.g., a neuron) with a second agent that acts to enhance neuronal outgrowth, e.g. an agent that blocks other regeneration inhibitors (e.g., a compound that blocks myelin-associated inhibition of neurite growth). Known inhibitors of neuronal outgrowth (e.g., of regeneration at a CNS injury site) are myelin-derived inhibitors (e.g., Nogo-A, MAG, OMgp, Ehprin B3, Sema 4D and Sema 5A), astrocyte derived inhibitors (e.g., CSPG, KSPG, Ephrin B2 and Slit), fibroblast derived inhibitors (e.g., Sema 3A). The second agent may be an antagonist to any of these inhibitors. In one embodiment, the cell is further contacted with one or more such second agents. In one embodiment, the agent inhibits a myelin inhibitor of neural regeneration (e.g., myelin-associated glycoprotein (MAG), Nogo, oligodendrocyte myelin glycoprotein (OMgp)). Inhibitors of MAG are disclosed in U.S. Pat. No. 5,932,542. Inhibitors of Nogo are disclosed in U.S. Patent Application Pub No. 2009/0215691. Inhibitors of OMgp are disclosed in U.S. Patent Application Pub. No. 2008/0188411. The cell can be contacted with this second agent before, after, and/or concurrently with the agent that inhibits the interaction of CSPG with PTPσ. The second agent can be formulated in a pharmaceutical composition with the first agent.

The second agent may be an agent that stimulates neuronal outgrowth. Such agents promote the intrinsic growth capability of a neuron. Such agents which promote neuronal outgrowth are known in the art. Such agents include, without limitation, agents that activate the growth pathway of neurons (e.g., CNS) are agents that are capable of producing a neurosalutary effect. As used herein, a "neurosalutary effect" means a response or result favorable to the health or function of a neuron, of a part of the nervous system, or of the nervous system generally. Examples of such effects include improvements in the ability of a neuron or portion of the nervous system to resist insult, to regenerate, to maintain desirable function, to grow or to survive. The phrase "producing a neurosalutary effect" includes producing or effecting such a response or improvement in function or resilience within a component of the nervous system. For example, examples of producing a neurosalutary effect would include stimulating axonal outgrowth after injury to a neuron; rendering a neuron resistant to apoptosis; rendering a neuron resistant to a toxic compound such as β-amyloid, ammonia, or other neurotoxins; reversing age-related neuronal atrophy or loss of function; or reversing age-related loss of cholinergic innervation.

Any agent that activates the growth pathway of neurons (e.g., CNS) is suitable for use in the methods of the present invention as a second agent. Examples of second agents include, but are not limited to, neurotrophic factors such as inosine, mannose, gulose, or glucose-6-phosphate, as described in Li et al., 23 J. Neurosci. 7830 (2003); Chen et al., 99 PNAS 1931 (2002); and Benowitz et al., 273 J. Biol. Chem. 29626 (1998). TGF-β, and oncomodulin as described in Yin et al., 23 J. Neurosci. 2284 (2003), are also such agents. In addition, polypeptide growth factors such as BDNF, NGF, NT-3, CNTF, LIF, and GDNF can be used. In one embodiment the methods of the present invention which comprise an agent that stimulates neuronal outgrowth further comprise contacting neurons (e.g., CNS) with a cAMP modulator that increases the concentration of intracellular cAMP (e.g., cAMP), and/or polyamines (Cai et al., 35 Neuron 711 (2002)). For example, the ability of mature rat retinal ganglionic cells to respond to mannose requires elevated cAMP (Li et. al., 2003).

Combinations of an agent (referred to herein as second agents) that blocks regeneration inhibitors, and an agent that stimulates neuronal outgrowth can also be used in conjunction with the agent that binds RPTPσ (referred to herein as the first agent). The cell can be contacted with one or more second agents before, after, and/or concurrently with the first agent, and/or before, after, and/or concurrently with the second agent. Administration to a subject to achieve the desired order of contacting the agents with the target cells is within the ability of the skilled artisan.

The agents described herein may further be modified (e.g., chemically modified). Such modification may be designed to facilitate manipulation or purification of the molecule, to increase solubility of the molecule, to facilitate administration, targeting to the desired location, to increase or decrease half life. A number of such modifications are known in the art and can be applied by the skilled practitioner.

In one embodiment, the agent is obtained or isolated from a source exogenouse to the subject to which it is being administered.

Targeted Cells

The agents and therapeutic pharmaceutical compositions described herein may be delivered to neurons of the CNS and/or the PNS to thereby stimulate neuronal outgrowth. In general, the targeted cell(s) will express RPTPσ. Such neurons may be injured or diseased. Such neurons may alternatively be healthy, uninjured neurons. Such neurons may be located at the site of injury or diseased tissue, or at a site incident to the injury or diseased tissue. The neurons to be targeted for therapeutic administration, delivery/contact of the agents and compositions described herein will be neurons from which neuronal outgrowth is thought to prove beneficial to the subject. Such determination is within the ability of the skilled practitioner through no more than routine experimentation. In one embodiment, the targeted cells are the actual injured neurons (e.g, to promote re-generation). In another embodiment, the targeted cells are neurons whose outgrowth produces compensatory neuronal function with respect to the neuronal injury. In another embodiment, both types of neurons (injured and compensatory) are targeted.

Treatments of Neuronal Disorders

In one embodiment, the agent described herein is administered to a subject for therapeutic purposes to promote neuronal outgrowth to thereby treat a neuronal disorder in the subject. As used herein, the term "neuronal disorder" includes a disease, disorder, or condition which directly or indirectly affects the normal functioning or anatomy of a subject's nervous system. The disorder may be an injury, or degeneration of the central nervous system and/or of peripheral nerves. The neuronal disorder may result from injury (e.g., traumatic injury) or from disease (e.g., neurodegenerative disease). Such injuries include stroke, traumatic brain injury, peripheral nerve injury, spinal cord injury, skin burn, and eye injury.

The term "stroke" is art-recognized and includes sudden diminution or loss of consciousness, sensation and voluntary motion caused by rupture or obstruction (for example, by a blood clot) of an artery of the brain. "Traumatic brain injury" is art-recognized and includes the condition in which a traumatic blow to the head causes damage to the brain or connecting spinal cord, with or without penetrating the skull. Usually, the initial trauma can result in expanding hematoma, subarachnoid hemorrhage, cerebral edema, raised intracranial pressure, and cerebral hypoxia, which can, in turn, lead to severe secondary events due to low cerebral blood flow.

The neuronal injury can be acute or chronic. Examples of acute injury are those that results from surgery, trauma, compression, contusion, transection or other physical injury, vascular pharmacologic or other insults including hemorrhagic or ischemic damage. Chronic neuronal injury may results from repetitive stress, inflammation/oxidative stress within a neural tissue caused by disease, neurodegenerative or other neurological diseases.

Neuronal degenerative diseases include, without limitation, amyotrophic lateral sclerosis (ALS), retinitis pigmentosa, glaucoma, multiple sclerosis, mild cognitive impairment, Alzheimer's disease, Pick's disease, senile dementia, progressive supranuclear palsy, subcortical dementias, Wilson disease, multiple infarct disease, arteriosclerotic dementia, AIDS associated dementia, cerebellar degeneration, spinocerebellar degeneration syndromes, Friedreichs ataxia, ataxia telangiectasia, epilepsy-related brain damage, spinal cord injury, restless legs syndrome, Huntington's disease, Parkinson's disease, striatonigral degeneration, cerebral vasculitis, mitochondrial encephalomyopathies, neuronal ceroid lipofuscinosis, spinal muscular atrophies, lysosomal storage disorders with central nervous system involvement, leukodystrophies, urea cycle defect disorders, hepatic encephalopathies, renal encephalopathies, metabolic encephalopathies, porphyria, bacterial meningitis, viral meningitis, meningoencephalitis, prion diseases, poisonings with neurotoxic compounds, Guillain Barre syndrome, chronic inflammatory neuropathies, polymyositis, dermatomyositis and radiation-induced brain damage. Included in the aspect is neurodegeneration including peripheral neuropathy due to therapeutic administration of cranial irradiation or chemotherapeutic agents.

Peripheral Nerve Damage

In one embodiment, the agent is administered to a subject to treat damage associated with peripheral neuropathies including, but not limited to, the following: diabetic neuropathies, virus-associated neuropathies, including acquired immunodeficiency syndrome (AIDS) related neuropathy, infectious mononucleosis with polyneuritis, viral hepatitis with polyneuritis; Guillian-Barre syndrome; botulism-related neuropathy; toxic polyneuropathies including lead and alcohol-related neuropathies; nutritional neuropathies including subacute combined degeneration; angiopathic neuropathies including neuropathies associated with systemic lupus erythematosis; sarcoid-associated neuropathy; carcinomatous neuropathy; compression neuropathy (e.g. carpal tunnel syndrome) and hereditary neuropathies, such as Charcot-Marie-Tooth disease. The agent is administered to thereby contact a peripheral nerve and induce neuronal outgrowth. The nerve may be an injured peripheral nerve, or a compensatory peripheral nerve.

Peripheral nerves such as dorsal root ganglia, otherwise known as spinal ganglia, are known to extend down the spinal column. These nerves can be injured as a result of spinal injury. Such peripheral nerve damage associated with spinal cord injury can also be treated using the present methods. The subject is treated in accordance with the present method for peripheral nerve damage as the result of peripheral neuropathies. The injury for treatment can be acute or chronic. The spinal cord injury may be a complete severing of the spinal cord, a partial severing of the spinal cord, or a crushing or compression injury of the spinal cord.

Transmembrane Protein Tyrosine Phosphatases (PTPs)

Transmembrane PTPs form a large and diverse molecular family, and have a structure typical of transmembrane cell surface receptors (Chagnon et al., Biochem Cell Biol 82, 664 (2004); Johnson et al., Physiol Rev 83, 1 (2003). PTPσ is a receptor type protein-tyrosine phosphatase that has been cloned and identified in mouse, in rat, and in human (Pulido et al., *Proc. Nat. Acad. Sci.* 92: 11686-11690, 1995; PubMed ID: 8524829). PTPσ and other PTPs in the LAR subfamily can act as receptors for heparan sulfate proteoglycans (HSPGs), and these PTPs are involved in axon guidance and synapse formation during development. In the adult, PTPσ gene disruption enhances regeneration in sciatic, facial and optic nerves.

PTPσ has two intracellular PTPase domains and an extracellular region having Ig-like and fibronectin type III-like domains. The specific location of the various domains of the PTPσ molecule are known in the art. Pulido et al., 92 PNAS 11686 (1995); PubMed ID: 8524829. Alternative splicing of PTPσ generates four isoforms; the long isoforms 1 and 2, which are expressed in a range of human tissues, contain an additional four fibronectin type III domains compared with the short isoforms 3 and 4, which are predominantly found in the brain (Naoto et al., J Bone Miner. Res. 11, 535 (1996)). Amino acid and nucleotide sequences for human and mouse PTPσ are shown in the Examples section below.

Administration

For the therapeutic methods described herein, the agent is administered to the subject to be treated. The term "administered" or "administering" to a subject includes dispensing, delivering or applying the agent to the subject by any suitable route for delivery of the agent to a site in the body where neuronal outgrowth is desired (e.g., the site of neuronal injury or neuronal degeneration) to thereby contact a neuron at that site. Contact can be to the cell body or cell process. The route of administration and the dosage regimen will be determined by skilled clinicians, based on factors such as the exact nature of the condition being treated, the severity of the condition, and the age and general physical condition of the patient. In one embodiment, administration is to thereby contact injured and/or non-injured neurons proximal to the injury site. In one embodiment, administration is such as to deliver the agent across the blood brain barrier. Pharmaceutical compositions described herein comprising one or more of the specific agents described herein are also envisioned as other aspects of the invention.

Typically the agent is administered in the context of a pharmaceutical composition. A pharmaceutical composition typically comprises the agent and a pharmaceutically acceptable carrier. A pharmaceutically acceptable carrier is one that is physiologically compatible with the intended route of administration, to deliver the agent in active form (e.g., not degraded). In one embodiment, the agent/pharmaceutical composition is in solution. In another embodiment, the agent is in a solid or in a semi-solid form (e.g., contained in a matrix). In one embodiment, the agent is in a liquid matrix that changes phase once injected into the body. In one embodiment, the pharmaceutical composition is a slow release implant that can be deposited at the site of injury or target site of contacting the neuron.

As the term is used herein, a matrix is a composition designed to localize/hold the agent in a specific desired location of the subject once administered. Such a matrix can be a gel, a paste, or a solid substance, that has the agent incorporated therein. The agent may be available in the matrix, or released from the matrix over time to thereby contact the neurons in the general location of the matrix. In one embodiment, the matrix is liquid at room temperature and more solid (e.g., a gel, paste, solid) once in the body. In one embodiment, the temperature of the body induces the phase shift. One such matrix is an injectable hydrogel. A variety of such hydrogels and routes/methods of administration are disclosed in Macaya et al., (Biomed. Mater. 7 (2012) 012001 (22 pp)). In one embodiment, the hydrogel is a thermogel (an aqueous monomer/polymer solution which has the ability to form a gel upon temperature change) such as is disclosed in Klouda et al., (Eur. J. Pharm. Biopharm. (2008) 68: 34-45).

Administration can be systemic or local. Local administration can be into the site of nerve or brain or cord injury, into a site of pain or neural degeneration, or intraocularly to contact neuroretinal cells. Administration can be directly into the neural tissue (e.g., the injured neural tissue). Routes of administration including delivery by either the parenteral or oral route, intramuscular injection, extradural, intramedullary, injection directly into neural tissue, subcutaneous/intradermal injection, intravenous injection, buccal administration, transdermal delivery and administration by the rectal, colonic, vaginal, intranasal or respiratory tract route. The agent can also be administered, topically, by inhalation (e.g., intrabronchial, intranasal, oral inhalation or intranasal drops). Other examples of local administration include delivery to the eye, such as by eyedrops, creams or erodible formulations to be placed under the eyelid, intraocular injection into the aqueous or the vitreous humor, injection into the external layers of the eye, such as via subconjunctival injection or subtenon injection.

A form of administration suitable for treatment of spinal cord injury is localized delivery (e.g., injection) into the spinal column or spinal canal. In certain aspects of the invention, the agent is introduced into the cerebrospinal fluid, a cerebral ventricle, the lumbar area, or the cisterna magna of a subject. The term "lumbar region" is intended to include the area between the third and fourth lumbar (lower back) vertebrae. The term "cisterna magna" is intended to include the area where the skull ends and the spinal cord begins at the back of the head. The term "cerebral ventricle" is intended to include the cavities in the brain that are continuous with the central canal of the spinal cord. Administration may be at the vertebrae closest to the injury site.

In another embodiment of the invention, the agent is administered to a subject intrathecally (e.g., to treat stroke). As used herein, the term "intrathecal administration" is intended to include delivering an active compound formulation directly into the cerebrospinal fluid of a subject, by techniques including lateral cerebroventricular injection through a burrhole or cisternal or lumbar puncture or the like (described in Lazorthes et al., 1991, and Ommaya A. K., 1984, the contents of which are incorporated herein by reference). In one embodiment, the administration is by way of deposition of a slow-release implant at the target site. In one embodiment, administration is by injection into the brain parenchyma.

Injections described herein can be, for example, rapid volume injection or slow infusion.

An additional means of administration is to intracranial tissue by application of the agent to the olfactory epithelium, with subsequent transmission to the olfactory bulb and transport to more proximal portions of the brain. Such administration can be by nebulized or aerosolized preparations.

Administration of the agent to any of the above mentioned sites can be achieved by direct implantation or injection of the agent or by the use of infusion pumps. Implantable or external pumps and catheter may be used.

For injection, the agent of the invention can be formulated in liquid solutions, preferably in physiologically compatible buffers such as Hank's solution or Ringer's solution. In addition, the agent may be formulated in solid form and re-dissolved or suspended immediately prior to use. Lyophilized forms are also included. The injection can be, for example, in the form of a bolus injection or continuous infusion (such as using infusion pumps) of the agent formulation.

Another method of administration is delivery of the agent contained within a matrix. Implantation of the matrix at the desired site results in delivery of the agent to the neurons to thereby promote outgrowth. The matrix can be a gel or a semi-solid or solid matrix. In one embodiment, the agent is dispersed from the matrix to the surrounding area. In one embodiment, the agent is present in the matrix in the absence of any extraneous agents e.g., a DNA encoding therapeutic agent. The matrix can be implanted via surgical implantation, or by topical application or injection into the injury site, such as with a matrix in the form of a gel or paste.

In one embodiment, the agent described herein is administered to the subject in the period from the time of, for example, an injury to the nervous system up to about 100 hours after the injury has occurred, for example within 24, 12, or 6 hours from the time of injury. In another embodiment of the invention, the active compound formulation is administered to a subject (e.g., at the site of injury), usually within 100 hours of when an injury occurs.

Another method of administration is via cells that express the agent described herein. Such cells are implanted at the administration sites described herein by the methods described herein (e.g., contained in a gel for implantation).

Dosage and Levels of Administration

Toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices, are preferred. As used herein, the term ED denotes effective dose and is used in connection with animal models. The term EC denotes effective concentration and is used in connection with in vitro models. The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized.

The therapeutically effective dose can be estimated initially from cell culture assays. A dose may be formulated in animal models to achieve a circulating plasma concentration range that includes the IC50 (i.e., the concentration of the therapeutic which achieves a half-maximal inhibition of symptoms) as determined in cell culture. Levels in plasma may be measured, for example, by high performance liquid chromatography. Levels within neural tissue of an experimental animal can be determined by procedures such as immunolocalization, or Western blot of tissue extracts, or by fluorescently tagging the therapeutic compound prior to administration. Once an appropriate level is effected in an experimental animal, the corresponding dose for a human subject can be extrapolated therefrom. The effects of any particular dosage can be monitored by a suitable bioassay, for example neuronal outgrowth or increased nerve function. Restoration of nerve function can be evidenced by restoration of nerve impulse conduction, a detectable increase in conduction action potentials, observation of anatomical continuity, restoration of more than one spinal root level, an increase in behavior or sensitivity, or a combination thereof.

In some embodiments the amount of neuronal outgrowth or increased nerve function produced by the in vitro contacting or in vivo administration of the agent, described herein, is increased by at least 5%, at least 10%, at least 20%, at least 30%, at least 40%, at least 50%, at least 60%, at least 70%, at least 80%, at least 90%, at least, 1-fold, 2-fold, 3-fold, 4-fold, 5-fold, 10-fold, 50-fold, or 100-fold or more, relative to reference level. A reference level an be obtained, for example, by using an appropriate control to generate a reference level, and can be, for example, a similar or identical subject who has experienced similar or identical conditions, but in the absence of the added agent.

The agent can be administered to a subject for an extended period of time to produce optimum axonal outgrowth. Sustained contact with the active compound can be achieved, for example, by repeated administration of the agent over a period of time, such as one week, several weeks, one month or longer. The pharmaceutically acceptable formulation used to administer the active compound(s) can also be formulated to provide sustained delivery of the active compound to a subject. For example, the formulation may deliver the active compound for at least one, two, three, or four weeks, inclusive, following initial administration to the subject. For example, a subject to be treated in accordance with the present invention is treated with the active compound for at least 30 days (either by repeated administration or by use of a sustained delivery system, or both).

Detecting Neurogenerative Effect

Neuronal outgrowth induced by the methods described herein can be determined by a variety of methods, such as by determination of the formation of axons (e.g., detecting the formation of neuronal branching microscopically, or by showing cytoplasmic transport of dyes). Neuronal outgrowth can also be detected by determination of the formation of neural connectivity. Outgrowth can also be determined by an increase or a restoration of function of the neuron. Neuronal function can be measured by standard assays such as detection of action potential or nerve impulse condition by standard assays.

The promotion of neural generation in a subject by the methods described herein may be assessed using any of a variety of known procedures and assays. For example, the determination of the establishment, or re-establishment of neural connectivity, and/or function after an injury. Such neural connectivity and/or function, may be determined visually (e.g., histologically by slicing neuronal tissue and looking at neuronal branching, or by showing cytoplasmic transport of dyes). Functional assays can also be used to determine neural generation, such as by detecting full or partial restoration of a neural function. Examples of such assays are, without limitation, use of an electroretinogram to detect restoration of function after damage to the neural retina or optic nerve; or measurement of the pupillary response to light in the damaged eye to detect restoration of the response.

Other tests that may be used include standard tests of neurological function in human subjects or in animal models of spinal injury (such as standard reflex testing, urologic tests, urodynamic testing, tests for deep and superficial pain appreciation, proprioceptive placing of the hind limbs, ambulation, and evoked potential testing). In addition, nerve impulse conduction can be measured in a subject, such as by measuring conduct action potentials, as an indication of restoration of neuronal function.

Animal models suitable for use in the assays of the present invention include the rat model of partial transaction (see Weidner et al., 2001), that tests how well a compound can enhance the survival and sprouting of the intact remaining fragment of an almost fully-transected cord. Another injury model is the rodent model for contusion which closely mimics the injury seen in the majority of human spinal cord injury patients. Accordingly, after administration of a candidate agent these animals may be evaluated for recovery of a certain function, such as how well the rats may manipulate food pellets with their forearms (to which the relevant cord had been cut 97%).

Another animal model suitable for use in the assays of the present invention includes the rat model of stroke (see Kawamata et al., 1997, for various tests that may be used to assess sensori motor function in the limbs as well as vestibulomotor function after an injury). Administration to these animals of the agents of the invention can be used to assess whether a given compound, route of administration, or dosage provides a neuroregenerative effect, such as increasing the level of function, or increasing the rate of regaining function or the degree of retention of function in the test animals.

Standard neurological evaluations used to assess progress in human patients after a stroke may also be used to evaluate the ability of an agent to produce a neurosalutary effect in a subject. Such standard neurological evaluations are routine in the medical arts, and are described in, for example, "Guide to Clinical Neurobiology" Edited by Mohr and Gautier (Churchill Livingstone Inc. 1995).

Another aspect of the present invention relates to a method for identifying an agent that induces neuronal outgrowth. The method comprises identifying a molecule that induces clustering of RPTPσ (e.g., through direct binding) by screening candidate agents. A candidate agent identified as inducing clustering of RPTPσ is expected to be an agent that will induce neuronal outgrowth, and thus be useful in the methods described herein. Such an identified candidate agent can further be verified as an agent useful in the methods described herein by determining its ability to induce neuronal outgrowth (e.g., by subjecting it to a neuronal outgrowth assay) as described herein.

Also encompassed by the present invention is an article of manufacture (e.g., a kit) comprising packaging material and compositions comprising the agents described herein (e.g. pharmaceutical compositions) contained within the packaging material. The packaging material comprises a label which indicates that the pharmaceutical may be administered, for a sufficient term at an effective dose, for inducing neuronal outgrowth in a subject, and/or treating neuronal injury or neurodegenerative diseases described herein. The present invention also encompasses pharmaceutical compositions described herein.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to described the present invention, in connection with percentages means ±1%, or ±5%.

In one respect, the present invention relates to the herein described compositions, methods, and respective component(s) thereof, as essential to the invention, yet open to the inclusion of unspecified elements, essential or not ("comprising). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The present invention may be as defined in any one of the following numbered paragraphs.

1. A method of inducing neuronal outgrowth of a neuron comprising, contacting the neuron with an agent that binds receptor protein tyrosine phosphatase σ (RPTPσ), to thereby induce neuronal outgrowth of the neuron.
2. The method of paragraph 1, wherein the agent induces clustering of RPTPσ.
3. The method of paragraph 1, wherein the agent inhibits binding of chondroitin sulfate proteoglycan (CSPG) to RPTPσ.
4. The method of any one of paragraphs 1-3, wherein the agent is selected from the group consisting of heparan sulfate proteoglycan, heparan sulfate, heparin oligosaccharide, and heparan sulfate oligosaccharide.
5. The method of paragraph 4, wherein the heparin oligosaccharide or the heparan sulfate oligosaccharide contains 8 or more saccharide units and less than 67 saccharide units.
6. The method of any one of paragraphs 1-5, wherein the heparin oligosaccharide or the heparan sulfate oligosaccharide contains 10 or more saccharide units and less than 67 saccharide units.
7. The method of paragraph 4, wherein the heparan sulfate proteoglycan is glypican 2 or a derivative thereof.
8. The method of any one of paragraphs 1-7, said agent binds to the first immunoglobulin-like domain of RPTPσ.
9. The method of any one of paragraphs 1-7 wherein the agent is in solution.
10. The method of any one of paragraphs 1-8, wherein the agent is contained in a matrix.
11. The method of any one of paragraphs 1-10, wherein the contacting occurs in vitro.
12. The method of any one of paragraphs 1-10, wherein the contacting occurs in vivo.
13. The method of paragraph 12, wherein said neuron is located at a site of injured or diseased tissue.
14. The method of any one of paragraphs 1-13, further comprising contacting said neuron with a second agent that promotes neuronal outgrowth.
15. The method of paragraph 14, wherein the second agent reduces inhibition of neuronal outgrowth.
16. The method of any one of paragraphs 1-15, wherein the neuron is a central nervous system neuron.
17. The method of any one of paragraphs 1-15, wherein the neuron is a peripheral nervous system neuron.
18. A method of treating neuronal injury in a subject comprising, administering to the subject an agent that binds RPTPσ to thereby induce neuronal outgrowth.
19. The method of paragraph 18, further comprising selecting a subject in need of treatment for neuronal injury prior to the administering.
20. The method of any one of paragraphs 18 or 19, wherein the agent is administered at a site of neuronal injury, to thereby induce neuronal outgrowth at the site of neuronal injury.
21. The method of any one of paragraphs 18-20 wherein the agent induces clustering of the RPTPσ.
22. The method of any one of paragraphs 18-20, wherein the agent inhibits binding of chondroitin sulfate proteoglycan (CSPG) to the RPTPσ.
23. The method of any one of paragraphs 18-22, wherein the neuronal injury is selected from the group consisting of stroke, spinal cord injury, traumatic brain injury, peripheral nerve injury, skin burn, and eye injury.
24. The method of any one of paragraphs 16-22 wherein the neuronal injury is acute.
25. The method of any one of paragraphs 16-22 wherein the neuronal injury is chronic.
26. The method of any one of paragraphs 16-22, wherein the agent is selected from the group consisting of heparan sulfate proteoglycan, heparan sulfate, heparin oligosaccharide, and heparan sulfate oligosaccharide.
27. The method of paragraph 26, wherein the heparin oligosaccharide or the heparan sulfate oligosaccharide contains 8 or more saccharide units and less than 67 saccharide units.
28. The method of any one of paragraphs 26 or 27, wherein the heparin oligosaccharide or the heparan sulfate oligosaccharide contains 10 or more saccharide units and less than 67 saccharide units.
29. The method of paragraph 26, wherein the heparan sulfate proteoglycan is glypican 2 or a derivative thereof.

30. The method of any one of paragraphs 19-20, further comprising contacting said neuron with a second agent that promotes neuronal outgrowth.
31. The method of any one of paragraphs 18-30 wherein the agent is soluble.
32. The method of any one of paragraphs 18-30 wherein the agent is contained in a matrix.
33. The method of any one of paragraphs 18-32 wherein the agent directly binds to the RPTPσ.
34. The method of any one of paragraphs 18-33, wherein the agent binds to the first immunoglobulin-like domain of RPTPσ.
35. The method of any one of paragraphs 18-34, wherein administering is systemic or localized.
36. The method of paragraph 35, wherein administration is by method selected from the group consisting of oral, intramuscular injection, subcutaneous or intradermal injection, intrathecal, extradural, intramedullary, injection directly into neural tissue, intravenous injection, buccal administration, transdermal, rectal, colonic, vaginal, intranasal, and inhalation.
37. The method of paragraph 35, wherein localized administration is by implantation of a matrix that contains the agent.
38. The method of paragraph 36, wherein implantation is by injection and the matrix is a gel that solidifies in the body of the subject.
39. A method of promoting neural outgrowth in the nervous system of a subject, comprising administering to the subject an agent that binds RPTPσ, to contact a neuron and thereby induce neural outgrowth of the neuron.
40. The method of paragraph 39, further comprising selecting a subject in need of promotion of neural outgrowth prior to the administering.
41. The method of any one of paragraphs 39-40, wherein the agent induces clustering of the RPTPσ.
42. The method of paragraph 39, wherein the agent inhibits binding of chondroitin sulfate proteoglycan (CSPG) to the RPTPσ.
43. The method of paragraph 39, wherein the agent is heparan sulfate proteoglycan, heparan sulfate, heparin oligosaccharide or heparan sulfate oligosaccharide.
44. The method of paragraph 43, wherein the heparin oligosaccharide or the heparan sulfate oligosaccharide contains 8 or more saccharide units and less than 67 saccharide units.
45. The method of paragraph 43, wherein the heparin oligosaccharide or the heparan sulfate oligosaccharide contains 10 or more saccharide units and less than 67 saccharide units.
46. The method of paragraph 43, wherein the heparan sulfate proteoglycan is glypican 2 or a derivative thereof.
47. The method of any one of paragraphs 39-46 wherein the agent is in solution.
48. The method of any one of paragraphs 39-46 wherein the agent is contained in a matrix.
49. The method of any one of paragraphs 39-48 wherein the neuron is located at or adjacent to a site of diseased or injured tissue.
50. The method of paragraph 49, wherein the injured tissue results from an injury selected from the group consisting of stroke, spinal cord injury, traumatic brain injury, peripheral nerve injury, skin burn, and eye injury affecting optic nerve fibers.
51. The method of paragraph 49, wherein the injured tissue results from an acute injury.
52. The method of paragraph 49, wherein the diseased tissue is a site of neuronal degeneration.
53. The method of paragraph 49, wherein the diseased tissue results from a neurodegenerative disease.
54. The method of any one of paragraphs 39-53, wherein administering is systemic or localized.
55. The method of paragraph 54, wherein administration is by method selected from the group consisting oral, intramuscular injection, subcutaneous or intradermal injection, intrathecal, extradural, intramedullary, injection directly into neural tissue, intravenous injection, buccal administration, transdermal, rectal, colonic, vaginal, intranasal, and inhalation.
56. The method of paragraph 54, wherein localized administration is by implantation of a matrix that contains the agent.
57. The method of paragraph 56, wherein implantation is by injection and the matrix is a gel that solidifies in the body of the subject.

The present invention is further illustrated by the following Examples. These Examples are provided to aid in the understanding of the invention and are not construed as a limitation thereof.

EXAMPLES

Example 1

Figure 1H:
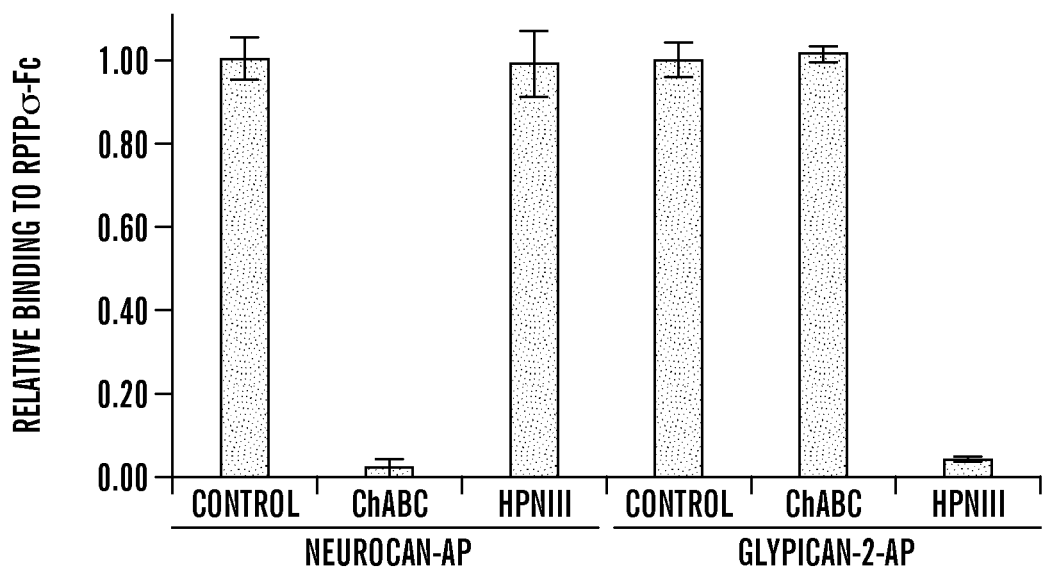
Figure 5:
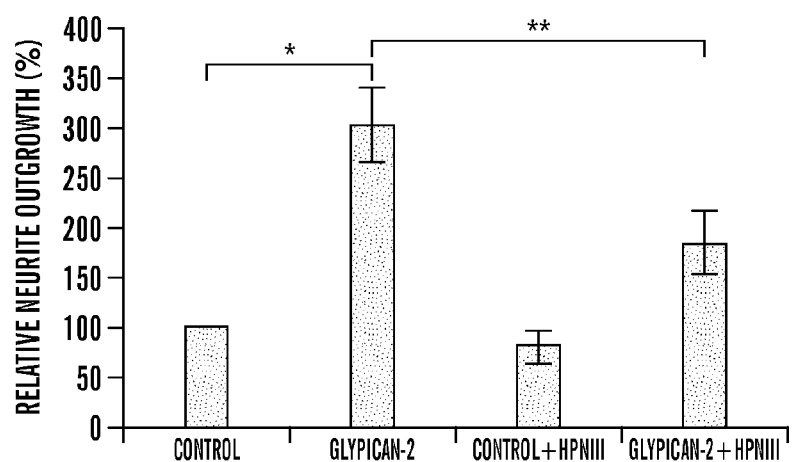
FIG. 5 is a bar graph of data from experiments that indicate Glypican-2 induced neurite outgrowth is largely dependent upon the presence of its heparan sulfate moieties. Wild-type P8 mouse dorsal root ganglion (DRG) neurons were grown on substrates containing a poly-D-lysine/laminin mixture (control) or supplemented with glypican-2, either with or without heparitinase III (HPNIII) treatment. The outgrowth of DRG neurons, relative to the control (assigned 100% outgrowth) was quantified. Treatment with HPNIII did not completely eliminate the growth promoting effect of the glypican-2 substrate, which may reflect either novel interactions involving the deglycosylated glypican core or incomplete enzymatic digestion of the heparan sulfate chains. Error bars show SEMs. **$p<0.005$ and *$p<0.05$, Student's t-test. The necessity of the chondroitin sulfate groups of neurocan for CSPG-mediated inhibition of DRG outgrowth, has been reported previously (S2).

Proteoglycan-Specific Molecular Switch for RPTPσ Clustering and Neuronal Extension Previous results led to alternative predictions for the potential effects, if any, of HSPGs acting via RPTPσ in DRG neurons: these might inhibit outgrowth, like CSPGs, or promote outgrowth, as suggested by the response of retinal ganglion cells to basal lamina. Neurocan, a CSPG, reduced outgrowth of wild-type DRG neurons by approximately 60%, as described previously (12), and this inhibitory effect was decreased in RPTPσ$^{-/-}$ neurons (P<0.001; FIGS. 1, A-D and G). In contrast, glypican-2, an HSPG, strongly promoted outgrowth of wild-type neurons. This promoting effect was reduced to undetectable levels in RPTPσ$^{-/-}$ neurons, showing a requirement for RPTPσ$^{-/-}$ (P<0.01; FIG. 1, E to G). Heparitinase III treatment of the glypican-2 significantly reduced its growth-promoting ability (P<0.005; FIG. 5), indicating that its glycosaminoglycan (GAG) chains are involved. Chondroitinase ABC and heparitinase III reduced RPTPσ$^{-/-}$ binding by neurocan and glypican-2 respectively, confirming the specific presence of HS and CS on these proteoglycans and the role of GAG chains in mediating interactions with RPTPσ$^{-/-}$ (FIG. 1H).

Figure 2A:
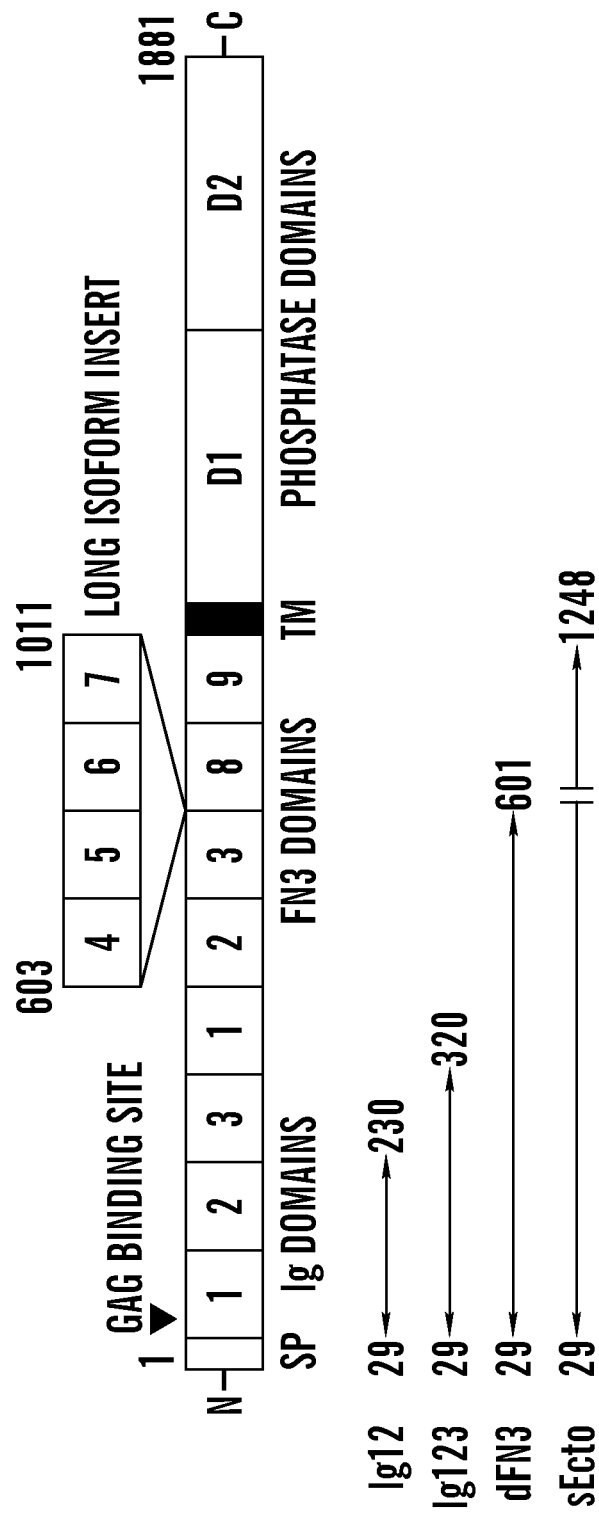
Figure 2B:
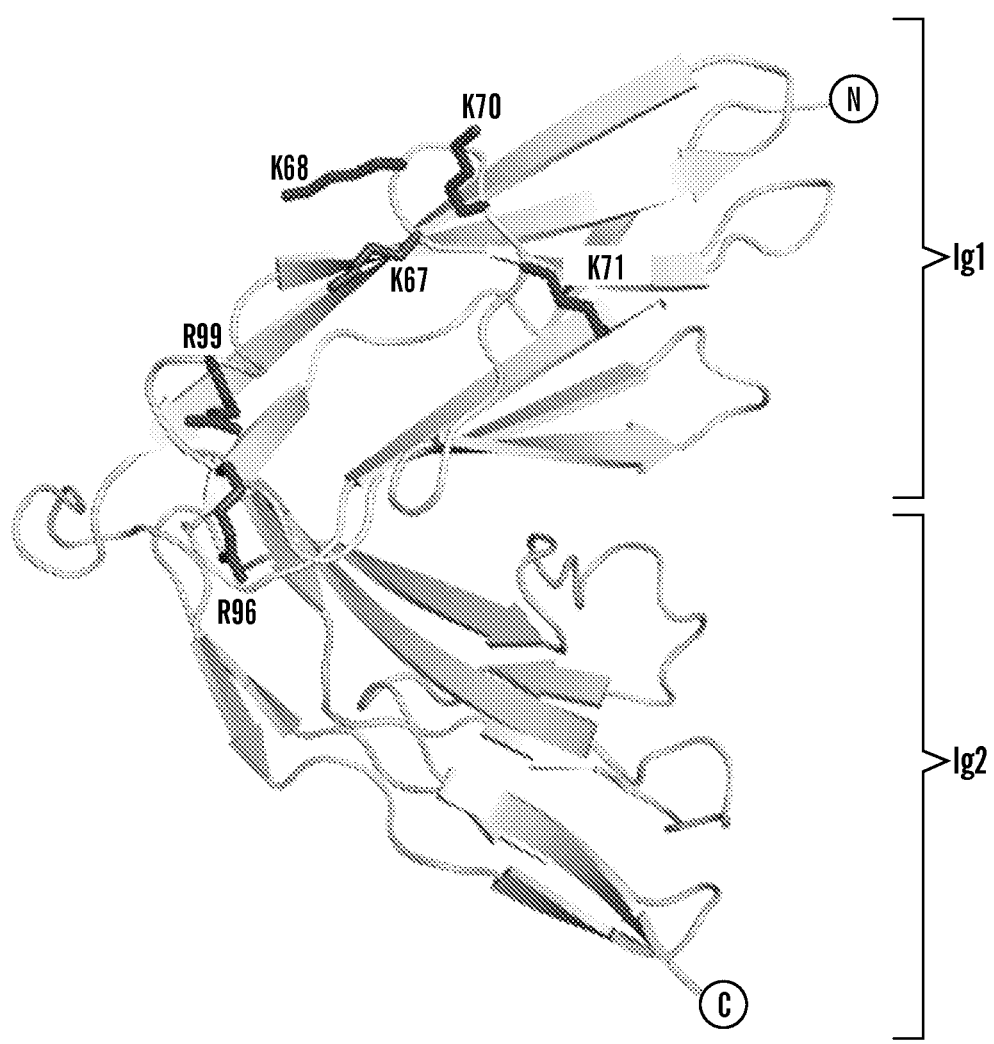
Figure 6:
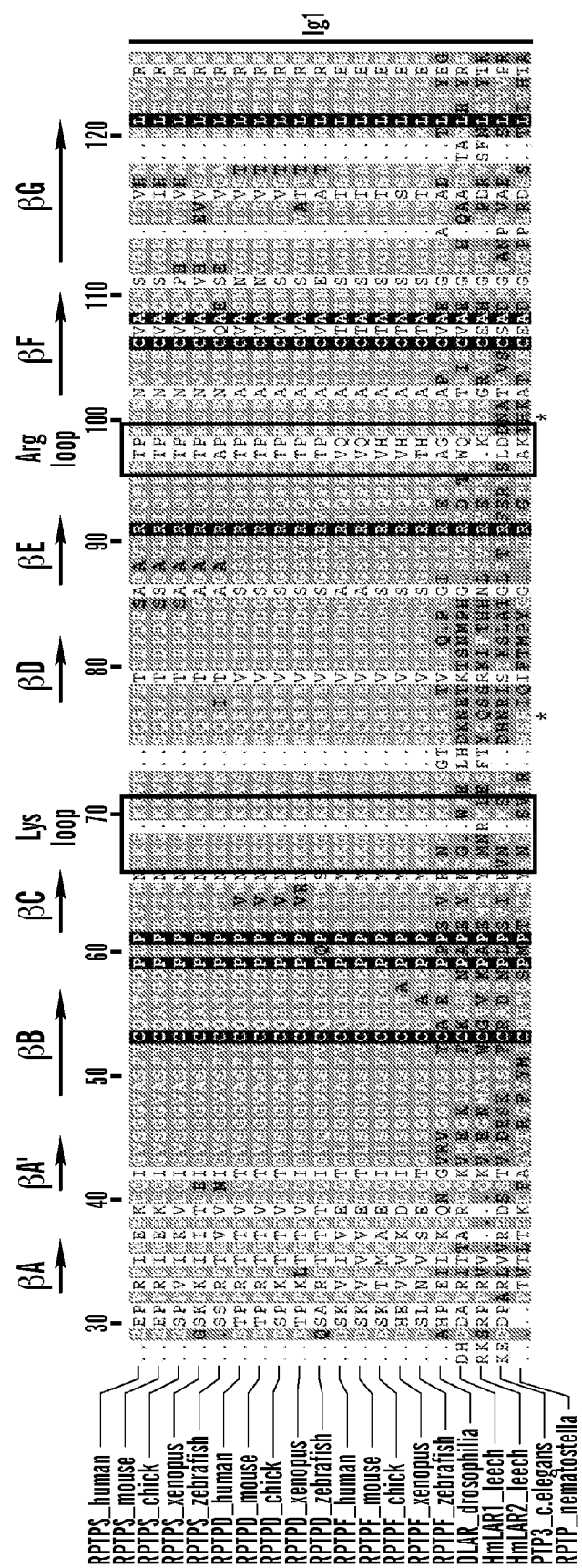
FIG. 6 is a sequence alignment of the two N-terminal Ig domains of the type IIa RPTP family members across species. Sequences correspond to the RPTP isoforms lacking the MeA and MeB exons, based on amino acid sequences taken from the following sources: RPTPσ human (NM_130854.2) (SEQ ID NO: 9), mouse (BCO52462.1) (SEQ ID NO: 10), chicken (NM_205407.1) (SEQ ID NO: 11), xenopus (NM_001141992.1) (SEQ ID NO: 12) and zebrafish (XP_002666198.1) (SEQ ID NO: 13); RPTPδ human (BC106713.1) (SEQ ID NO: 14), mouse (EDL31049.1) (SEQ ID NO: 15), chick (NP_990738.1) (SEQ ID NO: 16), xenopus (NM_001090381.1) (SEQ ID NO: 17) and zebrafish (NP_001159520.1) (SEQ ID NO: 18); RPTP LAR human (NM_002840.3) (SEQ ID NO: 19), mouse (NM_011213.2) (SEQ ID NO: 20), chicken (XP_001233494.1) (SEQ ID NO: 21), xenopus (NP_001081987) (SEQ ID NO: 22) and zebrafish (NP_001077045.1) (SEQ ID NO: 23); Drosophila LAR (NM_078880.3) (SEQ ID NO: 24), leech HmLAR1 (AF017084.1) (SEQ ID NO: 25) and HmLAR2 (AF017083.1) (SEQ ID NO: 26), C. elegans PTP-3A (AF316539.1) (SEQ ID NO: 27) and Nematostella RPTP (XP_001639024.1) (SEQ ID NO: 28). Numbers above the sequence alignment correspond to amino acid residue numbers relative to the chicken RPTPσ sequence, where residue 1 is the initial methionine. Black arrows above the sequence alignment indicate the location of the β-strands within the two immunoglobulin domains, based on the structure of chick Ig1-2, assigned using ksdssp (29). Blue boxes highlight the lysine loop between β strands C-D (containing K67, K68, K70 and K71) and the arginine loop between β strands E-F (containing R96 and R99). Black asterisks above the alignments highlight R76 and D100, the two residues forming the salt bridge which is disrupted upon binding of human LAR Ig1-2 to sucrose octasulfate.
Figure 6:
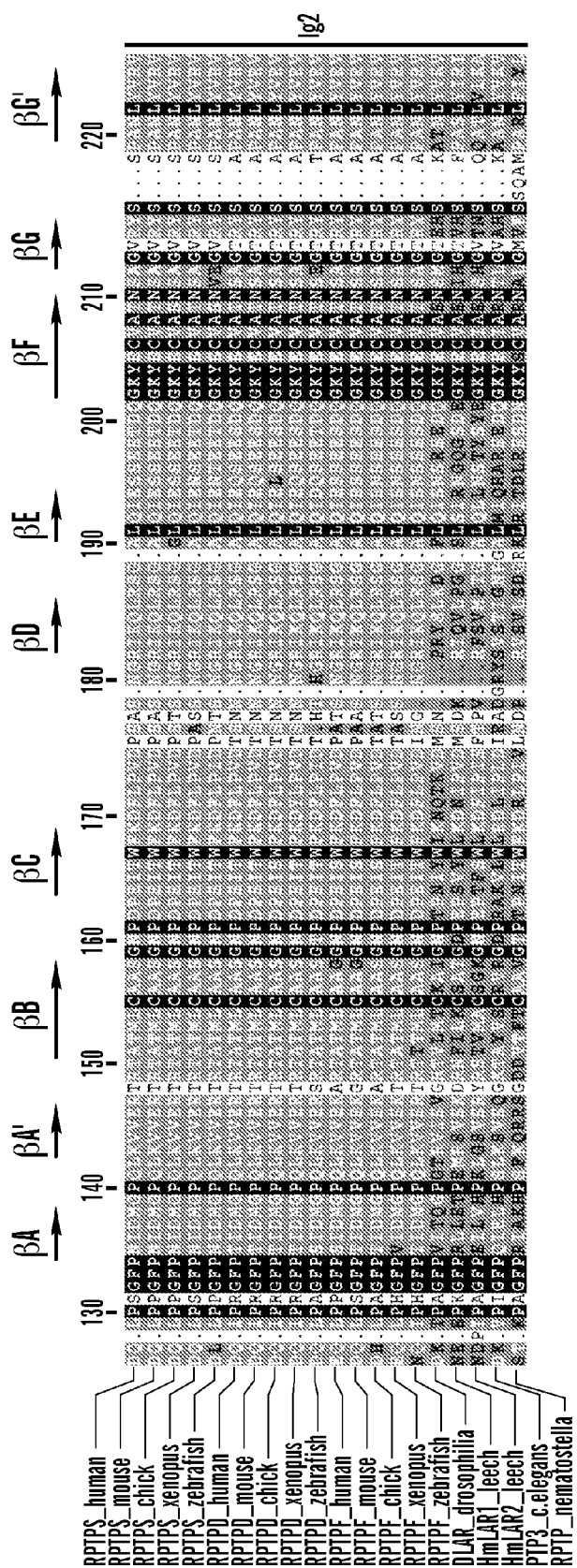
Figure 7B:
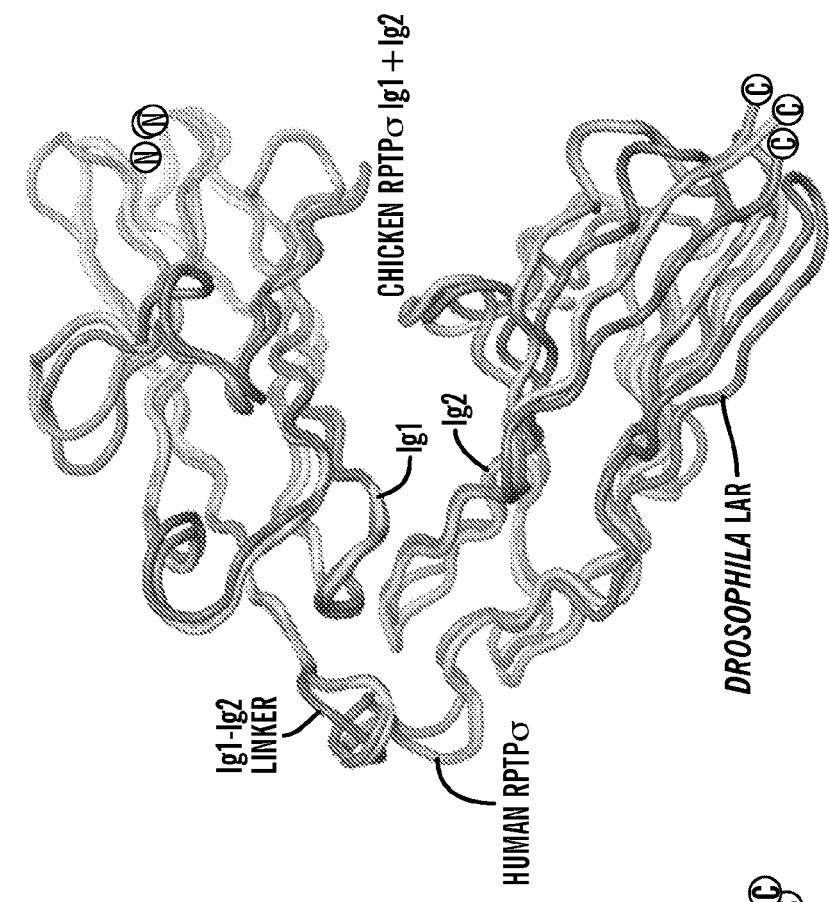
Figure 7A:
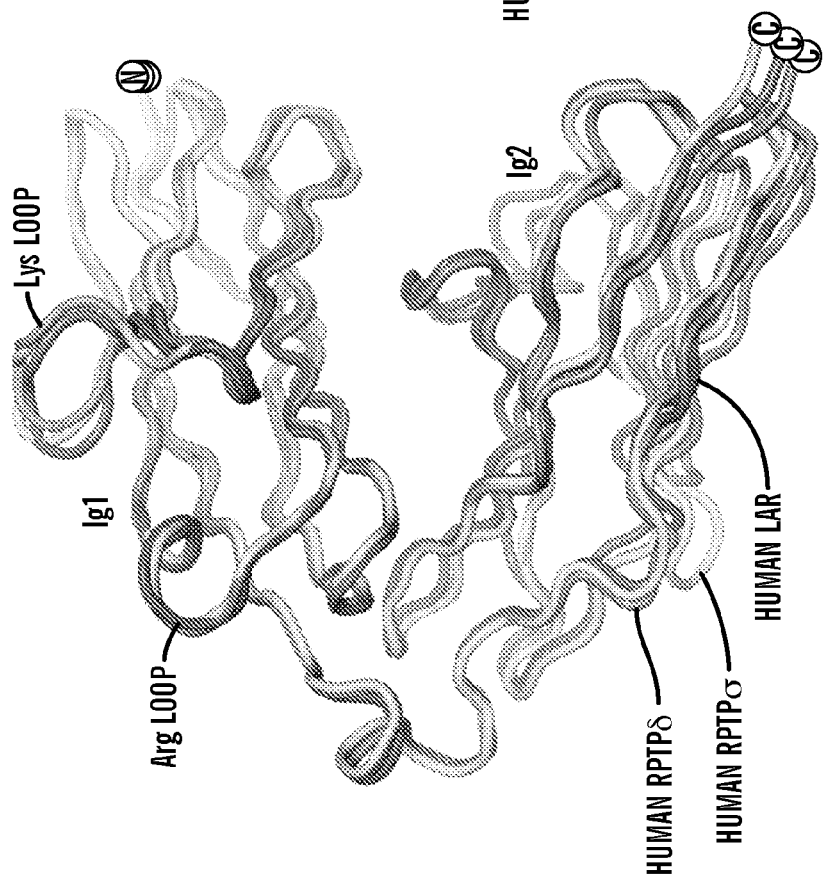
Figure 9:
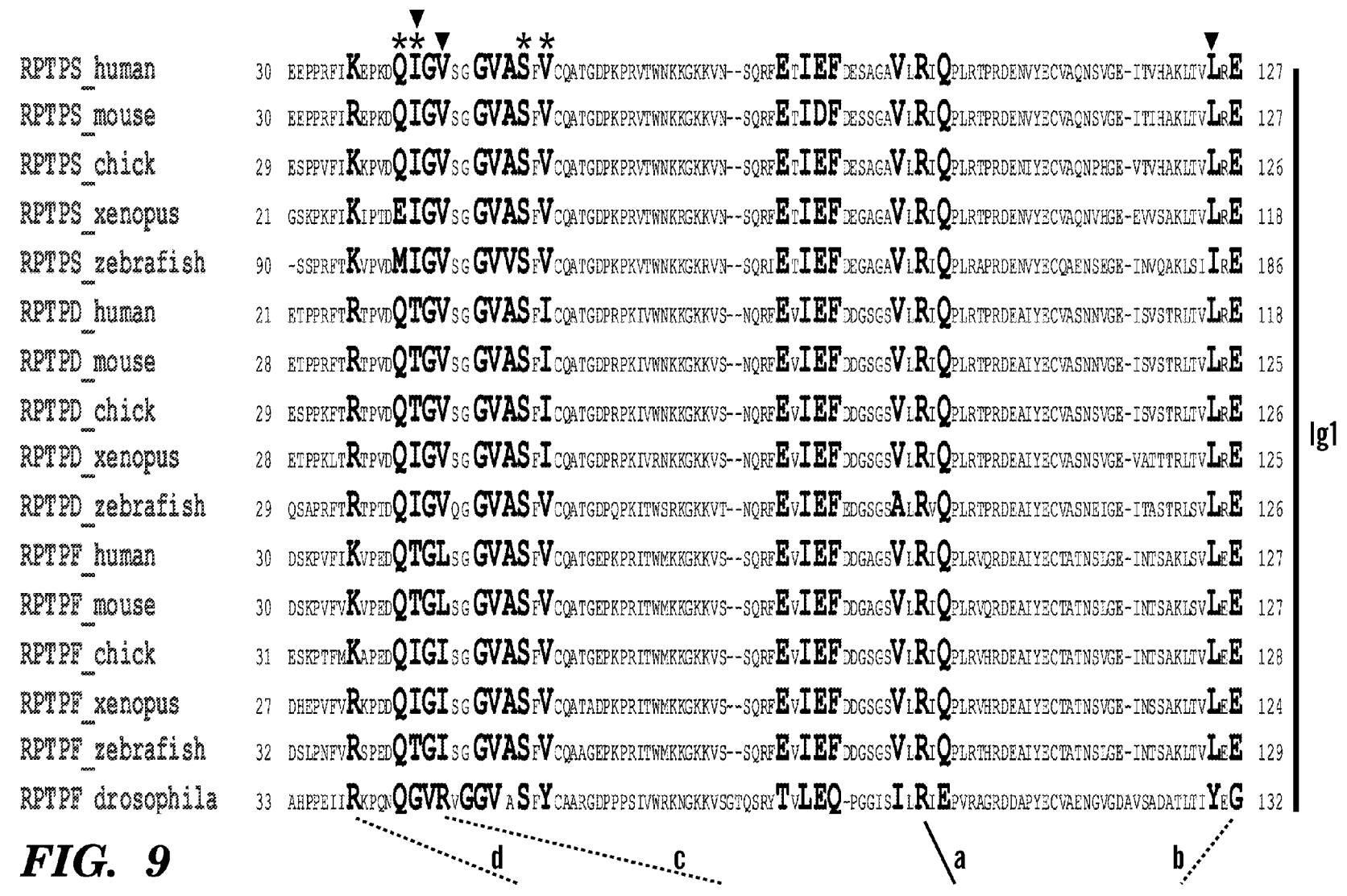
Figure 10A:
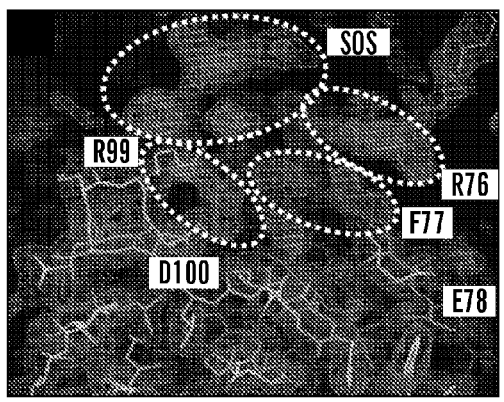
FIG. 10A-FIG. 10D is a collection of schematics that show model building for the 2.05 Å human LAR Ig1-2-sucrose octasulfate (SOS) crystal structure. (A) and (B): SigmaA-weighted electron density maps from refinement of the initial human LAR Ig1-2 model after molecular replacement in Phaser (S16). $2F_o$-$F_c$ C maps (blue) and $F_o$-$F_c$ C maps (green and red) are contoured at 1σ and ±3 σ respectively. Unmodelled features in the electron density maps are highlighted by white dashed lines. (C) and (D): SigmaA-weighted electron density maps after refinement in Phenix (S18) prior to addition of the SOS ligand to the model. $2F_o$-$F_c$ maps (purple) and $F_c$-$F_o$ maps (green and red) are contoured at σ and ±3 σ respectively. Asterisks mark the density into which three sulfate groups of the SOS ligand were initially placed, and onto which a full SOS molecule was superposed. The five-membered ring appeared to fit well into the electron density, but this left the six-membered ring of the ligand pointing into the solvent and consequently without electron density. Therefore the SOS ring was split at the disaccharide linker and just the five-membered ring was included in the model for refinement in Phenix (S18). The $R_{work}$ and $R_{free}$ decreased from 20.0% and 23.4% to 19.5% and 22.5% respectively upon addition of the five-membered ring from SOS to the model, supporting the inclusion of the ligand in the final crystal structure. Extensive co-crystallization attempts with fragments of chondroitin sulfate or heparin (widely-used to mimic highly sulfated regions of heparan sulfate) and various type IIa RPTP constructs did not produce interpretable electron density maps for the glycans, presumably due to their structural heterogeneity.
Figure 10B:
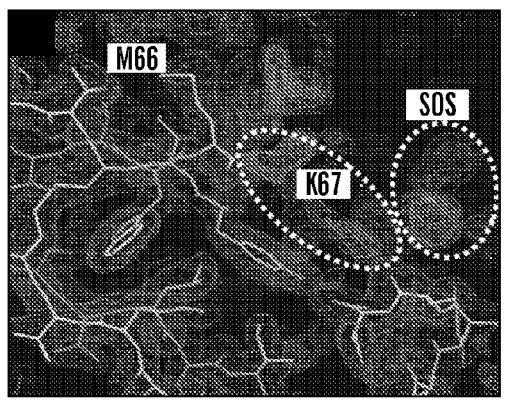
Figure 10C:
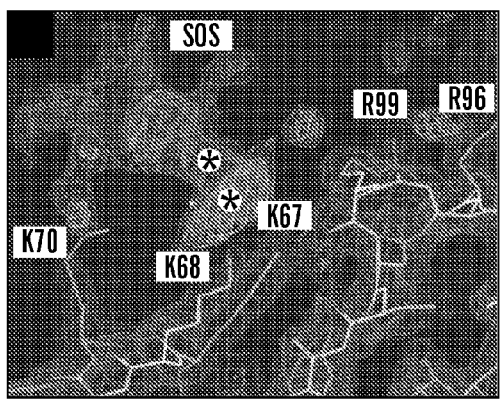
Figure 10D:
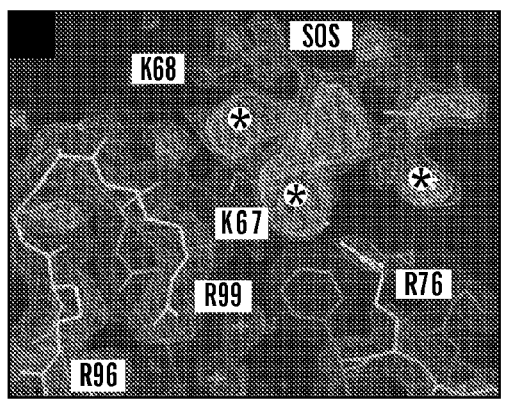
Figure 11:
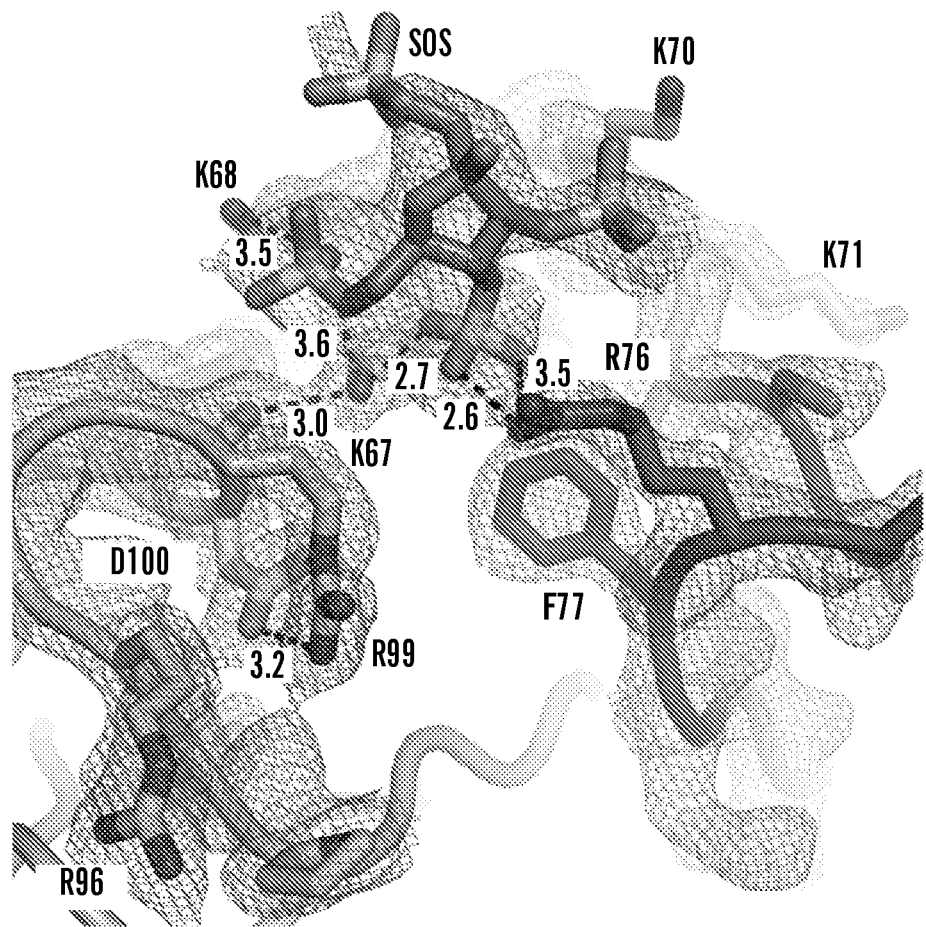
FIG. 11 is an illustration of an electron density map for the 2.05 Å crystal structure of human LAR Ig1-2 in complex with sucrose octasulfate (SOS). The flexible proteoglycan binding loop is coloured in purple while the remainder of the LAR protein is coloured in pink. The carbon backbone of the SOS ligand is shown in grey. Non-carbon atoms are highlighted as follows: nitrogen, blue; oxygen, red; sulphur, yellow. The sidechains of K67, K68 and R76 are well ordered in the SOS-bound LAR crystal structure and are suitably positioned to form electrostatic interactions with the negatively charged sulfate groups of the SOS ligand (distances less than 3.6 Å between oppositely charged groups are indicated by black dashed lines). R96 and R99 which lie on the Arg-loop are also well ordered, but play no role in SOS-binding in this crystal structure. R99 instead assumes the role of R76 in the apo-LAR crystal structure, by forming a salt bridge with D100 after the R76-D100 salt bridge is broken and R76 becomes involved in ligand binding. K70 is disordered and clear density is not visible for the sidechain. Blue mesh represents the SigmaAweighted $2F_o$-$F_c$ electron density map contoured at 1σ, after the final round of structure refinement in Phenix (S18).
Figure 12A:
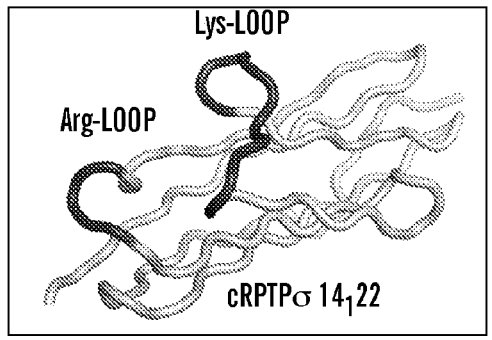
FIG. 12A-12F is a collection of illustrations that show conformational flexibility of the proteoglycan binding loop across type IIa RPTP structures. (A) Ribbon representation of the chicken RPTPσ Ig1 backbone. The "Lys"-loop and "Arg"-loop which harbour the crucial heparin binding residues, are highlighted in blue. The rmsd between the Ig1 $C_a$ positions of chicken RPTPσ ($I4_122$ space group) and either (B) human RPTPδ ($P3_221$ space group), (C) human LAR ($P3_221$ space group), (D) human RPTPσ ($I4_122$ space group), (E) human RPTPσ (C2 space group) or (F) DLAR (C2 space group) was measured using SHP (S22) and is plotted upon the chicken RPTPσ Ig1 structure; increasing rmsd values are shown using a rainbow scale (blue, low rmsd; red, high rmsd) and the increasing thickness of the protein backbone. The Lys-loop displays the greatest movement across crystal structures, indicating that this region has an inherent flexibility, which may facilitate binding of the type IIa RPTP receptors to different GAG ligands.
Figure 12D:
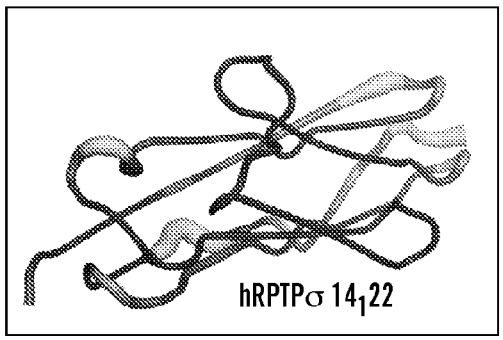
Figure 12B:
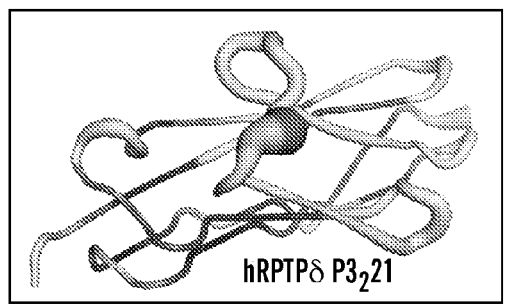
Figure 12E:
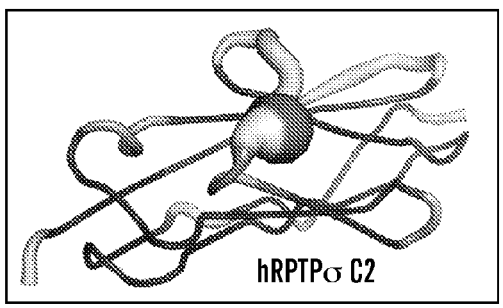
Figure 12C:
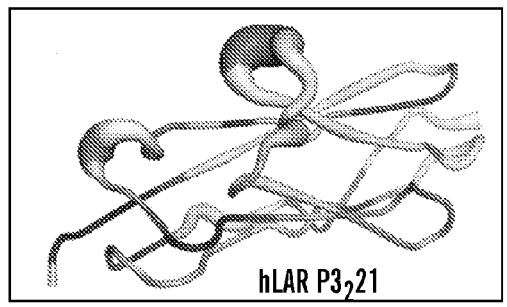
Figure 12F:
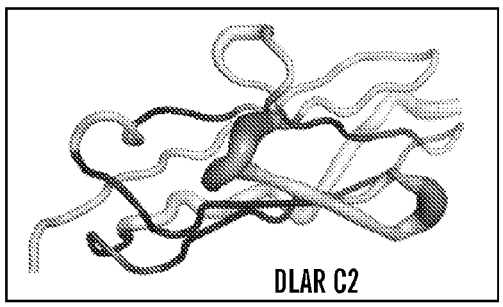
Figure 13A:
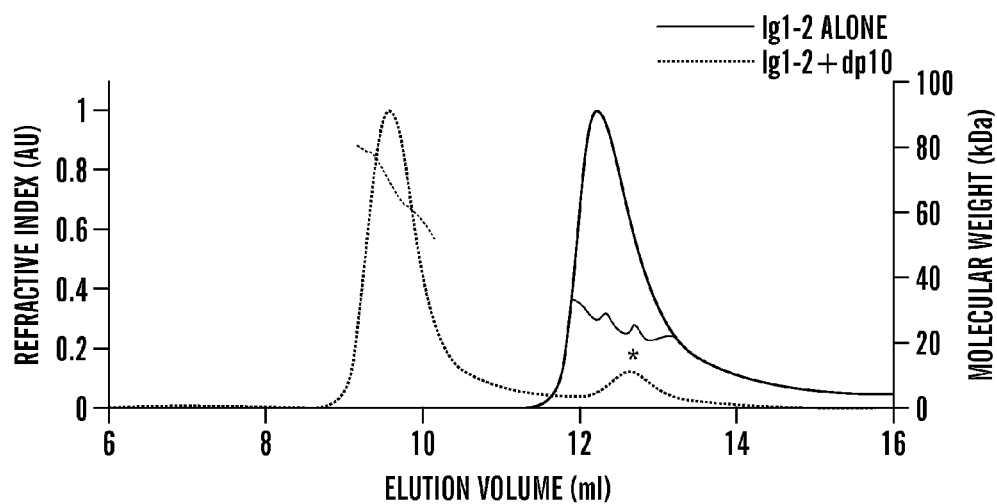
FIG. 13A-FIG. 13D are graphical representations of data from experiments that indicate Heparin-induced dimerisation of human RPTPσ ectodomain constructs. A series of human RPTPσ constructs were incubated with (blue) and without (red) a two-fold molar excess of heparin dp10 before SEC-MALS (size-exclusion chromatography-multi-angle light scattering) analysis; (A) Ig1-2, (B) Ig1-3, (C) Ig1-FN3, (D) sEcto. Refractive index traces (scaled within each panel) are shown by bold lines and the measured molecular weights are shown by dotted lines. Peaks in the refractive index that are indicated by an asterisk correspond to excess dp10 ligand. A Superdex 75 column (1 cm×30 cm) was used for the Ig1-2 construct (A) while all other constructs (B-D) were analysed using a Superdex 200 (1 cm×30 cm) column.
Figure 13B:
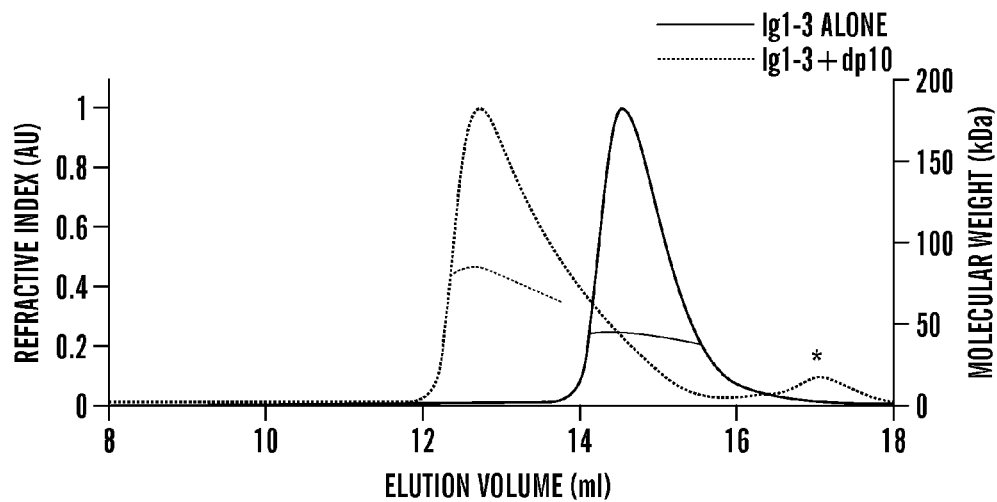
Figure 13C:
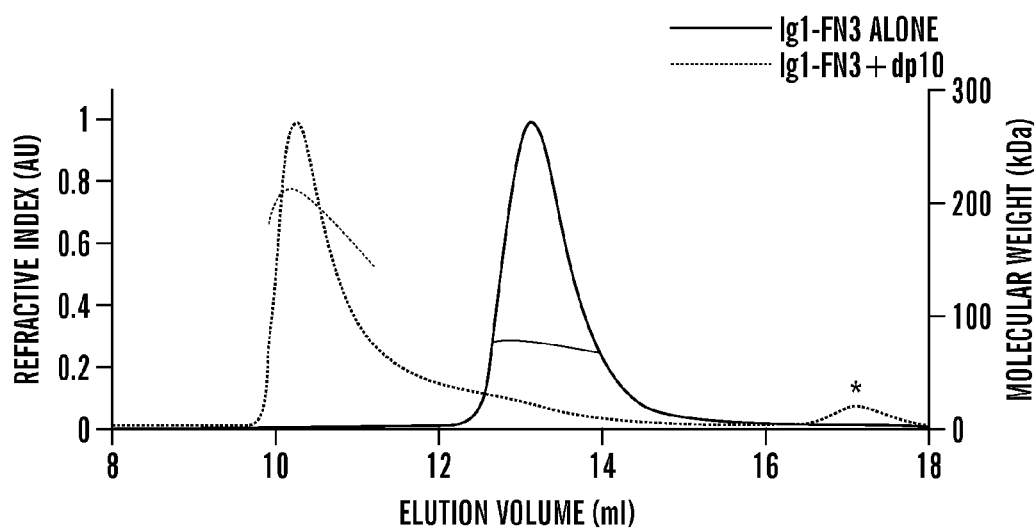
Figure 13D:
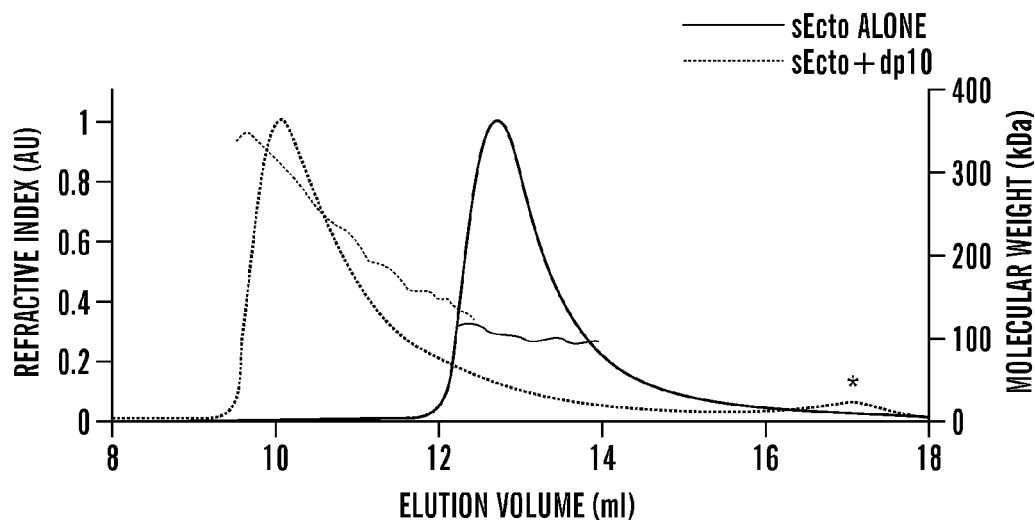
Figure 14A:
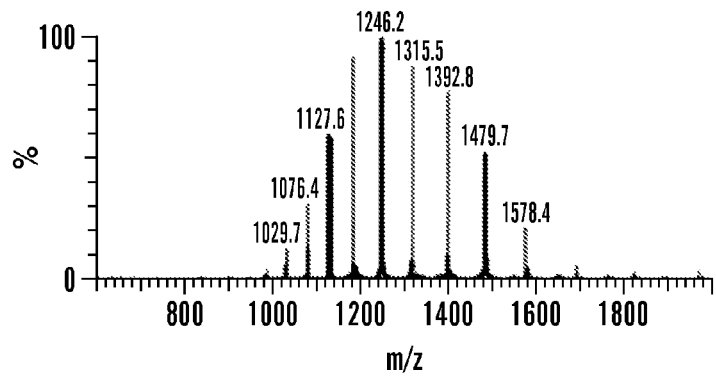
FIG. 14A-FIG. 14E present graphical representation of data from experiments for investigation of type IIa RPTP clustering in solution. After incubation of human RPTPσ alone or with heparin dp10 (Iduron H010), electrospray ionisation-mass spectrometry (ESI-MS) and analytical ultra-centrifugation (AUC) were used to analyse the oligomerisation state of the protein. The mass of human RPTPσ Ig1-2 alone was confirmed using ESI-MS under denaturing conditions; (A) an ion series corresponding to different charge states of the proteins was obtained and (B) this ion series was deconvoluted to give the molecular weight of the protein 23,660 Da (estimated molecular weight based on sequence is 23,676 Da). (C) Human RPTPσ Ig1-2 in complex with heparin dp10 and analysed using ESI-MS under native conditions. Two main ion series are observed; a series at lower m/z values corresponding to the protein alone (red) with a deconvoluted mass of 23, 672 Da and a series at higher m/z values (blue) with a deconvoluted mass of 53,104 Da which would correspond to a protein-dp10 complex. Further ion series at higher m/z values still are also present, which most likely represent higher order oligomers, but these series couldn't be deconvoluted to obtain mass values due to the overlapping arrangement and low abundance of the peaks. A series of sedimentation velocity AUC experiments were performed with the human RPTPσ Ig1-2 protein either alone (D) or in complex with heparin dp10 (E). The coloured circles represent the measured data points, while the black lines represent the fit of the data (the normal black lines correspond to the individual species included in the model and the bold lines to the fit of the overall model to the data). A single homogeneous species, with a Svedberg value indicating a monomeric protein was observed in the sample containing the protein alone. However the protein-heparin complex sample appears to contain three different species, which may match the monomeric, dimeric and higher order oligomeric states also observed in the native ESI-MS experiments.
Figure 14B:
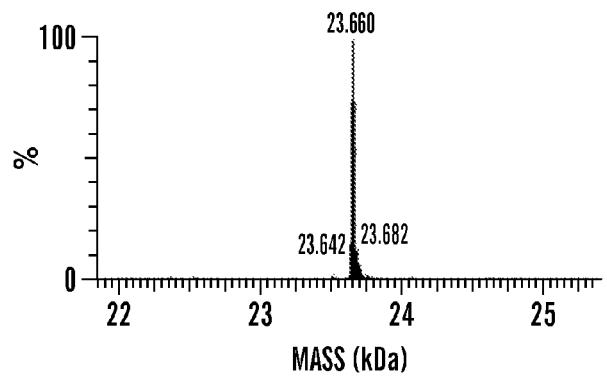
Figure 14C:
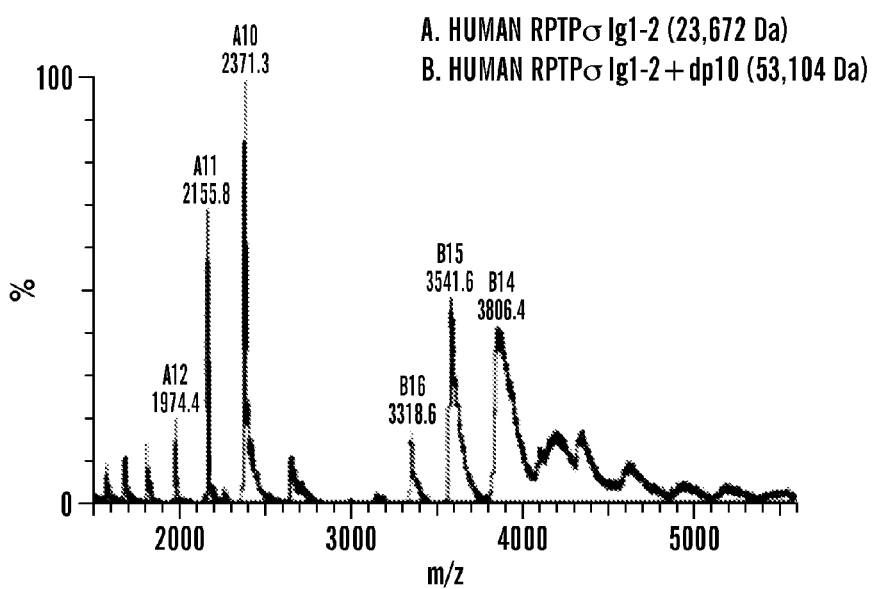
Figure 14D:
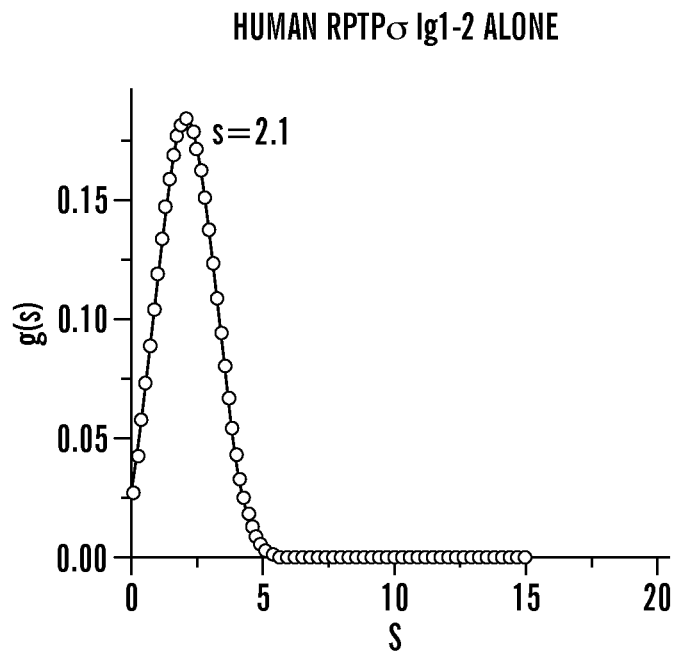
Figure 14E:
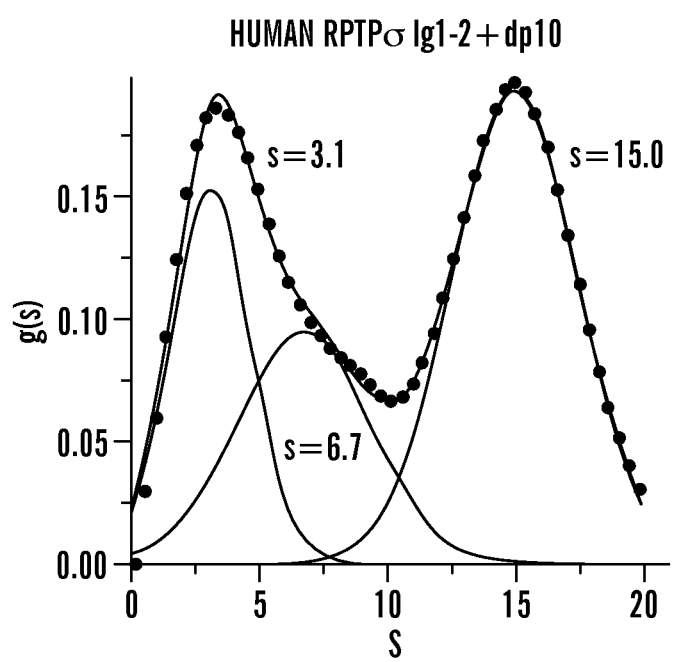

The observed dichotomy in CSPG/HSPG function, apparently mediated through a common receptor, RPTPσ, is intriguing given that mutagenesis studies indicate a common binding site for the two proteoglycan classes (12, 18). To investigate the structural basis of proteoglycan recognition in RPTPσ and type IIa RPTPs in general, crystallographic studies were undertaken. The type IIa RPTP ectodomain is predicted to consist of three I-set immunoglobulin (Ig)-like domains followed by either five or nine fibronectin (FN) type III repeats (FIG. 2A). A series of RPTPσ, RPTPδ and LAR deletion constructs were generated for structural and functional assays (27), all including the N-terminal Ig domain harbouring the putative GAG binding site (FIG. 2A) (12, 18). Crystal structures were determined of the two N-terminal Ig domains (Ig1-2), which formed the minimal stable unit, for examples across family members and species (chicken and human RPTPσ, human RPTPδ and LAR, *Drosophila* DLAR; see (28), Tables 1 and 2 and FIG. 6). A V-shape arrangement of Ig1 and Ig2 is stabilized by conserved interactions, irrespective of the crystallization conditions and packing (FIG. 2B and FIGS. 7 to 9).

RPTPσ residues previously shown to mediate GAG binding (K67, K68, K70, K71, R96 and R99) lie on loops between Ig1 β-strands C-D and E-F, forming an extended positively-charged surface (FIGS. 2, B and C). The determined crystal structures, supplemented by sequence comparisons, show this site is highly conserved across family members and species (FIG. 2C and FIG. 6) suggesting a common GAG binding mode. A 2.05 Å resolution crystal structure of human LAR Ig1-2 in complex with sucrose octasulfate (SOS), a synthetic heparin-mimic, confirmed the GAG-binding site location and revealed a conformational plasticity of the C-D ("Lys") loop (residues K67-F77; FIG. 2D, FIG. 10-12 and FIG. 36 and FIG. 37). SOS binding triggered an outwards movement of residues V72-F77, following rupture of the R76-D100 salt bridge. K67, K68 and R76 form electrostatic interactions with SOS whilst R99 interacts with D100, resulting in a modified topology of the GAG-binding surface but maintaining the overall positive charge (FIGS. 2, E and F). Thus, the combination of basic side chains deployed by the type IIa RPTP GAG-binding site may vary to match the sulfate chemistry of a particular disaccharide unit, conferring the ability to accommodate chemically diverse GAGs.

Figure 3A:
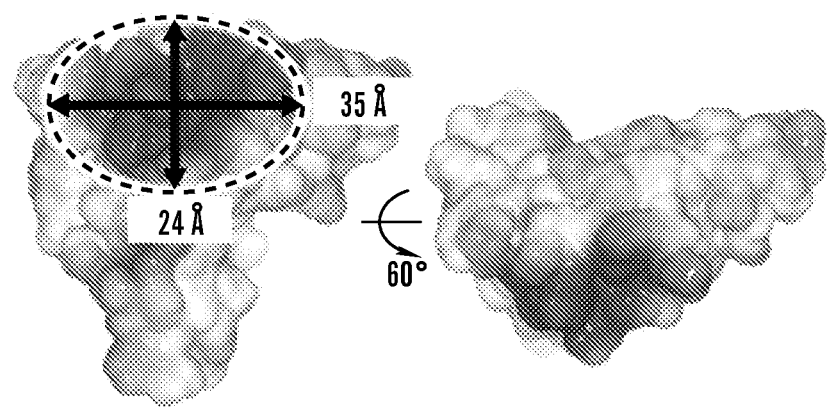
FIG. 3A-FIG. 3H show results from experiments which indicate GAG-induced oligomerisation of RPTPσ.
Figure 3B:
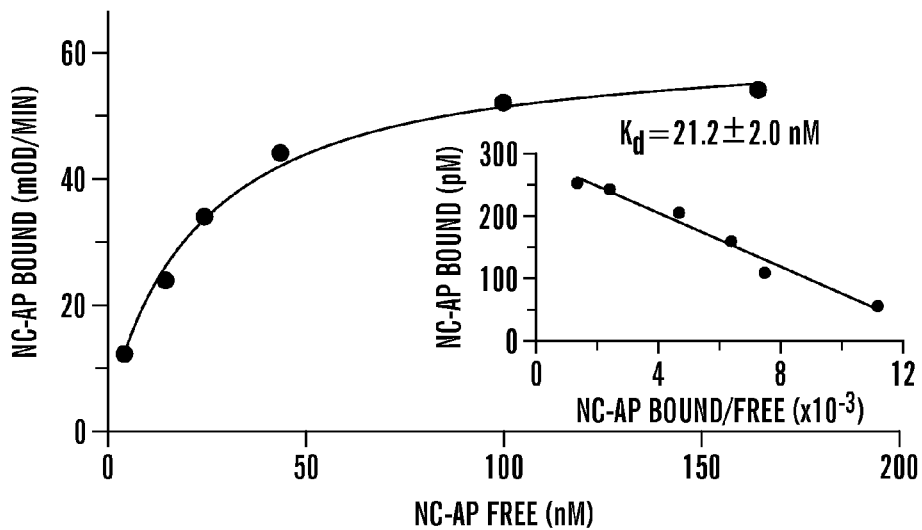
Figure 3C:
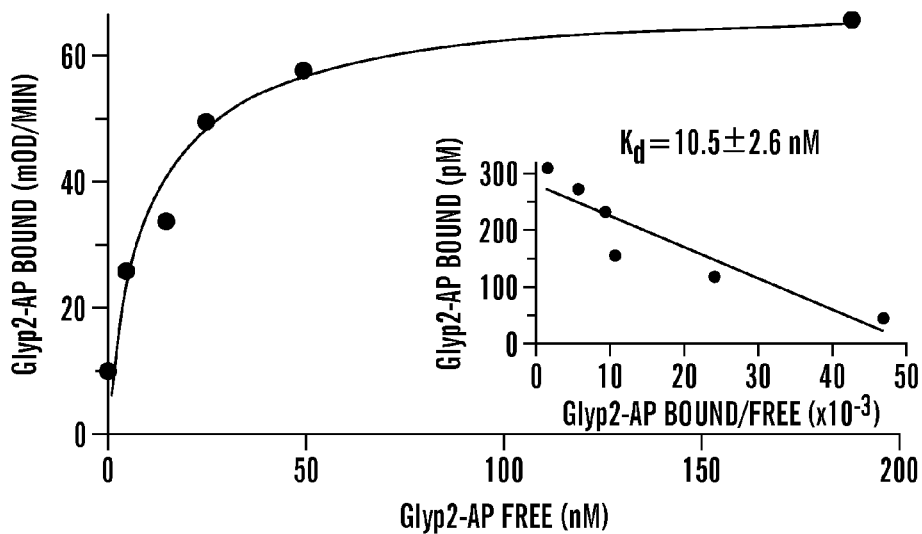
Figure 3D:
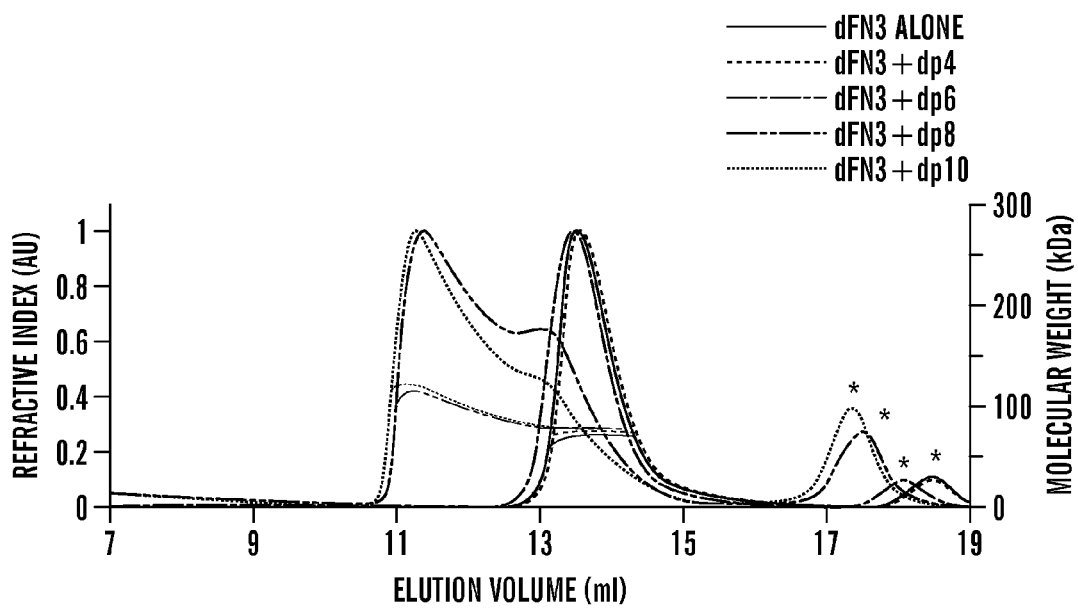
Figure 3E:
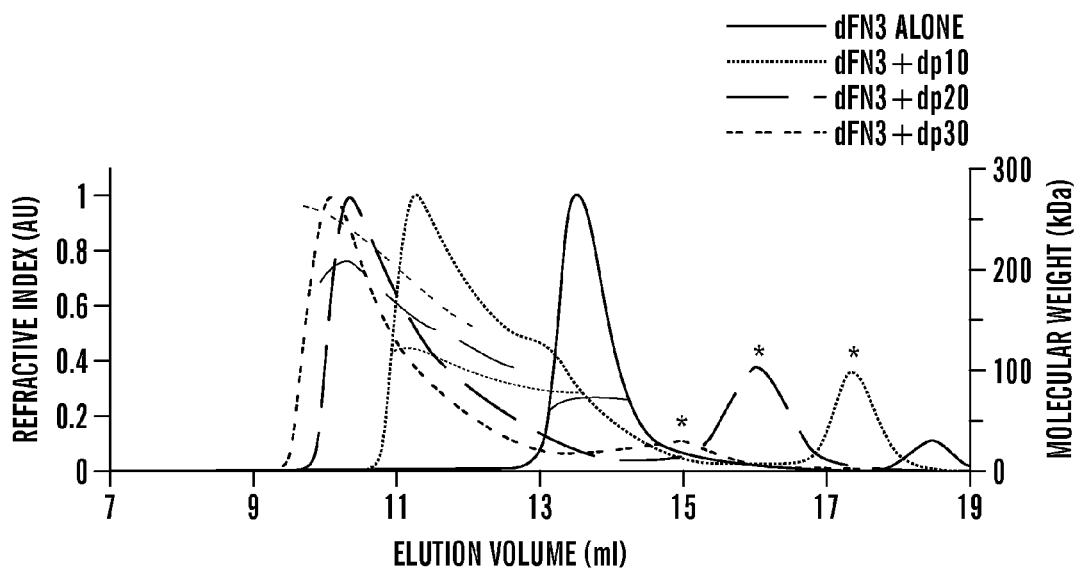
Figure 3F:
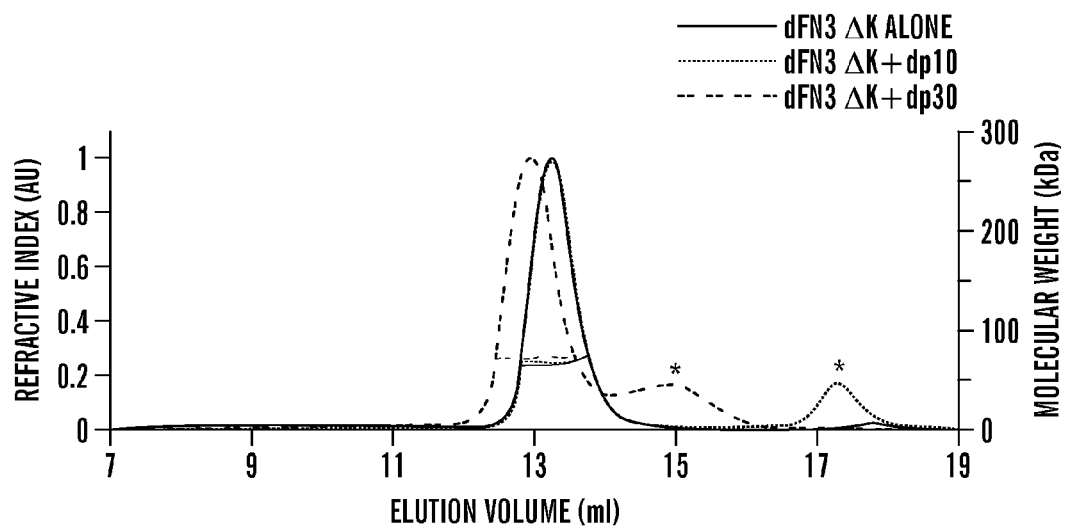
Figure 15:
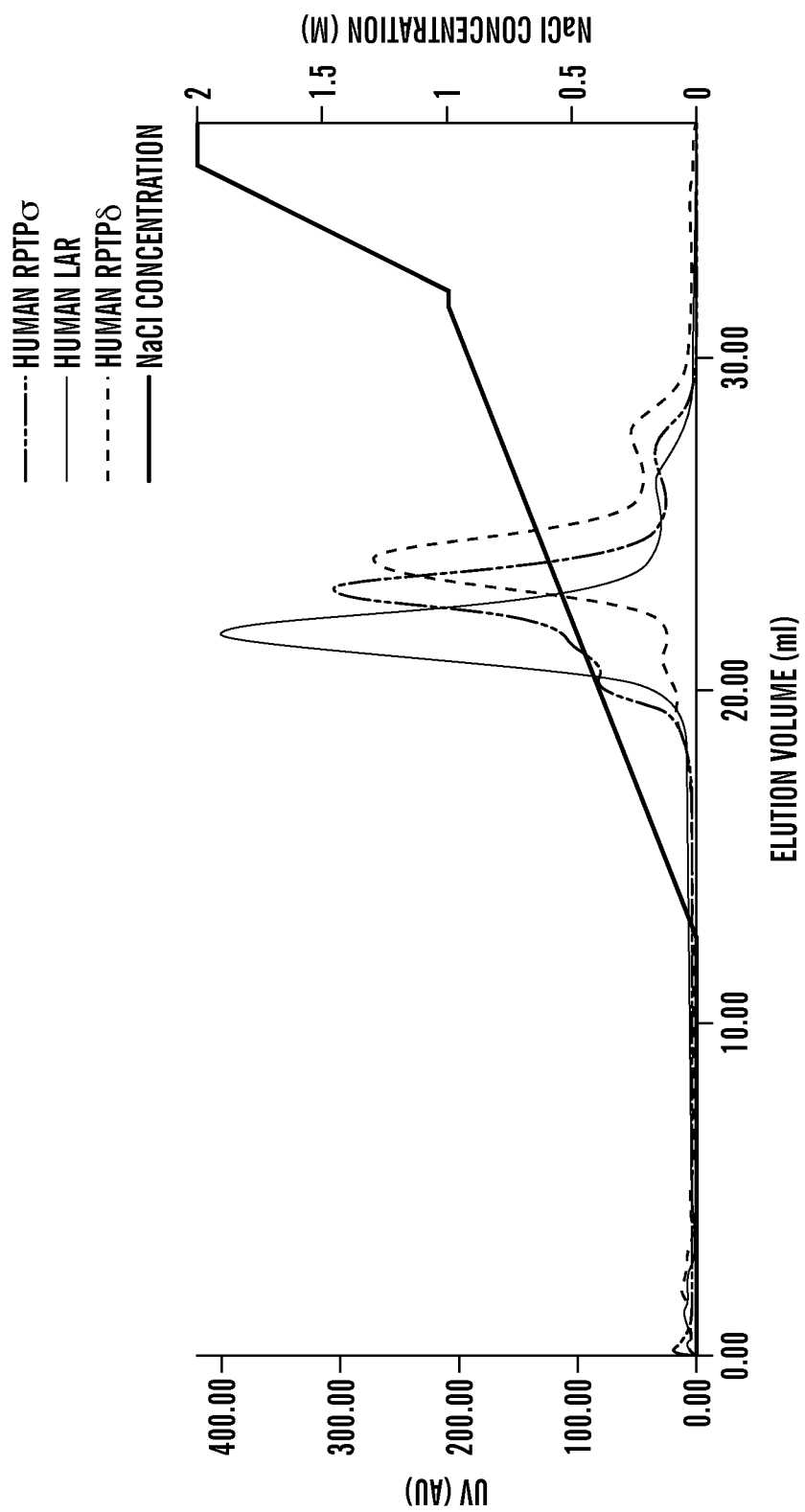
FIG. 15 is a graphical presentation of experimental results that measured the ability of the type IIa RPTPs to bind to a heparin affinity column. Purified Ig1-2 constructs of human RPTPσ (blue), RPTP LAR (red) and RPTPδ (yellow) were sequentially injected over the column and eluted upon addition of 550 mM, 490 mM and 600 mM sodium chloride respectively. All proteins were freshly purified by SEC, then desalted in 50 mM HEPES, 50 mM sodium chloride, pH 7.5 prior to injection onto a 1 ml heparin column, before elution with a gradient of 50 mM HEPES, 2M sodium chloride, pH 7.5 (black).
Figure 16A:
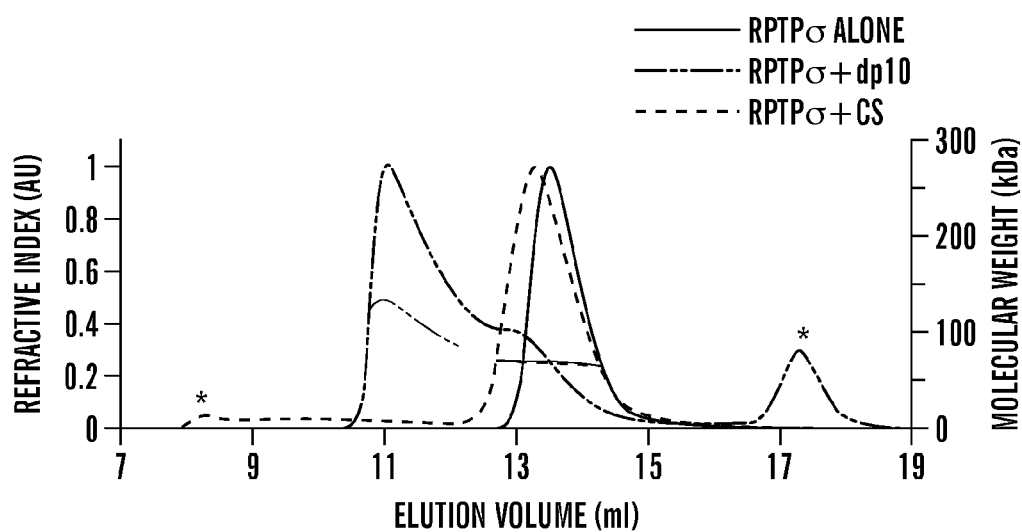
FIG. 16A-FIG. 16F are graphical representations of experimental results that indicate GAG-induced oligomerisation of the type IIa RPTP family. Alone (red), or after incubation with a five-fold molar excess of heparin dp10 (blue) or an equivalent amount of chondroitin sulfate (yellow), human RPTPσ Ig1-FN3 (A), RPTPδ Ig1-dFN3 (B) or LAR Ig1-dFN3 (C) were analysed by SEC-MALS. Similarly to RPTPσ, RPTPδ was observed to oligomerise upon addition of heparin dp10, however a longer oligosaccharide (dp30 in a fivefold molar excess, grey) was required to induce oligomerisation of LAR. In contrast to heparin, the introduction of chondroitin sulfate did not induce the oligomerisation of any of the human type IIa family members. Heparin promotes the oligomerisation of DLAR Ig1-FN3 (D), but this protein also requires a longer minimal heparin unit than RPTPσ. Incubating human RPTPσ Ig1-FN3 with a mixture of either heparin dp10 and a five-fold greater amount of chondroitin sulfate (E) or heparan sulfate and a five-fold greater amount of chondroitin sulfate (F) resulted in oligomers of reduced mass relative to the addition of heparin dp10 or heparan sulfate alone. Refractive index traces (scaled within each panel) are shown by bold lines and the measured molecular weights are shown by dotted lines. Peaks in the refractive index that are indicated by an asterisk correspond to excess oligosaccharide ligand. A Superdex 200 (1 cm×30 cm) column was used for all constructs.
Figure 16B:
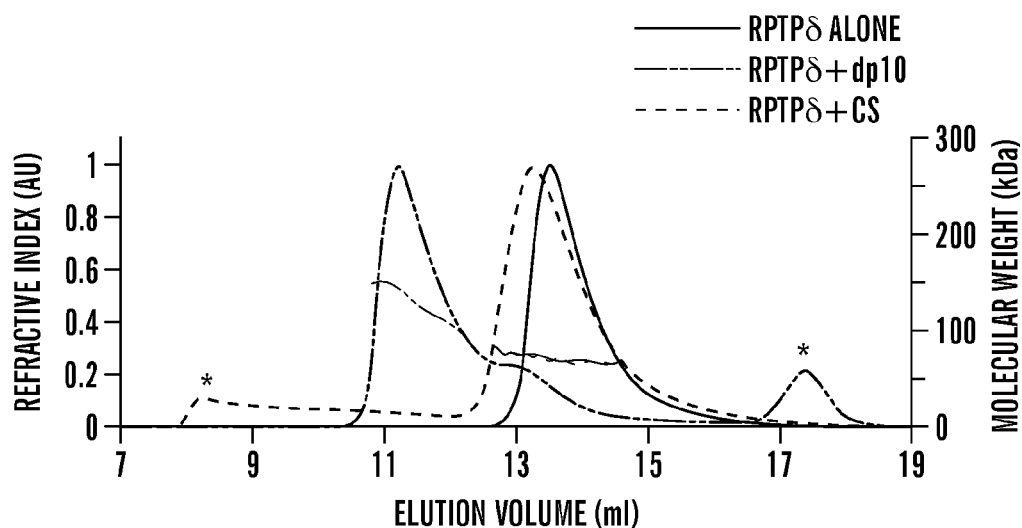
Figure 16C:
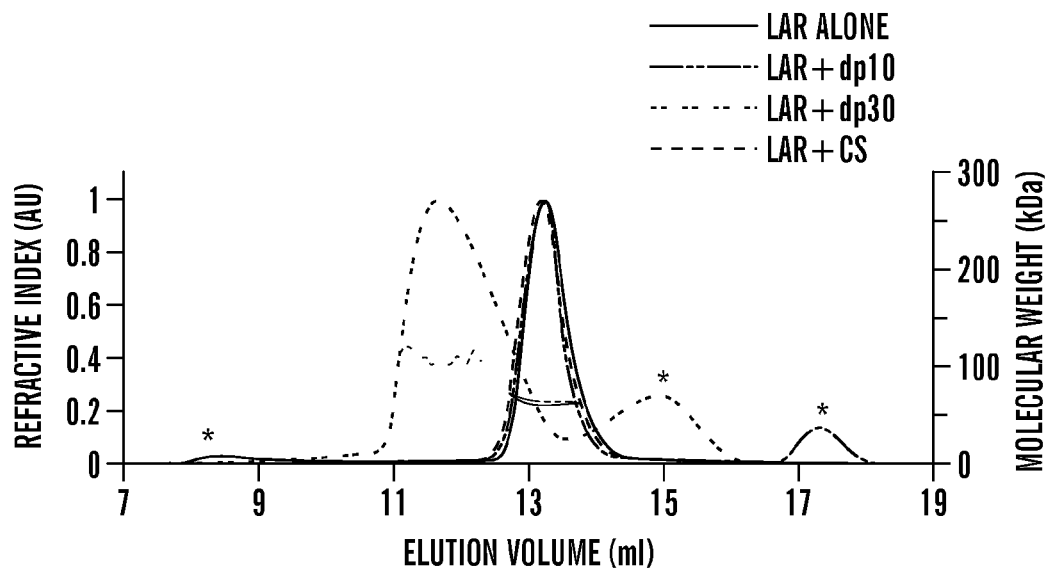
Figure 16D:
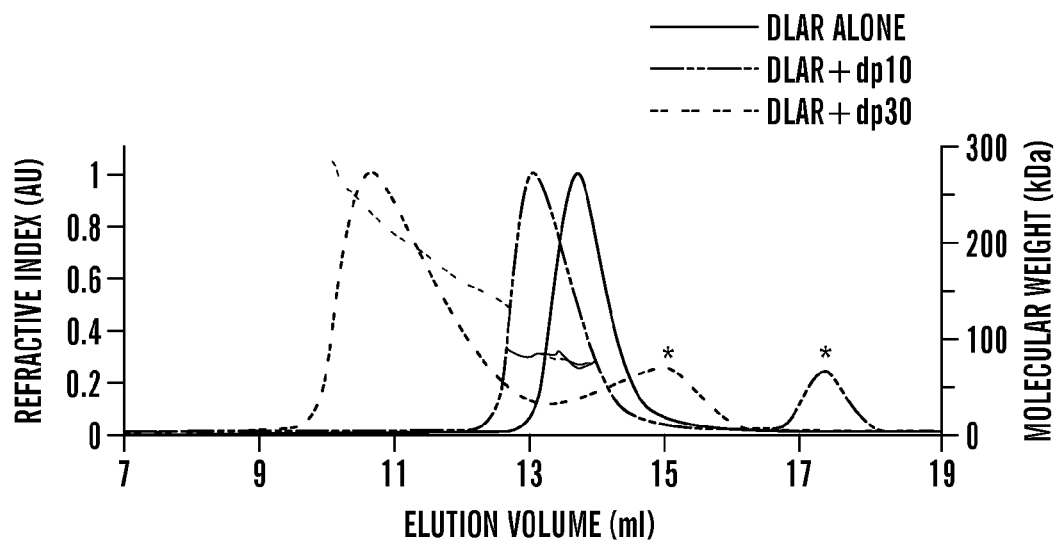
Figure 16E:
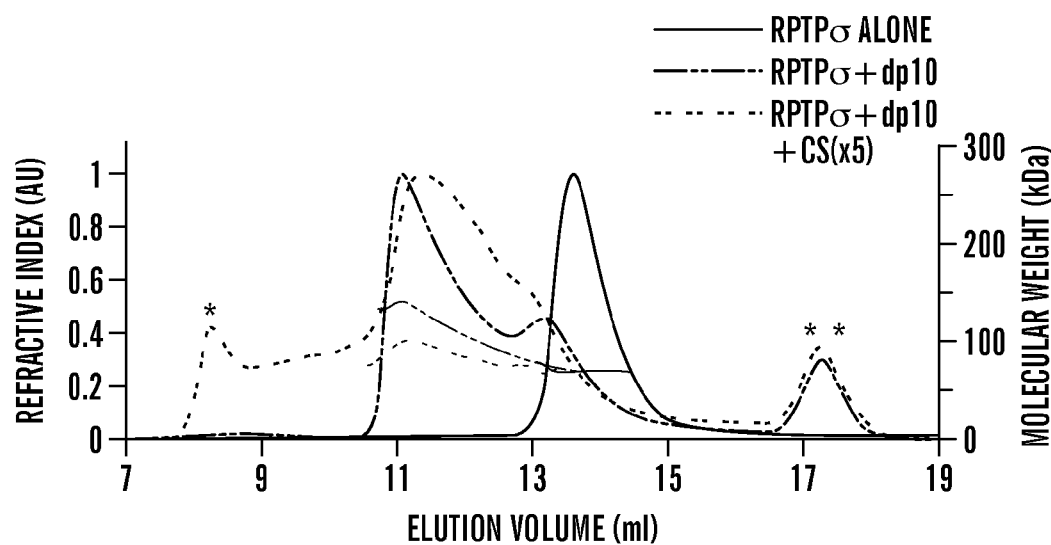
Figure 16F:
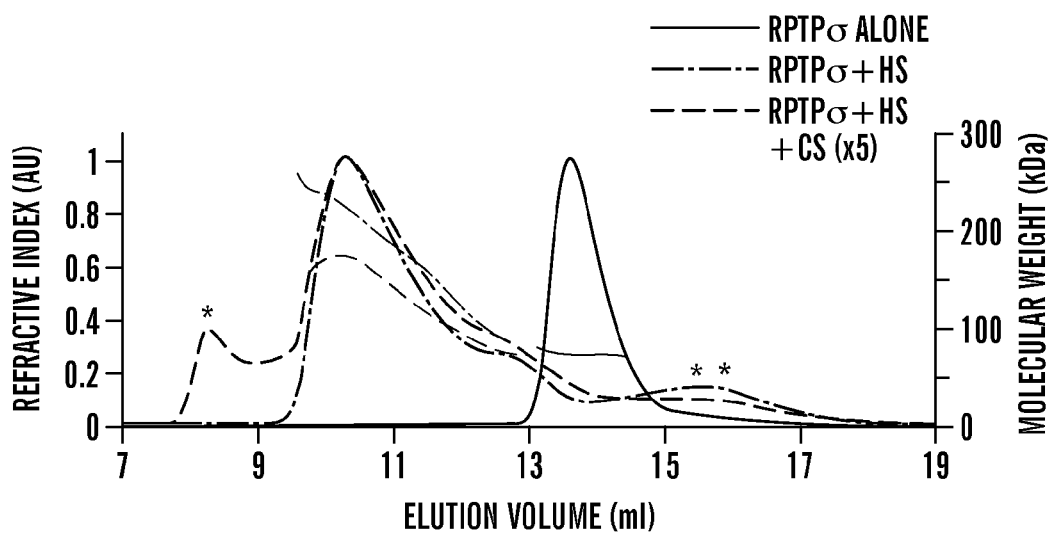
Figures 17A, 17B:
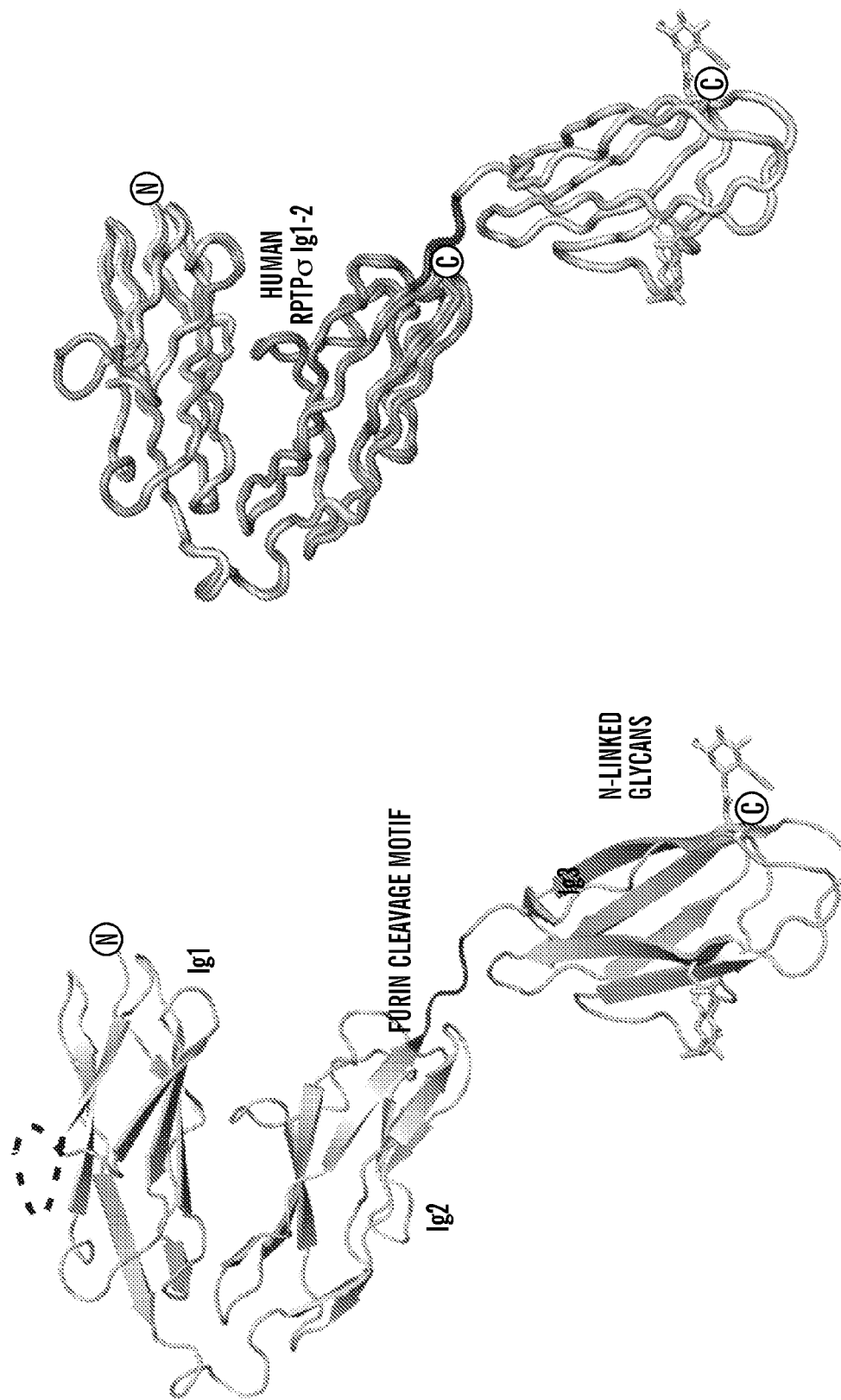
FIG. 17A-FIG. 17B are illustrations of the crystal structure of human RPTPσ Ig1-3. (A) Ribbon representation of the three Nterminal Ig domains of a human RPTPσ R227Q+ R228N double mutant. Only after introduction of these two point mutations to disrupt a potential furin cleavage motif RVRR, could crystals of intact Ig1-3 protein be obtained. The structure reveals that this motif is located in an exposed, flexible linker (black) between Ig domains 2 and 3. Residues 67-73 of the "Lys"-loop are not included in the structure as they were not well resolved in the electron density; they are indicated here by a dashed black line. (B) An overlay of human RPTPδ Ig1-2 (pink) and Ig1-3 illustrates the preserved architecture of the first two Ig domains in the Ig1-3 structure. Removal of Ig1-2, which contains the glycosaminoglycan binding site, either at or prior to arrival at the cell surface, could represent an additional mode of regulation of the type IIa RPTPs. However, RPTP isoforms which contain the MeB exon (which encodes four amino acid residues, ELRE, and lies within the RVRR motif), would be unable to utilise such a regulatory mechanism. For example, an isoform of RPTPδ lacking MeB is found to be expressed in the kidney, while an isoform with the MeB insert is expressed in the brain (S31, S32), therefore isoform expression patterns would determine whether this proteolytic cleavage event occurs in specific tissues. Additional membrane proximal and non-isoform dependent protease cleavage sites have been identified for type IIa RPTPs (S33), which result in the shedding of almost the entire ectodomain and would also desensitise the receptors to proteoglycans. A novel RPTPδ isoform lacking Ig3 has been identified in human ulcerative colitis patients (S34). The deletion of this domain may result in disruption of RPTPσ-ligand interactions, though as yet no binding partner for the Ig3 has been identified. Alternatively, it is possible that the resultant direct fusion of the rigid Ig1-2 unit onto the remainder of the ectodomain, limits the range of movement of the Ig1-2 unit, hampering efficient proteoglycan binding and receptor clustering.
Figure 18A:
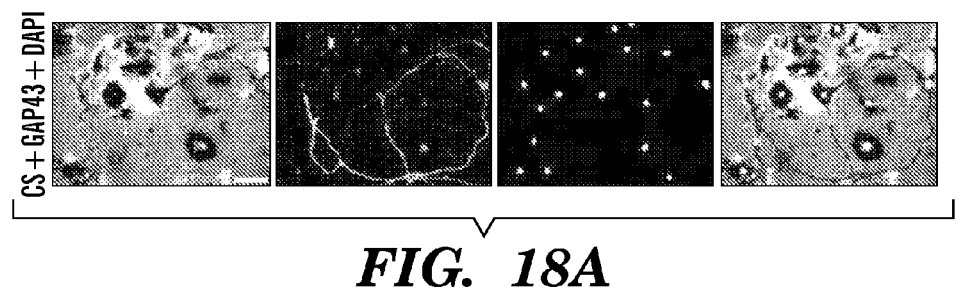
FIG. 18A-FIG. 18G is a collection of photographs that show immunolocalization of endogenous HS, CS and RPTPσ in DRG neuron cultures. Treatments are as described in FIG. 4 and (27), with additional controls shown here. (A and B) Immunolocalization of CS (red), with GAP43 neuronal marker (green) and DAPI nuclear stain (blue). Colors are merged in the right-hand panel.
Figure 18B:
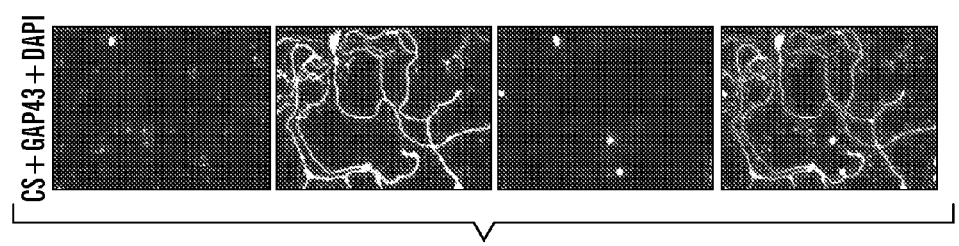
Figure 18C:
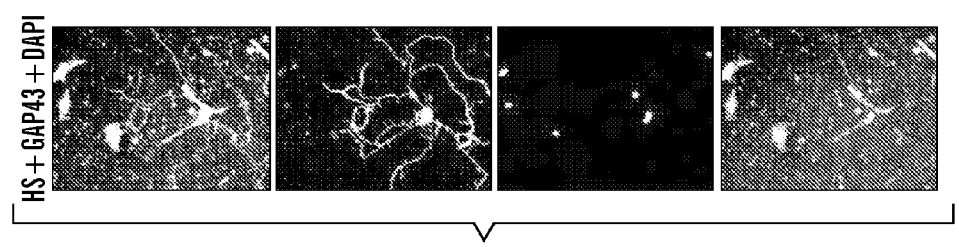
Figure 18D:
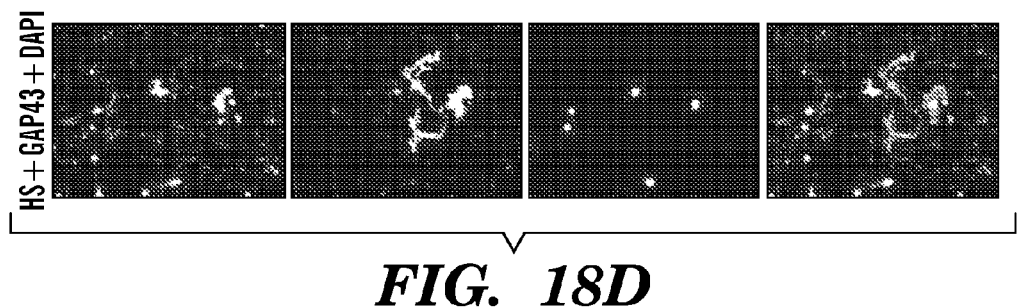
Figure 18E:
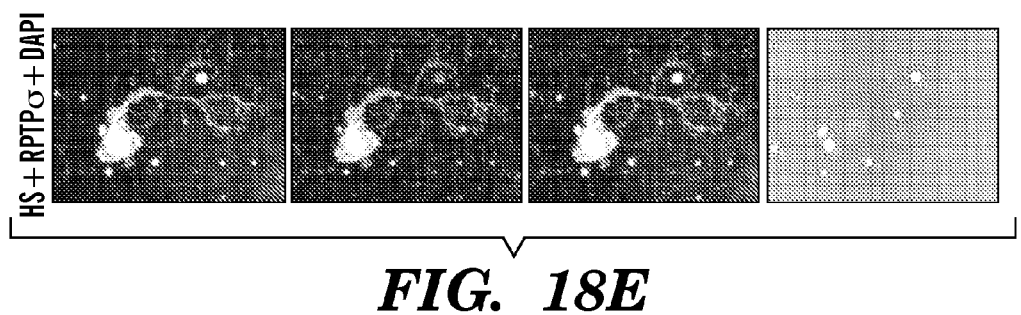
Figure 18F:
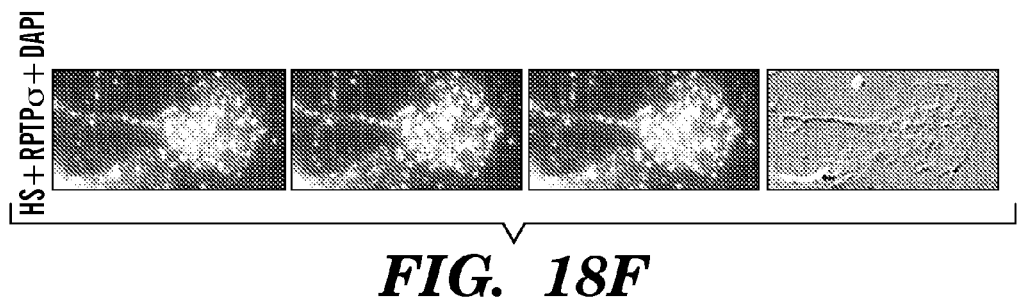
Figure 18G:
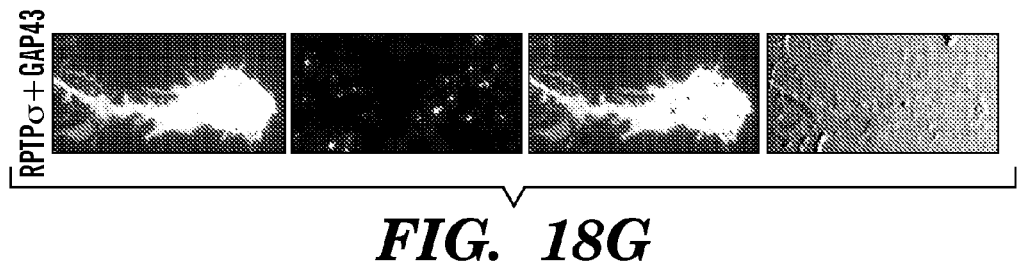

Interaction affinities of RPTPσ sEcto with neurocan and glypican-2, in solid phase binding assays, were in the same range (10-20 nM $K_d$; FIGS. 3B and C), similar to those determined in previous studies of CSPGs or HSPGs binding to type IIa RPTPs (7, 12), although weaker than measured previously for heparin-BSA (0.3 nM) (18). The glycan binding surface on Ig1 forms an elliptical area of ~35 Å×24 Å (FIG. 3A). Comparisons with a compact heparin structure, a helix with a 4 saccharide pitch of 17.5 Å (29), suggested that GAG chains could assemble RPTPσ oligomers. A series of size-defined heparin fragments were then incubated with a RPTPσ construct containing the six N-terminal domains (Ig1-FN3; FIG. 2A). Heparin fragments containing four [degree of polymerization 4 (dp4)] or six (dp6) saccharide residues did not alter the Ig1-FN3 oligomeric state, as assessed by size-exclusion chromatography coupled with multi-angle light scattering (MALS) (FIG. 3D to 3G and FIG. 37). However, fragments containing eight (dp8) or ten (dp10) saccharides induced a shift towards a dimeric Ig1-FN3 species (FIG. 3D and FIG. 37). This trend continued as heparin fragments of increasing length were tested; Ig1-FN3 mixed with dp20 and dp30 formed tri and tetrameric clusters, respectively (FIG. 3E and FIG. 37). A quadruple K67, K68, K70, K71 mutation to alanine, previously shown to impair binding to both CSPGs and HSPGs (12, 18), abolished the heparin-induced clustering effects (FIG. 3F and FIG. 37). The clustering behaviour was reproduced in MALS measurements for an RPTPσ domain deletion series (FIG. 2A and FIG. 13) and validated for Ig1-2 by analytical ultracentrifugation and native mass spectrometry (FIG. 14). These data provide compelling evidence that the Ig1 GAG-binding site is necessary and sufficient for receptor clustering dependent on heparin fragment length (FIG. 13, 14 and FIG. 37). Similar heparin-induced oligomerisation characteristics were demonstrated for other type IIa RPTPs, albeit with some variation (FIG. 15, 16 and FIG. 37).

Figure 3G:
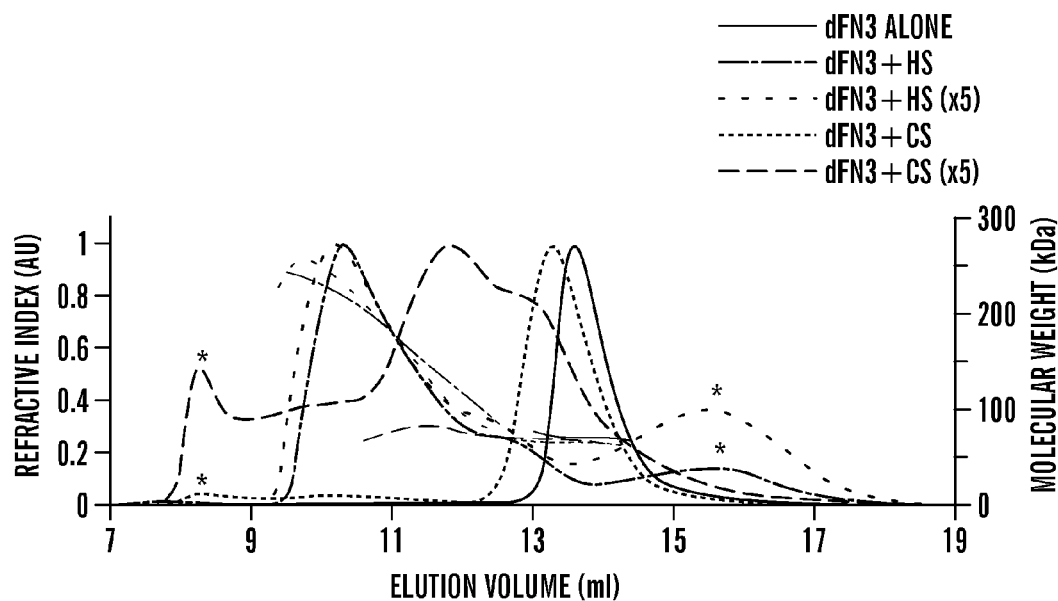
Figure 3H:
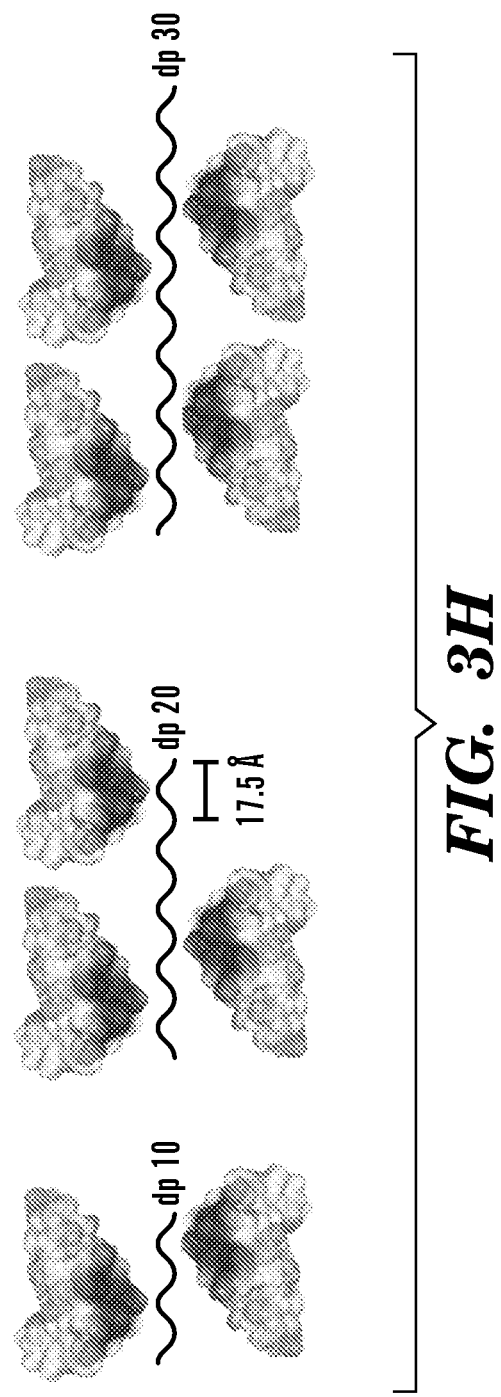

MALS was then used to compare the ability of chondroitin sulfate (CS) and heparan sulfate (HS) GAGs to induce oligomerization. HS (30-150 saccharide units) induced tetrameric clustering of RPTPσ Ig1-FN3, analogous to dp30 heparin fragments (FIG. 3G and FIG. 37). In striking contrast to heparin or HS, comparable CS (30-150 saccharide units) quantities did not induce clustering of any type IIa RPTP construct (FIG. 3E and FIG. 16). Using five-fold higher CS concentrations we were able to detect evidence of binding to RPTPσ Ig1-FN3, but the molecular mass did not shift to the levels seen for stable GAG-induced oligomers (FIG. 3G and FIG. 37). Since in our solid state assay CSPGs and HSPGs had shown comparable binding affinities to RPTPσ we tested whether CS could compete with HS in the MALS assay. Excess CS inhibited both HS- and heparin dp10-induced clustering (FIG. 16 and FIG. 37). Thus differences in GAG chemical structure must be responsible for the contrasting effects of HS and CS on RPTPσ oligomerisation (FIG. 3H).

Figure 4A:
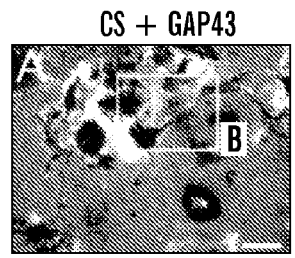
FIG. 4A-FIG. 4T is a collection of photographs and an illustration of a model. The collection presents experimental results that indicate immunolocalization of endogenous HS, CS and RPTPσ in DRG neuron cultures.
Figure 4D:
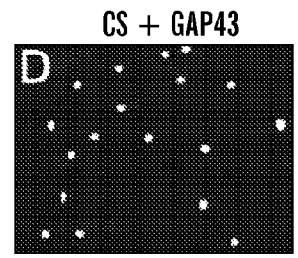
Figure 4B:
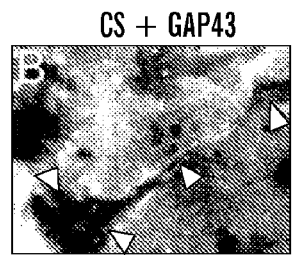
Figure 4E:
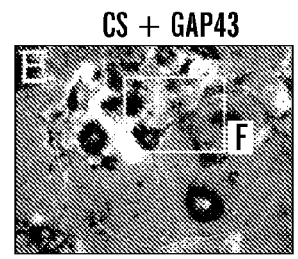
Figure 4C:
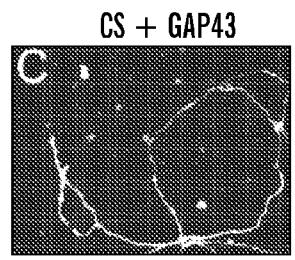
Figure 4F:
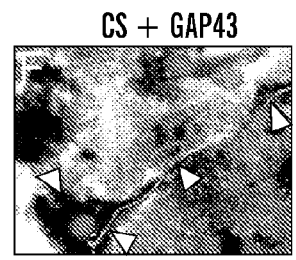
Figure 4G:
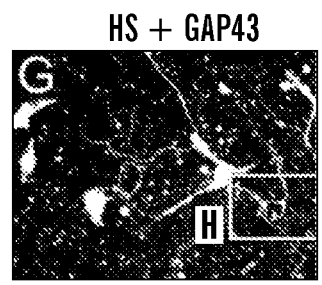
FIGS. 4G-L show HS (red), with GAP43 (green) and DAPI (blue). Colors are merged in FIGS. 4K and L. Boxed areas are enlarged in H and L. Arrowheads point to HS labeling over GAP43 labeled neuronal processes.
Figure 4J:
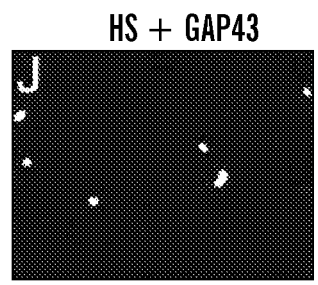
Figure 4H:
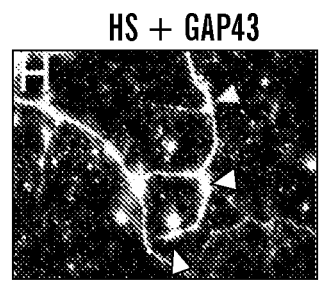
Figure 4K:
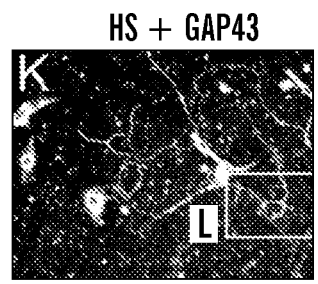
Figure 4I:
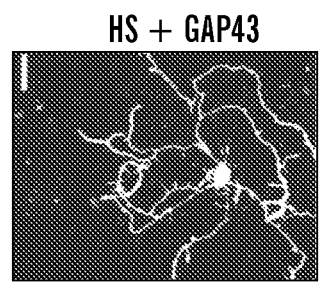
Figure 4L:
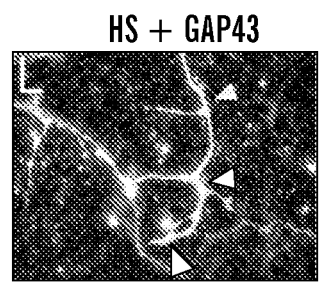
Figure 4M:
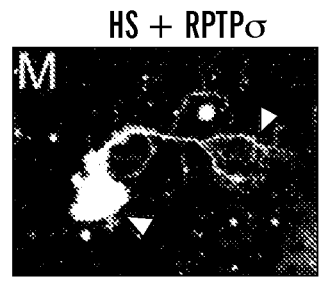
FIGS. 4M-S show immunolocalization of HS (red) with RPTPσ (green).
Figure 4N:
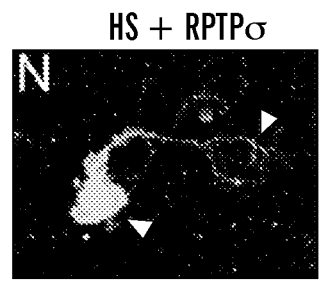
Figure 4O:
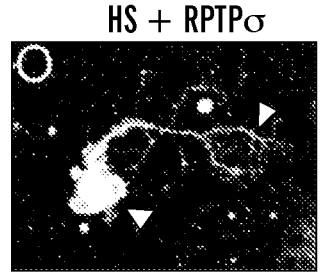
Figure 4P:
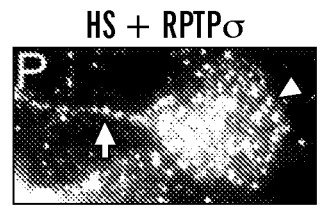
Figure 4Q:
Figure 4R:
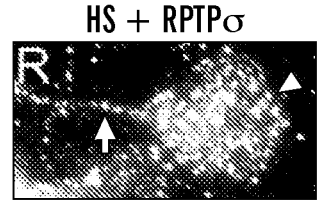
Figure 4S:
Figure 4T:
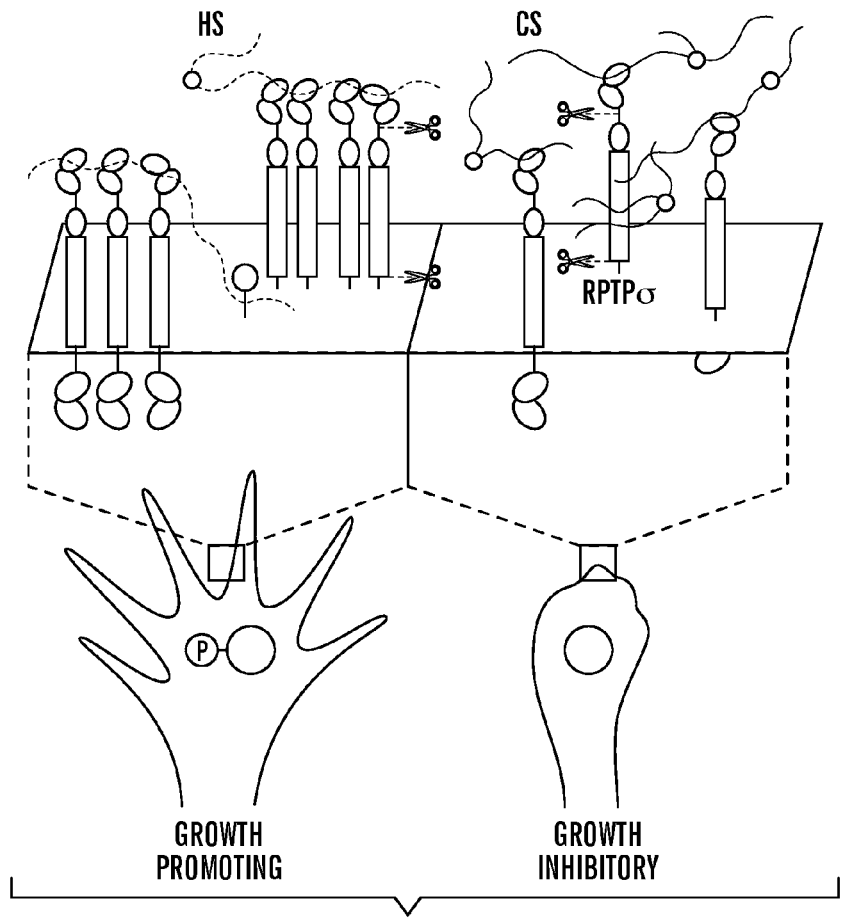
Figure 19:
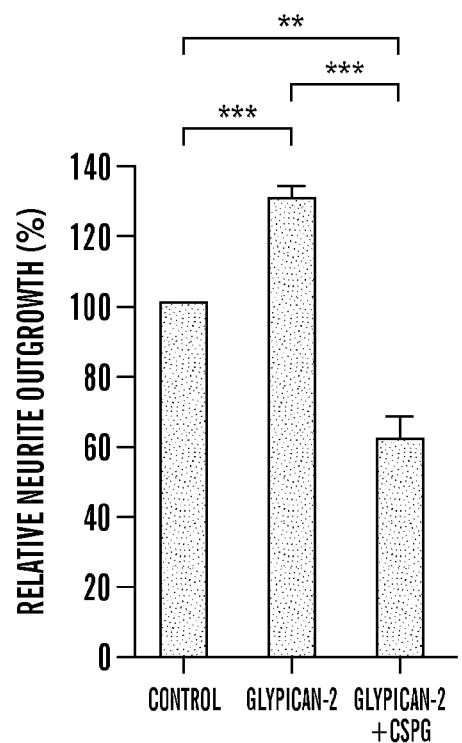
FIG. 19 is a bar graph of experimental results that show CSPG competition for HSPG-induced neurite outgrowth. Wild-type P10 mouse dorsal root ganglion (DRG) neurons were grown on substrates containing a poly-Dlysine/laminin mixture (control), or supplemented with either 5 μg/ml glypican-2, or with a mixture of 5 μg/ml glypican-2 plus 125 μg/ml CSPG. The outgrowth of DRG neurons, relative to control (assigned 100% outgrowth) was quantified. Treatment with glypican-2 promoted outgrowth to a lesser extent than the higher concentration (30 μg/ml) of glypican-2 used in FIGS. 1 and 5. CSPG out-competed the outgrowth promoting effect of glypican-2, leading to outgrowth inhibition relative to the control. Error bars show SEM. *$p<0.001$, $p<0.01$, Student's t-test.

The competing effects of CS and HS on RPTP oligomerization suggest axon outgrowth may be determined by relative amounts, rather than independent effects, of HSPG and CSPG acting on RPTPσ. To investigate this model, DRG neuron cultures were assessed for expression of endogenous HS and CS. Immunofluorescence showed both CS and HS are endogenously produced by these cultures. CS labeling was seen primarily over the extracellular matrix (ECM), where it was highest adjacent to non-neuronal cells, suggesting production of CSPG by these cells, whereas cell bodies and GAP43-labeled neurites showed little or no evidence of CS labeling and were typically aligned with dark areas in the immunofluorescence (FIGS. 4A-F and 18). HS labeling, in contrast, was highest over cell bodies and neurites, where RPTPσ labeling was also seen (FIGS. 4G-O and 18). At higher magnification, RPTPσ labeling revealed a punctate distribution over the growth cone, as described previously (15), and was similar (although not identical) to the HS pattern (FIG. 4P-S). These results thus support a model where endogeneous HSPGs in these cultures act predominantly in cis on the cell surface, while CSPGs are presented in trans by the ECM (FIG. 4T). Exogenous HSPG or CSPG addition (FIG. 1) would shift the HSPG:CSPG ratio. Consistent with this interpretation, and with the ability of CS to compete HS-mediated RPTPσ oligomerization (FIG. 16), addition of CSPG to DRG cultures could block the outgrowth-promoting effect of exogenous HSPG ($P<0.001$; FIG. 19).

Mechanistic parallels can be drawn for proteoglycan-specific regulation of other cell surface receptor systems. HS is known to play an essential role in fibroblast growth factor (FGF) signalling (30), and the number of FGF-FGFR protomers in a supramolecular assembly directly correlates with the size of the GAG chain (31). Opposing HSPG and CSPG effects have been reported in semaphorin-mediated axon guidance (22). HSPGs and CSPGs differ in the chemical composition of their GAG chains. The distribution of sulfate groups (typically 1-2 per disaccharide) along CS chains is relatively uniform, while HS has a distinct modular composition, with high sulfation regions (3 groups per disaccharide), flanked by intermediately modified transition zones and variably spaced by largely unmodified sections almost devoid of sulfation (32). Without being bound by theory, the observations reported herein suggest a model where islands of high sulfation present in HS, but not CS, may promote close packing of RPTPσ molecules.

RPTPσ clustering would translate into an uneven distribution of phosphatase activity on the cell surface, consistent with localization-based models for receptor action (33). Small regions depleted in phosphatase activity could enhance the extent and duration of a phosphorylated state for proteins stimulating neuronal extension (1, 34-35). The solution and cellular data presented herein are consistent with a model whereby increasing the CSPG:HSPG ratio shifts the balance away from growth-promoting RPTPσ clusters, stalling neuronal growth cones (FIG. 4T). This model predicts that molecules able to promote RPTPσ oligomerization may prove beneficial in strategies to facilitate plasticity and regeneration following nervous system injury. More generally, proteoglycan-binding is a common property of many cell surface signalling systems involved in normal biology and disease. Results presented herein point to a mechanism by which differences in the structure of GAG chains can serve as a stop/go molecular switch for cell motility and may provide a general paradigm in the biology of cell surface signalling.

REFERENCES FOR BACKGROUND, EXAMPLE 1 RESULTS, AND FIGS. 1-4

1. K. G. Johnson, D. Van Vactor, *Physiol. Rev.* 83, 1 (2003).
2. Y. Duan, R. J. Giger, *Sci. Signal.* 3, pe6 (2010).
3. N. K. Tonks, *Nat. Rev. Mol. Cell. Biol.* 7, 833 (2006).
4. F. Rashid-Doubell, I. McKinnell, A. R. Aricescu, G. Sajnani, A. Stoker, *J. Neurosci.* 22, 5024 (2002).
5. A. N. Fox, K. Zinn, *Curr. Biol.* 15, 1701 (2005).
6. A. W. Dunah et al., *Nat. Neurosci.* 8, 458 (2005).
7. K. G. Johnson et al., *Neuron* 49, 517 (2006).
8. J. Woo et al., *Nat. Neurosci.* 12, 428 (2009).
9. M. J. Wallace et al., *Nat. Genet.* 21, 334 (1999).
10. M. Elchebly et al., *Nat. Genet.* 21, 330 (1999).
11. J. McLean, J. Batt, L. C. Doering, D. Rotin, J. R. Bain, *J. Neurosci.* 22, 5481 (2002).
12. Y. Shen et al., *Science* 326, 592 (2009).
13. E. Fry, J. M. Chagnon, J. R. López-Vales, M. Tremblay, L. S. David, *Glia* 58, 423 (2010).
14. P. S. Sapieha et al., *Mol. Cell. Neuro.* 28, 625 (2005).
15. K. M. Thompson et al., *Mol. Cell. Neuro.* 23, 681 (2003).
16. N. Uetani et al., *EMBO J.* 19, 2775 (2000).
17. N. Uetani, M. J. Chagnon, T. E. Kennedy, Y. Iwakura, M. Tremblay, *J. Neurosci.* 26, 5872 (2006).
18. A. R. Aricescu, I. W. McKinnell, W. Halfter, A. W. Stoker, *Mol. Cell. Biol.* 22, 1881 (2002).
19. C. E. Bandtlow, D. R. Zimmermann, *Physiol. Rev.* 80, 1267 (2000).
20. D. Van Vactor, D. P. Wall, K. G. Johnson, *Curr. Opin. Neurobiol.* 16, 40 (2006).
21. J. Silver, J. H. Miller, *Nat. Rev. Neurosci.* 5, 146 (2004).
22. D. B. Kantor et al., *Neuron* 44, 961 (2004).
23. Y. Matsumoto, F. Irie, M. Inatani, M. Tessier-Lavigne, Y. Yamaguchi, *J Neurosci* 27, 4342 (2007).
24. C. M. Galtrey, J. W. Fawcett, *Brain Res. Rev.* 54, 1 (2007).
25. L. C. Case, M. Tessier-Lavigne, *Curr Biol* 15, R749 (2005).
26. M. Ledig, F. Haj, J. L. Bixby, A. W. Stoker, B. K. Mueller, *J. Cell Biol.* 147, 375 (1999).
27. A. R. Aricescu, W. Lu, E. Y. Jones, *Acta Crystallogr. D Biol. Crystallogr.* 62, 1243 (2006).
28. Materials and methods are provided herein.
29. B. Mulloy, M. J. Forster, C. Jones, D. B. Davies, *Biochem. J.* 293, 849 (1993).
30. T. Spivak-Kroizman et al., *Cell* 79, 1015 (1994).
31. N. J. Harmer et al., *Biochem J* 393, 741 (2006).
32. K. J. Murphy et al., *J Biol Chem* 279, 27239 (2004).
33. J. T. Groves, J. Kuriyan, *Nat Struct Mol Biol* 17, 659 (2010).
34. D. Y. Wu, D. J. Goldberg, *J. Cell Biol.* 123, 653 (1993).
35. E. Robles, S. Woo, T. M. Gomez, *J. Neurosci.* 25, 7669 (2005).
36. Coordinates and structure factors are deposited in the Protein Data Bank (see FIG. 37).

Materials and Methods
Construct Design and Cloning.

A series of type IIa RPTP constructs were cloned into the pHLsec vector (S1), introducing an N-terminal secretion signal sequence and a C-terminal hexahistidine tag. Human RPTPσ short isoform (NCBI Ref. Seq. NM_130853.2): Ig1-2 (amino acids 30-231), Ig1-3 (30-321), Ig1-FN3 (30-602), sEcto (30-839). Human RPTP LAR (NCBI Ref. Seq. NM_002840.3): Ig1-2 (30-231), Ig1-FN3 (30-602). Human RPTPδ (NCBI Ref. Seq. BC106713.1): Ig1-2 (21-220), Ig1-FN3 (21-594). *Drosophila* RPTP LAR (NCBI Ref. Seq. NM_078880.3): Ig1-2 (33-232), Ig1-FN3 (33-606). Chick RPTPσ (NCBI Ref. Seq. NM_205407.1) Ig1-229-226. A human RPTPσ Ig1-3 R227Q+R228N mutant construct was designed to prevent proteolytic cleavage during Ig1-3 crystallisation trials. This construct was generated by two-step overlapping PCRs. The Glypican2-AP construct was generated by subcloning the coding sequence for amino acids 1-555 of mouse Glypican-2 (NCBI Ref. Seq. BC083180) into the APTag5 vector. Mouse RPTPσ sEcto-Fc and Neurocan-AP fusion proteins were generated as described previously (S2).

Protein Purification and Crystallisation.

All Ig1-2 constructs were expressed in HEK-293T cells following transient transfection using polyethylenimine (S1). Human RPTPσ Ig1-3 R227Q+R228N was expressed in HEK-293T cells, in the presence of kifunensine (Toronto Research Chemicals), a specific inhibitor of α-mannosidase (S3, S4). Ig1-FN3 and sEcto constructs were expressed in either HEK-293T cells in the presence of kifunensine or in GnTI⁻ HEK293S cells (S5). All proteins were purified from filtered cell culture media by immobilised nickel affinity chromatography (Chelating Sepharose Fast Flow, GE Healthcare) followed by heparin affinity chromatography (HiTrap Heparin HP column, GE Healthcare) and finally gel filtration (Superdex resin, GE Healthcare) in 10 mM HEPES, 150 mM NaCl, pH 7.5. In addition, the human RPTPσ Ig1-3 R227Q+R228N protein, which contains two N-linked glycosylation sites, was incubated for 3 hours at 37° C. with endoglycosidase F1 (S4, S6) to cleave the N-linked Man$_9$GlcNAc$_2$ oligosaccharides to a single GlcNAc residue prior to the heparin affinity chromatography step of the purification. Expression of selenomethionine labelled protein was carried out as described previously (S1) and the protein was subsequently purified as described for native proteins.

Crystallisation trials, using 100 nl protein solution plus 100 nl reservoir solution in sitting drop vapour diffusion format were set up in 96-well Greiner plates using a Cartesian Technologies robot (S7). Crystallisation plates were maintained at 20.5° C. in a TAP Homebase storage vault and imaged via a Veeco visualisation system (S8). Crystallisation conditions for all proteins are provided in FIG. 35.

Data Collection and Processing.

All crystals obtained were cryo-protected as stated (FIG. 35) and then flash frozen at 100 K. X-ray diffraction data was collected at the Diamond Light Source, Oxfordshire, UK or the European Synchotron Radiation Facility, France as indicated. The diffraction images were indexed, integrated, scaled and merged using either the HKL2000 (S9) or the xia2 (S10) data processing suites. The chick RPTPσ Ig1-2 structure was determined by SAD analysis, using images collected from a selenomethionine labelled protein crystal at the selenium peak wavelength (λ=0.9783 Å). Using SHELXD (S11) via the autoSHARP interface (S12), the positions of two selenium atoms were determined, before subsequent phase calculation, improvement and preliminary model building was performed. These preliminary models were used together with a high resolution (1.65 Å) native dataset in iterative rounds of automatic model building using RESOLVE (S13), ARP/wARP (S14) and manual building using Coot (S15). The data obtained for all subsequent type IIa RPTP proteins were phased by molecular replacement using the chicken RPTPσ Ig1-2 solution as a search model in Phaser (S16). The resulting electron density maps were of high quality and enabled manual model adjustment in Coot (S15) and refinement in Refmac (517), Phenix (S18) and Buster (S19). For structural validation PROCHECK (S20) and MolProbity (S21) were used to assess the stereochemical properties of the models and refinement statistics are given in Table S2. The superimposition of atomic models to compare the domain architecture between different structures, was performed using SHP (S22), based on Cα positions. Crystallographic figures were created using PyMOL (S23) and APBS was used to calculate the electrostatic potential of solvent accessible surfaces (S24).

Multi-Angle Light Scattering (MALS).

MALS experiments were carried out on a Wyatt MALS/AFFFF System (Wyatt Technologies). All proteins were purified as described above, and samples were incubated alone or with an oligosaccharide ligand for an hour at room temperature prior to use in MALS analysis. For size defined heparin fragments (Iduron dp4-dp30; product codes HO04-HO30) a five-fold molar excess of oligosaccharide to protein was used, except for the series of experiments presented in FIG. 13, where a range of RPTPσ constructs were tested with a separate batch of dp10 at a two-fold molar excess (FIG. 37, highlighted in blue). Equivalent amounts (equal mg/ml concentrations) of HS (Iduron, GAG-HS01) and CS (Sigma, C4384) were used for MALS experiments as had been for heparin dp10 (in giving a five-fold molar excess). "×5" indicates that a five-fold greater quantity of HS or CS was used. All Ig1-FN3 proteins were injected at approximately 10 μM. Size exclusion chromatography was performed in 10 mM Tris, 50 mM NaCl, pH 7.5 on a Superdex75 or Superdex200 HR10/30 column (GE Healthcare), attached to an Agilent chromatography system. An Optilab rEX Refractive Index detector and a Dawn Helios II Multi-Angle Light Scattering (MALS) detector recorded the refractive index and light scattering of the samples upon elution from the size exclusion column. The Wyatt software ASTRA was used to analyse all the data collected.

Native Mass Spectrometry.

10 μM human RPTPσ Ig1-2 (desalted previously into 100 mM ammonium acetate pH 7.5) and 50 μM dp10 (ammonium salt) were incubated in a final volume of 500 μl for an hour. Gel filtration in 100 mM ammonium acetate pH 7.5 was carried out with this complex sample and the Ig1-2 protein alone, and fractions taken from the peaks on the UV traces and diluted to a concentration of 8 μM were used for analysis. Electrospray ionisation-mass spectrometry (ESI-MS) was carried out on a Waters Quadrupole Time-of-Flight (Q-T of) Micro instrument with direct infusion of the protein samples. For native analysis, the protein-heparin complex spectrum was obtained using a cone voltage of 200 V.

Analytical Ultracentrifugation.

Sedimentation equilibrium and velocity experiments were carried out at 20° C. in an Optima XL-I analytical ultracentrifuge (Beckman Instruments) utilising a scanning absorbance of 280 nm and interference optics. Samples of human RPTPσ Ig1-2 alone and in complex to heparin dp10, were taken directly from gel filtration in 20 mM Tris, 50 mM NaCl pH 7.5. Sedimentation velocity experiments were performed and analysed using the time derivative g(s*) method (25). Samples were equilibrated at 20° C. in the rotor, before the velocity was sequentially increased through speeds of 12, 18, 25, 35 and 50 krpm, 50 scans being made at each speed. ProFit (QuantumSoft) was used to fit Gaussian curves to the g(s*) plots obtained, and to describe the distribution of individual species.

Solid Phase Binding Assays.

Analysis of binding between RPTPσ sEcto-Fc and Glypican-2 or Neurocan alkaline phosphate (AP) fusion proteins was performed as described previously (S2, S26). All fusion proteins were produced in transiently transfected 293T cells. Briefly, the RPTPσ Fc-fusion protein was immobilised on 96-well Reactibind Protein A-coated plates (Pierce) and incubated with soluble proteoglycan-AP proteins which had been normalized for equal input AP activity. AP activity was determined by measuring substrate turnover on a microplate reader as described (S27, S28). For experiments involving treatment with chondroitinase ABC (Sigma) or heparitinase III (HPNIII, Sigma), chondoitinase-treated, heparitinase-treated or mock-treated proteoglycan-APs were incubated at 37° C. for 2 hours prior to addition to the RPTPσ-Fc coated plates. In FIG. 23, the binding between RPTPσ-Fc and heparin-derived size-fractionated oligosaccharides with different lengths (HS6, HS8, HS10, HS17, HS23, HS30 and HS67, corresponding to hexasaccharide, octasaccharide, decasaccharide, or approximately 17, 23, 30 and 67 saccharide units; molecular weights 1,800 Da, 3,000 Da, 5,000 Da, 7,000 Da, 9,000 Da, and 20,000 Da; Neoparin) was analyzed with RPTPσ-Fc immobilised on 96-well Reactibind Protein A-coated plates (Pierce) and incubated with soluble biotinalated HS. The bound HS was quantified by AP enzyme activity following incubation with streptavidin-AP (Promega). The effect of HS oligosaccharides on Neurocan-AP binding to RPTPσ-Fc was tested by adding HS oligosaccharides of various lengths as described above.

DRG Neurite Outgrowth Assay and Immunofluorescence.

DRGs of P8-12 RPTPσ+/+ or RPTPσ−/− mice were cut off from all roots. Neurons were dissociated and subjected to neurite outgrowth assays and analysis as described previously (S2). For experiments in FIG. 1, recombinant mouse Neurocan (5800-NC, R&D Systems) was used at 5 μg/ml and recombinant mouse Glypican-2 (2355-GP, R&D Systems) at 30 μg/ml. In FIG. 5, 30 μg/ml of Glypican-2 was pre-incubated with 1 unit/ml of Heparitinase III (HPNIII, H8891, Sigma) at 37° C. for 4 hrs where indicated, prior to use in outgrowth assays. For experiments in FIG. 19, recombinant mouse glypican-2 was used at 5 μg/ml, and Chondroitin Sulfate Proteoglycan mixture (CSPG, CC117, Millipore) was at 125 μg/ml. For experiments in FIGS. 24 and 25, Chondroitin Sulfate Proteoglycan mixture (CSPG, CC117, Millipore) was at 60 μg/ml, with or without the addition of HS at indicated length and concentration (1 μM for all HS in FIG. 21). Proteoglycans and heparin oligosaccharides were added to neuronal cultures 30 min after seeding and were replenished 24 hrs later. At 48 hrs after seeding, cells were fixed and immunostained with anti-GAP43 antibody (NB300-143, Novus). The whole of each well was scanned with a fluorescence microscope and the images were then analyzed for total neurite outgrowth using the Metamorph program.

For immunolocalization, dissociated DRG neurons were cultured without treatment then fixed and permeabilized, to allow co-staining with the cytoplasmic marker GAP43, at about 48 hrs after seeding. Where indicated, the fixed samples were then treated at 37° C. for 2 hrs with either 1 unit/ml of Chondroitinase ABC(C3667, Sigma) or a mixture of Heparinase I, II and III (H2519, H6512, H8891, Sigma), each at 1 unit/ml. Subsequently, samples were subjected to immunostaining using anti-chondroitin sulfate antibody (C8035, Sigma), anti-heparin/heparan sulfate antibody (OBT1698, AbD Serotec), anti-RPTPσ antibody (AF3430, R&D Systems) and anti-GAP43 antibody (NB300-143, Novus).

Statistics

Error bars show SEMs; P values were calculated by Student's t-test.

REFERENCES FOR MATERIALS AND METHODS, EXAMPLE 1, AND FIGS. 5-19, AND TABLES 1-3

S1. A. R. Aricescu, W. Lu, E. Y. Jones, *Acta Crystallogr. D Biol. Crystallogr.* 62, 1243 (2006).
S2. Y. Shen et al., *Science* 326, 592 (2009).
S3. A. D. Elbein, J. E. Tropea, M. Mitchell, G. P. Kaushal, *J. Biol. Chem.* 265, 15599 (1990).
S4. V. T. Chang et al., *Structure* 15, 267 (2007).
S5. P. J. Reeves, N. Callewaert, R. Contreras, H. G. Khorana, *Proc. Natl. Acad. Sci. U.S.A.* 99, 13419 (2002).
S6. F. Grueninger-Leitch, A. D'Arcy, B. D'Arcy, C. Chène, *Protein Sci.* 5, 2617 (1996).
S7. T. S. Walter et al., *Acta Crystallogr. D Biol. Crystallogr.* 61, 651 (2005).
S8. C. J. Mayo et al., *Structure* 13, 175 (2005).
S9. Z. Otwinowski, Minor, Wladek, *Methods Enzymol.*, 307 (1997).
S10. G. Winter, *J. Appl. Crystallogr.* 43, 186 (2010).
S11. G. Sheldrick, *Acta Crystallogr. A* 64, 112 (2008).
S12. E. B. C. Vonrhein, P. Roversi, G. Bricogne, *Methods Mol. Biol.*, 215 (2007).
S13. T. Terwilliger, *Acta Crystallogr. D Biol. Crystallogr.* 59, 45 (2003).
S14. A. Perrakis, R. Morris, V. S. Lamzin, *Nat. Struct. Mol. Biol.* 6, 458 (1999).
S15. P. Emsley, K. Cowtan, *Acta Crystallogr. D Biol. Crystallogr.* 60, 2126 (2004).
S16. A. J. McCoy, R. W. Grosse-Kunstleve, L. C. Storoni, R. J. Read, *Acta Crystallogr. D Biol. Crystallogr.* 61, 458 (2005).
S17. G. N. Murshudov, A. A. Vagin, E. J. Dodson, *Acta Crystallogr. D Biol. Crystallogr.* 53, 240 (1997).
S18. P. D. Adams et al., *Acta Crystallogr. D Biol. Crystallogr.* 66, 213 (2010).
S19. G. Bricogne, *Acta Crystallogr. D Biol. Crystallogr.* 49, 37 (1993).
S20. R. A. Laskowski, M. W. MacArthur, D. S. Moss, J. M. Thornton, *J. Appl. Crystallogr.* 26, 283 (1993).
S21.1. W. Davis et al., *Nucl. Acids Res.* 35, W375 (2007).
S22. D. I. Stuart, M. Levine, H. Muirhead, D. K. Stammers, *J. Mol. Biol.* 134, 109 (1979).
S23. W. L. DeLano, *DeLano Scientific LLC, Palo Alto, Calif., USA.* (2008).
S24. N. A. Baker, D. Sept, S. Joseph, M. J. Holst, J. A. McCammon, *Proc. Natl. Acad. Sci. U.S.A.* 98, 10037 (2001).
S25. W. F. Stafford, E. H. Braswell, *Biophys Chem.* 108, 273 (2004).
S26. K. G. Johnson et al., *Neuron* 49, 517 (2006).
S27. J. G. Flanagan, H.-J. Cheng, *Methods Enzymol.* 327, 198 (2000).
S28. J. G. Flanagan et al., *Methods Enzymol.* 327, 19 (2000).
S29. W. Kabsch, C. Sander, *Biopolymers* 22, 2577 (1983).
S30. M. C. Lawrence, P. M. Colman, *J. Mol. Biol.* 234, 946 (1993).
S31. R. Pulido, N. X. Krueger, C. Sena-Pagès, H. Saito, M. Streuli, *J. Biol. Chem.* 270, 6722 (1995).
S32. R. Pulido, C. Sena-Pagès, M. Tang, M. Streuli, *Proc. Natl. Acad. Sci. U.S.A.* 92, 11686 (1995).
S33. B. Aicher, M. M. Lerch, T. Muller, J. Schilling, A. Ullrich, *J. Cell Biol.* 138, 681 (1997).
S34. A. M. Muise et al., *Curr. Biol.* 17, 1212 (2007).
S35. K. M. Thompson et al., *Mol. Cell. Neuro.* 23, 681 (2003).

Additional information and sequences regarding PTPσ and its functional domains (e.g., first immunoglobulin-like domain) are available in Aricescu et al., 22 Mol. Cell. Biol. 1881 (2002), as well as the following GENBANK Accession Numbers: NM 130855, NM 130854, NM 130853, NM 002850 for human; and NM 011218 for mouse. For example, a purified PTPσ fragment that includes a first immunoglobulin-like domain comprises residues 47-109 or 33-123 of the amino acid sequence of NM 002850.

Example 2

Defined-Length Heparin Oligosaccharides Compete with CSPG and Promote Neurite Outgrowth The observed dichotomy in CSPG/HSPG function, mediated through a common receptor, PTPσ, is even more intriguing given that mutagenesis studies point towards a common binding site for the two proteoglycan classes [1, 2]. The affinities for the interaction of PTPσ sEcto with Neurocan and Glypican-2, as representative CSPGs and HSPGs, were measured in solid phase binding assays (data not shown). The affinities were in the same range as one another (10-20 nM $K_d$), and also similar to those determined in previous studies of CSPGs or HSPGs binding to type IIa PTPs [1, 4], although weaker than measured previously for heparin-BSA (0.3 nM) [2].

Figure 20:
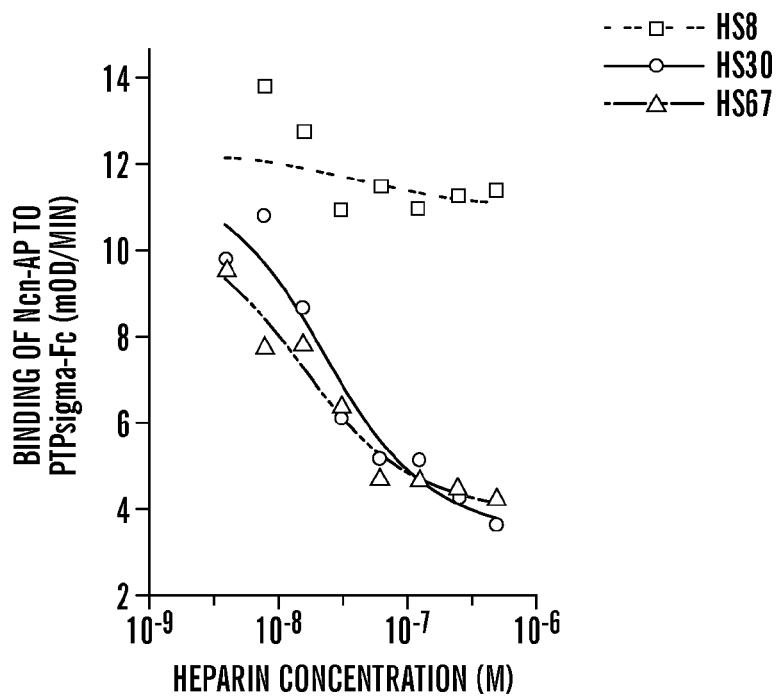
FIG. 20 is a graphical representation of data from experiments that indicate Heparin 30-mer and 67-mer inhibited interaction of the CSPG neurocan to PTPs-Fc in a solid phase binding assay. Heparin 8-mer produced little or no inhibition. IC50 values for Heparin30 and Heparin67 were 21 nM and 15 nM respectively.
Figure 21:
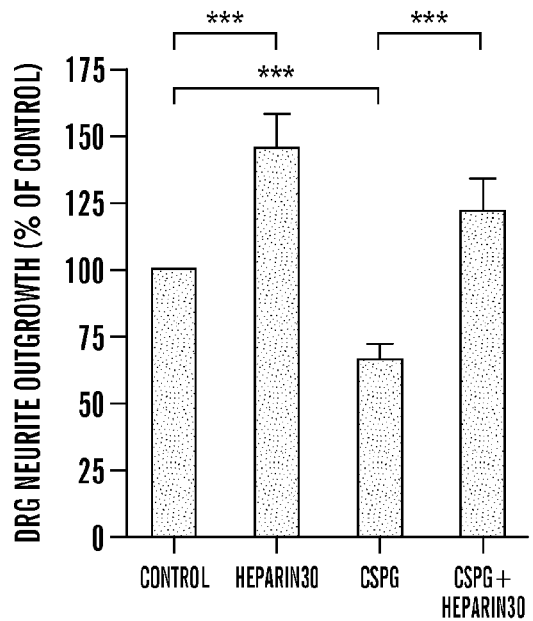
FIG. 21 is a bar graph of data from experiments that indicate Heparin 30-mer promoted neurite outgrowth in presence or absence of CSPG. ***$p \leq 0.001$
Figure 22:
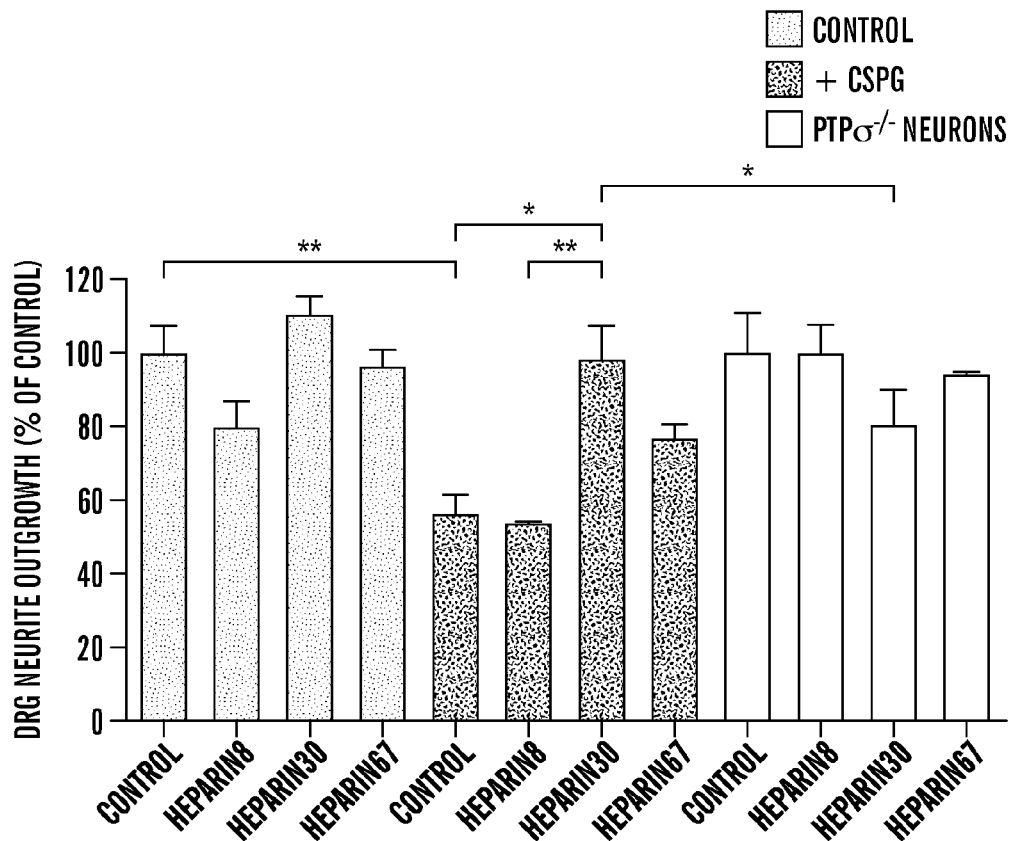
FIG. 22 is a bar graph of data from experiments that indicate Heparin8, in contrast to heparin 30, did not promote neurite outgrowth on CSPG. *$p \leq 0.5$, **$p \leq 0.01$.

The ability of defined length heparin oligosaccharides to compete with CSPGs and promote neurite outgrowth was tested. If heparins compete with CSPGs, they would have to bind to PTPσ with comparable affinity. In initial binding experiments, heparin oligosaccharides were seen to bind to PTPσ with affinities ($K_D$) of approximately 10 nM (data not shown). This is similar to the affinity of HSPGs and CSPGs binding to PTPσ, indicating that oligosaccharides should be capable of competing effectively with endogenous proteoglycans. In further experiments, the ability of heparin oligosaccharides to act as competitive inhibitors for the binding of CSPG to PTPσ was directly tested. Heparin oligosaccharides were seen to inhibit binding of the CSPG neurocan to PTPσ (FIG. 20). For heparin 30-mer and 67-mer, the IC50 for inhibition of neurocan-PTPσ binding in a solid phase assay was approximately 20 nM, very consistent with their affinity of binding to PTPσ. When a heparin 30-mer was tested in DRG neuron culture, it was observed to promote neurite outgrowth (p=0.001). Furthermore, it completely counteracted CSPG inhibition of outgrowth (p<0.001) (FIG. 21). Interestingly, a heparin 8-mer did not promote outgrowth or counteract CSPG inhibition (data not shown). As described in the previous section, heparin 8-mers were able to promote dimerization of the PTPσ ectodomain. It may be that these in vitro assays are not sensitive enough to detect neurite outgrowth induction by heparin 8-mers, or alternatively PTPσ signaling that promotes neurite outgrowth is not triggered by receptor dimerization, and instead may require higher-order clustering of the receptor. Given that heparin is in wide therapeutic use for other purposes already, defined length heparin oligosaccharides provide useful therapeutics to promote neural regeneration. These results indicate that heparin oligosaccharides can be used to promote of recovery from neuronal (e.g., CNS) injury in vivo.

REFERENCES FOR EXAMPLE 2

1. Shen, Y., Tenney, A. P., Busch, S. A., Horn, K. P., Cuascut, F. X., Liu, K., He, Z., Silver, J., and Flanagan, J. G. PTPsigma is a receptor for Chondroitin Sulfate Proteoglycan, an inhibitor of neural regeneration. *Science,* 2009. 326: p. 592-6.
2. Aricescu, A. R., McKinnell, I. W., Halfter, W., and Stoker, A. W. Heparan sulfate proteoglycans are ligands for receptor protein tyrosine phosphatase sigma. *Mol Cell Biol,* 2002. 22(6): p. 1881-92.
3. Ledig, M. M., Haj, F., Bixby, J. L., Stoker, A. W., and Mueller, B. K. The receptor tyrosine phosphatase CRYP alpha promotes intraretinal axon growth. *Journal of Cell Biology,* 1999. 147(2): p. 375-388.
4. Johnson, K. G., Tenney, A. P., Ghose, A., Duckworth, A. M., Higashi, M. E., Parfitt, K., Marcu, O., Heslip, T. R., Marsh, J. L., Schwarz, T. L., Flanagan, J. G., and Van Vactor, D. The HSPGs Syndecan and Dallylike bind the receptor phosphatase LAR and exert distinct effects on synaptic development. *Neuron,* 2006. 49(4): p. 517-31.

Example 3

Figure 23A:
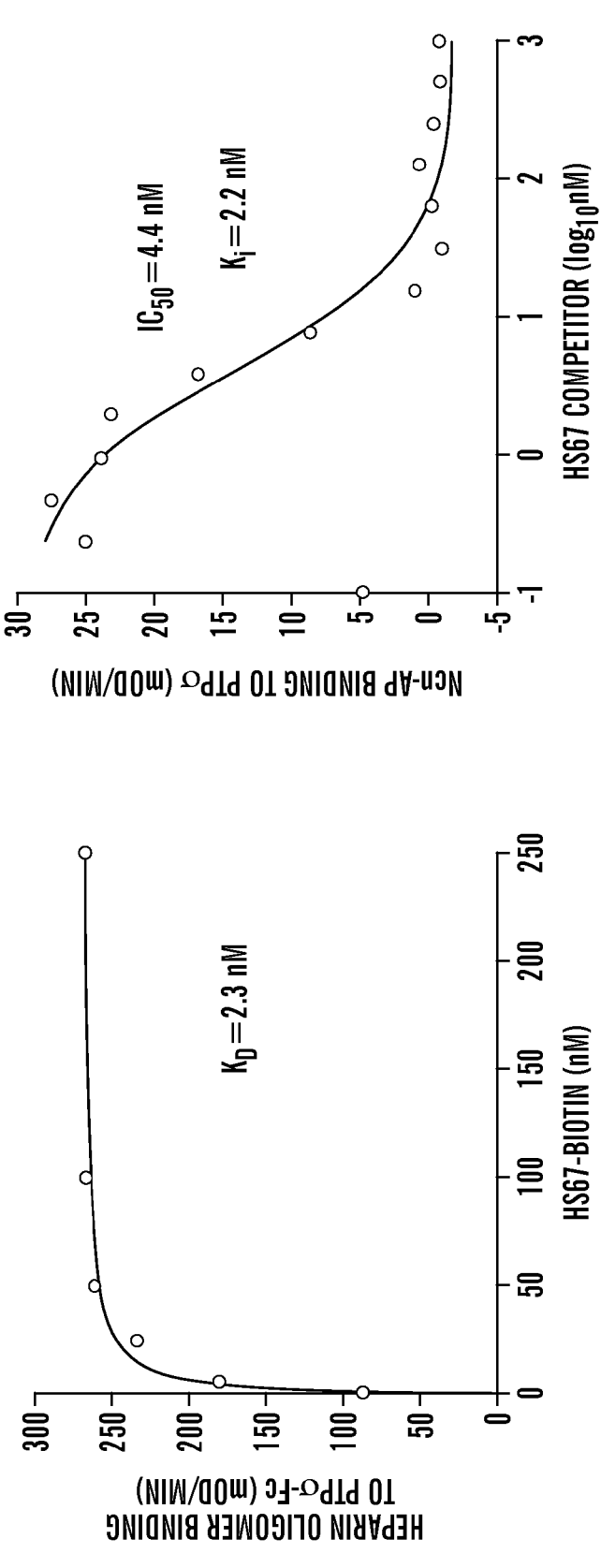
FIG. 23A and FIG. 23B are the results of experiments showing that heparin oligosaccharides bind to the extracellular domain of PTPσ, and compete for binding with CSPG.
Figure 23B:
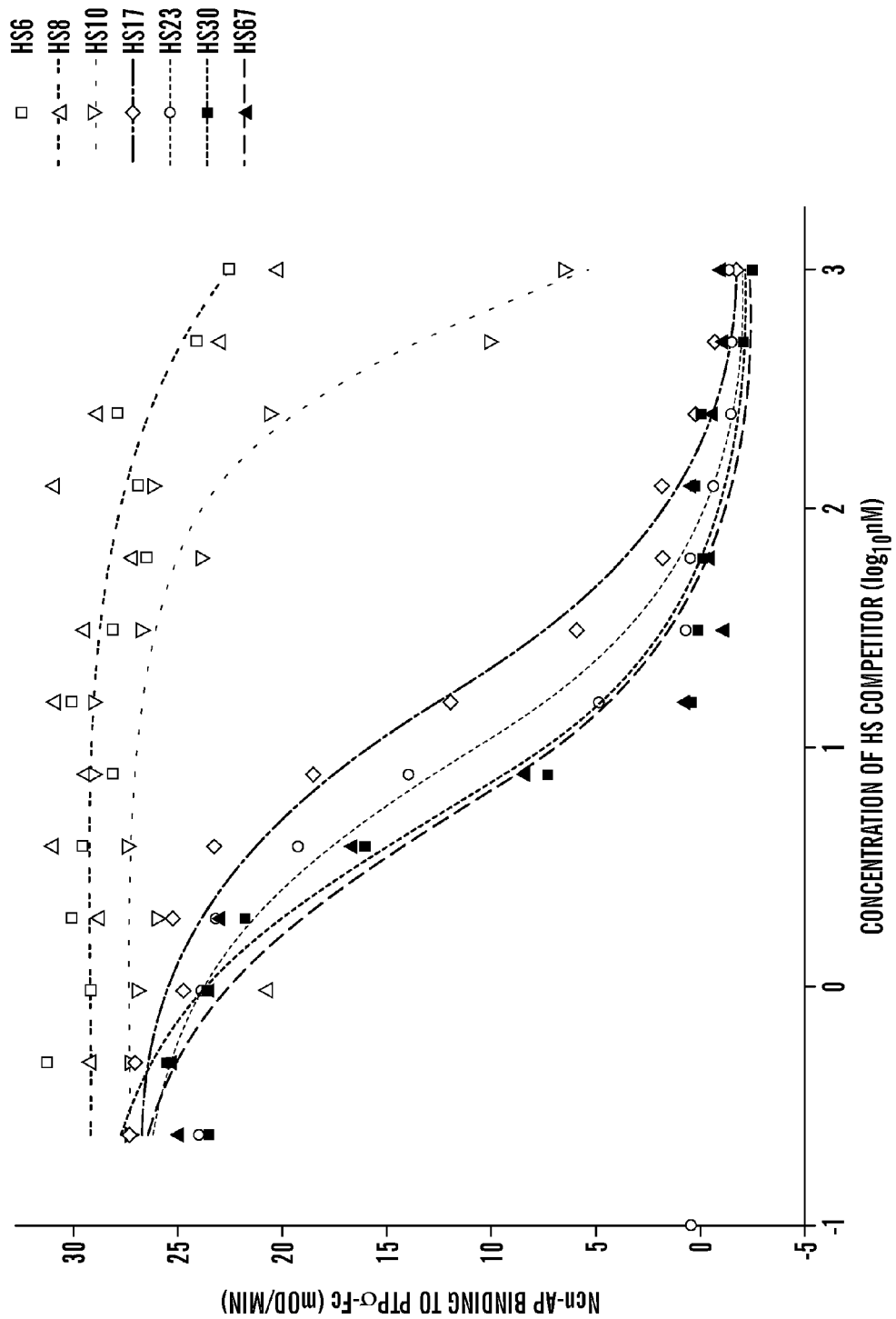

Defined-Length Heparin Oligosaccharides Compete with CSPG and Promote Axon Extension The finding that HSPG can promote axon extension through PTPσ in a manner competitive with CSPG raised a question: is the core protein of the HSPG necessary for a functional effect on axons, or might it be possible to achieve promotion of axon growth using sulfated carbohydrate chains alone? To investigate this, binding experiments were initially performed, reasoning that if heparin oligosaccharides are to reverse the functional effects of CSPG, they would need to bind to PTPσ with high affinity. The results of these experiments indeed showed that heparin oligosaccharides bound to PTPσ with high affinity, and that they inhibited the binding of CSPG to PTPσ (FIG. 23). Moreover, the affinities of oligosaccharides for PTPσ were up to 5-10 fold tighter than observed for HSPG or CSPG (FIG. 23A). This high affinity is very promising in regard to therapeutic applications, since it indicates that oligosaccharides should be capable of competing effectively with endogenous proteoglycans. The ability of oligosaccharides to compete with CSPG was dependent on length, with chains greater than 10 saccharide units showing strong competition, with inhibition constants ($K_i$) in the low nanomolar range, whereas shorter oligosaccharides competed with CSPG more weakly (FIG. 23B).

Figure 24:
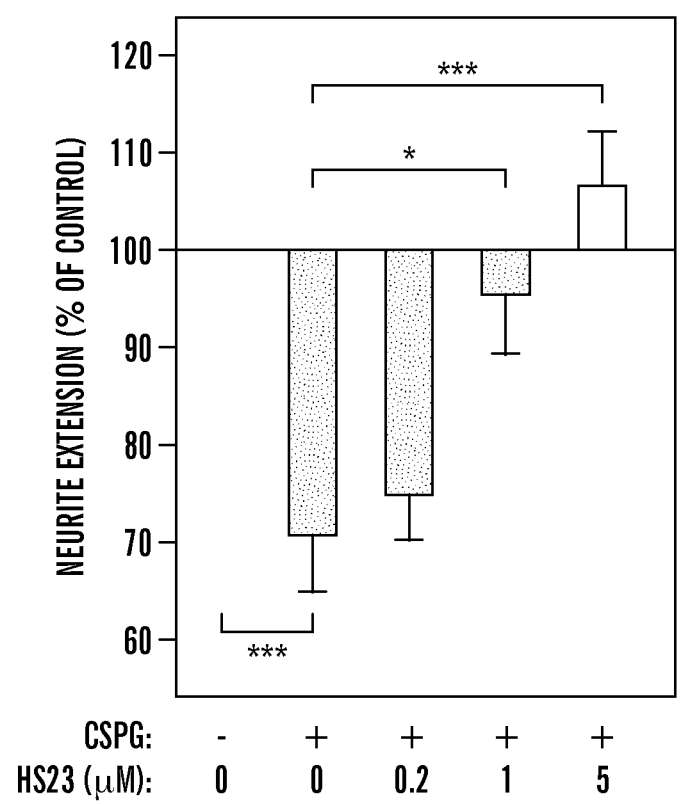
FIG. 24 shows that a heparin oligosaccharide can overcome CSPG inhibition and promote neurite extension, in a dose-dependent manner. Neurite outgrowth of dissociated mouse DRG neurons with or without CSPGs (60 µg/ml), and with HS23 at the indicated concentrations, was measured and normalized against control without CSPG or HS23. Increasing doses of HS23 incrementally reversed the CSPG inhibitory effect on neurite extension. As with the HSPG glypican 2 (FIG. 1), higher concentrations of HS23 promoted axon extension relative to control. *$p<0.05$, ***$p<0.001$.
Figure 25:
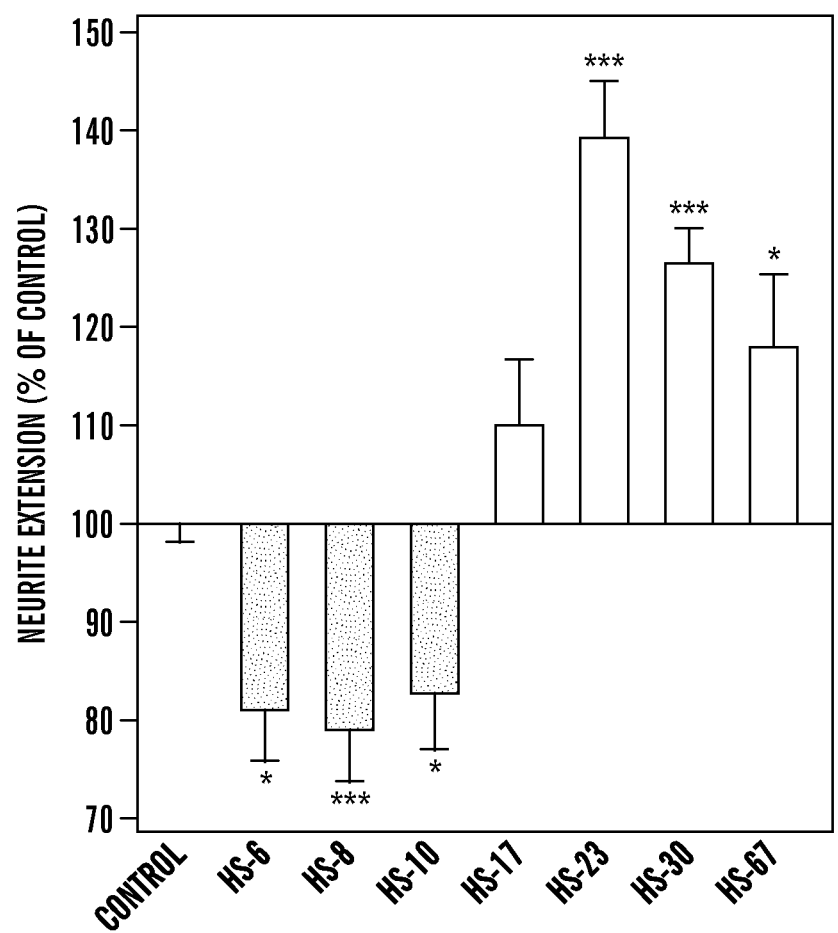
FIG. 25 shows that the effect of heparin oligosaccharides in reversing CSPG inhibition and promoting neurite outgrowth is dependent on the length of the oligosaccharides. The neurite outgrowth of dissociated mouse DRG neurons in the presence of CSPGs (60 µg/ml) and heparin oligosaccharides of indicated lengths was measured and normalized against control with CSPG and without HS. The results showed that heparin oligosaccharides with lengths greater than 10 saccharide units overcame the inhibitory effect of CSPG and promoted neurite extension; these were the same oligosaccharide lengths that were found to compete strongly with CSPG for binding to PTPσ in FIG. 23B. Shorter heparin oligosaccharides did not overcome CSPG inhibition, but rather were found to further inhibit neurite extension. *$p<0.05$, ***$p<0.001$.

The functional effect of heparin oligosaccharides on axon extension of cultured dorsal root ganglion (DRG) neurons were then tested. The results showed that heparin oligosaccharide could completely overcome the inhibition of outgrowth caused by CSPG, in a dose-dependent manner (FIG. 24). This effect on axon outgrowth was found to be strongly dependent on chain length. Oligosaccharide chains greater than 10 saccharide units in length were found to promote axon extension (FIG. 25). This length dependence is very consistent with the ability of these same oligosaccharide chains to compete at high affinity with CSPG for PTPσ binding (FIG. 23). The strongest growth promoting effects were seen for HS23 and HS30, while a promoting effect was also seen with HS67 although less strongly than HS23 in this assay ($p<0.05$ for HS23 versus HS67). In contrast, heparin chains less than or equal to 10 saccharide units in length were not found to reverse the inhibitory effects of CSPG, and instead caused further inhibition of axon extension (FIG. 25). It is interesting that heparin chains of 8 and 10 saccharide units did not promote axon growth, considering that chains of this length were able to cause dimerization of the PTPσ ectodomain (FIG. 3). These results imply that dimerization of PTPσ may not be sufficient to promote axon growth, and that higher-order oligomerization or large-scale clustering of the receptor may be required to transduce a growth-promoting signal. Given that heparin is in wide therapeutic use for other purposes already, defined length heparin oligosaccharides provide useful therapeutics to promote neural regeneration. These results indicate that heparin oligosaccharides can be used to promote of recovery from neuronal (e.g., CNS) injury in vivo.

What is claimed is:

1. A method of inducing neuronal outgrowth of a neuron comprising, contacting the neuron with glypican 2, wherein glypican 2 binds receptor protein tyrosine phosphatase σ (RPTPσ) and induces clustering of RPTPσ to induce neuronal outgrowth of the neuron.

2. The method of claim 1, wherein glypican 2 inhibits binding of chondroitin sulfate proteoglycan (CSPG) to RPTPσ.

3. The method of claim 1, wherein the method is in a human subject.

4. The method of claim 3, wherein the human subject has a spinal cord injury or stroke.

5. A method of treating neuronal injury in the spinal cord of a subject comprising, administering to the subject glypican 2, wherein glypican 2 contacts the neuron and binds RPTPσ and induces clustering of RPTPσ, to induce spinal cord neuronal outgrowth.

6. The method of claim 5, wherein the glypican 2 is administered at a site of neuronal injury, to thereby induce neuronal outgrowth at the site of neuronal injury.

7. The method of claim 5, wherein the glypican 2 inhibits binding of chondroitin sulfate proteoglycan (CSPG) to the RPTPσ.

8. A method of promoting neural outgrowth in the nervous system of a subject, comprising administering to the subject glypican 2, wherein glypican 2 contacts a neuron and binds RPTPσ and induces clustering of RPTPσ to induce neural outgrowth of the neuron.

9. The method of claim 8, wherein the neuron is located at or adjacent to a site of diseased or injured tissue.

\* \* \* \* \*

SEQUENCE LISTING

```
<160> NUMBER OF SEQ ID NOS: 31

<210> SEQ ID NO 1
<211> LENGTH: 1505
<212> TYPE: PRT
<213> ORGANISM: Homo sapiens

<400> SEQUENCE: 1

Met Ala Pro Thr Trp Gly Pro Gly Met Val Ser Val Val Gly Pro Met
1               5                   10                  15

Gly Leu Leu Val Val Leu Leu Val Gly Gly Cys Ala Ala Glu Glu Pro
            20                  25                  30

Pro Arg Phe Ile Lys Glu Pro Lys Asp Gln Ile Gly Val Ser Gly Gly
        35                  40                  45

Val Ala Ser Phe Val Cys Gln Ala Thr Gly Asp Pro Lys Pro Arg Val
    50                  55                  60
```

```
Thr Trp Asn Lys Lys Gly Lys Lys Val Asn Ser Gln Arg Phe Glu Thr
 65                  70                  75                  80
Ile Glu Phe Asp Glu Ser Ala Gly Ala Val Leu Arg Ile Gln Pro Leu
                 85                  90                  95
Arg Thr Pro Arg Asp Glu Asn Val Tyr Glu Cys Val Ala Gln Asn Ser
            100                 105                 110
Val Gly Glu Ile Thr Val His Ala Lys Leu Thr Val Leu Arg Glu Asp
        115                 120                 125
Gln Leu Pro Ser Gly Phe Pro Asn Ile Asp Met Gly Pro Gln Leu Lys
130                 135                 140
Val Val Glu Arg Thr Arg Thr Ala Thr Met Leu Cys Ala Ala Ser Gly
145                 150                 155                 160
Asn Pro Asp Pro Glu Ile Thr Trp Phe Lys Asp Phe Leu Pro Val Asp
                165                 170                 175
Pro Ser Ala Ser Asn Gly Arg Ile Lys Gln Leu Arg Ser Gly Ala Leu
            180                 185                 190
Gln Ile Glu Ser Ser Glu Glu Thr Asp Gln Gly Lys Tyr Glu Cys Val
        195                 200                 205
Ala Thr Asn Ser Ala Gly Val Arg Tyr Ser Ser Pro Ala Asn Leu Tyr
210                 215                 220
Val Arg Glu Leu Arg Glu Val Arg Arg Val Ala Pro Arg Phe Ser Ile
225                 230                 235                 240
Leu Pro Met Ser His Glu Ile Met Pro Gly Gly Asn Val Asn Ile Thr
                245                 250                 255
Cys Val Ala Val Gly Ser Pro Met Pro Tyr Val Lys Trp Met Gln Gly
            260                 265                 270
Ala Glu Asp Leu Thr Pro Glu Asp Asp Met Pro Val Gly Arg Asn Val
        275                 280                 285
Leu Glu Leu Thr Asp Val Lys Asp Ser Ala Asn Tyr Thr Cys Val Ala
290                 295                 300
Met Ser Ser Leu Gly Val Ile Glu Ala Val Ala Gln Ile Thr Val Lys
305                 310                 315                 320
Ser Leu Pro Lys Ala Pro Gly Thr Pro Met Val Thr Glu Asn Thr Ala
                325                 330                 335
Thr Ser Ile Thr Ile Thr Trp Asp Ser Gly Asn Pro Asp Pro Val Ser
            340                 345                 350
Tyr Tyr Val Ile Glu Tyr Lys Ser Lys Ser Gln Asp Gly Pro Tyr Gln
        355                 360                 365
Ile Lys Glu Asp Ile Thr Thr Thr Arg Tyr Ser Ile Gly Gly Leu Ser
370                 375                 380
Pro Asn Ser Glu Tyr Glu Ile Trp Val Ser Ala Val Asn Ser Ile Gly
385                 390                 395                 400
Gln Gly Pro Pro Ser Glu Ser Val Val Thr Arg Thr Gly Glu Gln Ala
                405                 410                 415
Pro Ala Ser Ala Pro Arg Asn Val Gln Ala Arg Met Leu Ser Ala Thr
            420                 425                 430
Thr Met Ile Val Gln Trp Glu Glu Pro Val Glu Pro Asn Gly Leu Ile
        435                 440                 445
Arg Gly Tyr Arg Val Tyr Tyr Thr Met Glu Pro Glu His Pro Val Gly
            450                 455                 460
Asn Trp Gln Lys His Asn Val Asp Asp Ser Leu Leu Thr Thr Val Gly
465                 470                 475                 480
```

```
Ser Leu Leu Glu Asp Glu Thr Tyr Thr Val Arg Val Leu Ala Phe Thr
                485                 490                 495

Ser Val Gly Asp Gly Pro Leu Ser Asp Pro Ile Gln Val Lys Thr Gln
            500                 505                 510

Gln Gly Val Pro Gly Gln Pro Met Asn Leu Arg Ala Glu Ala Arg Ser
            515                 520                 525

Glu Thr Ser Ile Thr Leu Ser Trp Ser Pro Pro Arg Gln Glu Ser Ile
        530                 535                 540

Ile Lys Tyr Glu Leu Leu Phe Arg Glu Gly Asp His Gly Arg Glu Val
545                 550                 555                 560

Gly Arg Thr Phe Asp Pro Thr Thr Ser Tyr Val Val Glu Asp Leu Lys
                565                 570                 575

Pro Asn Thr Glu Tyr Ala Phe Arg Leu Ala Ala Arg Ser Pro Gln Gly
            580                 585                 590

Leu Gly Ala Phe Thr Pro Val Val Arg Gln Arg Thr Leu Gln Ser Ile
            595                 600                 605

Ser Pro Lys Asn Phe Lys Val Lys Met Ile Met Lys Thr Ser Val Leu
        610                 615                 620

Leu Ser Trp Glu Phe Pro Asp Asn Tyr Asn Ser Pro Thr Pro Tyr Lys
625                 630                 635                 640

Ile Gln Tyr Asn Gly Leu Thr Leu Asp Val Asp Gly Arg Thr Thr Lys
                645                 650                 655

Lys Leu Ile Thr His Leu Lys Pro His Thr Phe Tyr Asn Phe Val Leu
            660                 665                 670

Thr Asn Arg Gly Ser Ser Leu Gly Gly Leu Gln Gln Thr Val Thr Ala
            675                 680                 685

Trp Thr Ala Phe Asn Leu Leu Asn Gly Lys Pro Ser Val Ala Pro Lys
        690                 695                 700

Pro Asp Ala Asp Gly Phe Ile Met Val Tyr Leu Pro Asp Gly Gln Ser
705                 710                 715                 720

Pro Val Pro Val Gln Ser Tyr Phe Ile Val Met Val Pro Leu Arg Lys
                725                 730                 735

Ser Arg Gly Gly Gln Phe Leu Thr Pro Leu Gly Ser Pro Glu Asp Met
            740                 745                 750

Asp Leu Glu Glu Leu Ile Gln Asp Ile Ser Arg Leu Gln Arg Arg Ser
            755                 760                 765

Leu Arg His Ser Arg Gln Leu Glu Val Pro Arg Pro Tyr Ile Ala Ala
        770                 775                 780

Arg Phe Ser Val Leu Pro Pro Thr Phe His Pro Gly Asp Gln Lys Gln
785                 790                 795                 800

Tyr Gly Gly Phe Asp Asn Arg Gly Leu Glu Pro Gly His Arg Tyr Val
                805                 810                 815

Leu Phe Val Leu Ala Val Leu Gln Lys Ser Glu Pro Thr Phe Ala Ala
            820                 825                 830

Ser Pro Phe Ser Asp Pro Phe Gln Leu Asp Asn Pro Asp Pro Gln Pro
        835                 840                 845

Ile Val Asp Gly Glu Glu Gly Leu Ile Trp Val Ile Gly Pro Val Leu
850                 855                 860

Ala Val Val Phe Ile Ile Cys Ile Val Ile Ala Ile Leu Leu Tyr Lys
865                 870                 875                 880

Asn Lys Pro Asp Ser Lys Arg Lys Asp Ser Glu Pro Arg Thr Lys Cys
                885                 890                 895

Leu Leu Asn Asn Ala Asp Leu Ala Pro His His Pro Lys Asp Pro Val
```

-continued

```
                900             905             910
Glu Met Arg Arg Ile Asn Phe Gln Thr Pro Gly Met Leu Ser His Pro
        915             920             925
Pro Ile Pro Ile Ala Asp Met Ala Glu His Thr Glu Arg Leu Lys Ala
        930             935             940
Asn Asp Ser Leu Lys Leu Ser Gln Glu Tyr Glu Ser Ile Asp Pro Gly
945             950             955             960
Gln Gln Phe Thr Trp Glu His Ser Asn Leu Glu Val Asn Lys Pro Lys
            965             970             975
Asn Arg Tyr Ala Asn Val Ile Ala Tyr Asp His Ser Arg Val Ile Leu
            980             985             990
Gln Pro Ile Glu Gly Ile Met Gly Ser Asp Tyr Ile Asn Ala Asn Tyr
        995             1000            1005
Val Asp Gly Tyr Arg Cys Gln Asn Ala Tyr Ile Ala Thr Gln Gly
    1010            1015            1020
Pro Leu Pro Glu Thr Phe Gly Asp Phe Trp Arg Met Val Trp Glu
    1025            1030            1035
Gln Arg Ser Ala Thr Ile Val Met Met Thr Arg Leu Glu Glu Lys
    1040            1045            1050
Ser Arg Ile Lys Cys Asp Gln Tyr Trp Pro Asn Arg Gly Thr Glu
    1055            1060            1065
Thr Tyr Gly Phe Ile Gln Val Thr Leu Leu Asp Thr Ile Glu Leu
    1070            1075            1080
Ala Thr Phe Cys Val Arg Thr Phe Ser Leu His Lys Asn Gly Ser
    1085            1090            1095
Ser Glu Lys Arg Glu Val Arg Gln Phe Gln Phe Thr Ala Trp Pro
    1100            1105            1110
Asp His Gly Val Pro Glu Tyr Pro Thr Pro Phe Leu Ala Phe Leu
    1115            1120            1125
Arg Arg Val Lys Thr Cys Asn Pro Pro Asp Ala Gly Pro Ile Val
    1130            1135            1140
Val His Cys Ser Ala Gly Val Gly Arg Thr Gly Cys Phe Ile Val
    1145            1150            1155
Ile Asp Ala Met Leu Glu Arg Ile Lys Pro Glu Lys Thr Val Asp
    1160            1165            1170
Val Tyr Gly His Val Thr Leu Met Arg Ser Gln Arg Asn Tyr Met
    1175            1180            1185
Val Gln Thr Glu Asp Gln Tyr Ser Phe Ile His Glu Ala Leu Leu
    1190            1195            1200
Glu Ala Val Gly Cys Gly Asn Thr Glu Val Pro Ala Arg Ser Leu
    1205            1210            1215
Tyr Ala Tyr Ile Gln Lys Leu Ala Gln Val Glu Pro Gly Glu His
    1220            1225            1230
Val Thr Gly Met Glu Leu Glu Phe Lys Arg Leu Ala Asn Ser Lys
    1235            1240            1245
Ala His Thr Ser Arg Phe Ile Ser Ala Asn Leu Pro Cys Asn Lys
    1250            1255            1260
Phe Lys Asn Arg Leu Val Asn Ile Met Pro Tyr Glu Ser Thr Arg
    1265            1270            1275
Val Cys Leu Gln Pro Ile Arg Gly Val Glu Gly Ser Asp Tyr Ile
    1280            1285            1290
Asn Ala Ser Phe Ile Asp Gly Tyr Arg Gln Gln Lys Ala Tyr Ile
    1295            1300            1305
```

```
Ala Thr Gln Gly Pro Leu Ala Glu Thr Thr Glu Asp Phe Trp Arg
    1310            1315                1320
Met Leu Trp Glu Asn Asn Ser Thr Ile Val Val Met Leu Thr Lys
    1325            1330                1335
Leu Arg Glu Met Gly Arg Glu Lys Cys His Gln Tyr Trp Pro Ala
    1340            1345                1350
Glu Arg Ser Ala Arg Tyr Gln Tyr Phe Val Val Asp Pro Met Ala
    1355            1360                1365
Glu Tyr Asn Met Pro Gln Tyr Ile Leu Arg Glu Phe Lys Val Thr
    1370            1375                1380
Asp Ala Arg Asp Gly Gln Ser Arg Thr Val Arg Gln Phe Gln Phe
    1385            1390                1395
Thr Asp Trp Pro Glu Gln Gly Val Pro Lys Ser Gly Glu Gly Phe
    1400            1405                1410
Ile Asp Phe Ile Gly Gln Val His Lys Thr Lys Glu Gln Phe Gly
    1415            1420                1425
Gln Asp Gly Pro Ile Ser Val His Cys Ser Ala Gly Val Gly Arg
    1430            1435                1440
Thr Gly Val Phe Ile Thr Leu Ser Ile Val Leu Glu Arg Met Arg
    1445            1450                1455
Tyr Glu Gly Val Val Asp Ile Phe Gln Thr Val Lys Met Leu Arg
    1460            1465                1470
Thr Gln Arg Pro Ala Met Val Gln Thr Glu Asp Glu Tyr Gln Phe
    1475            1480                1485
Cys Tyr Gln Ala Ala Leu Glu Tyr Leu Gly Ser Phe Asp His Tyr
    1490            1495                1500
Ala Thr
    1505

<210> SEQ ID NO 2
<211> LENGTH: 6018
<212> TYPE: DNA
<213> ORGANISM: Homo sapiens

<400> SEQUENCE: 2
cctcgcgccg cccgcccggc agcccggccg gcgcgcgcac gccgcgagcc gctggcgctc      60
gggctccgct cggatcccat gcaacagcca cgatgtgaag cggggcagag ccggggagc     120 ccagcccagc cagcctccag acgttgcccc atctgacgct cggctcgagg cctctctgtg    180
agggaccggg gggccatccc cctccagggc ggagatcgga ggtcgctgcc aagcatggcg    240
cccacctggg gcctggcat ggtgtctgtg gttggtccca tgggcctcct tgtggtcctg    300
ctcgttggag gctgtgcagc agaagagccc cccaggttta tcaaagaacc caaggaccag    360
atcggcgtgt cggggggtgt ggcctctttc gtgtgtcagg ccacgggtga ccccaagcca    420
cgagtgacct ggaacaagaa gggcaagaag gtcaactctc agcgctttga cgcgattgag    480
tttgatgaga gtgcaggggc agtgctgagg atccagccgc tgaggacacc gcgggatgaa    540
aacgtgtacg agtgtgtggc ccagaactcg gttggggaga tcacagtcca tgccaagctt    600
actgtcctcc gagaggacca gctgccctct ggcttcccca acatcgacat gggcccacag    660
ttgaaggtgg tggagcggac acggacagcc accatgctct gtgcagccag cggcaaccct    720
gaccctgaga tcacctggtt caaggactc ctgcctgtgg atcctagtgc cagcaatgga    780
cgcatcaaac agctgcgatc aggagccctg cagattgaaa gcagtgagga aaccgaccag    840
```

```
ggcaaatatg agtgtgtggc caccaacagc gccggcgtgc gctactcctc acctgccaac    900
ctctacgtgc gagagcttcg agaagtccgc cgcgttctc catcctgccc               960
atgagccacg agatcatgcc agggggcaac gtgaacatca cctgcgtggc cgtgggctcg   1020
cccatgccat acgtgaagtg gatgcagggg gccgaggacc tgaccccga ggatgacatg    1080
cccgtgggtc ggaacgtgct ggaactcaca gatgtcaagg actcggccaa ctacacctgc   1140
gtggccatgt ccagcctggg cgtcattgag gcggttgctc agatcacggt gaaatctctc   1200
cccaaagctc ccgggactcc catggtgact gagaacacag ccaccagcat caccatcacg   1260
tgggactcgg gcaacccaga tcctgtgtcc tattacgtca tcgaatataa atccaagagc   1320
caagacgggc cgtatcagat aaagaggac atcaccacca cacgttacag catcggcggc    1380
ctgagcccca actcggagta cgagatctgg gtgtcggccg tcaactccat cggccagggg   1440
cccccccagcg agtccgtggt caccgcaca ggcgagcagg cccggccag cgcgccgcgg    1500
aacgtgcaag cccggatgct cagcgcgacc accatgattg tgcagtggga ggagccggtg   1560
gagcccaacg gcctgatccg cggctaccgc gtctactaca ccatggaacc ggagcacccc   1620
gtgggcaact ggcagaagca caacgtggac gacagcctgc tgaccaccgt gggcagcctg   1680
ctggaggacg agacctacac cgtgcgggtg ctcgccttca cctccgtcgg cgacgggccc   1740
ctctcggacc ccatccaggt caagacgcag cagggagtgc cgggccagcc catgaacctg   1800
cgggccgagg ccaggtcgga gaccagcatc acgctgtcct ggagccccc gcggcaggag    1860
agtatcatca gtacgagct cctcttccgg gaaggcgacc atggccggga ggtgggaagg   1920
accttcgacc cgacgacttc ctacgtggtg gaggacctga agcccaacac ggagtacgcc   1980
ttccgcctgg cggcccgctc gccgcagggc ctgggcgcct tcacccccgt ggtgcggcag   2040
cgcacgctgc agtccatctc gcccaagaac ttcaaggtga aaatgatcat gaagacatca   2100
gttctgctca gctgggagtt ccctgacaac tacaactcac ccacacccta caagatccag   2160
tacaatgggc tcacactgga gtggatggc cgtaccacca gaagctcat cacgcacctc     2220
aagcccccaca ccttctacaa ctttgtgctg accaatcgcg gcagcagcct gggcggcctc   2280
cagcagacgg tcaccgcctg gactgccttc aacctgctca acggcaagcc cagcgtcgcc   2340
cccaagcctg atgctgacgg cttcatcatg gtgtatcttc ctgacggcca gagccccgtg   2400
cctgtccaga gctatttcat tgtgatggtg ccactgcgca gtctcgtgg aggccaattc    2460
ctgaccccgc tgggtagccc agaggacatg gatctggaag agctcatcca ggacatctca   2520
cggctacaga ggcgcagcct gcggcactcg cgtcagctgg aggtgccccg gccctatatt   2580
gcagctcgct tctctgtgct gccacccacg ttccatcccg gcgaccagaa gcagtatggc   2640
ggcttcgata accggggcct ggagcccggc caccgctatg tcctcttcgt gcttgccgtg   2700
cttcagaaga gcgagcctac ctttgcagcc agtcccttct cagacccctt ccagctggat   2760
aacccggacc cccagcccat cgtggatggc gaggaggggc ttatctgggt gatcgggcct   2820
gtgctggccg tggtcttcat aatctgcatt gtcattgcta tcctgctcta caagaacaaa   2880
cccgacagta acgcaagga ctcagaaccc cgcaccaaat gcctcctgaa caatgccgac   2940
ctcgcccctc accacccaa ggaccctgtg gaaatgagac gcattaactt ccagactcca   3000
ggcatgctta gccacccgcc aattcccatc gcagacatgg cggagcacac ggagcggctc   3060
aaggccaacg acagcctcaa gctctcccag gagtatgagt ccatcgaccc tggacagcag   3120
ttcacatggg aacattccaa cctggaagtg aacaagccga gaaccgcta tgccaacgtc   3180
atcgcctatg accactcccg tgtcatcctc cagcccattg aaggcatcat gggcagtgat   3240
```

```
tacatcaatg ccaactacgt ggacggctac cggtgtcaga acgcgtacat tgccacgcag    3300
gggccgctgc ctgagacctt tggggacttc tggcgtatgg tgtgggagca gcggtcggcg    3360
accatcgtca tgatgacgcg gctggaggag aagtcacgga tcaagtgtga tcagtattgg    3420
cccaacagag gcacggagac ctacggcttc atccaggtca cgttgctaga taccatcgag    3480
ctggccacat tctgcgtcag gacattctct ctgcacaaga atggctccag tgagaaacgc    3540
gaggtccgcc agttccagtt tacggcgtgg ccggaccatg gcgtgcccga atacccaacg    3600
cccttcctgg ctttcctgcg gagagtcaag acctgcaacc cgccagatgc cggccccatc    3660
gtggttcact gcagtgccgg tgtgggccgc acaggctgct ttatcgtcat cgacgccatg    3720
cttgagcgga tcaagccaga aagacagtc gatgtctatg ccacgtgac gctcatgagg    3780 tcccagcgca actacatggt gcagacggag accagtaca gcttcatcca cgaggccctg    3840
ctggaggccg tgggctgtgg caacacagaa gtgcccgcac gcagcctcta tgcctacatc    3900
cagaagctgg cccaggtgga gcctggcgaa acgtcactg gcatggaact cgagttcaag    3960
cggctggcta actccaaggc ccacacgtca cgcttcatca gtgccaatct gccttgtaac    4020
aagttcaaga accgcctggt gaacatcatg ccctatgaga gcacacgggt ctgtctgcaa    4080
cccatccggg gtgtggaggg ctctgactac atcaacgcca gcttcattga tggctacagg    4140
cagcagaagg cctacatcgc gacacagggg ccgctggcgg agaccacgga agacttctgg    4200
cgcatgctgt gggagaacaa ttcgacgatc gtggtgatgc tgaccaagct gcgggagatg    4260
ggccgggaga agtgtcacca gtactggccg gccgagcgct ctgcccgcta ccagtacttt    4320
gtggtagatc cgatggcaga atacaacatg cctcagtata tcctgcgaga gttcaaggtc    4380
acagatgccc gggatggcca gtcccggact gtccggcagt tccagttcac agactggccg    4440
gaacagggtg tgccaaagtc gggggagggc ttcatcgact tcattggcca agtgcataag    4500
actaaggagc agtttggcca ggacggcccc atctctgtcc actgcagtgc cggcgtgggc    4560
aggacgggcg tcttcatcac gcttagcatc gtgctggagc ggatgcggta tgaaggcgtg    4620
gtggacatct ttcagacggt gaagatgcta cgaacccagc ggccggccat ggtgcagaca    4680
gaggatgagt accagttctg ttaccaggcg gcactggagt acctcggaag ctttgaccac    4740
tatgcaacct aaagccatgg ttcccccag gcccgacacc actggccccg gatgcctctg    4800
cccctcccgg gcggacctcc tgaggcctgg accccagtg gcagggcag gaggtggcag    4860 cggcagcagc tgtgtttctg caccatttcc gaggacgacg cagcccctcg agccccccca    4920
ccggccccgg ccgccccagc gacctccctg gcaccggccg ccgccttcaa atacttggca    4980
cattcctcct ttccttccaa ttccaaaacc agattccggg gtggggggtg gggggatggt    5040
gagcaaatag gagtgctccc cagaaccaga ggagggtggg gcacagacca tagacggacc    5100
cctcgtcctc ccccagcggt ggtaggggga cccggggggc tcctccccgc tctgcagcct    5160
ggggacactg ggctgggacc agaatccagc tttcttttaa aactctcagt gtaactgtat    5220
cccgtgacat tcatttttt taaatagtg tatttttttt tccattttt tttttaagag    5280 aaacaaacaa aagactcgcc agtcaatgac tttcaaagag aactaacttt ggcttattca    5340
tattctgttc aaagacagtc tattttttca ctgtagaaaa cgtccttgtg tgatagttac    5400
gttcgcaaac gcgcacgcca ggccatggc tgtaccttgg ctttttttt tttttttttt    5460 tttttaattt ttcctaccat cagaaagtgt gctttgctca cagaagaatg ggatgtcctt    5520
ttttctttct tggcttttt tttccccctt tttgtttcat tttataaat taaattttca    5580
```

-continued

```
gacatatcaa atacagttct gagggtaagg tcatgggga gctcggaccc agtggcgttg    5640
ggtgcggttg agggggacgc tgctgtaaga ggagagagat gacagtggtc ctcctctgag    5700
agcctgagct gtctccccgt ctcccgcccc aaggagaca gagaggatcc tacttcttcg    5760
gggacagtgg ctgtatggct gtgctgcccc acatcaggga ccctttcccc ctgggactgt    5820
ggggcagttt gggagcaaaa ccagaaggac aggccccct ctacccgcct accctgagca    5880
agcgagttgt tcctctttgt acaagggcag gtctgcggtt actttcaaca ctgtttattc    5940
cagcggaagc agccgggtgg ttttcccacc cccgtgtatg tagatatatc gactttgtat    6000
taaaggaaga tcgtctga                                                 6018
```

<210> SEQ ID NO 3
<211> LENGTH: 1501
<212> TYPE: PRT
<213> ORGANISM: Homo sapiens

<400> SEQUENCE: 3

```
Met Ala Pro Thr Trp Gly Pro Gly Met Val Ser Val Val Gly Pro Met
1               5                   10                  15

Gly Leu Leu Val Val Leu Val Gly Gly Cys Ala Ala Glu Glu Pro
            20                  25                  30

Pro Arg Phe Ile Lys Glu Pro Lys Asp Gln Ile Gly Val Ser Gly Gly
        35                  40                  45

Val Ala Ser Phe Val Cys Gln Ala Thr Gly Asp Pro Lys Pro Arg Val
    50                  55                  60

Thr Trp Asn Lys Lys Gly Lys Lys Val Asn Ser Gln Arg Phe Glu Thr
65                  70                  75                  80

Ile Glu Phe Asp Glu Ser Ala Gly Ala Val Leu Arg Ile Gln Pro Leu
                85                  90                  95

Arg Thr Pro Arg Asp Glu Asn Val Tyr Glu Cys Val Ala Gln Asn Ser
            100                 105                 110

Val Gly Glu Ile Thr Val His Ala Lys Leu Thr Val Leu Arg Glu Asp
        115                 120                 125

Gln Leu Pro Ser Gly Phe Pro Asn Ile Asp Met Gly Pro Gln Leu Lys
    130                 135                 140

Val Val Glu Arg Thr Arg Thr Ala Thr Met Leu Cys Ala Ala Ser Gly
145                 150                 155                 160

Asn Pro Asp Pro Glu Ile Thr Trp Phe Lys Asp Phe Leu Pro Val Asp
                165                 170                 175

Pro Ser Ala Ser Asn Gly Arg Ile Lys Gln Leu Arg Ser Gly Ala Leu
            180                 185                 190

Gln Ile Glu Ser Ser Glu Glu Thr Asp Gln Gly Lys Tyr Glu Cys Val
        195                 200                 205

Ala Thr Asn Ser Ala Gly Val Arg Tyr Ser Ser Pro Ala Asn Leu Tyr
    210                 215                 220

Val Arg Val Arg Arg Val Ala Pro Arg Phe Ser Ile Leu Pro Met Ser
225                 230                 235                 240

His Glu Ile Met Pro Gly Gly Asn Val Asn Ile Thr Cys Val Ala Val
                245                 250                 255

Gly Ser Pro Met Pro Tyr Val Lys Trp Met Gln Gly Ala Glu Asp Leu
            260                 265                 270

Thr Pro Glu Asp Asp Met Pro Val Gly Arg Asn Val Leu Glu Leu Thr
        275                 280                 285

Asp Val Lys Asp Ser Ala Asn Tyr Thr Cys Val Ala Met Ser Ser Leu
```

```
            290                 295                 300
Gly Val Ile Glu Ala Val Ala Gln Ile Thr Val Lys Ser Leu Pro Lys
305                 310                 315                 320

Ala Pro Gly Thr Pro Met Val Thr Glu Asn Thr Ala Thr Ser Ile Thr
                325                 330                 335

Ile Thr Trp Asp Ser Gly Asn Pro Asp Pro Val Ser Tyr Tyr Val Ile
                340                 345                 350

Glu Tyr Lys Ser Lys Ser Gln Asp Gly Pro Tyr Gln Ile Lys Glu Asp
                355                 360                 365

Ile Thr Thr Thr Arg Tyr Ser Ile Gly Gly Leu Ser Pro Asn Ser Glu
                370                 375                 380

Tyr Glu Ile Trp Val Ser Ala Val Asn Ser Ile Gly Gln Gly Pro Pro
385                 390                 395                 400

Ser Glu Ser Val Val Thr Arg Thr Gly Glu Gln Ala Pro Ala Ser Ala
                405                 410                 415

Pro Arg Asn Val Gln Ala Arg Met Leu Ser Ala Thr Thr Met Ile Val
                420                 425                 430

Gln Trp Glu Glu Pro Val Glu Pro Asn Gly Leu Ile Arg Gly Tyr Arg
                435                 440                 445

Val Tyr Tyr Thr Met Glu Pro Glu His Pro Val Gly Asn Trp Gln Lys
                450                 455                 460

His Asn Val Asp Asp Ser Leu Leu Thr Thr Val Gly Ser Leu Leu Glu
465                 470                 475                 480

Asp Glu Thr Tyr Thr Val Arg Val Leu Ala Phe Thr Ser Val Gly Asp
                485                 490                 495

Gly Pro Leu Ser Asp Pro Ile Gln Val Lys Thr Gln Gln Gly Val Pro
                500                 505                 510

Gly Gln Pro Met Asn Leu Arg Ala Glu Ala Arg Ser Glu Thr Ser Ile
                515                 520                 525

Thr Leu Ser Trp Ser Pro Pro Arg Gln Glu Ser Ile Ile Lys Tyr Glu
                530                 535                 540

Leu Leu Phe Arg Glu Gly Asp His Gly Arg Glu Val Gly Arg Thr Phe
545                 550                 555                 560

Asp Pro Thr Thr Ser Tyr Val Val Glu Asp Leu Lys Pro Asn Thr Glu
                565                 570                 575

Tyr Ala Phe Arg Leu Ala Ala Arg Ser Pro Gln Gly Leu Gly Ala Phe
                580                 585                 590

Thr Pro Val Val Arg Gln Arg Thr Leu Gln Ser Ile Ser Pro Lys Asn
                595                 600                 605

Phe Lys Val Lys Met Ile Met Lys Thr Ser Val Leu Leu Ser Trp Glu
610                 615                 620

Phe Pro Asp Asn Tyr Asn Ser Pro Thr Pro Tyr Lys Ile Gln Tyr Asn
625                 630                 635                 640

Gly Leu Thr Leu Asp Val Asp Gly Arg Thr Thr Lys Lys Leu Ile Thr
                645                 650                 655

His Leu Lys Pro His Thr Phe Tyr Asn Phe Val Leu Thr Asn Arg Gly
                660                 665                 670

Ser Ser Leu Gly Gly Leu Gln Gln Thr Val Thr Ala Trp Thr Ala Phe
                675                 680                 685

Asn Leu Leu Asn Gly Lys Pro Ser Val Ala Pro Lys Pro Asp Ala Asp
                690                 695                 700

Gly Phe Ile Met Val Tyr Leu Pro Asp Gly Gln Ser Pro Val Pro Val
705                 710                 715                 720
```

```
Gln Ser Tyr Phe Ile Val Met Val Pro Leu Arg Lys Ser Arg Gly Gly
                725                 730                 735

Gln Phe Leu Thr Pro Leu Gly Ser Pro Glu Asp Met Asp Leu Glu Glu
                740                 745                 750

Leu Ile Gln Asp Ile Ser Arg Leu Gln Arg Arg Ser Leu Arg His Ser
                755                 760                 765

Arg Gln Leu Glu Val Pro Arg Pro Tyr Ile Ala Ala Arg Phe Ser Val
770                 775                 780

Leu Pro Pro Thr Phe His Pro Gly Asp Gln Lys Gln Tyr Gly Gly Phe
785                 790                 795                 800

Asp Asn Arg Gly Leu Glu Pro Gly His Arg Tyr Val Leu Phe Val Leu
                805                 810                 815

Ala Val Leu Gln Lys Ser Glu Pro Thr Phe Ala Ala Ser Pro Phe Ser
                820                 825                 830

Asp Pro Phe Gln Leu Asp Asn Pro Asp Pro Gln Pro Ile Val Asp Gly
                835                 840                 845

Glu Gly Leu Ile Trp Val Ile Gly Pro Val Leu Ala Val Val Phe
850                 855                 860

Ile Ile Cys Ile Val Ile Ala Ile Leu Leu Tyr Lys Asn Lys Pro Asp
865                 870                 875                 880

Ser Lys Arg Lys Asp Ser Glu Pro Arg Thr Lys Cys Leu Leu Asn Asn
                885                 890                 895

Ala Asp Leu Ala Pro His His Pro Lys Asp Pro Val Glu Met Arg Arg
                900                 905                 910

Ile Asn Phe Gln Thr Pro Gly Met Leu Ser His Pro Pro Ile Pro Ile
                915                 920                 925

Ala Asp Met Ala Glu His Thr Glu Arg Leu Lys Ala Asn Asp Ser Leu
                930                 935                 940

Lys Leu Ser Gln Glu Tyr Glu Ser Ile Asp Pro Gly Gln Gln Phe Thr
945                 950                 955                 960

Trp Glu His Ser Asn Leu Glu Val Asn Lys Pro Lys Asn Arg Tyr Ala
                965                 970                 975

Asn Val Ile Ala Tyr Asp His Ser Arg Val Ile Leu Gln Pro Ile Glu
                980                 985                 990

Gly Ile Met Gly Ser Asp Tyr Ile Asn Ala Asn Tyr Val Asp Gly Tyr
                995                 1000                1005

Arg Cys Gln Asn Ala Tyr Ile Ala Thr Gln Gly Pro Leu Pro Glu
    1010                1015                1020

Thr Phe Gly Asp Phe Trp Arg Met Val Trp Glu Gln Arg Ser Ala
    1025                1030                1035

Thr Ile Val Met Met Thr Arg Leu Glu Glu Lys Ser Arg Ile Lys
    1040                1045                1050

Cys Asp Gln Tyr Trp Pro Asn Arg Gly Thr Glu Thr Tyr Gly Phe
    1055                1060                1065

Ile Gln Val Thr Leu Leu Asp Thr Ile Glu Leu Ala Thr Phe Cys
    1070                1075                1080

Val Arg Thr Phe Ser Leu His Lys Asn Gly Ser Ser Glu Lys Arg
    1085                1090                1095

Glu Val Arg Gln Phe Gln Phe Thr Ala Trp Pro Asp His Gly Val
    1100                1105                1110

Pro Glu Tyr Pro Thr Pro Phe Leu Ala Phe Leu Arg Arg Val Lys
    1115                1120                1125
```

Thr Cys Asn Pro Pro Asp Ala Gly Pro Ile Val Val His Cys Ser
    1130            1135            1140

Ala Gly Val Gly Arg Thr Gly Cys Phe Ile Val Ile Asp Ala Met
    1145            1150            1155

Leu Glu Arg Ile Lys Pro Glu Lys Thr Val Asp Val Tyr Gly His
    1160            1165            1170

Val Thr Leu Met Arg Ser Gln Arg Asn Tyr Met Val Gln Thr Glu
    1175            1180            1185

Asp Gln Tyr Ser Phe Ile His Glu Ala Leu Leu Glu Ala Val Gly
    1190            1195            1200

Cys Gly Asn Thr Glu Val Pro Ala Arg Ser Leu Tyr Ala Tyr Ile
    1205            1210            1215

Gln Lys Leu Ala Gln Val Glu Pro Gly Glu His Val Thr Gly Met
    1220            1225            1230

Glu Leu Glu Phe Lys Arg Leu Ala Asn Ser Lys Ala His Thr Ser
    1235            1240            1245

Arg Phe Ile Ser Ala Asn Leu Pro Cys Asn Lys Phe Lys Asn Arg
    1250            1255            1260

Leu Val Asn Ile Met Pro Tyr Glu Ser Thr Arg Val Cys Leu Gln
    1265            1270            1275

Pro Ile Arg Gly Val Glu Gly Ser Asp Tyr Ile Asn Ala Ser Phe
    1280            1285            1290

Ile Asp Gly Tyr Arg Gln Gln Lys Ala Tyr Ile Ala Thr Gln Gly
    1295            1300            1305

Pro Leu Ala Glu Thr Thr Glu Asp Phe Trp Arg Met Leu Trp Glu
    1310            1315            1320

Asn Asn Ser Thr Ile Val Val Met Leu Thr Lys Leu Arg Glu Met
    1325            1330            1335

Gly Arg Glu Lys Cys His Gln Tyr Trp Pro Ala Glu Arg Ser Ala
    1340            1345            1350

Arg Tyr Gln Tyr Phe Val Val Asp Pro Met Ala Glu Tyr Asn Met
    1355            1360            1365

Pro Gln Tyr Ile Leu Arg Glu Phe Lys Val Thr Asp Ala Arg Asp
    1370            1375            1380

Gly Gln Ser Arg Thr Val Arg Gln Phe Gln Phe Thr Asp Trp Pro
    1385            1390            1395

Glu Gln Gly Val Pro Lys Ser Gly Glu Gly Phe Ile Asp Phe Ile
    1400            1405            1410

Gly Gln Val His Lys Thr Lys Glu Gln Phe Gly Gln Asp Gly Pro
    1415            1420            1425

Ile Ser Val His Cys Ser Ala Gly Val Gly Arg Thr Gly Val Phe
    1430            1435            1440

Ile Thr Leu Ser Ile Val Leu Glu Arg Met Arg Tyr Glu Gly Val
    1445            1450            1455

Val Asp Ile Phe Gln Thr Val Lys Met Leu Arg Thr Gln Arg Pro
    1460            1465            1470

Ala Met Val Gln Thr Glu Asp Glu Tyr Gln Phe Cys Tyr Gln Ala
    1475            1480            1485

Ala Leu Glu Tyr Leu Gly Ser Phe Asp His Tyr Ala Thr
    1490            1495            1500

<210> SEQ ID NO 4
<211> LENGTH: 6006
<212> TYPE: DNA

<213> ORGANISM: Homo sapiens

<400> SEQUENCE: 4

```
cctcgcgccg cccgcccggc agcccggccg gcgcgcgcac gccgcgagcc gctggcgctc        60
gggctccgct cggatcccat gcaacagcca cgatgtgaag cggggcagag ccggggagc        120
ccagcccagc cagcctccag acgttgcccc atctgacgct cggctcgagg cctctctgtg       180
agggaccggg gggccatccc cctccagggc ggagatcgga ggtcgctgcc aagcatggcg       240
cccacctggg gccctggcat ggtgtctgtg gttggtccca tgggcctcct tgtggtcctg       300
ctcgttggag gctgtgcagc agaagagccc ccaggttta tcaaagaacc caaggaccag        360
atcggcgtgt cggggggtgt ggcctctttc gtgtgtcagg ccacgggtga ccccaagcca       420
cgagtgacct ggaacaagaa gggcaagaag gtcaactctc agcgctttga cgcgattgag       480
tttgatgaga gtgcaggggc agtgctgagg atccagccgc tgaggacacc gcgggatgaa       540
aacgtgtacg agtgtgtggc ccagaactcg gttggggaga tcacagtcca tgccaagctt       600
actgtcctcc gagaggacca gctgccctct ggcttcccca acatcgacat gggcccacag       660
ttgaaggtgg tggagcggac acggacagcc accatgctct gtgcagccag cggcaacccct      720
gaccctgaga tcacctggtt caaggacttc ctgcctgtgg atcctagtgc cagcaatgga      780
cgcatcaaac agctgcgatc aggagccctg cagattgaaa gcagtgagga aaccgaccag       840
ggcaaatatg agtgtgtggc caccaacagc gccggcgtgc gctactcctc acctgccaac       900
ctctacgtgc gagtccgccg cgtggccccg cgcttctcca tcctgcccat gagccacgag       960
atcatgccag ggggcaacgt gaacatcacc tgcgtggccg tgggctcgcc catgccatac      1020
gtgaagtgga tgcaggggcc cgaggacctg accccgagg atgacatgcc cgtgggtcgg       1080
aacgtgctgg aactcacaga tgtcaaggac tcggccaact acacctgcgt ggccatgtcc      1140
agcctgggcg tcattgaggc ggttgctcag atcacggtga aatctctccc caaagctccc      1200
gggactccca tggtgactga aacacagcc accagcatca ccatcacgtg ggactcgggc      1260
aacccagatc ctgtgtccta ttacgtcatc gaatataaat ccaagagcca agacgggccg      1320
tatcagatta agaggacat caccaccaca cgttacagca tcggcggcct gagccccaac      1380
tcggagtacg agatctgggt gtcggccgtc aactccatcg ccaggggggcc cccagcgag      1440
tccgtggtca cccgcacagg cgagcaggcc cggccagcg cgccgcggaa cgtgcaagcc      1500
cggatgctca gcgcgaccac catgattgtg cagtgggagg agcggtggga gcccaacggc      1560
ctgatccgcg gctaccgcgt ctactacacc atggaaccgg agcacccgt gggcaactgg      1620
cagaagcaca acgtggacga cagcctgctg accaccgtgg gcagcctgct ggaggacgag      1680
acctacaccg tgcgggtgct cgccttcacc tccgtcggcg acgggcccct ctcggacccc      1740
atccaggtca agacgcagca gggagtgccg ggccagccca tgaacctgcg ggccgaggcc      1800
aggtcggaga ccagcatcac gctgtcctgg agccccccgc ggcaggagag tatcatcaag      1860
tacgagctcc tcttccggga aggcgaccat ggccgggagt tgggaaggac cttcgacccg      1920
acgacttcct acgtggtgga ggacctgaag cccaacacgg agtacgcctt ccgcctggcg      1980
gcccgctcgc gcagggcct gggcgccttc accccgtgg tgcggcagcg cacgctgcag      2040
tccatctcgc ccaagaactt caaggtgaaa atgatcatga gacatcagt tctgctcagc      2100
tgggagttcc ctgacaacta caactcaccc acaccctaca agatccagta caatgggctc      2160
acactggatg tggatggccg taccaccaag aagctcatca cgcacctcaa gccccacacc      2220
ttctacaact tgtgctgac caatcgcggc agcagcctgg gcggcctcca gcagacggtc      2280
```

```
accgcctgga ctgccttcaa cctgctcaac ggcaagccca gcgtcgcccc caagcctgat    2340
gctgacggct tcatcatggt gtatcttcct gacggccaga gccccgtgcc tgtccagagc    2400
tatttcattg tgatggtgcc actgcgcaag tctcgtggag ccaattcct gaccccgctg     2460 ggtagcccag aggacatgga tctggaagag ctcatccagg acatctcacg gctacagagg    2520
cgcagcctgc ggcactcgcg tcagctggag gtgccccggc cctatattgc agctcgcttc    2580
tctgtgctgc cacccacgtt ccatcccggc gaccagaagc agtatggcgg cttcgataac    2640
cggggcctgg agcccggcca ccgctatgtc ctcttcgtgc ttgccgtgct tcagaagagc    2700
gagcctacct ttgcagccag tcccttctca gaccccttcc agctggataa cccggacccc    2760
cagcccatcg tggatggcga ggaggggctt atctgggtga tcgggcctgt gctggccgtg    2820
gtcttcataa tctgcattgt cattgctatc ctgctctaca agaacaaacc cgacagtaaa    2880
cgcaaggact cagaaccccg caccaaatgc ctcctgaaca atgccgacct cgcccctcac    2940 cacccccaagg accctgtgga aatgagacgc attaacttcc agactccagg catgcttagc    3000
cacccgccaa ttcccatcgc agacatggcg gagcacacgg agcggctcaa ggccaacgac    3060
agcctcaagc tctcccagga gtatgagtcc atcgaccctg acagcagtt cacatgggaa     3120 cattccaacc tggaagtgaa caagccgaag aaccgctatg ccaacgtcat cgcctatgac    3180
cactcccgtg tcatcctcca gcccattgaa ggcatcatgg gcagtgatta tcatcaatgcc   3240 aactacgtgg acggctaccg tgtcagaaac gcgtacattg ccacgcaggg gccgctgcct    3300
gagacctttg gggacttctg gcgtatggtg tgggagcagc ggtcggcgac catcgtcatg    3360
atgacgcggc tggaggagaa gtcacggatc aagtgtgatc agtattggcc caacagaggc    3420
acggagacct acggcttcat ccaggtcacg ttgctagata ccatcgagct ggccacattc    3480
tgcgtcagga cattctctct gcacaagaat ggctccagtg agaaacgcga ggtccgccag    3540
ttccagttta cggcgtggcc ggaccatggc gtgcccgaat acccaacgcc cttcctggct    3600
ttcctgcgga gagtcaagac ctgcaacccg ccagatgccg gccccatcgt ggttcactgc    3660
agtgccggtg tgggccgcac aggctgcttt atcgtcatcg acgccatgct tgagcggatc    3720
aagccagaga agacagtcga tgtctatggc cacgtgacgc tcatgaggtc ccagcgcaac    3780
tacatggtgc agacgaggac ccagtacagc ttcatccacg aggccctgct ggaggccgtg    3840
ggctgtggca acacagaagt gcccgcacgc agcctctatg cctacatcca gaagctggcc    3900
caggtggagc ctggcgaaca cgtcactggc atggaactcg agttcaagcg gctggctaac    3960
tccaaggccc acacgtcacg cttcatcagt gccaatctgc cttgtaacaa gttcaagaac    4020
cgcctggtga acatcatgcc ctatgagagc acacgggtct gtctgcaacc catccggggt    4080
gtggagggct ctgactacat caacgccagc ttcattgatg gctacaggca gcagaaggcc    4140
tacatcgcga cacaggggcc gctggcggag accacggaag acttctggcg catgctgtgg    4200
gagaacaatt cgacgatcgt ggtgatgctg accaagctgc gggagatggg ccgggagaag    4260
tgtcaccagt actggccggc cgagcgctct gcccgctacc agtactttgt ggtagatccg    4320
atggcagaat acaacatgcc tcagtatatc ctgcgagagt tcaaggtcac agatgcccgg    4380
gatgccagtc ccggactgt ccggcagttc cagttcacag actggccgga acagggtgtg     4440
ccaaagtcgg gggagggctt catcgacttc attggccaag tgcataagac taaggagcag    4500
tttggccagg acgccccat ctctgtccac tgcagtgccg cgtgggcag gacgggcgtc      4560 ttcatcacgc ttagcatcgt gctggagcgg atgcggtatg aaggcgtggt ggacatcttt    4620
```

```
cagacggtga agatgctacg aacccagcgg ccggccatgg tgcagacaga ggatgagtac    4680
cagttctgtt accaggcggc actggagtac ctcggaagct ttgaccacta tgcaacctaa    4740
agccatggtt ccccccaggc ccgacaccac tggccccgga tgcctctgcc cctcccgggc    4800
ggacctcctg aggcctggac ccccagtggg cagggcagga ggtggcagcg cagcagctg    4860 tgtttctgca ccatttccga ggacgacgca gcccctcgag cccccccacc ggccccggcc    4920
gccccagcga cctccctggc accggccgcc gccttcaaat acttggcaca ttcctccttt    4980
ccttccaatt ccaaaaccag attccggggt gggggtgggg gggatggtga gcaaatagga    5040
gtgctcccca gaaccagagg agggtgggge acagaccata gacggacccc tcgtcctccc    5100
ccagcggtgg taggggggacc cgggggggctc ctccccgctc tgcagcctgg ggacactggg    5160
ctgggaccag aatccagctt tcttttaaaa ctctcagtgt aactgtatcc cgtgacattt    5220 cattttttt aaatagtgta tttttttttc catttttttt tttaagagaa acaaacaaaa    5280
gactcgccag tcaatgactt tcaaagagaa ctaactttgg cttattcata ttctgttcaa    5340
agacagtcta ttttttcact gtagaaagcg tccttgtgtg atagttacgt tcgcaaacgc    5400
gcacgccagg cccatggctg taccttggct tttttttttt tttttttttt tttaatttt    5460 cctaccatca gaaagtgtgc tttgctcaca gaagaatggg atgtccttt ttctttcttg    5520 gcttttttt tccccctttt tgtttcattt ttataaatta aattttcaga catatcaaat    5580
acagttctga gggtaaggtc atgggggagc tcggacccag tggcgttggg tgcggttgag    5640
ggggacgctg ctgtaagagg agagagatga cagtggtcct cctctgagag cctgagctgt    5700
ctccccgtct cccgccccca aggagacaga gaggatccta cttcttcggg gacagtggct    5760
gtatggctgt gctgccccac atcagggacc cttttccccct gggactgtgg ggcagtttgg    5820
gagcaaaacc agaaggacag gccccctct acccgcctac cctgagcaag cgagttgttc    5880
ctctttgtac aagggcaggt ctgcggttac tttcaacact gtttattcca gcggaagcag    5940
ccgggtggtt tcccacccc cgtgtatgta gatatatcga ctttgtatta aaggaagatc    6000
gtctga                                                               6006
```

<210> SEQ ID NO 5
<211> LENGTH: 1948
<212> TYPE: PRT
<213> ORGANISM: Homo sapiens

<400> SEQUENCE: 5

Met Ala Pro Thr Trp Gly Pro Gly Met Val Ser Val Val Gly Pro Met
1               5                   10                  15

Gly Leu Leu Val Val Leu Val Gly Gly Cys Ala Ala Glu Glu Pro
            20                  25                  30

Pro Arg Phe Ile Lys Glu Pro Lys Asp Gln Ile Gly Val Ser Gly Gly
        35                  40                  45

Val Ala Ser Phe Val Cys Gln Ala Thr Gly Asp Pro Lys Pro Arg Val
    50                  55                  60

Thr Trp Asn Lys Lys Gly Lys Lys Val Asn Ser Gln Arg Phe Glu Thr
65                  70                  75                  80

Ile Glu Phe Asp Glu Ser Ala Gly Ala Val Leu Arg Ile Gln Pro Leu
                85                  90                  95

Arg Thr Pro Arg Asp Glu Asn Val Tyr Glu Cys Val Ala Gln Asn Ser
            100                 105                 110

Val Gly Glu Ile Thr Val His Ala Lys Leu Thr Val Leu Arg Glu Asp
        115                 120                 125

```
Gln Leu Pro Ser Gly Phe Pro Asn Ile Asp Met Gly Pro Gln Leu Lys
    130                 135                 140

Val Val Glu Arg Thr Arg Thr Ala Thr Met Leu Cys Ala Ala Ser Gly
145                 150                 155                 160

Asn Pro Asp Pro Glu Ile Thr Trp Phe Lys Asp Phe Leu Pro Val Asp
                165                 170                 175

Pro Ser Ala Ser Asn Gly Arg Ile Lys Gln Leu Arg Ser Glu Thr Phe
            180                 185                 190

Glu Ser Thr Pro Ile Arg Gly Ala Leu Gln Ile Glu Ser Ser Glu Glu
        195                 200                 205

Thr Asp Gln Gly Lys Tyr Glu Cys Val Ala Thr Asn Ser Ala Gly Val
210                 215                 220

Arg Tyr Ser Ser Pro Ala Asn Leu Tyr Val Arg Glu Leu Arg Glu Val
225                 230                 235                 240

Arg Arg Val Ala Pro Arg Phe Ser Ile Leu Pro Met Ser His Glu Ile
                245                 250                 255

Met Pro Gly Gly Asn Val Asn Ile Thr Cys Val Ala Val Gly Ser Pro
            260                 265                 270

Met Pro Tyr Val Lys Trp Met Gln Gly Ala Glu Asp Leu Thr Pro Glu
        275                 280                 285

Asp Asp Met Pro Val Gly Arg Asn Val Leu Glu Leu Thr Asp Val Lys
290                 295                 300

Asp Ser Ala Asn Tyr Thr Cys Val Ala Met Ser Ser Leu Gly Val Ile
305                 310                 315                 320

Glu Ala Val Ala Gln Ile Thr Val Lys Ser Leu Pro Lys Ala Pro Gly
                325                 330                 335

Thr Pro Met Val Thr Glu Asn Thr Ala Thr Ser Ile Thr Ile Thr Trp
            340                 345                 350

Asp Ser Gly Asn Pro Asp Pro Val Ser Tyr Tyr Val Ile Glu Tyr Lys
        355                 360                 365

Ser Lys Ser Gln Asp Gly Pro Tyr Gln Ile Lys Glu Asp Ile Thr Thr
370                 375                 380

Thr Arg Tyr Ser Ile Gly Gly Leu Ser Pro Asn Ser Glu Tyr Glu Ile
385                 390                 395                 400

Trp Val Ser Ala Val Asn Ser Ile Gly Gln Gly Pro Pro Ser Glu Ser
                405                 410                 415

Val Val Thr Arg Thr Gly Glu Gln Ala Pro Ala Ser Ala Pro Arg Asn
            420                 425                 430

Val Gln Ala Arg Met Leu Ser Ala Thr Thr Met Ile Val Gln Trp Glu
        435                 440                 445

Glu Pro Val Glu Pro Asn Gly Leu Ile Arg Gly Tyr Arg Val Tyr Tyr
450                 455                 460

Thr Met Glu Pro Glu His Pro Val Gly Asn Trp Gln Lys His Asn Val
465                 470                 475                 480

Asp Asp Ser Leu Leu Thr Thr Val Gly Ser Leu Leu Glu Asp Glu Thr
                485                 490                 495

Tyr Thr Val Arg Val Leu Ala Phe Thr Ser Val Gly Asp Gly Pro Leu
            500                 505                 510

Ser Asp Pro Ile Gln Val Lys Thr Gln Gln Gly Val Pro Gly Gln Pro
        515                 520                 525

Met Asn Leu Arg Ala Glu Ala Arg Ser Glu Thr Ser Ile Thr Leu Ser
530                 535                 540
```

-continued

```
Trp Ser Pro Pro Arg Gln Glu Ser Ile Ile Lys Tyr Glu Leu Leu Phe
545                 550                 555                 560

Arg Glu Gly Asp His Gly Arg Glu Val Gly Arg Thr Phe Asp Pro Thr
                565                 570                 575

Thr Ser Tyr Val Val Glu Asp Leu Lys Pro Asn Thr Glu Tyr Ala Phe
            580                 585                 590

Arg Leu Ala Ala Arg Ser Pro Gln Gly Leu Gly Ala Phe Thr Pro Val
        595                 600                 605

Val Arg Gln Arg Thr Leu Gln Ser Lys Pro Ser Ala Pro Pro Gln Asp
    610                 615                 620

Val Lys Cys Val Ser Val Arg Ser Thr Ala Ile Leu Val Ser Trp Arg
625                 630                 635                 640

Pro Pro Pro Pro Glu Thr His Asn Gly Ala Leu Val Gly Tyr Ser Val
                645                 650                 655

Arg Tyr Arg Pro Leu Gly Ser Glu Asp Pro Glu Pro Lys Glu Val Asn
                660                 665                 670

Gly Ile Pro Pro Thr Thr Thr Gln Ile Leu Leu Glu Ala Leu Glu Lys
            675                 680                 685

Trp Thr Gln Tyr Arg Ile Thr Thr Val Ala His Thr Glu Val Gly Pro
690                 695                 700

Gly Pro Glu Ser Ser Pro Val Val Arg Thr Asp Glu Asp Val Pro
705                 710                 715                 720

Ser Ala Pro Pro Arg Lys Val Glu Ala Glu Ala Leu Asn Ala Thr Ala
                725                 730                 735

Ile Arg Val Leu Trp Arg Ser Pro Ala Pro Gly Arg Gln His Gly Gln
            740                 745                 750

Ile Arg Gly Tyr Gln Val His Tyr Val Arg Met Glu Gly Ala Glu Ala
        755                 760                 765

Arg Gly Pro Pro Arg Ile Lys Asp Val Met Leu Ala Asp Ala Gln Trp
    770                 775                 780

Glu Thr Asp Asp Thr Ala Glu Tyr Glu Met Val Ile Thr Asn Leu Gln
785                 790                 795                 800

Pro Glu Thr Ala Tyr Ser Ile Thr Val Ala Ala Tyr Thr Met Lys Gly
                805                 810                 815

Asp Gly Ala Arg Ser Lys Pro Lys Val Val Thr Lys Gly Ala Val
                820                 825                 830

Leu Gly Arg Pro Thr Leu Ser Val Gln Gln Thr Pro Glu Gly Ser Leu
            835                 840                 845

Leu Ala Arg Trp Glu Pro Pro Ala Gly Thr Ala Glu Asp Gln Val Leu
850                 855                 860

Gly Tyr Arg Leu Gln Phe Gly Arg Glu Asp Ser Thr Pro Leu Ala Thr
865                 870                 875                 880

Leu Glu Phe Pro Pro Ser Glu Asp Arg Tyr Thr Ala Ser Gly Val His
                885                 890                 895

Lys Gly Ala Thr Tyr Val Phe Arg Leu Ala Ala Arg Ser Arg Gly Gly
                900                 905                 910

Leu Gly Glu Glu Ala Ala Glu Val Leu Ser Ile Pro Glu Asp Thr Pro
            915                 920                 925

Arg Gly His Pro Gln Ile Leu Glu Ala Ala Gly Asn Ala Ser Ala Gly
        930                 935                 940

Thr Val Leu Leu Arg Trp Leu Pro Pro Val Pro Ala Glu Arg Asn Gly
945                 950                 955                 960

Ala Ile Val Lys Tyr Thr Val Ala Val Arg Glu Ala Gly Ala Leu Gly
```

-continued

```
                965                 970                 975
Pro Ala Arg Glu Thr Glu Leu Pro Ala Ala Ala Glu Pro Gly Ala Glu
                    980                 985                 990

Asn Ala Leu Thr Leu Gln Gly Leu Lys Pro Asp Thr Ala Tyr Asp Leu
                    995                 1000                1005

Gln Val Arg Ala His Thr Arg Arg Gly Pro Gly Pro Phe Ser Pro
    1010                1015                1020

Pro Val Arg Tyr Arg Thr Phe Leu Arg Asp Gln Val Ser Pro Lys
    1025                1030                1035

Asn Phe Lys Val Lys Met Ile Met Lys Thr Ser Val Leu Leu Ser
    1040                1045                1050

Trp Glu Phe Pro Asp Asn Tyr Asn Ser Pro Thr Pro Tyr Lys Ile
    1055                1060                1065

Gln Tyr Asn Gly Leu Thr Leu Asp Val Asp Gly Arg Thr Thr Lys
    1070                1075                1080

Lys Leu Ile Thr His Leu Lys Pro His Thr Phe Tyr Asn Phe Val
    1085                1090                1095

Leu Thr Asn Arg Gly Ser Ser Leu Gly Gly Leu Gln Gln Thr Val
    1100                1105                1110

Thr Ala Trp Thr Ala Phe Asn Leu Leu Asn Gly Lys Pro Ser Val
    1115                1120                1125

Ala Pro Lys Pro Asp Ala Asp Gly Phe Ile Met Val Tyr Leu Pro
    1130                1135                1140

Asp Gly Gln Ser Pro Val Pro Val Gln Ser Tyr Phe Ile Val Met
    1145                1150                1155

Val Pro Leu Arg Lys Ser Arg Gly Gly Gln Phe Leu Thr Pro Leu
    1160                1165                1170

Gly Ser Pro Glu Asp Met Asp Leu Glu Glu Leu Ile Gln Asp Ile
    1175                1180                1185

Ser Arg Leu Gln Arg Arg Ser Leu Arg His Ser Arg Gln Leu Glu
    1190                1195                1200

Val Pro Arg Pro Tyr Ile Ala Ala Arg Phe Ser Val Leu Pro Pro
    1205                1210                1215

Thr Phe His Pro Gly Asp Gln Lys Gln Tyr Gly Gly Phe Asp Asn
    1220                1225                1230

Arg Gly Leu Glu Pro Gly His Arg Tyr Val Leu Phe Val Leu Ala
    1235                1240                1245

Val Leu Gln Lys Ser Glu Pro Thr Phe Ala Ala Ser Pro Phe Ser
    1250                1255                1260

Asp Pro Phe Gln Leu Asp Asn Pro Asp Pro Gln Pro Ile Val Asp
    1265                1270                1275

Gly Glu Glu Gly Leu Ile Trp Val Ile Gly Pro Val Leu Ala Val
    1280                1285                1290

Val Phe Ile Ile Cys Ile Val Ile Ala Ile Leu Leu Tyr Lys Asn
    1295                1300                1305

Lys Pro Asp Ser Lys Arg Lys Asp Ser Glu Pro Arg Thr Lys Cys
    1310                1315                1320

Leu Leu Asn Asn Ala Asp Leu Ala Pro His His Pro Lys Asp Pro
    1325                1330                1335

Val Glu Met Arg Arg Ile Asn Phe Gln Thr Pro Asp Ser Gly Leu
    1340                1345                1350

Arg Ser Pro Leu Arg Glu Pro Gly Phe His Phe Glu Ser Met Leu
    1355                1360                1365
```

-continued

```
Ser His Pro Pro Ile Pro Ile Ala Asp Met Ala Glu His Thr Glu
    1370            1375                1380

Arg Leu Lys Ala Asn Asp Ser Leu Lys Leu Ser Gln Glu Tyr Glu
    1385            1390                1395

Ser Ile Asp Pro Gly Gln Gln Phe Thr Trp Glu His Ser Asn Leu
    1400            1405                1410

Glu Val Asn Lys Pro Lys Asn Arg Tyr Ala Asn Val Ile Ala Tyr
    1415            1420                1425

Asp His Ser Arg Val Ile Leu Gln Pro Ile Glu Gly Ile Met Gly
    1430            1435                1440

Ser Asp Tyr Ile Asn Ala Asn Tyr Val Asp Gly Tyr Arg Cys Gln
    1445            1450                1455

Asn Ala Tyr Ile Ala Thr Gln Gly Pro Leu Pro Glu Thr Phe Gly
    1460            1465                1470

Asp Phe Trp Arg Met Val Trp Glu Gln Arg Ser Ala Thr Ile Val
    1475            1480                1485

Met Met Thr Arg Leu Glu Glu Lys Ser Arg Ile Lys Cys Asp Gln
    1490            1495                1500

Tyr Trp Pro Asn Arg Gly Thr Glu Thr Tyr Gly Phe Ile Gln Val
    1505            1510                1515

Thr Leu Leu Asp Thr Ile Glu Leu Ala Thr Phe Cys Val Arg Thr
    1520            1525                1530

Phe Ser Leu His Lys Asn Gly Ser Ser Glu Lys Arg Glu Val Arg
    1535            1540                1545

Gln Phe Gln Phe Thr Ala Trp Pro Asp His Gly Val Pro Glu Tyr
    1550            1555                1560

Pro Thr Pro Phe Leu Ala Phe Leu Arg Arg Val Lys Thr Cys Asn
    1565            1570                1575

Pro Pro Asp Ala Gly Pro Ile Val Val His Cys Ser Ala Gly Val
    1580            1585                1590

Gly Arg Thr Gly Cys Phe Ile Val Ile Asp Ala Met Leu Glu Arg
    1595            1600                1605

Ile Lys Pro Glu Lys Thr Val Asp Val Tyr Gly His Val Thr Leu
    1610            1615                1620

Met Arg Ser Gln Arg Asn Tyr Met Val Gln Thr Glu Asp Gln Tyr
    1625            1630                1635

Ser Phe Ile His Glu Ala Leu Leu Glu Ala Val Gly Cys Gly Asn
    1640            1645                1650

Thr Glu Val Pro Ala Arg Ser Leu Tyr Ala Tyr Ile Gln Lys Leu
    1655            1660                1665

Ala Gln Val Glu Pro Gly Glu His Val Thr Gly Met Glu Leu Glu
    1670            1675                1680

Phe Lys Arg Leu Ala Asn Ser Lys Ala His Thr Ser Arg Phe Ile
    1685            1690                1695

Ser Ala Asn Leu Pro Cys Asn Lys Phe Lys Asn Arg Leu Val Asn
    1700            1705                1710

Ile Met Pro Tyr Glu Ser Thr Arg Val Cys Leu Gln Pro Ile Arg
    1715            1720                1725

Gly Val Glu Gly Ser Asp Tyr Ile Asn Ala Ser Phe Ile Asp Gly
    1730            1735                1740

Tyr Arg Gln Gln Lys Ala Tyr Ile Ala Thr Gln Gly Pro Leu Ala
    1745            1750                1755
```

| | | | | | | | | | | | | |
|---|---|---|---|---|---|---|---|---|---|---|---|---|
|Glu|Thr|Thr|Glu|Asp|Phe|Trp|Arg|Met|Leu|Trp|Glu|Asn Asn Ser|
|1760| | | | |1765| | | |1770| | | |
|Thr|Ile|Val|Val|Met|Leu|Thr|Lys|Leu|Arg|Glu|Met|Gly Arg Glu|
|1775| | | | |1780| | | |1785| | | |
|Lys|Cys|His|Gln|Tyr|Trp|Pro|Ala|Glu|Arg|Ser|Ala|Arg Tyr Gln|
|1790| | | | |1795| | | |1800| | | |
|Tyr|Phe|Val|Val|Asp|Pro|Met|Ala|Glu|Tyr|Asn|Met|Pro Gln Tyr|
|1805| | | | |1810| | | |1815| | | |
|Ile|Leu|Arg|Glu|Phe|Lys|Val|Thr|Asp|Ala|Arg|Asp|Gly Gln Ser|
|1820| | | | |1825| | | |1830| | | |
|Arg|Thr|Val|Arg|Gln|Phe|Gln|Phe|Thr|Asp|Trp|Pro|Glu Gln Gly|
|1835| | | | |1840| | | |1845| | | |
|Val|Pro|Lys|Ser|Gly|Glu|Gly|Phe|Ile|Asp|Phe|Ile|Gly Gln Val|
|1850| | | | |1855| | | |1860| | | |
|His|Lys|Thr|Lys|Glu|Gln|Phe|Gly|Gln|Asp|Gly|Pro|Ile Ser Val|
|1865| | | | |1870| | | |1875| | | |
|His|Cys|Ser|Ala|Gly|Val|Gly|Arg|Thr|Gly|Val|Phe|Ile Thr Leu|
|1880| | | | |1885| | | |1890| | | |
|Ser|Ile|Val|Leu|Glu|Arg|Met|Arg|Tyr|Glu|Gly|Val|Val Asp Ile|
|1895| | | | |1900| | | |1905| | | |
|Phe|Gln|Thr|Val|Lys|Met|Leu|Arg|Thr|Gln|Arg|Pro|Ala Met Val|
|1910| | | | |1915| | | |1920| | | |
|Gln|Thr|Glu|Asp|Glu|Tyr|Gln|Phe|Cys|Tyr|Gln|Ala|Ala Leu Glu|
|1925| | | | |1930| | | |1935| | | |
|Tyr|Leu|Gly|Ser|Phe|Asp|His|Tyr|Ala|Thr| | | |
|1940| | | | |1945| | | | | | | |

<210> SEQ ID NO 6
<211> LENGTH: 7347
<212> TYPE: DNA
<213> ORGANISM: Homo sapiens

<400> SEQUENCE: 6

```
cctcgcgccg cccgcccggc agcccggccg gcgcgcgcac gccgcgagcc gctggcgctc      60
gggctccgct cggatcccat gcaacagcca cgatgtgaag cggggcagag ccggggagc     120
ccagcccagc cagcctccag acgttgcccc atctgacgct cggctcgagg cctctctgtg    180
agggaccggg gggccatccc cctccagggc ggagatcgga ggtcgctgcc aagcatggcg    240
cccacctggg gcctggcat ggtgtctgtg gttggtccca tgggcctcct tgtggtcctg     300
ctcgttggag gctgtgcagc agaagagccc ccaggttta tcaaagaacc caaggaccag     360
atcggcgtgt cgggggggtgt ggcctctttc gtgtgtcagg ccacgggtga ccccaagcca    420
cgagtgacct ggaacaagaa gggcaagaag gtcaactctc agcgctttga acgcattgag    480
tttgatgaga gtgcaggggc agtgctgagg atccagccgc tgaggacacc gcgggatgaa    540
aacgtgtacg agtgtgtggc ccagaactcg gttggggaga tcacagtcca tgccaagctt    600
actgtcctcc gagaggacca gctgcctct ggcttcccca acatcgacat gggcccacag    660
ttgaaggtgg tggagcggac acggacagcc accatgctct gtgcagccag cggcaaccct    720
gaccctgaga tcacctggtt caaggactc ctgcctgtgg atcctagtgc cagcaatgga    780
cgcatcaaac agctgcgatc agaaaccttt gaaagcactc cgattcgagg agccctgcag    840
attgaaagca gtgaggaaac cgaccagggc aaatatgagt gtgtggccac caacagcgcc    900
ggcgtgcgct actcctcacc tgccaacctc tacgtgcgag agcttcgaga agtccgccgc    960
```

-continued

```
gtggcccgc gcttctccat cctgcccatg agccacgaga tcatgccagg gggcaacgtg    1020
aacatcacct gcgtggccgt gggctcgccc atgccatacg tgaagtggat gcaggggggcc   1080 gaggacctga cccccgagga tgacatgccc gtgggtcgga acgtgctgga actcacagat   1140
gtcaaggact cggccaacta cacctgcgtg gccatgtcca gcctgggcgt cattgaggcg   1200
gttgctcaga tcacggtgaa atctctcccc aaagctcccg ggactcccat ggtgactgag   1260
aacacagcca ccagcatcac catcacgtgg gactcgggca acccagatcc tgtgtcctat   1320
tacgtcatcg aatataaatc caagagccaa gacgggccgt atcagattaa agaggacatc   1380
accaccacac gttacagcat cggcggcctg agccccaact cggagtacga gatctgggtg   1440
tcggccgtca actccatcgg ccaggggccc cccagcgagt ccgtggtcac ccgcacaggc   1500
gagcaggccc cggccagcgc gccgcggaac gtgcaagccc ggatgctcag cgcgaccacc   1560
atgattgtgc agtgggagga gccggtggag cccaacggcc tgatccgcgg ctaccgcgtc   1620
tactacacca tggaaccgga gcaccccgtg ggcaactggc agaagcacaa cgtggacgac   1680
agcctgctga ccaccgtggg cagcctgctg gaggacgaga cctacaccgt gcgggtgctc   1740
gccttcacct ccgtcggcga cgggcccctc tcggacccca tccaggtcaa gacgcagcag   1800
ggagtgccgg gccagcccat gaacctgcgg gccgaggcca ggtcggagac cagcatcacg   1860
ctgtcctgga gccccccgcg gcaggagagt atcatcaagt acgagctcct cttccgggaa   1920
ggcgaccatg gccgggaggt gggaaggacc ttcgacccga cgacttccta cgtggtggag   1980
gacctgaagc ccaacacgga gtacgccttc cgcctggcgg cccgctcgcc gcagggcctg   2040
ggcgccttca ccccgtggt gcggcagcgc acgctgcagt ccaaaccgtc agccccccct   2100
caagacgtta aatgtgtcag cgtgcgctcc acggccattt tggtaagttg gcgcccgccg   2160
ccgccggaaa cgcacaacgg ggccctggtg ggctacagcg tccgctaccg accgctgggc   2220
tcagaggacc cggaacccaa ggaggtgaac ggcatccccc cgaccaccac tcagatcctg   2280
ctggaggcct tggagaagtg gacccagtac cgcatcacga ctgtcgctca cacagaggtg   2340
ggaccagggc ccgagagctc gcccgtggtc gtccgcaccg acgaggatgt gcccagcgcg   2400
ccgccgcgga aggtggaggc ggaggcgctc aacgccacgg ccatccgcgt gctgtggcgc   2460
tcgcccgcgc ccggccggca gcacggccag atccgcggct accaggtcca ctacgtgcgc   2520
atggagggcg ccgaggcccg cgggccgccg cgcatcaagg acgtcatgct ggccgatgcc   2580
cagtgggaga cggatgacac ggccgaatat gagatggtca tcacaaactt gcagcctgag   2640
accgcgtact ccatcacggt agccgcctac accatgaagg gcgatggcgc tcgcagcaaa   2700
cccaaggtgg ttgtgaccaa gggagcagtg ctgggccgcc caaccctgtc ggtgcagcag   2760 accccgagg gcagcctgct ggcacgctgg gagcccccgg ctggcaccgc ggaggaccag   2820
gtgctgggct accgcctgca gtttggccgt gaggactcga cgcccctggc cacctggag   2880 ttccgccct ccgaggaccg ctacacggca tcaggcgtgc acaaggggc cacgtatgtg   2940 ttccggcttg cggcccggag ccgcggcggc ctgggcgagg aggcagccga ggtcctgagc   3000
atcccggagg acacgccccg tggccacccg cagattctgg aggcggccgg caacgcctcg   3060
gccgggaccg tccttctccg ctggctgcca ccgtgcccg ccgagcgcaa cggggccatc   3120
gtcaaataca cggtggccgt gcgggaggcc ggtgccctgg gcctgcccg agagactgag   3180 ctgccggcag cggctgagcc gggcgcggag aacgcgctca cgctgcaggg cctgaagccc   3240
gacacggcct atgacctcca agtgcgagcc cacacgcgcc ggggccctgg ccccttcagc   3300 cccccgtcc gctaccggac gttcctgcgg gaccaagtct cgcccaagaa cttcaaggtg   3360
```

```
aaaatgatca tgaagacatc agttctgctc agctgggagt tccctgacaa ctacaactca   3420
cccacaccct acaagatcca gtacaatggg ctcacactgg atgtggatgg ccgtaccacc   3480
aagaagctca tcacgcacct caagccccac accttctaca actttgtgct gaccaatcgc   3540
ggcagcagcc tgggcggcct ccagcagacg gtcaccgcct ggactgcctt caacctgctc   3600
aacggcaagc ccagcgtcgc ccccaagcct gatgctgacg gcttcatcat ggtgtatctt   3660
cctgacggcc agagccccgt gcctgtccag agctatttca ttgtgatggt gccactgcgc   3720
aagtctcgtg gaggccaatt cctgaccccg ctgggtagcc cagaggacat ggatctggaa   3780
gagctcatcc aggacatctc acggctacag aggcgcagcc tgcggcactc gcgtcagctg   3840
gaggtgcccc ggccctatat tgcagctcgc ttctctgtgc tgccacccac gttccatccc   3900
ggcgaccaga agcagtatgg cggcttcgat aaccggggcc tggagcccgg ccaccgctat   3960
gtcctcttcg tgcttgccgt gcttcagaag agcgagccta cctttgcagc cagtcccttc   4020
tcagacccct tccagctgga taacccggac ccccagccca tcgtggatgg cgaggagggg   4080
cttatctggg tgatcgggcc tgtgctggcc gtggtcttca taatctgcat tgtcattgct   4140
atcctgctct acaagaacaa acccgacagt aaacgcaagg actcagaacc ccgcaccaaa   4200
tgcctcctga acaatgccga cctcgcccct caccacccca aggaccctgt ggaaatgaga   4260
cgcattaact tccagactcc agattcaggc ctcaggagcc ccctcaggga gccggggttt   4320
cactttgaaa gcatgcttag ccacccgcca attcccatcg cagacatggc ggagcacacg   4380
gagcggctca aggccaacga cagcctcaag ctctcccagg agtatgagtc catcgacccct   4440 ggacagcagt tcacatggga acattccaac ctggaagtga acaagccgaa gaaccgctat   4500
gccaacgtca tcgcctatga ccactcccgt gtcatcctcc agcccattga aggcatcatg   4560
ggcagtgatt acatcaatgc caactacgtg gacggctacc ggtgtcagaa cgcgtacatt   4620
gccacgcagg ggccgctgcc tgagaccttt ggggacttct ggcgtatggt gtgggagcag   4680
cggtcggcga ccatcgtcat gatgacgcgg ctggaggaga agtcacggat caagtgtgat   4740
cagtattggc ccaacagagg cacggagacc tacggcttca tccaggtcac gttgctagat   4800
accatcgagc tggccacatt ctgcgtcagg acattctctc tgcacaagaa tggctccagt   4860
gagaaacgcg aggtccgcca gttccagttt acggcgtggc cggaccatgg cgtgcccgaa   4920
tacccaacgc ccttcctggc tttcctgcgg agagtcaaga cctgcaaccc gccagatgcc   4980
ggccccatcg tggttcactg cagtgccggt gtgggccgca caggctgctt tatcgtcatc   5040
gacgccatgc ttgagcggat caagccagag aagacagtcg atgtctatgg ccacgtgacg   5100
ctcatgaggt cccagcgcaa ctacatggtg cagacggagg accagtacag cttcatccac   5160
gaggccctgc tggaggccgt gggctgtggc aacacagaag tgcccgcacg cagcctctat   5220
gcctacatcc agaagctggc ccaggtggag cctggcgaac acgtcactgg catggaactc   5280
gagttcaagc ggctggctaa ctccaaggcc cacacgtcac gcttcatcag tgccaatctg   5340
ccttgtaaca agttcaagaa ccgcctggtg aacatcatgc cctatgagag cacacgggtc   5400
tgtctgcaac ccatccgggg tgtggagggc tctgactaca tcaacgccag cttcattgat   5460
ggctacaggc agcagaaggc ctacatcgcg acacagggcc gctggcgga gaccacggaa   5520 gacttctggc gcatgctgtg ggagaacaat tcgacgatcg tggtgatgct gaccaagctg   5580
cgggagatgg gccgggagaa gtgtcaccag tactggccgg ccgagcgctc tgcccgctac   5640
cagtactttg tggtagatcc gatggcagaa tacaacatgc ctcagtatat cctgcgagag   5700
```

-continued

```
ttcaaggtca cagatgcccg ggatggccag tcccggactg tccggcagtt ccagttcaca    5760
gactggccgg aacagggtgt gccaaagtcg ggggagggct tcatcgactt cattggccaa    5820
gtgcataaga ctaaggagca gtttggccag gacggcccca tctctgtcca ctgcagtgcc    5880
ggcgtgggca ggacgggcgt cttcatcacg cttagcatcg tgctggagcg gatgcggtat    5940
gaaggcgtgg tggacatctt tcagacggtg aagatgctac gaacccagcg gccggccatg    6000
gtgcagacag aggatgagta ccagttctgt taccaggcgg cactggagta cctcggaagc    6060
tttgaccact atgcaaccta agccatggtt ccccccagg cccgacacca ctggccccgg     6120
atgcctctgc ccctcccggg cggacctcct gaggcctgga cccccagtgg gcagggcagg    6180
aggtggcagc ggcagcagct gtgtttctgc accatttccg aggacgacgc agcccctcga    6240
gccccccac cggccccggc cgccccagcg acctccctgg caccggccgc cgccttcaaa     6300
tacttggcac attcctcctt tccttccaat tccaaaacca gattccgggg tgggggtgg    6360
ggggatggtg agcaaatagg agtgctcccc agaaccagag gagggtgggg cacagaccat    6420
agacggaccc ctcgtcctcc cccagcggtg gtaggggac ccgggggct cctcccgct       6480
ctgcagcctg ggacactgg gctgggacca gaatccagct ttcttttaaa actctcagtg     6540
taactgtatc ccgtgacatt tcatttttt taaatagtgt atttttttt ccattttttt     6600
ttttaagaga acaaacaaa agactcgcca gtcaatgact ttcaaagaga actaactttg     6660
gcttattcat attctgttca aagacagtct attttttcac tgtagaaagc gtccttgtgt    6720
gatagttacg ttcgcaaacg cgcacgccag gcccatggct gtaccttggc ttttttttt    6780
tttttttt ttttaattt tcctaccatc agaaagtgtg ctttgctcac agaagaatgg      6840
gatgtccttt tttctttctt ggctttttt ttcccccttt ttgtttcatt tttataaatt    6900
aaattttcag acatatcaaa tacagttctg agggtaaggt catggggag ctcggaccca    6960
gtggcgttgg gtgcggttga gggggacgct gctgtaagag gagagagatg acagtggtcc    7020
tcctctgaga gcctgagctg tctccccgtc tcccgccccc aaggagacag agaggatcct    7080
acttcttcgg ggacagtggc tgtatggctg tgctgcccca catcagggac cctttccccc    7140
tgggactgtg gggcagtttg ggagcaaaac cagaaggaca ggccccctc tacccgccta    7200
ccctgagcaa gcgagttgtt cctctttgta caagggcagg tctgcggtta cttttcaacac  7260
tgtttattcc agcggaagca gccgggtggt tttcccaccc ccgtgtatgt agatatatcg   7320
actttgtatt aaaggaagat cgtctga                                       7347
```

<210> SEQ ID NO 7
<211> LENGTH: 1907
<212> TYPE: PRT
<213> ORGANISM: Mus musculus

<400> SEQUENCE: 7

Met Ala Pro Thr Trp Ser Pro Val Val Ser Val Val Gly Pro Val
1               5                   10                  15

Gly Leu Phe Leu Val Leu Leu Ala Arg Gly Cys Leu Ala Glu Glu Pro
                20                  25                  30

Pro Arg Phe Ile Arg Glu Pro Lys Asp Gln Ile Gly Val Ser Gly Gly
            35                  40                  45

Val Ala Ser Phe Val Cys Gln Ala Thr Gly Asp Pro Lys Pro Arg Val
        50                  55                  60

Thr Trp Asn Lys Lys Gly Lys Lys Val Asn Ser Gln Arg Phe Glu Thr
65                  70                  75                  80

```
Ile Asp Phe Asp Glu Ser Ser Gly Ala Val Leu Arg Ile Gln Pro Leu
                85                  90                  95

Arg Thr Pro Arg Asp Glu Asn Val Tyr Glu Cys Val Ala Gln Asn Ser
            100                 105                 110

Val Gly Glu Ile Thr Ile His Ala Lys Leu Thr Val Leu Arg Glu Asp
        115                 120                 125

Gln Leu Pro Pro Gly Phe Pro Asn Ile Asp Met Gly Pro Gln Leu Lys
    130                 135                 140

Val Val Glu Arg Thr Arg Thr Ala Thr Met Leu Cys Ala Ala Ser Gly
145                 150                 155                 160

Asn Pro Asp Pro Glu Ile Thr Trp Phe Lys Asp Phe Leu Pro Val Asp
                165                 170                 175

Pro Ser Ala Ser Asn Gly Arg Ile Lys Gln Leu Arg Ser Gly Ala Leu
            180                 185                 190

Gln Ile Glu Ser Ser Glu Glu Thr Asp Gln Gly Lys Tyr Glu Cys Val
        195                 200                 205

Ala Thr Asn Ser Ala Gly Val Arg Tyr Ser Ser Pro Ala Asn Leu Tyr
    210                 215                 220

Val Arg Val Arg Arg Val Ala Pro Arg Phe Ser Ile Leu Pro Met Ser
225                 230                 235                 240

His Glu Ile Met Pro Gly Gly Asn Val Asn Ile Thr Cys Val Ala Val
                245                 250                 255

Gly Ser Pro Met Pro Tyr Val Lys Trp Met Gln Gly Ala Glu Asp Leu
            260                 265                 270

Thr Pro Glu Asp Asp Met Pro Val Gly Arg Asn Val Leu Glu Leu Thr
        275                 280                 285

Asp Val Lys Asp Ser Ala Asn Tyr Thr Cys Val Ala Met Ser Ser Leu
    290                 295                 300

Gly Val Ile Glu Ala Val Ala Gln Ile Thr Val Lys Ser Leu Pro Lys
305                 310                 315                 320

Ala Pro Gly Thr Pro Val Val Thr Glu Asn Thr Ala Thr Ser Ile Thr
                325                 330                 335

Val Thr Trp Asp Ser Gly Asn Pro Asp Pro Val Ser Tyr Tyr Val Ile
            340                 345                 350

Glu Tyr Lys Ser Lys Ser Gln Asp Gly Pro Tyr Gln Ile Lys Glu Asp
        355                 360                 365

Ile Thr Thr Thr Arg Tyr Ser Ile Gly Gly Leu Ser Pro Asn Ser Glu
    370                 375                 380

Tyr Glu Ile Trp Val Ser Ala Val Asn Ser Ile Gly Gln Gly Pro Pro
385                 390                 395                 400

Ser Glu Ser Val Val Thr Arg Thr Gly Glu Gln Ala Pro Ala Ser Ala
                405                 410                 415

Pro Arg Asn Val Gln Ala Arg Met Leu Ser Ala Thr Thr Met Ile Val
            420                 425                 430

Gln Trp Glu Glu Pro Val Glu Pro Asn Gly Leu Ile Arg Gly Tyr Arg
        435                 440                 445

Val Tyr Tyr Thr Met Glu Pro Glu His Pro Val Gly Asn Trp Gln Lys
    450                 455                 460

His Asn Val Asp Asp Ser Leu Leu Thr Thr Val Gly Ser Leu Leu Glu
465                 470                 475                 480

Asp Glu Thr Tyr Thr Val Arg Val Leu Ala Phe Thr Ser Val Gly Asp
                485                 490                 495

Gly Pro Leu Ser Asp Pro Ile Gln Val Lys Thr Gln Gln Gly Val Pro
```

```
            500             505             510
Gly Gln Pro Met Asn Leu Arg Ala Glu Ala Lys Ser Glu Thr Ser Ile
            515             520             525

Gly Leu Ser Trp Ser Ala Pro Arg Gln Glu Ser Val Ile Lys Tyr Glu
            530             535             540

Leu Leu Phe Arg Glu Gly Asp Arg Gly Arg Glu Val Gly Arg Thr Phe
545             550             555             560

Asp Pro Thr Thr Ala Phe Val Val Glu Asp Leu Lys Pro Asn Thr Glu
                565             570             575

Tyr Ala Phe Arg Leu Ala Ala Arg Ser Pro Gln Gly Leu Gly Ala Phe
            580             585             590

Thr Ala Val Val Arg Gln Arg Thr Leu Gln Ala Lys Pro Ser Ala Pro
            595             600             605

Pro Gln Asp Val Lys Cys Thr Ser Leu Arg Ser Thr Ala Ile Leu Val
            610             615             620

Ser Trp Arg Pro Pro Pro Glu Thr His Asn Gly Ala Leu Val Gly
625             630             635             640

Tyr Ser Val Arg Tyr Arg Pro Leu Gly Ser Glu Asp Pro Asp Pro Lys
                645             650             655

Glu Val Asn Asn Ile Pro Pro Thr Thr Gln Ile Leu Leu Glu Ala
                660             665             670

Leu Glu Lys Trp Thr Glu Tyr Arg Val Thr Ala Val Ala Tyr Thr Glu
            675             680             685

Val Gly Pro Gly Pro Glu Ser Ser Pro Val Val Arg Thr Asp Glu
            690             695             700

Asp Val Pro Ser Ala Pro Pro Arg Lys Val Glu Ala Glu Ala Leu Asn
705             710             715             720

Ala Thr Ala Ile Arg Val Leu Trp Arg Ser Pro Thr Pro Gly Arg Gln
                725             730             735

His Gly Gln Ile Arg Gly Tyr Gln Val His Tyr Val Arg Met Glu Gly
                740             745             750

Ala Glu Ala Arg Gly Pro Pro Arg Ile Lys Asp Ile Met Leu Ala Asp
            755             760             765

Ala Gln Glu Met Val Ile Thr Asn Leu Gln Pro Glu Thr Ala Tyr Ser
            770             775             780

Ile Thr Val Ala Ala Tyr Thr Met Lys Gly Asp Gly Ala Arg Ser Lys
785             790             795             800

Pro Lys Val Val Val Thr Lys Gly Ala Val Leu Gly Arg Pro Thr Leu
                805             810             815

Ser Val Gln Gln Thr Pro Glu Gly Ser Leu Leu Ala Arg Trp Glu Pro
            820             825             830

Pro Ala Asp Ala Ala Glu Asp Pro Val Leu Gly Tyr Arg Leu Gln Phe
            835             840             845

Gly Arg Glu Asp Ala Ala Pro Ala Thr Leu Glu Leu Ala Ala Trp Glu
            850             855             860

Arg Arg Phe Ala Ala Pro Ala His Lys Gly Ala Thr Tyr Val Phe Arg
865             870             875             880

Leu Ala Ala Arg Gly Arg Ala Gly Leu Gly Glu Glu Ala Ala Ala
                885             890             895

Leu Ser Ile Pro Glu Asp Ala Pro Arg Gly Phe Pro Gln Ile Leu Gly
            900             905             910

Ala Ala Gly Asn Val Ser Ala Gly Ser Val Leu Leu Arg Trp Leu Pro
            915             920             925
```

-continued

Pro Val Pro Ala Glu Arg Asn Gly Ala Ile Ile Lys Tyr Thr Val Ser
930                 935                 940

Val Arg Glu Ala Gly Ala Pro Gly Pro Ala Thr Glu Thr Glu Leu Ala
945                 950                 955                 960

Ala Ala Ala Gln Pro Gly Ala Glu Thr Ala Leu Thr Leu Arg Gly Leu
            965                 970                 975

Arg Pro Glu Thr Ala Tyr Glu Leu Arg Val Arg Ala His Thr Arg Arg
            980                 985                 990

Gly Pro Gly Pro Phe Ser Pro Pro Leu Arg Tyr Arg Leu Ala Arg Asp
        995                 1000                1005

Pro Val Ser Pro Lys Asn Phe Lys Val Lys Met Ile Met Lys Thr
    1010                1015                1020

Ser Val Leu Leu Ser Trp Glu Phe Pro Asp Asn Tyr Asn Ser Pro
    1025                1030                1035

Thr Pro Tyr Lys Ile Gln Tyr Asn Gly Leu Thr Leu Asp Val Asp
    1040                1045                1050

Gly Arg Thr Thr Lys Lys Leu Ile Thr His Leu Lys Pro His Thr
    1055                1060                1065

Phe Tyr Asn Phe Val Leu Thr Asn Arg Gly Ser Ser Leu Gly Gly
    1070                1075                1080

Leu Gln Gln Thr Val Thr Ala Arg Thr Ala Phe Asn Met Leu Ser
    1085                1090                1095

Gly Lys Pro Ser Val Ala Pro Lys Pro Asp Asn Asp Gly Phe Ile
    1100                1105                1110

Val Val Tyr Leu Pro Asp Gly Gln Ser Pro Val Thr Val Gln Asn
    1115                1120                1125

Tyr Phe Ile Val Met Val Pro Leu Arg Lys Ser Arg Gly Gly Gln
    1130                1135                1140

Phe Pro Val Leu Leu Gly Ser Pro Glu Asp Met Asp Leu Glu Glu
    1145                1150                1155

Leu Ile Gln Asp Ile Ser Arg Leu Gln Arg Arg Ser Leu Arg His
    1160                1165                1170

Ser Arg Gln Leu Glu Val Pro Arg Pro Tyr Ile Ala Ala Arg Phe
    1175                1180                1185

Ser Ile Leu Pro Ala Val Phe His Pro Gly Asn Gln Lys Gln Tyr
    1190                1195                1200

Gly Gly Phe Asp Asn Arg Gly Leu Glu Pro Gly His Arg Tyr Val
    1205                1210                1215

Leu Phe Val Leu Ala Val Leu Gln Lys Asn Glu Pro Thr Phe Ala
    1220                1225                1230

Ala Ser Pro Phe Ser Asp Pro Phe Gln Leu Asp Asn Pro Asp Pro
    1235                1240                1245

Gln Pro Ile Val Asp Gly Glu Glu Gly Leu Ile Trp Val Ile Gly
    1250                1255                1260

Pro Val Leu Ala Val Val Phe Ile Ile Cys Ile Val Ile Ala Ile
    1265                1270                1275

Leu Leu Tyr Lys Asn Lys Pro Asp Ser Lys Arg Lys Asp Ser Glu
    1280                1285                1290

Pro Arg Thr Lys Cys Leu Leu Asn Asn Ala Asp Leu Ala Pro His
    1295                1300                1305

His Pro Lys Asp Pro Val Glu Met Arg Arg Ile Asn Phe Gln Thr
    1310                1315                1320

-continued

Pro Gly Met Leu Ser His Pro Pro Ile Pro Ile Thr Asp Met Ala
1325              1330              1335

Glu His Met Glu Arg Leu Lys Ala Asn Asp Ser Leu Lys Leu Ser
1340              1345              1350

Gln Glu Tyr Glu Ser Ile Asp Pro Gly Gln Gln Phe Thr Trp Glu
1355              1360              1365

His Ser Asn Leu Glu Ala Asn Lys Pro Lys Asn Arg Tyr Ala Asn
1370              1375              1380

Val Ile Ala Tyr Asp His Ser Arg Val Ile Leu Gln Pro Leu Glu
1385              1390              1395

Gly Ile Met Gly Ser Asp Tyr Ile Asn Ala Asn Tyr Val Asp Gly
1400              1405              1410

Tyr Arg Arg Gln Asn Ala Tyr Ile Ala Thr Gln Gly Pro Leu Pro
1415              1420              1425

Glu Thr Phe Gly Asp Phe Trp Arg Met Val Trp Glu Gln Arg Ser
1430              1435              1440

Ala Thr Val Val Met Met Thr Arg Leu Glu Glu Lys Ser Arg Ile
1445              1450              1455

Lys Cys Asp Gln Tyr Trp Pro Asn Arg Gly Thr Glu Thr Tyr Gly
1460              1465              1470

Phe Ile Gln Val Thr Leu Leu Asp Thr Met Glu Leu Ala Thr Phe
1475              1480              1485

Cys Val Arg Thr Phe Ser Leu His Lys Asn Gly Ser Ser Glu Lys
1490              1495              1500

Arg Glu Val Arg His Phe Gln Phe Thr Ala Trp Pro Asp His Gly
1505              1510              1515

Val Pro Glu Tyr Pro Thr Pro Phe Leu Ala Phe Leu Arg Arg Val
1520              1525              1530

Lys Thr Cys Asn Pro Pro Asp Ala Gly Pro Ile Val Val His Cys
1535              1540              1545

Ser Ala Gly Val Gly Arg Thr Gly Cys Phe Ile Val Ile Asp Ala
1550              1555              1560

Met Leu Glu Arg Ile Lys Thr Glu Lys Thr Val Asp Val Tyr Gly
1565              1570              1575

His Val Thr Leu Met Arg Ser Gln Arg Asn Tyr Met Val Gln Thr
1580              1585              1590

Glu Asp Gln Tyr Gly Phe Ile His Glu Ala Leu Leu Glu Ala Val
1595              1600              1605

Gly Cys Gly Asn Thr Glu Val Pro Ala Arg Ser Leu Tyr Thr Tyr
1610              1615              1620

Ile Gln Lys Leu Ala Gln Val Glu Pro Gly Glu His Val Thr Gly
1625              1630              1635

Met Glu Leu Glu Phe Lys Arg Leu Ala Ser Ser Lys Ala His Thr
1640              1645              1650

Ser Arg Phe Ile Thr Ala Ser Leu Pro Cys Asn Lys Phe Lys Asn
1655              1660              1665

Arg Leu Val Asn Ile Leu Pro Tyr Glu Ser Ser Arg Val Cys Leu
1670              1675              1680

Gln Pro Ile Arg Gly Val Glu Gly Ser Asp Tyr Ile Asn Ala Ser
1685              1690              1695

Phe Ile Asp Gly Tyr Arg Gln Gln Lys Ala Tyr Ile Ala Thr Gln
1700              1705              1710

Gly Pro Leu Ala Glu Thr Thr Glu Asp Phe Trp Arg Ala Leu Trp

```
                1715                1720                1725
Glu Asn Asn Ser Thr Ile Val Val Met Leu Thr Lys Leu Arg Glu
        1730                1735                1740
Met Gly Arg Glu Lys Cys His Gln Tyr Trp Pro Ala Glu Arg Ser
    1745                1750                1755
Ala Arg Tyr Gln Tyr Phe Val Val Asp Pro Met Ala Glu Tyr Asn
    1760                1765                1770
Met Pro Gln Tyr Ile Leu Arg Glu Phe Lys Val Thr Asp Ala Arg
    1775                1780                1785
Asp Gly Gln Ser Arg Thr Val Arg Gln Phe Gln Phe Thr Asp Trp
    1790                1795                1800
Pro Glu Gln Gly Ala Pro Lys Ser Gly Glu Gly Phe Ile Asp Phe
    1805                1810                1815
Ile Gly Gln Val His Lys Thr Lys Glu Gln Phe Gly Gln Asp Gly
    1820                1825                1830
Pro Ile Ser Val His Cys Ser Ala Gly Val Gly Arg Thr Gly Val
    1835                1840                1845
Phe Ile Thr Leu Ser Ile Val Leu Glu Arg Met Arg Tyr Glu Gly
    1850                1855                1860
Val Val Asp Ile Phe Gln Thr Val Lys Val Leu Arg Thr Gln Arg
    1865                1870                1875
Pro Ala Met Val Gln Thr Glu Asp Glu Tyr Gln Phe Cys Phe Gln
    1880                1885                1890
Ala Ala Leu Glu Tyr Leu Gly Ser Phe Asp His Tyr Ala Thr
    1895                1900                1905

<210> SEQ ID NO 8
<211> LENGTH: 6874
<212> TYPE: DNA
<213> ORGANISM: Mus musculus

<400> SEQUENCE: 8
aggggtgacg tcaccggctg ggggcgcgcg agccgcagtg gggttttgcc ccgcccgcca    60
ggcagctcgg gccgcgcgca cacgcggagc cgccggagcc cgggccgacc cggtgccggg   120
agcagcatgc ggagcccgca gacgctgccc ctctggacac ctcagcctga ggcctctccg   180
tgagtcacgg gggtaccatc ccccaccagg gcagaggctg gaggccactg ccaagcatgg   240
cgcccacctg gagtcccagc gtggtgtctg tggtgggtcc tgtggggctc ttcctcgtac   300
tgctggccag aggatgcttg gctgaagaac cacccaggtt tatcagagag cccaaggatc   360
agattggagt gtcgggaggc gtggcctcct tcgtgtgcca ggccacgggt gatcctaagc   420
cacgggtgac ctggaacaag aagggcaaga aagtgaactc acagcgcttc gagaccattg   480
actttgacga gagctctggg gcggtcctga ggatccagcc acttcggacg cctcgggatg   540
agaacgtgta cgagtgtgtg cccagaacct cggtgggcga aatcacaatt catgcaaagc   600
tcaccgtcct tcgagaggac cagctgcctc ctggcttccc caacattgac atgggccccc   660
agttgaaggt tgtagagcgc acacgcacag ccaccatgct ctgtgctgcc agcgggaacc   720
cggaccctga gatcacctgg tttaaggact tcctgcctgt ggaccccagt gccagcaacg   780
ggcggatcaa gcagcttcga tcaggtgccc tgcagattga gagcagcgag agacagacc    840
agggcaagta cgagtgtgtg gccaccaaca gcgctggggt gcgctactca tcacctgcca   900
acctctacgt gcgagtccgc cgtgtggccc acgcttctc catcctgccc atgagccacg   960
agatcatgcc cggtgggaat gtgaatatca cttgtgtggc cgtgggctca cccatgcct   1020
```

```
acgtgaaatg gatgcagggg gccgaggacc tgacgcctga ggatgacatg cccgtgggtc    1080
ggaatgttct agaactcacg gatgtcaagg actcagctaa ctacacttgt gtggccatgt    1140
ccagcctggg tgtgatcgag gccgtggccc agatcactgt aaaatctctc cccaaagccc    1200
ctgggactcc tgtggtgacg gagaacactg ccaccagtat cactgtcaca tgggactcgg    1260
gcaaccctga ccccgtgtcc tactacgtaa ttgagtataa gtccaaaagc caggatgggc    1320
cgtatcagat caaagaagac atcaccacca cgcgctacag catcggaggc ctgagcccca    1380
attctgagta tgagatctgg gtgtcagctg tcaactccat tggccagggc cctcccagtg    1440
aatcggtggt gacccgcaca ggtgagcagg caccagccag cgctcccagg aatgttcagg    1500
cccgcatgct cagcgccacc accatgatcg tgcagtggga ggagcctgtg agcccaatg     1560 gcctgatccg tggctaccgt gtctactata ccatggagcc ggaacaccca gtgggcaact    1620
ggcagaaaca caatgtggac gacagtctcc tgaccactgt gggcagcctg ctggaagacg    1680
agacctacac cgtgcgcgtg ctcgccttca cgtcggtggg cgacggacca ctgtcagacc    1740
ccatccaggt caagacccag cagggagttc ctggccagcc catgaacttg cgggctgagg    1800
ccaagtcaga gaccagcatt gggctctcgt ggagtgcacc acgacaggag agtgtcatta    1860
agtatgaact gctcttccgg gagggcgacc gaggccgaga ggtggggcga accttcgacc    1920
caaccacagc ctttgtggtg gaggacctca agcccaatac ggagtatgcg ttccggctgg    1980
cggcgcgctc gccgcagggc ctgggcgcct tcaccgcggt cgtgcgccag cgcacgctgc    2040
aggccaaacc gtcagccccc cctcaagacg ttaagtgcac cagcttgcgc tccacggcca    2100
tattggtaag ttggcgcccg ccaccgccag aaactcacaa cggggccctc gtgggctaca    2160
gcgtccgcta ccgaccgctg ggctcagagg acccggaccc caaggaggtg aacaacatac    2220
ccccgaccac cactcagatc cttctggaag cttttggagaa atggacggag taccgtgtca    2280
ccgccgtggc ttacacagag gtgggaccag ggcccgagag ctcgcccgtg gtcgtccgca    2340
ccgatgagga cgtgcccagc gcgcccccgc ggaaggtgga ggcggaggcg ctcaacgcca    2400
cagccatccg agtgctgtgg cgctcgccca cgcccggccg gcagcacggg cagatccgcg    2460
gctaccaggt ccactatgtg cgcatggagg gtgccgaggc ccgcgggcca ccgcgcatca    2520
aggacatcat gctggcggat gcccaggaaa tggtgataac gaacctccag cctgagactg    2580
cttactctat cacagtagcc gcgtatacca tgaaaggcga tggcgctcgc agcaaaccga    2640
aggtggtggt gaccaaggga gcagtgctgg gccgccccac cctgtcggtg cagcagaccc    2700
ccgagggcag cctgctggcg cgctgggagc ccccgcgga cgcggccgag gacccggtgc    2760
ttggctaccg cctgcagttt gggcgcgaag acgcggcccc ggccacgttg gagctggctg    2820
cgtgggagcg gcggttcgcg gcgcctgcac acaagggcgc cacctatgtg ttccggctgg    2880
cagcgcgggg ccgcgcgggg ttgggcgagg aggccgcggc agcgctgagc atccccgagg    2940
acgctccgcg cggcttcccg cagatcttgg gcgccgcggg caacgtgtcc gcgggctccg    3000
tgctactgcg ctggctgcca cccgtgcccg ccgagcgcaa cggcgccatc atcaagtaca    3060
cggtgtccgt gcgggaggcc ggcgcccctg ggccgcgac cgagacggag ctggcggcgg    3120
ccgcccagcc gggggccgag acagcgctca cgctgcgagg gctgcggccg agacggcct    3180 acgagttacg cgtgcgcgca cacacgcgtc gcggcccggg ccccttctca ccccgctgc    3240 gctacaggct cgcgcgggac ccagtctccc caaagaactt caaggtgaag atgatcatga    3300
agacttcagt gctgctgagc tgggagttcc ccgacaacta taactcaccc acaccctaca    3360
```

```
agattcagta caatgggctc accctggatg tggacggccg cacgaccaag aagctgatca    3420
cacacctcaa gccacacacc ttctataatt tcgtgctcac caaccgtggc agcagcctgg    3480
ggggcctgca gcagacggtc actgccagga ccgcctttaa catgctcagt ggcaagccta    3540
gcgtcgcccc gaagcccgac aatgacggtt tcatcgtggt ctacctgcct gatggccaga    3600
gtcctgtgac cgtgcagaac tacttcattg tgatggtccc acttcggaag tctcgaggtg    3660
gccagttccc tgtcctacta ggtagtccag aggacatgga tctggaggag ctcatccagg    3720
acatctcccg gctgcagagg cgcagcctgc gccactccag acagctggag gtgcctcggc    3780
cctacatcgc cgctcgattc tccatcctgc cagctgtctt ccatcctggg aaccagaagc    3840
aatatggtgg ctttgacaac aggggcttgg agccaggcca ccgctatgtc ctctttgtgc    3900
ttgctgtgtt gcagaagaat gagcctacat ttgcagccag tcccttctca gacccCttcc    3960
agctggacaa cccggaccct cagcccattg tggacggcga ggagggcctc atctgggtga    4020
ttgggcctgt gctggccgtg gtcttcatca tctgcatcgt gattgccatc ctgctgtaca    4080
agaacaaacc tgacagcaaa cgcaaggact cagagccccg caccaaatgc ttactgaaca    4140
atgccgacct tgccccccat caccccaagg accctgtgga aatgcgacgc atcaacttcc    4200
agacaccagg tatgctcagc caccaccca tccccatcac agacatggcg gagcacatgg    4260
agagactcaa agccaacgac agcctgaagc tctcccagga gtacgagtcc attgaccccg    4320
ggcagcaatt cacgtgggaa cattcgaacc tggaggccaa caagcccaag aaccgctatg    4380
ccaacgtcat cgcctatgac cactcacgag tcatcctgca gccCctagaa ggcatcatgg    4440
gtagtgatta catcaatgcc aactatgtgg acggctaccg gcggcagaat gcatacattg    4500
ccacgcaggg gcccctgcct gagacctttg ggacttctg gcggatggtg tgggagcagc    4560
gatcggccac tgtggtcatg atgacgcgac tggaggagaa atcacggatc aaatgtgacc    4620
aatactggcc taaccgaggc accgagacat acggcttcat ccaggtcacc ctactagata    4680
ccatggagct ggctaccttc tgcgtcagga ctttttctct acacaagaat ggctctagcg    4740
agaagcgtga ggtgcgacat ttccagttca cggcatggcc cgaccacggg gtacctgagt    4800
accccacgcc cttcctggca ttcctgcgaa gagtcaagac ctgcaacccg cctgatgctg    4860
gccccattgt ggtccactgc agcgcgggtg tggggcgcac tggctgcttc atcgtaattg    4920
acgccatgct agagcgcatc aagacagaga agaccgtgga tgtgtatgga catgtgacac    4980
tcatgcggtc gcagcgcaac tacatggtgc agacagagga tcagtatggc ttcatccacg    5040
aggcgctgct ggaggctgtg ggctgcggca ataccgaggt ccctgctcgc agcctctaca    5100
cctacatcca gaagctggcc caggtggagc ctggcgagca cgtcacgggc atggagcttg    5160
agttcaagag gctcgccagt tccaaggcac acacttcgcg cttcatcacc gccagcctgc    5220
cttgcaacaa gtttaagaac cgactggtga acatcctgcc gtacgagagc tcgcgtgtct    5280
gcctgcagcc catccgcggt gtggagggct ctgactacat caatgccagc tttatcgacg    5340
gctatagaca gcagaaagcc tacattgcaa cacagggggcc actggcagag accacagagg    5400
acttctggcg agctctgtgg gagaacaact ctactattgt cgtaatgctc accaagctcc    5460
gagaaatggg ccgggaaaag tgccaccagt actggccagc cgagcgctct gccCgctacc    5520
agtactttgt ggttgacccg atggcagagt ataacatgcc acagtacatt ctgcgtgagt    5580
ttaaggtcac agatgcccgg gatgccagt cccggaccgt ccgacagttc cagttcacgg    5640
actggccaga gcagggtgca cccaagtcag gggaaggctt cattgacttc atcggccaag    5700
tgcataagac caaggagcag tttggccagg acggacccat ctcagtgcac tgcagcgccg    5760
```

```
gagtgggcag gaccggagtg ttcatcaccc tgagcatcgt gcttgagcgg atgcgctacg    5820
agggcgtggt ggacattttc cagacagtga aggtgcttcg gacccagagg cctgccatgg    5880
tgcagacaga ggacgagtac cagttctgct tccaggcggc tttggaatac ctgggcagtt    5940
ttgatcatta tgcaacataa gccatgggcc ccgcccaaca cctcagccct gcgccaagtg    6000
ccctggatgt gagcctaggc ccgccgctgg gcaggatgcg gcccagggag acctcctctt    6060
cgcggagaca ggcgctgcct tcctcattcc cttctgattc caaaacgagg ttccaggggtg   6120 gggggttggg gtggagagag aaggagccac tgctccccag gctggggtca cacagggacc    6180
gacctctgct tccgcactcc cctgcctgcc ttttggcaac attttttttc ttattttttt    6240
ttaatagtgt atattttttt tcttttttctt tttttcttttt tttttttttaa gaaaaaaaca  6300 aaatcgtgcc ggtcaaaact ttgaaaaaga aacaagatca ctgtttgtgc ctctgtggga    6360
ggcctatttt ttcatagtta gtgtgccgtg tggcggctat gtgcggccac ttcgacggct    6420
tctgtgtgtg catctttccc acatgcccga cactgccccc atccccatgt gaatggtgcg    6480
cttagttttt atttttaacc ttttttacttt tttttttaatc aatcttcaga catatcagat   6540
atggagggtg aggcgctggg ggcactcggg ccagactaca gggacatggc caccaaggac    6600
acagtggctg gccttgctgc tccagtccct ggcacaccag ggagggtcct cgtctactca    6660
tgacctctgt gccccgcatg gaggacctgg gactacggga cacttggggg atatccaacc    6720
ccctggagca actgaggtct ctctttgtag gagagtgggt cagtactcgt ccccgctgtt    6780
ttttgggcag aagcagcagg tgacgcccct gtatgtagat aaaccaactt tgtattaaag    6840
aaagattcgt ccgacctaga aaaaaaaaaa aaaa                                6874
```

<210> SEQ ID NO 9
<211> LENGTH: 198
<212> TYPE: PRT
<213> ORGANISM: Homo sapiens

<400> SEQUENCE: 9

```
Glu Glu Pro Pro Arg Phe Ile Lys Glu Pro Lys Asp Gln Ile Gly Val
1               5                   10                  15

Ser Gly Gly Val Ala Ser Phe Val Cys Gln Ala Thr Gly Asp Pro Lys
            20                  25                  30

Pro Arg Val Thr Trp Asn Lys Lys Gly Lys Lys Val Asn Ser Gln Arg
        35                  40                  45

Phe Glu Thr Ile Glu Phe Asp Glu Ser Ala Gly Ala Val Leu Arg Ile
    50                  55                  60

Gln Pro Leu Arg Thr Pro Arg Asp Glu Asn Val Tyr Glu Cys Val Ala
65                  70                  75                  80

Gln Asn Ser Val Gly Glu Ile Thr Val His Ala Lys Leu Thr Val Leu
                85                  90                  95

Arg Glu Asp Gln Leu Pro Ser Gly Phe Pro Asn Ile Asp Met Gly Pro
            100                 105                 110

Gln Leu Lys Val Val Glu Arg Thr Arg Thr Ala Thr Met Leu Cys Ala
        115                 120                 125

Ala Ser Gly Asn Pro Asp Pro Glu Ile Thr Trp Phe Lys Asp Phe Leu
    130                 135                 140

Pro Val Asp Pro Ser Ala Ser Asn Gly Arg Ile Lys Gln Leu Arg Ser
145                 150                 155                 160

Gly Ala Leu Gln Ile Glu Ser Ser Glu Glu Thr Asp Gln Gly Lys Tyr
                165                 170                 175
```

```
Glu Cys Val Ala Thr Asn Ser Ala Gly Val Arg Tyr Ser Ser Pro Ala
            180                 185                 190
Asn Leu Tyr Val Arg Val
            195

<210> SEQ ID NO 10
<211> LENGTH: 198
<212> TYPE: PRT
<213> ORGANISM: Mus musculus

<400> SEQUENCE: 10

Glu Glu Pro Pro Arg Phe Ile Arg Glu Pro Lys Asp Gln Ile Gly Val
1               5                   10                  15

Ser Gly Gly Val Ala Ser Phe Val Cys Gln Ala Thr Gly Asp Pro Lys
            20                  25                  30

Pro Arg Val Thr Trp Asn Lys Lys Gly Lys Lys Val Asn Ser Gln Arg
            35                  40                  45

Phe Glu Thr Ile Asp Phe Asp Glu Ser Gly Ala Val Leu Arg Ile
    50                  55                  60

Gln Pro Leu Arg Thr Pro Arg Asp Glu Asn Val Tyr Glu Cys Val Ala
65                  70                  75                  80

Gln Asn Ser Val Gly Glu Ile Thr Ile His Ala Lys Leu Thr Val Leu
            85                  90                  95

Arg Glu Asp Gln Leu Pro Pro Gly Phe Pro Asn Ile Asp Met Gly Pro
            100                 105                 110

Gln Leu Lys Val Val Glu Arg Thr Arg Thr Ala Thr Met Leu Cys Ala
            115                 120                 125

Ala Ser Gly Asn Pro Asp Pro Glu Ile Thr Trp Phe Lys Asp Phe Leu
            130                 135                 140

Pro Val Asp Pro Ser Ala Ser Asn Gly Arg Ile Lys Gln Leu Arg Ser
145                 150                 155                 160

Gly Ala Leu Gln Ile Glu Ser Ser Glu Glu Thr Asp Gln Gly Lys Tyr
            165                 170                 175

Glu Cys Val Ala Thr Asn Ser Ala Gly Val Arg Tyr Ser Ser Pro Ala
            180                 185                 190

Asn Leu Tyr Val Arg Val
            195

<210> SEQ ID NO 11
<211> LENGTH: 198
<212> TYPE: PRT
<213> ORGANISM: Gallus gallus

<400> SEQUENCE: 11

Glu Ser Pro Pro Val Phe Ile Lys Lys Pro Val Asp Gln Ile Gly Val
1               5                   10                  15

Ser Gly Gly Val Ala Ser Phe Val Cys Gln Ala Thr Gly Asp Pro Lys
            20                  25                  30

Pro Arg Val Thr Trp Asn Lys Lys Gly Lys Lys Val Asn Ser Gln Arg
            35                  40                  45

Phe Glu Thr Ile Glu Phe Asp Glu Ser Ala Gly Ala Val Leu Arg Ile
    50                  55                  60

Gln Pro Leu Arg Thr Pro Arg Asp Glu Asn Ile Tyr Glu Cys Val Ala
65                  70                  75                  80

Gln Asn Pro His Gly Glu Val Thr Val His Ala Lys Leu Thr Val Leu
            85                  90                  95
```

```
Arg Glu Asp Gln Leu Pro Pro Gly Phe Pro Asn Ile Asp Met Gly Pro
            100                 105                 110

Gln Leu Lys Val Val Glu Arg Thr Arg Thr Ala Thr Met Leu Cys Ala
            115                 120                 125

Ala Ser Gly Asn Pro Asp Pro Glu Ile Thr Trp Phe Lys Asp Phe Leu
            130                 135                 140

Pro Val Asp Pro Ser Thr Ser Asn Gly Arg Ile Lys Gln Leu Arg Ser
145                 150                 155                 160

Gly Gly Leu Gln Ile Glu Ser Ser Glu Glu Thr Asp Gln Gly Lys Tyr
                165                 170                 175

Glu Cys Val Ala Ser Asn Ser Ala Gly Val Arg Tyr Ser Ser Pro Ala
            180                 185                 190

Asn Leu Tyr Val Arg Val
            195

<210> SEQ ID NO 12
<211> LENGTH: 198
<212> TYPE: PRT
<213> ORGANISM: Xenopus tropicalis

<400> SEQUENCE: 12

Gly Ser Lys Pro Lys Phe Ile Lys Ile Pro Thr Asp Glu Ile Gly Val
1               5                   10                  15

Ser Gly Gly Val Ala Ser Phe Val Cys Gln Ala Thr Gly Asp Pro Lys
            20                  25                  30

Pro Arg Val Thr Trp Asn Lys Arg Gly Lys Lys Val Asn Ser Gln Arg
            35                  40                  45

Phe Glu Thr Ile Glu Phe Asp Glu Gly Ala Gly Ala Val Leu Arg Ile
        50                  55                  60

Gln Pro Leu Arg Thr Pro Arg Asp Glu Asn Val Tyr Glu Cys Val Ala
65                  70                  75                  80

Gln Asn Val His Gly Glu Glu Val Val Ser Ala Lys Leu Thr Val Leu
                85                  90                  95

Arg Glu Asp Gln Leu Pro Ser Gly Phe Pro Asn Ile Asp Met Gly Pro
            100                 105                 110

Gln Leu Lys Val Val Glu Arg Thr Arg Thr Ala Thr Met Leu Cys Ala
            115                 120                 125

Ala Ser Gly Asn Pro Asp Pro Glu Ile Thr Trp Phe Lys Asp Phe Leu
            130                 135                 140

Pro Val Asp Pro Ala Ser Ser Asn Gly Arg Ile Lys Gln Leu Arg Ser
145                 150                 155                 160

Gly Ala Leu Gln Ile Glu Asn Ser Glu Glu Thr Asp Gln Gly Lys Tyr
                165                 170                 175

Glu Cys Val Ala Thr Asn Ser Ala Gly Val Arg Tyr Ser Ser Pro Ala
            180                 185                 190

Asn Leu Tyr Val Arg Val
            195

<210> SEQ ID NO 13
<211> LENGTH: 197
<212> TYPE: PRT
<213> ORGANISM: Danio rerio

<400> SEQUENCE: 13

Ser Ser Pro Arg Phe Thr Lys Val Pro Val Asp Met Ile Gly Val Ser
1               5                   10                  15
```

```
Gly Gly Val Val Ser Phe Val Cys Gln Ala Thr Gly Asp Pro Lys Pro
            20                  25                  30

Lys Val Thr Trp Asn Lys Lys Gly Arg Val Asn Ser Gln Arg Ile
        35                  40                  45

Glu Thr Ile Glu Phe Asp Glu Gly Ala Gly Ala Val Leu Arg Ile Gln
 50                  55                  60

Pro Leu Arg Ala Pro Arg Asp Glu Asn Val Tyr Glu Cys Gln Ala Glu
 65                  70                  75                  80

Asn Ser Glu Gly Glu Ile Asn Val Gln Ala Lys Leu Ser Ile Ile Arg
                85                  90                  95

Glu Asp Leu Leu Pro Pro Gly Phe Pro Asn Ile Asp Met Gly Pro Gln
                100                 105                 110

Leu Lys Val Val Glu Arg Thr Arg Thr Ala Thr Met Leu Cys Ala Ala
                115                 120                 125

Ser Gly Asn Pro Asp Pro Glu Ile Thr Trp Phe Lys Asp Phe Leu Pro
130                 135                 140

Ile Asp Pro Asn Thr Ser Asn Gly Arg Ile Lys Gln Leu Arg Ser Gly
145                 150                 155                 160

Ala Leu Gln Ile Glu Asn Thr Glu Glu Thr Asp Gln Gly Lys Tyr Glu
                165                 170                 175

Cys Val Ala Ser Asn Val Glu Gly Val Arg Tyr Ser Ser Pro Ala Asn
                180                 185                 190

Leu Tyr Val Arg Val
            195

<210> SEQ ID NO 14
<211> LENGTH: 198
<212> TYPE: PRT
<213> ORGANISM: Homo sapiens

<400> SEQUENCE: 14

Glu Thr Pro Pro Arg Phe Thr Arg Thr Pro Val Asp Gln Thr Gly Val
 1               5                  10                  15

Ser Gly Gly Val Ala Ser Phe Ile Cys Gln Ala Thr Gly Asp Pro Arg
                20                  25                  30

Pro Lys Ile Val Trp Asn Lys Lys Gly Lys Lys Val Ser Asn Gln Arg
                35                  40                  45

Phe Glu Val Ile Glu Phe Asp Asp Gly Ser Gly Ser Val Leu Arg Ile
 50                  55                  60

Gln Pro Leu Arg Thr Pro Arg Asp Glu Ala Ile Tyr Glu Cys Val Ala
 65                  70                  75                  80

Ser Asn Asn Val Gly Glu Ile Ser Val Ser Thr Arg Leu Thr Val Leu
                85                  90                  95

Arg Glu Asp Gln Ile Pro Arg Gly Phe Pro Thr Ile Asp Met Gly Pro
                100                 105                 110

Gln Leu Lys Val Val Glu Arg Thr Arg Thr Ala Thr Met Leu Cys Ala
                115                 120                 125

Ala Ser Gly Asn Pro Asp Pro Glu Ile Thr Trp Phe Lys Asp Phe Leu
130                 135                 140

Pro Val Asp Thr Ser Asn Asn Gly Arg Ile Lys Gln Leu Arg Ser
145                 150                 155                 160

Gly Ala Leu Gln Ile Glu Gln Ser Glu Glu Ser Asp Gln Gly Lys Tyr
                165                 170                 175

Glu Cys Val Ala Thr Asn Ser Ala Gly Thr Arg Tyr Ser Ala Pro Ala
```

```
Asn Leu Tyr Val Arg Val
            195

<210> SEQ ID NO 15
<211> LENGTH: 198
<212> TYPE: PRT
<213> ORGANISM: Mus musculus

<400> SEQUENCE: 15

Glu Thr Pro Pro Arg Phe Thr Arg Thr Pro Val Asp Gln Thr Gly Val
1               5                   10                  15

Ser Gly Gly Val Ala Ser Phe Ile Cys Gln Ala Thr Gly Asp Pro Arg
            20                  25                  30

Pro Lys Ile Val Trp Asn Lys Lys Gly Lys Lys Val Ser Asn Gln Arg
        35                  40                  45

Phe Glu Val Ile Glu Phe Asp Asp Gly Ser Gly Ser Val Leu Arg Ile
    50                  55                  60

Gln Pro Leu Arg Thr Pro Arg Asp Glu Ala Ile Tyr Glu Cys Val Ala
65                  70                  75                  80

Ser Asn Asn Val Gly Glu Ile Ser Val Ser Thr Arg Leu Thr Val Leu
                85                  90                  95

Arg Glu Asp Gln Ile Pro Arg Gly Phe Pro Thr Ile Asp Met Gly Pro
            100                 105                 110

Gln Leu Lys Val Val Glu Arg Thr Arg Thr Ala Thr Met Leu Cys Ala
        115                 120                 125

Ala Ser Gly Asn Pro Asp Pro Glu Ile Thr Trp Phe Lys Asp Phe Leu
    130                 135                 140

Pro Val Asp Thr Ser Asn Asn Asn Gly Arg Ile Lys Gln Leu Arg Ser
145                 150                 155                 160

Gly Ala Leu Gln Ile Glu Gln Ser Glu Glu Ser Asp Gln Gly Lys Tyr
                165                 170                 175

Glu Cys Val Ala Thr Asn Ser Ala Gly Thr Arg Tyr Ser Ala Pro Ala
            180                 185                 190

Asn Leu Tyr Val Arg Val
            195

<210> SEQ ID NO 16
<211> LENGTH: 198
<212> TYPE: PRT
<213> ORGANISM: Gallus gallus

<400> SEQUENCE: 16

Glu Ser Pro Pro Lys Phe Thr Arg Thr Pro Val Asp Gln Thr Gly Val
1               5                   10                  15

Ser Gly Gly Val Ala Ser Phe Ile Cys Gln Ala Thr Gly Asp Pro Arg
            20                  25                  30

Pro Lys Ile Val Trp Asn Lys Lys Gly Lys Lys Val Ser Asn Gln Arg
        35                  40                  45

Phe Glu Val Ile Glu Phe Asp Asp Gly Ser Gly Ser Val Leu Arg Ile
    50                  55                  60

Gln Pro Leu Arg Thr Pro Arg Asp Glu Ala Ile Tyr Glu Cys Val Ala
65                  70                  75                  80

Ser Asn Ser Val Gly Glu Ile Ser Val Ser Thr Arg Leu Thr Val Leu
                85                  90                  95

Arg Glu Asp Gln Ile Pro Arg Gly Phe Pro Thr Ile Asp Met Gly Pro
```

```
            100                 105                 110
Gln Leu Lys Val Val Glu Arg Thr Arg Thr Ala Thr Met Leu Cys Ala
        115                 120                 125

Ala Ser Gly Asn Pro Asp Pro Glu Ile Ser Trp Phe Lys Asp Phe Leu
    130                 135                 140

Pro Val Asp Thr Ser Asn Asn Gly Arg Ile Lys Gln Leu Arg Ser
145                 150                 155                 160

Gly Ala Leu Gln Ile Glu Leu Ser Glu Glu Ser Asp Gln Gly Lys Tyr
                165                 170                 175

Glu Cys Val Ala Thr Asn Ser Ala Gly Thr Arg Tyr Ser Ala Pro Ala
            180                 185                 190

Asn Leu Tyr Val Arg Val
        195

<210> SEQ ID NO 17
<211> LENGTH: 198
<212> TYPE: PRT
<213> ORGANISM: Xenopus laevis

<400> SEQUENCE: 17

Glu Thr Pro Pro Lys Leu Thr Arg Thr Pro Val Asp Gln Ile Gly Val
1               5                   10                  15

Ser Gly Gly Val Ala Ser Phe Ile Cys Gln Ala Thr Gly Asp Pro Arg
            20                  25                  30

Pro Lys Ile Val Arg Asn Lys Lys Gly Lys Lys Val Ser Asn Gln Arg
        35                  40                  45

Phe Glu Val Ile Glu Phe Asp Asp Gly Ser Gly Ser Val Leu Arg Ile
    50                  55                  60

Gln Pro Leu Arg Thr Pro Arg Asp Glu Ala Ile Tyr Glu Cys Val Ala
65                  70                  75                  80

Ser Asn Ser Val Gly Glu Val Ala Thr Thr Thr Arg Leu Thr Val Leu
                85                  90                  95

Arg Glu Asp Gln Ile Pro Arg Gly Phe Pro Thr Ile Asp Met Gly Pro
            100                 105                 110

Gln Leu Lys Val Val Glu Arg Thr Arg Thr Ala Thr Met Leu Cys Ala
        115                 120                 125

Ala Ser Gly Asn Pro Asp Pro Glu Ile Thr Trp Phe Lys Asp Tyr Leu
    130                 135                 140

Pro Val Asp Thr Ser Asn Asn Gly Arg Ile Lys Gln Leu Arg Ser
145                 150                 155                 160

Gly Ala Leu Gln Ile Glu Gln Ser Glu Glu Ser Asp Gln Gly Lys Tyr
                165                 170                 175

Glu Cys Val Ala Thr Asn Ser Ala Gly Thr Arg Tyr Ser Ala Pro Ala
            180                 185                 190

Asn Leu Tyr Val Arg Val
        195

<210> SEQ ID NO 18
<211> LENGTH: 197
<212> TYPE: PRT
<213> ORGANISM: Danio rerio

<400> SEQUENCE: 18

Gln Ser Ala Pro Arg Phe Thr Arg Thr Pro Thr Asp Gln Ile Gly Val
1               5                   10                  15

Gln Gly Gly Val Ala Ser Phe Val Cys Gln Ala Thr Gly Asp Pro Gln
```

```
                    20                  25                  30
Pro Lys Ile Thr Trp Ser Arg Lys Gly Lys Lys Val Thr Asn Gln Arg
            35                  40                  45
Phe Glu Val Ile Glu Phe Asp Gly Ser Gly Ser Ala Leu Arg Val
    50                  55                  60
Gln Pro Leu Arg Thr Pro Arg Asp Glu Ala Ile Tyr Glu Cys Val Ala
65                  70                  75                  80
Ser Asn Glu Ile Gly Glu Ile Thr Ala Ser Thr Arg Leu Ser Val Leu
                85                  90                  95
Arg Glu Asp Gln Leu Pro Ala Gly Phe Pro Ser Ile Asp Met Gly Pro
            100                 105                 110
Gln Leu Lys Val Val Glu Arg Ser Arg Thr Ala Thr Met Leu Cys Ala
            115                 120                 125
Ala Ser Gly Thr Pro Asp Pro Glu Ile Thr Trp Phe Lys Asp Phe Leu
        130                 135                 140
Pro Ile Asp Thr His Thr His Gly Arg Ile Lys Gln Leu Arg Ser Gly
145                 150                 155                 160
Ala Leu Gln Ile Asp Gln Ser Glu Glu Thr Asp Gln Gly Lys Tyr Glu
                165                 170                 175
Cys Val Ala Thr Asn Ser Glu Gly Thr Arg Tyr Ser Thr Pro Ala Asn
            180                 185                 190
Leu Tyr Val Arg Val
            195

<210> SEQ ID NO 19
<211> LENGTH: 198
<212> TYPE: PRT
<213> ORGANISM: Homo sapiens

<400> SEQUENCE: 19

Asp Ser Lys Pro Val Phe Ile Lys Val Pro Glu Asp Gln Thr Gly Leu
1               5                   10                  15
Ser Gly Gly Val Ala Ser Phe Val Cys Gln Ala Thr Gly Glu Pro Lys
                20                  25                  30
Pro Arg Ile Thr Trp Met Lys Lys Gly Lys Lys Val Ser Ser Gln Arg
            35                  40                  45
Phe Glu Val Ile Glu Phe Asp Asp Gly Ala Gly Ser Val Leu Arg Ile
    50                  55                  60
Gln Pro Leu Arg Val Gln Arg Asp Glu Ala Ile Tyr Glu Cys Thr Ala
65                  70                  75                  80
Thr Asn Ser Leu Gly Glu Ile Asn Thr Ser Ala Lys Leu Ser Val Leu
                85                  90                  95
Glu Glu Glu Gln Leu Pro Pro Gly Phe Pro Ser Ile Asp Met Gly Pro
            100                 105                 110
Gln Leu Lys Val Val Glu Lys Ala Arg Thr Ala Thr Met Leu Cys Ala
            115                 120                 125
Ala Gly Gly Asn Pro Asp Pro Glu Ile Ser Trp Phe Lys Asp Phe Leu
        130                 135                 140
Pro Val Asp Pro Ala Thr Ser Asn Gly Arg Ile Lys Gln Leu Arg Ser
145                 150                 155                 160
Gly Ala Leu Gln Ile Glu Ser Ser Glu Glu Ser Asp Gln Gly Lys Tyr
                165                 170                 175
Glu Cys Val Ala Thr Asn Ser Ala Gly Thr Arg Tyr Ser Ala Pro Ala
            180                 185                 190
```

```
Asn Leu Tyr Val Arg Val
        195

<210> SEQ ID NO 20
<211> LENGTH: 198
<212> TYPE: PRT
<213> ORGANISM: Mus musculus

<400> SEQUENCE: 20

Asp Ser Lys Pro Val Phe Val Lys Val Pro Glu Asp Gln Thr Gly Leu
1               5                   10                  15

Ser Gly Gly Val Ala Ser Phe Val Cys Gln Ala Thr Gly Glu Pro Lys
            20                  25                  30

Pro Arg Ile Thr Trp Met Lys Lys Gly Lys Lys Val Ser Ser Gln Arg
        35                  40                  45

Phe Glu Val Ile Glu Phe Asp Asp Gly Ala Gly Ser Val Leu Arg Ile
    50                  55                  60

Gln Pro Leu Arg Val Gln Arg Asp Glu Ala Ile Tyr Glu Cys Thr Ala
65                  70                  75                  80

Thr Asn Ser Leu Gly Glu Ile Asn Thr Ser Ala Lys Leu Ser Val Leu
                85                  90                  95

Glu Glu Asp Gln Leu Pro Ser Gly Phe Pro Thr Ile Asp Met Gly Pro
            100                 105                 110

Gln Leu Lys Val Val Glu Lys Gly Arg Thr Ala Thr Met Leu Cys Ala
        115                 120                 125

Ala Gly Gly Asn Pro Asp Pro Glu Ile Ser Trp Phe Lys Asp Phe Leu
    130                 135                 140

Pro Val Asp Pro Ala Ala Ser Asn Gly Arg Ile Lys Gln Leu Arg Ser
145                 150                 155                 160

Gly Ala Leu Gln Ile Glu Ser Ser Glu Glu Ser Asp Gln Gly Lys Tyr
                165                 170                 175

Glu Cys Val Ala Thr Asn Ser Ala Gly Thr Arg Tyr Ser Ala Pro Ala
            180                 185                 190

Asn Leu Tyr Val Arg Val
        195

<210> SEQ ID NO 21
<211> LENGTH: 198
<212> TYPE: PRT
<213> ORGANISM: Gallus gallus

<400> SEQUENCE: 21

Glu Ser Lys Pro Thr Phe Met Lys Ala Pro Glu Asp Gln Ile Gly Ile
1               5                   10                  15

Ser Gly Gly Val Ala Ser Phe Val Cys Gln Ala Thr Gly Glu Pro Lys
            20                  25                  30

Pro Arg Ile Thr Trp Met Lys Lys Gly Lys Lys Val Ser Ser Gln Arg
        35                  40                  45

Phe Glu Val Ile Glu Phe Asp Asp Gly Ser Gly Ser Val Leu Arg Ile
    50                  55                  60

Gln Pro Leu Arg Val His Arg Asp Glu Ala Ile Tyr Glu Cys Thr Ala
65                  70                  75                  80

Thr Asn Ser Val Gly Glu Ile Asn Thr Ser Ala Lys Leu Thr Val Leu
                85                  90                  95

Glu Glu Asp His Leu Pro Ala Gly Phe Pro Thr Ile Asp Met Gly Pro
            100                 105                 110
```

```
Gln Leu Lys Val Val Glu Lys Ala Arg Thr Ala Thr Met Leu Cys Ala
            115                 120                 125

Ala Ser Gly Asn Pro Asp Pro Glu Ile Ser Trp Phe Lys Asp Phe Leu
130                 135                 140

Pro Val Asp Thr Ala Thr Ser Asn Gly Arg Ile Lys Gln Leu Arg Ser
145                 150                 155                 160

Gly Ala Leu Gln Ile Glu Asn Ser Glu Glu Ser Asp Gln Gly Lys Tyr
                165                 170                 175

Glu Cys Val Ala Thr Asn Ser Ala Gly Thr Arg Tyr Ser Ala Pro Ala
            180                 185                 190

Asn Leu Tyr Val Arg Val
            195

<210> SEQ ID NO 22
<211> LENGTH: 198
<212> TYPE: PRT
<213> ORGANISM: Xenopus laevis

<400> SEQUENCE: 22

Asp His Glu Pro Val Phe Val Arg Lys Pro Asp Asp Gln Ile Gly Ile
1               5                   10                  15

Ser Gly Gly Val Ala Ser Phe Val Cys Gln Ala Thr Ala Asp Pro Lys
                20                  25                  30

Pro Arg Ile Thr Trp Met Lys Lys Gly Lys Lys Val Ser Ser Gln Arg
            35                  40                  45

Phe Glu Val Ile Glu Phe Asp Asp Gly Ser Gly Ser Val Leu Arg Ile
    50                  55                  60

Gln Pro Leu Arg Val His Arg Asp Glu Ala Ile Tyr Glu Cys Thr Ala
65                  70                  75                  80

Thr Asn Ser Val Gly Glu Ile Asn Ser Ser Ala Lys Leu Thr Val Leu
                85                  90                  95

Glu Glu Glu Gln Leu Pro His Gly Phe Pro Val Ile Asp Met Gly Pro
            100                 105                 110

Gln Leu Lys Val Val Glu Lys Thr Arg Thr Ala Thr Met Leu Cys Ala
            115                 120                 125

Ala Ser Gly Asn Pro Asp Pro Glu Ile Thr Trp Phe Lys Asp Phe Leu
130                 135                 140

Pro Val Asp Thr Ala Ser Ser Asn Gly Arg Ile Lys Gln Leu Arg Ser
145                 150                 155                 160

Gly Ala Leu Gln Ile Glu Asn Ser Glu Glu Ser Asp Gln Gly Lys Tyr
                165                 170                 175

Glu Cys Val Ala Thr Asn Ser Ala Gly Thr Arg Tyr Ser Ala Pro Ala
            180                 185                 190

Asn Leu Tyr Val Arg Val
            195

<210> SEQ ID NO 23
<211> LENGTH: 197
<212> TYPE: PRT
<213> ORGANISM: Danio rerio

<400> SEQUENCE: 23

Asp Ser Leu Pro Asn Phe Val Arg Ser Pro Glu Asp Gln Thr Gly Ile
1               5                   10                  15

Ser Gly Gly Val Ala Ser Phe Val Cys Gln Ala Ala Gly Glu Pro Lys
                20                  25                  30
```

Pro Arg Ile Thr Trp Met Lys Lys Gly Lys Lys Val Ser Gln Arg
           35                  40                  45

Phe Glu Val Ile Glu Phe Asp Asp Gly Ser Gly Ser Val Leu Arg Ile
 50                  55                  60

Gln Pro Leu Arg Thr His Arg Asp Glu Ala Ile Tyr Glu Cys Thr Ala
 65                  70                  75                  80

Thr Asn Ser Leu Gly Glu Ile Asn Thr Ser Ala Lys Leu Thr Val Leu
                 85                  90                  95

Glu Glu Asn Gln Ile Pro His Gly Phe Pro Thr Ile Asp Met Gly Pro
            100                 105                 110

Gln Leu Lys Val Val Glu Arg Thr Arg Thr Thr Met Leu Cys Ala
            115                 120                 125

Ala Ser Gly Asn Pro Asp Pro Glu Ile Thr Trp Phe Lys Asp Phe Leu
130                 135                 140

Pro Val Asp Ile Asn Gly Asn Gly Arg Ile Lys Gln Leu Arg Ser Gly
145                 150                 155                 160

Ala Leu Gln Ile Glu Asn Ser Glu Glu Ser Asp Gln Gly Lys Tyr Glu
                165                 170                 175

Cys Val Ala Thr Asn Ser Ala Gly Thr Arg Tyr Ser Ala Pro Ala Asn
            180                 185                 190

Leu Tyr Val Arg Val
        195

<210> SEQ ID NO 24
<211> LENGTH: 197
<212> TYPE: PRT
<213> ORGANISM: Drosophila melanogaster

<400> SEQUENCE: 24

Ala His Pro Pro Glu Ile Ile Arg Lys Pro Gln Asn Gln Gly Val Arg
 1               5                  10                  15

Val Gly Gly Val Ala Ser Phe Tyr Cys Ala Ala Arg Gly Asp Pro Pro
                20                  25                  30

Pro Ser Ile Val Trp Arg Lys Asn Gly Lys Lys Val Ser Gly Thr Gln
            35                  40                  45

Ser Arg Tyr Thr Val Leu Glu Gln Pro Gly Gly Ile Ser Ile Leu Arg
 50                  55                  60

Ile Glu Pro Val Arg Ala Gly Arg Asp Asp Ala Pro Tyr Glu Cys Val
 65                  70                  75                  80

Ala Glu Asn Gly Val Gly Asp Ala Val Ser Ala Asp Ala Thr Leu Thr
                 85                  90                  95

Ile Tyr Glu Gly Asp Lys Thr Pro Ala Gly Phe Pro Val Ile Thr Gln
            100                 105                 110

Gly Pro Gly Thr Arg Val Ile Glu Val Gly His Thr Val Leu Met Thr
            115                 120                 125

Cys Lys Ala Ile Gly Asn Pro Thr Pro Asn Ile Tyr Trp Ile Lys Asn
130                 135                 140

Gln Thr Lys Val Asp Met Ser Asn Pro Arg Tyr Ser Leu Lys Asp Gly
145                 150                 155                 160

Phe Leu Gln Ile Glu Asn Ser Arg Glu Glu Asp Gln Gly Lys Tyr Glu
                165                 170                 175

Cys Val Ala Glu Asn Ser Met Gly Thr Glu His Ser Lys Ala Thr Asn
            180                 185                 190

Leu Tyr Val Lys Val
        195

<210> SEQ ID NO 25
<211> LENGTH: 200
<212> TYPE: PRT
<213> ORGANISM: Hirudo medicinalis

<400> SEQUENCE: 25

Asp His Asp Asp Ala Pro Arg Ile Thr Thr Ala Pro Arg Asp Gln Lys
1               5                   10                  15

Val Met Glu Gly Lys Ile Ala Ser Phe Phe Cys Lys Ala Ser Gly Asn
            20                  25                  30

Pro Ala Pro Glu Val Tyr Trp Lys Arg Gly Trp Lys Glu Ser Leu His
        35                  40                  45

Asp Lys Asn Glu Thr Lys Thr Ser Asn Met Pro His Gly Ser Val Leu
    50                  55                  60

Arg Val Asp Pro Thr Lys Trp Gln Lys Asp Glu Thr Ile Ile Glu Cys
65                  70                  75                  80

Val Ala Glu Ser Gly Ile Gly His Gln Ala Ala Thr Ala Thr Ala Arg
            85                  90                  95

Leu His Ile Tyr Arg Glu Asn Glu Glu Pro Lys Gly Phe Pro Arg Leu
        100                 105                 110

Leu Glu Thr Pro Glu Met Arg Ser Val Glu Lys Asp Arg Asn Phe Ile
    115                 120                 125

Leu Lys Cys Ser Ala Thr Gly Asp Pro Glu Pro Ser Val Tyr Trp Leu
130                 135                 140

Lys Asp Asn Ile Pro Val Asp Met Ser Asp Lys Arg Ile Gln Val Leu
145                 150                 155                 160

Pro Gly Gly Ser Leu Ser Ile Arg Asn Gly Gln Gly Ser Asp Glu Gly
            165                 170                 175

Lys Tyr Glu Cys Val Ala Glu Asn Ile His Gly Thr Val His Ser Phe
        180                 185                 190

Pro Ala Ser Leu Tyr Ile Arg Ile
    195                 200

<210> SEQ ID NO 26
<211> LENGTH: 197
<212> TYPE: PRT
<213> ORGANISM: Hirudo medicinalis

<400> SEQUENCE: 26

Arg Lys Ser Arg Pro Pro Arg Val Val Gln Lys Val Met Glu Gly Asn
1               5                   10                  15

Met Ala Thr Phe Trp Cys Gly Val Val Gly Lys Pro Ala Pro Glu Met
            20                  25                  30

Thr Trp Tyr His Met Asn Arg Lys Leu Glu Ser Phe Thr Tyr Gln Gln
        35                  40                  45

Ser Ser Arg Lys Ile Phe Thr His His Asn Leu Ser Val Leu Arg Val
    50                  55                  60

Glu Pro Val Lys Lys Arg Asp Glu Gly Arg Tyr Glu Cys Glu Ala His
65                  70                  75                  80

Asn Gly Val Gly Val Pro Asp Arg Val Ser Phe Asn Leu Ser Val Tyr
            85                  90                  95

Thr Lys Asn Asp Pro Ile Pro Ala Gly Phe Pro Glu Ile Leu Val His
        100                 105                 110

Pro Lys Leu Gly Ser Val Glu Arg Tyr Arg Ser Thr Val Met Ala Cys
    115                 120                 125

```
Ser Gly Lys Gly Asn Pro Glu Pro Thr Phe Ser Trp Leu Lys Asp Phe
        130                 135                 140

Ile Pro Ile Glu Phe Thr Pro Val Arg Phe Ser Val Met Pro Thr Gly
145                 150                 155                 160

Ala Leu Gln Leu Leu Asn Ser Thr Tyr Ser Tyr Glu Gly Lys Tyr Glu
                165                 170                 175

Cys Ile Ala Glu Asn Ser His Gly Val Thr Asn Ser Gln Gln Ala Thr
                180                 185                 190

Leu Val Leu Lys Ala
            195

<210> SEQ ID NO 27
<211> LENGTH: 203
<212> TYPE: PRT
<213> ORGANISM: Caenorhabditis elegans

<400> SEQUENCE: 27

Lys Glu Asp Asp Pro Ala Arg Leu Val Val Arg Pro Asp Ser Ser Thr
1               5                   10                  15

Val Val Asp Glu Ser Lys Ile Ser Phe Phe Cys Arg Ala Asp Gly Asn
                20                  25                  30

Pro Leu Pro Ser Val Ile Trp Arg Val Asn Gly Lys Ser Ile Thr Asp
            35                  40                  45

His Asn Arg Ile Ser Ile Lys Ser Leu Ala Thr Gly Leu Ser Thr Leu
        50                  55                  60

Arg Phe Glu Arg Val Ser Leu Asp Asp Asn Ala Thr Val Val Ser Cys
65                  70                  75                  80

Ser Ala Asp Asn Gly Val Ala Asn Pro Val Val Ala Glu Ala Ser Leu
                85                  90                  95

Thr Val Val Pro Arg Asp Lys Val Pro Ile Gly Phe Pro Gln Ile Glu
                100                 105                 110

Leu His Pro Ser Leu Lys Ser Val Glu Gln Gly Lys Thr Ala Tyr Val
            115                 120                 125

Ser Cys Arg Val Arg Gly Asp Pro Arg Ala Lys Val Leu Trp Leu Arg
        130                 135                 140

Asp Leu Ile Pro Leu Asp Ile Arg Ala Asp Gly Arg Tyr Ser Val Ser
145                 150                 155                 160

Thr Ile Gly Asn Pro Gly Ala Leu Met Ile Gln His Ala Arg Glu Glu
                165                 170                 175

Asp Gln Gly Lys Tyr Glu Cys Ile Ala Arg Asn Thr Leu Gly Val Ala
            180                 185                 190

His Ser Lys Ala Ala Asn Leu Tyr Val Lys Val
        195                 200

<210> SEQ ID NO 28
<211> LENGTH: 196
<212> TYPE: PRT
<213> ORGANISM: Nematostella vectensis

<400> SEQUENCE: 28

Pro Thr Val Thr Leu Thr Pro Lys Asp Phe Ala Gly Val Thr Arg Gly
1               5                   10                  15

Phe Val Tyr Met Ile Cys Asn Val Thr Gly Ser Pro Met Pro Thr Leu
                20                  25                  30

Thr Trp Tyr Lys Asn Gly Ser Val Ile Arg Asn Ser Arg Ile Gln Ile
            35                  40                  45
```

```
Phe Thr Met Pro Tyr Gly Gly Leu Ile Arg Ile Gly Pro Leu Arg Ala
    50                  55                  60

Lys Ile His Lys Ala Thr Tyr Glu Cys Glu Ala Asp Asn Gly Val Gly
 65                  70                  75                  80

Pro Pro Leu Arg Asp Ser Ser Thr Leu Ile Val His Thr Ala Ser Thr
                 85                  90                  95

Lys Pro Ala Gly Phe Pro Arg Ile Ala Lys His Pro Ser Phe Lys Gln
                100                 105                 110

Arg Arg Ser Gly Asp Asp Val Thr Phe Thr Cys Ala Ala Val Gly Thr
            115                 120                 125

Pro Thr Pro Asn Ile Thr Trp Phe Lys Asp Arg Leu Pro Ile Val Leu
    130                 135                 140

Asn Asp Pro Arg Val Ser Val Leu Ser Asp Gly Arg Lys Leu Arg Ile
145                 150                 155                 160

Thr Asp Leu Arg Glu Ser Asp Asn Gly Lys Tyr Ser Cys Val Ala Arg
                165                 170                 175

Asn Ala Leu Gly Met Val Phe Ser Ser Gln Ala Met Pro Ala Arg Leu
                180                 185                 190

Phe Ile Tyr Leu
        195

<210> SEQ ID NO 29
<211> LENGTH: 4
<212> TYPE: PRT
<213> ORGANISM: Homo sapiens

<400> SEQUENCE: 29

Arg Val Arg Arg
1

<210> SEQ ID NO 30
<211> LENGTH: 4
<212> TYPE: PRT
<213> ORGANISM: Homo sapiens

<400> SEQUENCE: 30

Glu Leu Arg Glu
1

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 31

His His His His His His
1               5
```

UNITED STATES PATENT AND TRADEMARK OFFICE
CERTIFICATE OF CORRECTION

PATENT NO.         : 9,744,188 B2
APPLICATION NO.    : 13/985629
DATED              : August 29, 2017
INVENTOR(S)        : Flanagan et al.

Page 1 of 1

It is certified that error appears in the above-identified patent and that said Letters Patent is hereby corrected as shown below:

In the Specification

At Column 1, under the heading GOVERNMENT SUPPORT:
"This invention was supported by the National Institutes for Health (NIH) Grant No. EY11559 and HD29417 and the Government of the United States has certain rights thereto."

Should be replaced with:
— This invention was made with government support under EY011559 and HD029417 awarded by the National Institutes of Health. The government has certain rights in the invention. —

Signed and Sealed this
Twelfth Day of May, 2020

Andrei Iancu
*Director of the United States Patent and Trademark Office*